US008344208B2

(12) United States Patent
Kearney et al.

(10) Patent No.: US 8,344,208 B2
(45) Date of Patent: Jan. 1, 2013

(54) HIGHLY EFFICIENT SUPPRESSOR-DEPENDENT PROTEIN EXPRESSION IN PLANTS WITH A VIRAL VECTOR

(75) Inventors: Christopher M. Kearney, Woodway, TX (US); Zun Liu, Maiden, MA (US)

(73) Assignee: Baylor University, Waco, TX (US)

( * ) Notice: Subject to any disclaimer, the term of this patent is extended or adjusted under 35 U.S.C. 154(b) by 33 days.

(21) Appl. No.: 12/714,057

(22) Filed: Feb. 26, 2010

(65) Prior Publication Data
US 2010/0306878 A1 Dec. 2, 2010

Related U.S. Application Data

(60) Provisional application No. 61/155,810, filed on Feb. 26, 2009.

(51) Int. Cl.
*C12N 15/34* (2006.01)
*C12N 15/83* (2006.01)
*C12N 5/10* (2006.01)

(52) U.S. Cl. .................................... 800/280; 435/320.1

(58) Field of Classification Search .................. 800/278
See application file for complete search history.

(56) References Cited

U.S. PATENT DOCUMENTS 7,217,854 B1 * 5/2007 Baulcombe et al. .......... 800/278

FOREIGN PATENT DOCUMENTS
WO 2008/094512 A2 8/2008

OTHER PUBLICATIONS

Gelvin et al. Agrobacterium-mediated plant transformation: the biology behind the "gene-jockeying" tool (2003) Micorbiol. and Molec. Biol. Rev. 67: 16-37.*
Brunn-Rasmussen et al. Revised sequence of foxtail mosaic virus reveals a triple gene block structure similar to potato virus X (2008) Arch. Virol. 153: 223-226.*
Skryabin et al. Conserved and variable elements in RNA genomes of potexviruses (1998) Febs letters 240: 33-40.*
Paulson et al. Purification and properties of foxtail mosaic virus (1977) Phytopathology 67: 1346-1351.*
Brand et al. A versatile and reliable two-component system for tissue-specific gene induction in Arabidopsis (2006) Plant Phys. 141: 1194-1204.*
European Patent Office, International Search Report, Application No. PCT/US10/025615, Feb. 17, 2011.
Beck, David L., et al.; "Infectious Transcripts and Nucleotide Sequence of Cloned cDNA of the Potexvirus White Clover Mosaic Virus," Virology 177, (1990), pp. 152-158.
Bruun-Rasmussen, M., et al.; "Revised sequence of foxtail mosaic virus reveals a triple gene block structure similar to potato virus X," Archives of Virology, vol. 153, No. 1, (2008), pp. 223-226.
Gleba, Y., et al.; "Magnifection—a new platform for expressing recombinant vaccines in plants," Science Direct, Vaccine 23, (2005), pp. 2042-2048.
Komarova, T. V., et al.; "New Viral Vector for Efficient Production of Target Proteins in Plants," Biochemistry (Moscow), vol. 71, No. 8, Aug. 2006, pp. 846-850.
Lindbo, John A., et al.; "High-efficiency protein expression in plants from agroinfection-compatible Tobacco Mosaic virus expression vectors," BMC Biotechnology 2007, 7:52, pp. 1-11.
Lindo, John A., et al; "TRBO: A High-Efficiency Tobacco Mosaic Virus RNA-Based Overexpression Vector," Plant Physiology, Dec. 2007, vol. 145, pp. 1232-1240.
Plesha, Michael A., et al.; "High-Level Transient Production of a Heterologous Protein in Plants by Optimizing Induction of a Chemically Inducible Viral Amplicon Expression System," Biotechnology Progress, vol. 23, No. 6, Nov. 2007, pp. 1277-1285.

Robertson, N. L., et al.; "The open reading frame 5A of foxtail mosaic virus is expressed in vivo and is dispensable for systemic infection," Archives of Virology, vol. 145, No. 8, 2000, pp. 1685-1698.

Zuo, Jianru, et al.; "An estrogen receptor-based transactivator XVE mediates highly inducible gene expression in transgenic plants," The Plant Journal, (2000), 24(2),pp. 265-273.

European Patent Office, Invitation to Pay Additional Fees and, Where Applicable, Protest Fee, Partial International Search, Application No. PCT/US2010/025615, Nov. 10, 2010.

* cited by examiner

*Primary Examiner* — David H Kruse
*Assistant Examiner* — Steven Bernacki
(74) *Attorney, Agent, or Firm* — Jackson Walker L.L.P.

(57) ABSTRACT

A series of viral vectors derived from foxtail mosaic virus, sunn hemp mosaic virus and white clover mosaic virus sequences, and which are capable of expressing heterologous proteins in plants, including the tobacco, *Nicotiana benthamiana*, and cowpea, bean, and other legumes with the properties of unusually limited expression in the absence of gene silencing suppressors and high level expression in their presence. In a preferred embodiment, these viral vectors may be introduced via agroinoculation, and expression of the heterologous gene may be inducible with little or no leakiness in the absence of induction.

20 Claims, 9 Drawing Sheets

JBest: parent inducible binary
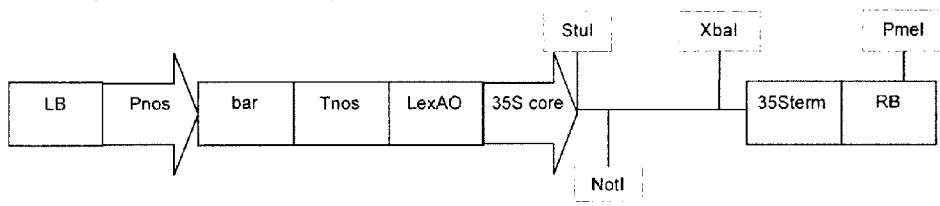
TBest: inducible TMV binary
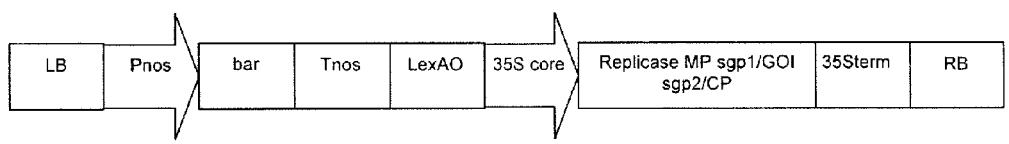
FBest: inducible FECT
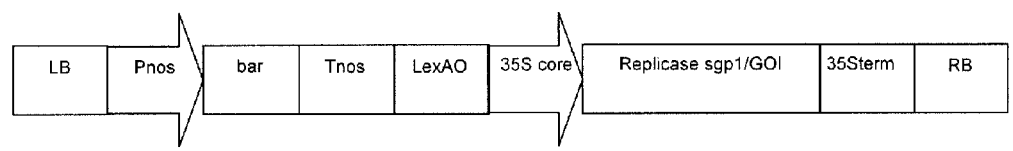
pER8/p19: inducible p19 binary
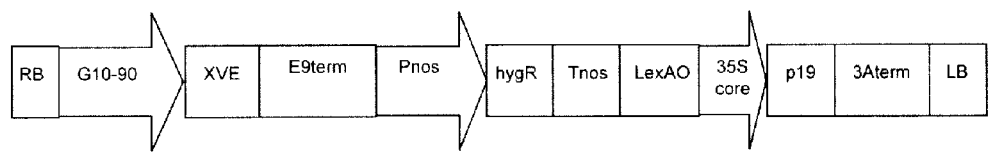
Figure 3

EcoLex Up
Adds EcoRI site upstream of LexAO promoter
5' GGAAAG GAATTC ATGTTACTAGATCGGGGAAT 3'
    Eco RI     pER8 3792-3811 (LexA operator)

35term Up
3' end of pJL24's 35S promoter, sense; overlap PCR
5' AAGTTCATTTCATTTGGAGAGG 3'

35termAS Down
3' end of pJL24's 35S promoter, antisense; overlap PCR
5' CCTCTCCAAATGAAATGAACTT 3'

JL22 RB Down
Downstream of PmeI site in JL22 T-DNA right border. Nts. 827-800 in pJL22.
5' TCTAATAAACGCTCTTTTCTCTTAGGTT 3'

TMV p1-21 UP
Phosphorylated 5' primer co-terminal with 5' end of TMV (nt. 1-21).
5'-p-GTATTTTTACAACAATTACC -3'

TMV1008 NotDN
Primer (TMVnts 1027-1008) with *Not* I site added
5' ATTATT GCGGCCGC TTGTACAAAAGAAAAGTATC
    Not I      TMVnts 1027-1008

FoMV 5'term UP
Phosphorylated 5' primer co-terminal with 5' end of FoMV (nts.1-21)
5' P--GAAAACTCTTCCGAAACCGAA 3'

FoMV756 NotI DOWN
For cloning 5' end of FECT
5' TTTTTT GCGGCCGC TTAGCCAGTTTAGGTCCTTA 3'
    *Not* I     FoMVnts 756-737 p19XhoI UP
Puts XhoI at 5' end of p19 ORF from TBSV
5' TAATAA CTCGAG ATGGAACGAGCTATACAAG 3' p19SpeI DOWN
Puts SpeI at 3' end of p19 ORF from TBSV
5' TTTTTT ACTAGT TTACTCGCTTTCTTTTTCGAAGG

Figure 4

HIGHLY EFFICIENT SUPPRESSOR-DEPENDENT PROTEIN EXPRESSION IN PLANTS WITH A VIRAL VECTOR

This application claims priority to U.S. Provisional Patent Application Ser. No. 61/155,810, filed on Feb. 26, 2009, entitled HIGHLY EFFICIENT SUPPRESSOR-DEPENDENT PROTEIN EXPRESSION IN PLANTS WITH A VIRAL VECTOR, the entire content of which is hereby incorporated by reference.

FIELD OF THE INVENTION

The present invention relates to a viral vector system, and more specifically to an inducible viral vector system for expressing heterologous genes with low risk of detrimental effect of either the viral vector or of toxic protein genes carried by the vector.

The content of text file BAYU 0023 ST25.txt (created Jul. 14, 2010, having a size of 182,271 bytes) is hereby incorporated by reference in its entirety.

BACKGROUND

Plant expression systems have been developed as a production platform for therapeutic proteins in the past two decades. Plants have some advantages over other expression systems, such as mammalian cell culture and bacterial fermentation. The application of plant systems means a lower cost of production and large-volume production, and cultivation is much less expensive and easier without sterile conditions of cell culture. Like mammalian systems, plant expression systems have the advantage of being able to produce active forms of complex proteins with post-translational modifications, such as glycosylation, which are necessary for human therapeutic proteins for correct function in vivo. Plant systems are also free of human pathogens potentially associated with mammalian cell cultures.

Although much work has been done with transgenic plants, their creation is time-consuming and labor-intensive. Plant viral vectors have emerged as the most efficient approach to achieving more rapid and higher-level expression of recombinant proteins, although protein expression is transient. Viral vectors systems take advantage of high levels of replication and maximum levels of foreign gene expression in a short time period from an engineered viral genome, with results within a week or two post-inoculation. A number of different plant viruses have been developed into protein production vectors, the most commercially useful being tobacco mosaic virus (TMV) of the Tobamovirus family and potato virus X (PVX) of the Potexvirus family.

Over the last two decades, plant virus-based expression systems have been successfully developed and utilized for high-yield production of heterologous proteins in plants. Viral vectors as transient gene expression systems provide increased speed and flexibility during early phases of experimentation. However, the potential widespread use of recombinant viruses raises concerns about possible risks to the environment. The bio-safety issues have to be considered to control the spread of the genetically engineered virus from experimental plants to susceptible wild plants. Intact viral vectors have the potential to spread and infect non-target plants, but replication-defective or movement-defective viruses avoid these problems. These deleted viral vectors can be safely used in the laboratory and, in large scale application, can be used to inoculate an entire greenhouse at once. In the field, it may be possible to achieve high expression in transgenic plants carrying an inducible virus as a transgene. In all of these cases, deleted virus vectors would be greatly preferred over full virus vectors for their lower environmental risk. However, one disadvantage of the deleted virus approach is that the vector cannot spread past the originally inoculated cells.

Several innovations have led to dramatic improvements in plant viral vectors. The early versions of these vectors cited used in vitro transcription to create infectious RNA, which is expensive and not amenable to large scale production in contrast to a more recent method named "agroinfection" (Gleba et al., 2005). Agroinfection involves syringe or vacuum infiltration of an *Agrobacterium tumefaciens* suspension harboring T-DNA carrying the viral genome into plant leaves, resulting in the local transformation of the infiltrated leaf with the cDNA form of the virus as a part of the T-DNA of the Ti plasmid. *Agrobacterium* infects each cell in the inoculated zone and inserts its T-DNA into the plant chromosome of each cell. A plant promoter placed upstream of the viral cDNA induces the transcription of viral genome in the plant nucleus and viral RNA is transported to cytoplasm for viral replication. Agroinfection results in almost 100% of the plant cells being infected transformed by *Agrobacterium* in the infiltrated zone. Therefore, agroinoculation also gives a preview as to how expression would look in a permanently transgenic plant. For both agroinoculation and transgenic use, systemic spread becomes an unnecessary property.

Agroinfection was developed originally for DNA plant viruses. As DNA viruses have disadvantages for foreign sequences insertion, RNA viruses were introduced into agroinfection system and developed with a number of different RNA viruses. Another development was the use of RNA silencing suppressors to increase expression. For example, a recently developed TMV vector, driven by a 35S promoter in a binary vector, was delivered via agroinfection along with an *Agrobacterium* culture carrying a 35S-driven p19 suppressor. This system produced 0.6-1.2 mg of recombinant protein per gram of infiltrated plant tissue, which is 10-25 times higher than the 35S promoter driven transient expression systems (Lindbo, 2007a).

Agroinfection allows the replacement of the MP and/or CP genes of vector viruses with heterologous sequences in some virus species. Tobacco mosaic virus (TMV) lacking the CP gene has been used to produce large amounts of foreign proteins and agroinfection greatly increased infectivity of the TMV cDNA, since every cell in the infiltrated area contained the TMV transgene in its nucleus. In the potato virus X (PVX) replacement virus vector, both the triple gene block (TGB) and coat protein (CP) viral genes were removed, leaving only the replicase gene, and were replaced with GFP. The expression levels of GFP from this vector were about 2.5-fold higher than that of full-length PVX vector with the GFP encoding sequence between the triple gene block and the CP genes. Removal of the movement proteins prevents systemic movement of TMV and PVX in above examples and inhibits the spread of the genetically modified virus, which is positive from the biosafety point of view.

*Agrobacterium* infiltration-mediated transient expression can be greatly enhanced by suppression of gene silencing. An RNA silencing suppressor (such as P19 encoded by tomato bushy stunt virus or HcPro expressed by potato virus A) is co-inoculated in a separate strain of *Agrobacterium* along with the *Agrobacterium* carrying the viral cDNA. Using this approach, highly efficient production of GFP from a TMV-based vector was achieved with up to 100-fold increase of the overexpression level (Lindbo, 2007a). As well, potexvirus expression was greatly increased (Komorova et al., 2006). Both of these viral vectors expressed GFP efficiently in the absence of GFP; however, the addition of GFP greatly increased this efficiency.

Foxtail Mosaic Virus (FoMV)

Foxtail mosaic virus (FoMV) is a member of the genus Potexvirus. Potexvirus is a large group of flexous and filamentous plant viruses with a single-stranded, positive-sense genomic RNA, with a cap structure at the 5' terminus and a poly-(A) tail at the 3' terminus. The FoMV genome structure resembles that of PVX, the type species of the genus Potexvirus, and the gene functions are presumed to be similar as well. The genome of FoMV contains five open reading frames (ORFs), and two subgenomic promoters directing transcription of subgenomic RNAs 1 and 2 (sgRNA1 and sgRNA2). The genomic RNA allows the expression of ORF1 encoding for the RNA-dependent RNA polymerase (RdRP) with methyltransferase, helicase, and polymerase motifs. ORF2, 3 and 4 code for the triple gene block (TGB) proteins TGB1, TGB2 and TGB3, which are required for virus cell-to-cell movement. ORF2 codes for a multifunctional protein that has RNA helicase activity, promotes translation of viral RNAs, increases plasmodesmal size exclusion limits, and acts as a suppressor of RNA-mediated post-transcriptional gene silencing (PTGS). ORF5 encodes the coat protein, which is required for viral encapsidation and long distance movement. FoMV has a broad host range, infecting 56 species of the Gramineae and at least 35 dicot species. The sequence of FoMV genomic RNA was first published in 1991. Infectious full-length clones were constructed based on the same FoMV isolate and some corrections to the published sequence were noted. The significant difference between the gene organizations of FoMV and PVX is the presence of ORF 5A upstream of the CP gene in FoMV. ORF 5A initiates 143 nts upstream of the CP and extends the reading frame of CP gene. The 5A protein was produced in vivo, but it was not required for either replication or productive infection of plants. Recently, the revised full-length sequence of Foxtail mosaic virus clone was published in 2008 (Bruun-Rasmussen et al.), and reveals a triple gene block structure similar to potato virus.

Foundational potexvirus vector work was done first not with FoMV but with PVX, the type species of the genus Potexvirus. PVX was engineered to express reporter proteins such as GFP and GUS, which were cloned just upstream of the CP gene and expressed from a duplicated copy of the coat protein (CP) subgenomic promoter. The reporter protein is translated from a sgRNA separate from the other viral proteins. Because PVX has a linear helical capsid, rather than an icoshedral capsid, the longer than wild type recombinant viral genome can still be encapsidated into infectious virus particles. However, GUS encoding sequence was deleted, because of recombination between the homologous sequences of the duplicated subgenomic promoters (81 nt).

The potexvirus replicase is the only protein translated directly from the full-length genomic RNA, but other viral proteins are translated from 3' coterminal subgenomic RNAs (sgRNAs). The two sgRNAs of approximately 2.1 and 0.9 kb in length have their 5' termini upstream of the TGB and CP genes, respectively. The integrity of subgenomic promoter is very important for the accumulation of subgenomic RNA and target protein. However, the boundaries of sgRNA promoters have not been delineated for FoMV.

Therefore, what is needed in either a greenhouse or field setting is a viral vector which expresses protein at a very high level and yet is intrinsically crippled, greatly facilitating decontamination and lowering environmental risk. As well, an inducible version of such a viral vector which expresses an exogenous gene at high levels in the presence of a silencing suppressor, and expresses the exogenous gene at negligible levels in the absence of a silencing suppressor would further lower environmental risk and would facilitate the manipulation of plant material transformed with such a viral vector, such as in the production of transgenic plants.

SUMMARY

In a preferred embodiment, the present invention comprises a viral vector derived from Foxtail mosaic potexvirus, wherein the triple gene block and coat protein genes have been removed, specifically with partial removal of the TGB1 and CP open reading frames, and wherein expression is driven by a CaMV 35S promoter. The invention further comprises a method of expressing a gene in a plant comprising inserting the gene into the viral vector and delivering the viral vector to a plant using agroinoculation of *Agrobacterium tumefaciens*. In a preferred embodiment, the plant may be *Nicotiana benthamiana*. In a further preferred embodiment, the method may include the step of co-inoculating with silencing suppressor genes carried in a separate agrobacterial strain.

In a further preferred embodiment, the present invention comprises a viral vector derived from Sunn hemp mosaic virus (SHMV), wherein the coat protein open reading frame has been partially removed, and wherein expression is by a CaMV 35S promoter. The endogenous coat protein may be replaced by the coat protein open reading frame and subgenomic promoter from another tobamovirus. The invention further comprises a method of expressing a gene in a plant comprising the steps of inserting the gene into the viral vector and delivering the viral vector to a plant using agroinoculation of *Agrobacterium tumefaciens*. In a preferred embodiment, the plant may be *Nicotiana benthamiana*. In a further preferred embodiment, the method may include the step of co-inoculating with silencing suppressor genes carried in a separate agrobacterial strain. The silencing suppressor genes may be RNA silencing suppressor p19 or HcPro.

In a further preferred embodiment, the present invention comprises a viral vector derived from White clover mosaic potexvirus, wherein the triple gene block and coat protein genes have been removed, specifically with partial removal of the TGB1 and CP open reading frames, and wherein expression is driven by a CaMV 35S promoter. The invention further comprises a method of expressing a gene in a plant comprising inserting the gene into the viral vector and delivering the viral vector to a plant using agroinoculation of *Agrobacterium tumefaciens*. In a preferred embodiment, the plant may be *Nicotiana benthamiana*. In a further preferred embodiment, the method may include the step of co-inoculating with silencing suppressor genes carried in a separate agrobacterial strain.

In a further preferred embodiment, the invention comprises an inducible viral vector system derived from the Foxtail mosaic virus, carried on one binary vector, wherein the triple gene block and coat protein genes have been removed, specifically with partial removal of the TGB1 and CP open reading frames, and wherein viral vector transcription is driven by a constitutive promoter, such as the CaMV 35S promoter, or an inducible promoter, such as an estradiol-inducible promoter, and wherein a second binary vector is included, comprising an inducible promoter, such as an estradiol-inducible promoter, which allows for expression of a silencing suppressor, such as p19, and may also include a gene constitutively expressing the XVE transcription factor. This method may further include the steps of co-agroinoculating the two *Agro-* bacterium cultures into a plant, preferably *Nicotiana benthamiana*, and delivering estradiol to the plant.

It is herein disclosed that these vectors would serve as an enabling technology for the development of transgenic plants which would produce foreign proteins upon induction. Since the process of agroinoculation creates a zone of leaf tissue comprising transgenic plant cells while retaining the mature leaf morphology, and since this transgenic leaf tissue was capable of expressing large quantities of foreign protein, and since this transgenic leaf tissue was capable of being induced by estradiol, it would be expected that transgenic whole plants would express the quantities of protein seen in this study and would be capable of expressing this in an inducible fashion. Furthermore, since there was little or no leakiness of expression of GFP or toxic glycanases by these viral vector in the absence of p19, we disclosed that it should be possible to create such transgenic plants carrying these vectors, driven by either constitutive or inducible promoters, because any detrimental effect of either the viral vector or of toxic protein genes carried by the vector would be mitigated by the very low level of leakiness.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3 shows diagrams of the key estradiol-inducible binary vectors agroinoculated in this study. JBest was constructed here to be the parent of TBest and FBest. pER8 (Zuo et al., 2000) was the parent of pER8/p19. LB, RB: left and right T-DNA borders; Pnos, Tnos: promoter and transcriptional terminator from nopaline synthase gene; LexAO: regulatory element that binds to estradiol-inducible XVE transcription factor; 35S core: combined with LexAO as inducible promoter; replicase: viral methylase, helicase and RdRp; MP, viral movement protein, sgp1: subgenomic promoter driving gene of interest (GOI); sgp2: subgenomic promoter driving viral coat protein (CP) gene; 35Sterm: transcription terminator; G10-90: synthetic promoter; XVE: estradiol-inducible transcription activator; E9term: pea rbcS E9 terminator; hygR: hygromycin resistance; p19: silencing suppressor; 3Aterm: pea3A terminator;

FIG. 4 shows primers used in vector constructions. EcoLex Up (SEQ ID NO:86), 35term Up (SEQ ID NO:87), 35termAS Down (SEQ ID NO:88), JL22 RB Down (SEQ ID NO:89). TMV p1-21 UP (SEQ ID NO:90). TMV1008 NotDN (SEQ ID NO:91), FoMV 5 term UP (SEQ ID NO:92). FoMV756 NotI DOWN (SEQ ID NO:93). p19XhoI UP (SEQ ID NO:94), p19SpeI DOWN (SEQ ID NO:95);

DETAILED DESCRIPTION OF PREFERRED EMBODIMENTS

Figure 1A:
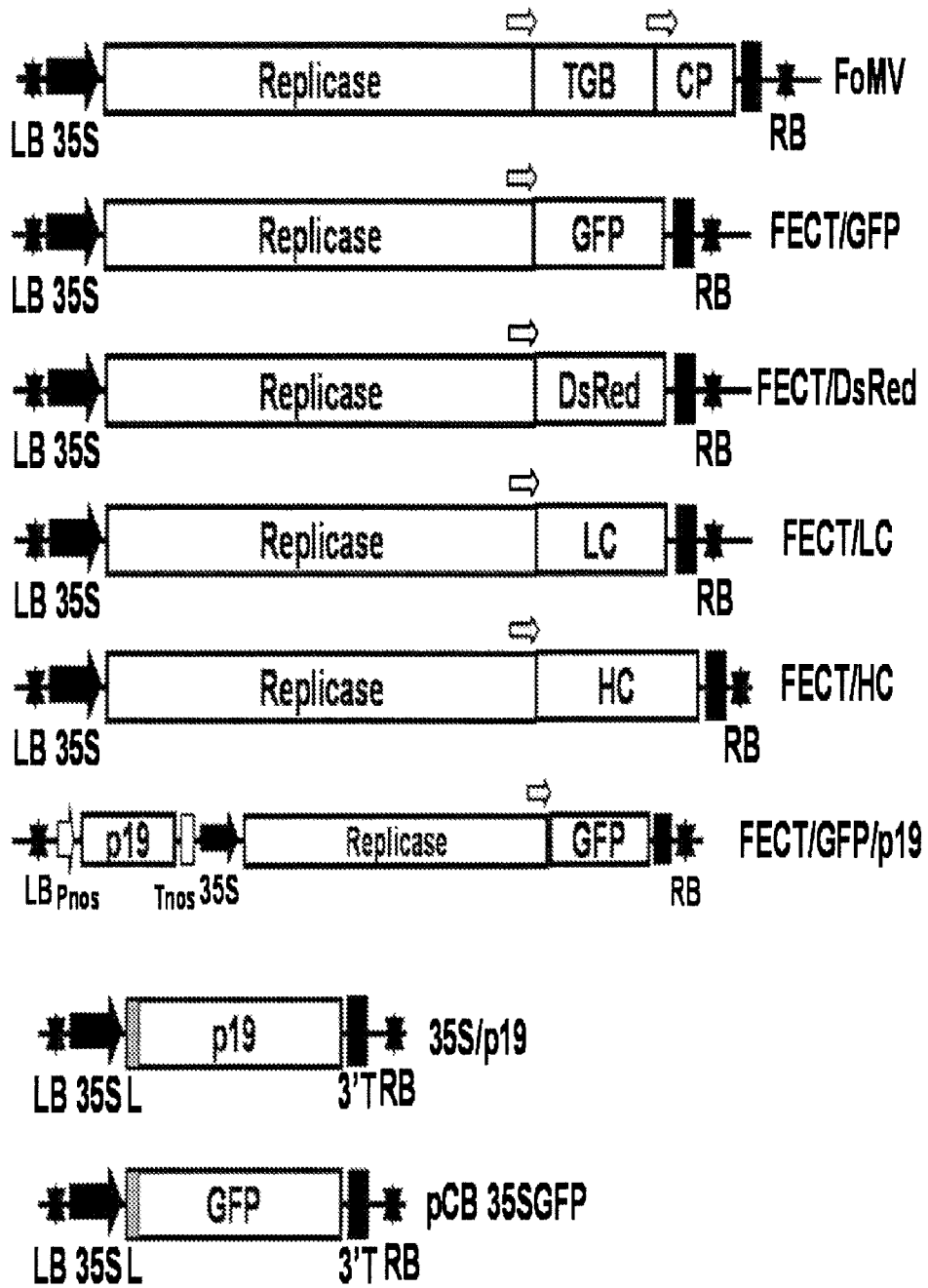
FIG. 1 shows a schematic diagram of the T-DNA regions of binary plasmid used in this study (A) and the genomic organization of FoMV-based replicon (B). (A)—Cauliflower mosaic virus (CaMV) 35S promoter driven versions of Foxtail mosaic virus (FoMV) vector cDNAs or FECT as viral vector to express GFP, GUS and antibody LC, HC and 35S driven versions of GFP, p19 were constructed. All plasmids were based on the binary vector pCB301 backbone. Open boxes represent open reading frames; black stars: left border and right border of T-DNA; block arrows: CaMV duplicated 35S promoter; black boxes: CaMV 3' terminator sequence; gray arrows, subgenomic promoters; white arrow: nos promoter (Pnos); white box: nos terminator (Tnos); dark grey boxes: Tobacco etch virus 5' non-translated leader sequence (L); RB: T-DNA right border sequences; LB: T-DNA left border sequences; TGB: triple gene block; CP, coat protein; LC, antibody light chain; HC, antibody heavy chain. (B)—Shows FECT0/GFP (SEQ ID NO:149), FECT22/GFP (SEQ ID NO:150). FECT40/GFP (SEQ ID NO:151), and FECT/GFP CP 3' (SEQ I D NO:152). All TGB and CP deletion mutants have the root "FECT" (Foxtail Elimination of CP and TGB). In the start codon of 5'TGB, ATG were mutated to ATC, shown as underlined. Restriction sites PacI and AvrII were introduced at the flank of GFP ORF as cloning sites for other foreign inserts. The numbering indicates the number of nucleotides from the TGB ORF presented as upstream of the GFP ORF. For example, FECT40 remains the 5" end 40 nts of FoMV TGB to reserve the subgenomic promoter to drive the expression of GFP.

The present invention relates to an inducible viral vector which expresses an exogenous gene at high levels in the presence of a silencing suppressor, and expresses the gene at negligible levels in the absence of a silencing suppressor.

In this study, vectors were constructed which exhibited two advantageous properties: (1) compared to other viral vectors factors, the environmental risks are greatly lowered and (2) the expression rate of foreign proteins is among the highest achieved in plant systems to date. To achieve lowered environmental risk, the TGB and CP genes of FoMV were removed and replaced with heterologous sequences while the subgenomic promoter of one of the TGB genes was reserved to direct the transcription of the heterologous coding sequence. The FoMV expression vectors driven by the cauliflower mosaic virus (CaMV) 35S promoter were delivered as a T-DNA to plant cells by *Agrobacterium* tumefaciens. This viral vector is unprotected by a coat protein, was not able to infect *Nicotiana benthamiana* systemically, replicates very poorly, and has had its genome size reduced by 29%. On the other hand, in the presence of gene silencing suppressor, the virus-mediated expression of the reporter protein GFP was up to 1.4 ug/g fresh weight of plant leaf (40% total soluble protein).

In a preferred embodiment of the invention, these vectors would be useful in the development of transgenic plants which would produce foreign proteins upon induction. Since the process of agroinoculation creates a zone of leaf tissue comprising transgenic plant cells while retaining the mature leaf morphology, and since this transgenic leaf tissue was capable of expressing large quantities of foreign protein, and since this transgenic leaf tissue was capable of being induced by estradiol, transgenic whole plants would also express the quantities of protein described in this application and would be capable of expressing this in an inducible fashion. Furthermore, since there was little or no leakiness of expression of GFP or toxic glycanases by these viral vector in the absence of p19, transgenic plants carrying these vectors, driven by either constitutive or inducible promoters, would not experience detrimental effects of either the viral vector or of toxic protein genes carried by the vector because these effects would be mitigated by the very low level of leakiness.

Sunn Hemp Mosaic Virus (SHMV)

By far, the current emphasis in commercial and scientific use of viral vectors lies with the tobacco host *Nicotiana benthamiana*. Future development needs to focus on the creation of new vectors that can be used in different hosts, such as hosts amenable to oral delivery of vaccines, including cereals and legumes. Sunn Hemp Mosaic virus (SHMV) is a good candidate for such a vector, since it is closely related to the commercially robust TMV but it infect a wide range of legumes as well as *N. benthamiana.*

SHMV, being a member of the Tobamovirus group, is a plus-strand RNA virus with the same genomic arrangement as TMV. The 3' 1.8 kb of sequence were determined in initial reports, while the final 4.6 kb at the 5' end were given in a separate report, completing the sequence (Silver et al., 1996). Belonging to the tobamovirus group, SHMV is a positive strand RNA virus consisting of 6483 nucleotides. Like TMV, the SHMV genome consists of genes coding for two replicase proteins, a movement protein and a coat protein (CP). The first two open reading frames (ORF) produce two replicase proteins, a 129 kDa and an 186 kDa protein. An amber stop codon at the end of the 126 kDa replicase undergoes a translational read-through to produce the 183 kDa replicase. The movement and coat proteins are translated from 3' coterminal subgenomic mRNAs. The movement protein is a 31 kDa protein produced early in the infection cycle, which is required for virus cell to cell movement. The coat protein is 18 kDa protein produced at high levels later in the infection cycle, and is required for virus long distance movement.

By deletion of the CP gene, a viral vector has been constructed, SHEC (Sunn Hemp Elimination of Coat protein), that is incapable of long distance movement and is unprotected by a coat protein. The coat protein subgenomic promoter was used in this vector to drive foreign genes, using three different potential promoter lengths. The use of co-agroinoculation with a silencing suppressor gene was found to be critical for successful marker gene expression. In the absence of the suppressor, the expression level was negligible, similar to the FECT vector of foxtail mosaic virus. This is in contrast to a similar CP-deletion mutant derived from tobacco mosaic virus (TMV), also a tobamovirus family member, which expressed well even in the absence of a silencing suppressor (Lindbo, 2007b). A full length vector was also created. A subgenomic promoter from a different tobamovirus was needed to drive the coat protein gene (in addition to the SHMV coat protein promoter driving the foreign gene), since recombination between identical subgenomic promoters has be shown to severely destabilize TMV vectors. This chimeric viral vector with an Alternate Coat protein (SHAC) systemically infected *N. benthamiana* and expressed GFP.

White Clover Mosaic Virus (WCLMV)

White clover mosaic virus (WClMV) is a member of the genus Potexvirus like foxtail mosaic virus (FoMV) mentioned previously. It contains all the basic features in its genome, replication and expression strategy, and virus particle as already described for FoMV. It is distinguished from FoMV, and is similar to SHMV, in that it has a much broader host range in Fabaceae, the legume family, which includes a wide variety of plants critical to human nutrition such as beans, peas, and cowpeas and forage crops such as clover. WClMV was chosen in this project as a base for the construction of an agroinfection viral vector because of its host range in legumes, its success as a nonagroinfection viral vector (Beck et al, 1990), and its similarity to FoMV. Because the deleted version of FoMV (FECT) demonstrated very high expression of the presence of a gene silencing suppressor and yet is nearly environmentally inert in its absence, and yet a similar potato virus X vector (Komorova et al., 2006), from the same potexvirus family, did not display this stark "on/off" capacity, it was investigated whether this effect could be duplicated in another member of the potexvirus family. Similar to the FECT construction, the TGB and CP genes of WClMV were removed and replaced with heterologous sequences while the subgenomic promoter of one of the TGB genes was reserved to direct the transcription of the heterologous coding sequence. The WClMV expression vector driven by the cauliflower mosaic virus (CaMV) 35S promoter was delivered as a T-DNA to plant cells by *Agrobacterium tumefaciens* via agroinfection. As with the FECT vector, high levels of GFP expression were seen in the presence of silencing suppressor while almost no expression occurred in the absence of silencing suppressor.

Inducible Viral Vectors

Inducible expression systems are desirable when a protein detrimental to the host organism is to be expressed. In plants, several inducible promoters have been used successfully, including those induced by copper, dexamethasone, ethanol, estradiol (Zuo et al., 2000), and ecdysone. Of these the estradiol and ecdysone systems report the highest expression of marker genes, with several-fold higher expression than the CaMV 35S promoter.

Since viral vectors provide much higher expression than this, there has been an impetus to produce inducible viral vectors. This concept has two potential problems, however. First, viral vectors come with some concerns regarding environmental safety, since they are capable of replication and transmission in the field. Second, there is the potential for leakiness in the uninduced plant, since a single viral replicon transcribed from the inducible viral transgene is a self-amplifying replicon which can move from cell to cell.

Four inducible viral systems have already been developed. Two consist of full-length viral vectors: a dexamethasone-inducible Brome mosaic virus (BMV) vector and an estradiol-inducible Cucumber mosaic virus (CuMV) vector (Sudarshana et al., 2006). Two others utilize a deleted virus system: an ethanol-inducible Bean yellow dwarf virus (BYDV) vector (Zhang and Mason, 2006) and an estradiol-inducible Tomato mosaic virus (ToMV) vector. The BMV and BYDV vector systems were demonstrated in transgenic whole plants, while the ToMV system used transgenic tobacco cell cultures. The CuMV vector system was demonstrated via agroinoculation.

As described herein, a highly deleted viral vector from Foxtail mosaic virus (Potexvirus family) has been created, which is a virus noteworthy in causing mild symptoms in its hosts. This FECT vector (FoMV elimination of coat protein and triple gene block) would be an excellent candidate for development into an inducible viral vector of enhanced environmental safety. FECT is capable of expressing GFP in *Nicotiana benthamiana* at up to 40% total soluble protein but only with co-expression of a silencing suppressor such as p19. In the absence of suppressors, FECT expresses little or no protein. FECT has 29% of its genome removed and retains only the replicase complex, the 5' and 3' UTRs and the TGB1 subgenomic promoter.

Described herein is an estradiol-inducible FECT vector, herein named FBest (FECT/bar estradiol-inducible). Agroinoculation was used as a model anticipating the properties that would be seen in stably transgenic plants. In agroinoculation, the cells in the infiltrated zone are made transgenic, with the genes contained within the TDNA, including the viral vector, inserted into a chromosome of the plant cell. FBest expressed GFP with fluorescence similar to the FECT vector and dependent on p19 co-expression like FECT. Furthermore, FBest can express a toxic gene product (xylanase) with total necrosis of the leaf occurring only after induction with estradiol. The several safety features of the FBest vector would be valuable for large scale agroinoculation in greenhouses or in any potential use of the vector in stably transgenic plants. In this latter case, the ability to express proteins toxic to plants would be most useful, permitting the survival of the plants during tissue culture, seed production and initial growth in the field.

I Viral Vector Derived from Foxtail Mosaic Potexvirus (FoMV)

The present invention comprises a viral vector derived from Foxtail mosaic potexvirus (FoMV), wherein the TGB2, TGB3, and most of the TGB1 and coat protein (CP) genes have been removed, and wherein expression is driven by a CaMV 35S promoter. The invention further comprises a method of expressing a gene in a plant comprising inserting the gene into the viral vector and delivering the viral vector to a plant using agroinoculation of *Agrobacterium tumefaciens*.

In a preferred embodiment, the plant may be *Nicotiana benthamiana*. In a further preferred embodiment, the method may include the step of co-inoculating with silencing suppressor genes carried on the same or a separate agrobacterial strain.

In a preferred embodiment, the invention comprises a viral vector comprising a binary vector which includes a multiple cloning site, a CaMV 35S promoter at the 5' end of the multiple cloning site, and a 35S polyA signal/transcription terminator at the 3' end of the multiple cloning site. The binary vector may be pJL22. The viral vector further comprises a foxtail mosaic virus full length cDNA inserted into the multiple cloning site of the binary vector. The foxtail mosaic virus full length cDNA may have had the majority of the Triple Gene Block (TGB) deleted, while retaining the subgenomic promoter of subgenomic RNA I retained including approximately the first 30% or less of the TGB1 ORF, preferably the first 20% of the TGB1 ORF, most preferably approximately 6% of the TGB1 ORF comprising the first 40 bp out of the 711 bp in the full sequence. The foxtail mosaic virus full length cDNA may have had the majority of the coat protein (CP) removed, while retaining the final sequence of the CP ORF including approximately 30% or less of the terminal sequence of the CP ORF, preferably approximately 20% or less of the terminal sequence of the CP ORF, most preferably approximately 6% of the terminal sequence of the CP ORF comprising the final 42 bp out of the 648 bp sequence.

The invention further comprises the insertion of a heterologous gene into a restriction site at the 3' end of the subgenomic promoter of subgenomic RNA1 in the foxtail mosaic virus full length cDNA within the binary vector.

In a further preferred embodiment, the invention also comprises a process for expressing a gene in a plant comprising the step of: agroinoculating the plant with the viral vector described above. In this embodiment, the plant could be *Nicotiana benthamiana*, cowpea, lentil, bean, switchgrass, foxtail millet, barley, wheat, oat or corn, and the gene could be a marker gene, such as glucuronidase, DsRed, GFP, a gene for a cell wall modifying agent such as cellulase, glycanase, pectinase or LTP, or an antibody fragment such as anti-langerin mAb IgG4 heavy chain or the anti-langerin mAb IgG4 light chain.

II Viral Vector Derived from Sunn Hemp Mosaic Virus (SHMV)

The present invention comprises a viral vector derived from Sunn hemp mosaic virus (SHMV), wherein at least 70% of the coat protein (CP) open reading frame has been removed, and wherein 20% or less of the initial portion and 10% or less of the final portion of the open reading frame of the coat protein has been retained, and wherein transcription of the viral vector is driven by a CaMV 35S promoter. The gene of interest is inserted between the initial and final CP ORF sequences. The start codon of the coat protein may be mutated to be nonfunctional. The endogenous coat protein may be replaced by the coat protein open reading frame from another tobamovirus. The invention further comprises a method of expressing a gene in a plant comprising the steps of inserting the gene into the viral vector and delivering the viral vector, contained in a binary vector, to a plant using agroinoculation of *Agrobacterium tumefaciens*. In a preferred embodiment, the plant may be *Nicotiana benthamiana*. In a further preferred embodiment, the method may include the step of co-inoculating with silencing suppressor genes carried in a separate agrobacterial strain. The silencing suppressor genes may be RNA silencing suppressor p19 or HcPro.

In a preferred embodiment, the invention comprises a viral vector comprising a binary vector which includes a multiple cloning site, a CaMV 35S promoter at the 5' end of the multiple cloning site, and a 35S polyA signal/transcription terminator at the 3' end of the multiple cloning site. The binary vector may be pJL22. The viral vector further comprises a Sunn hemp mosaic virus full length cDNA inserted into the multiple cloning site of the binary vector. The Sunn hemp mosaic virus full length cDNA may have had the majority of the coat protein (CP) deleted, while retaining approximately 30% or less of the of the initial sequence of the CP ORF, preferably approximately 20% or less of the initial sequence of the CP ORF, most preferably approximately 15% of the CP ORF comprising the initial 74 bp out of the 495 bp sequence. The Sunn hemp mosaic virus full length cDNA may have had the majority of the coat protein (CP) deleted, while retaining the subgenomic promoter of CP subgenomic RNA will be retained, comprising approximately 20% or less of the of the final sequence of the CP ORF, preferably approximately 10% or less of the final sequence of the CP ORF, most preferably approximately 0% to 5% of the CP ORF comprising the final 0 bp to 25 bp out of the 495 bp sequence.

The invention further comprises the insertion of a heterologous gene into a restriction site at the 3' end of the subgenomic promoter of subgenomic RNA1 in the Sunn-hemp mosaic virus full length cDNA within the binary vector.

In a further preferred embodiment, the invention also comprises a process for expressing a gene in a plant comprising the step of agroinoculating the plant with the viral vector described above. In this embodiment, the plant could be *Nicotiana benthamiana*, pinto bean, or cowpea, and the gene may be GFP or GUS.

III Inducible Viral Vector System

The present invention comprises an inducible viral vector system derived from the Foxtail mosaic virus (SEQ ID NO: 7). The Foxtail mosaic virus comprises a 5' untranslated region (UTR) (SEQ ID NO:1), a replicase (SEQ ID NO:2), a TGB1 open reading frame (SEQ ID NO: 3), TGB2 and TGB3 genes (SEQ ID NO: 4), a CP gene (SEQ ID NO:5), and a 3' UTR (SEQ ID NO: 6). In the present invention, the triple gene block (TGB) and coat protein (CP) genes have been removed, leaving approximately the first 30% or less of the TGB1 ORF, preferably the first 20% or less of the TGB1 ORF, most preferably the first 6% or less of the TGB1 ORF, and also retaining approximately 30% of the final sequence of the CP ORF, preferably approximately 20% of the final sequence of the CP ORF, and most preferably 6% of the final sequence of the CP ORF, and wherein transcription of the viral vector is driven by a CaMV 35S promoter or by an inducible promoter, preferably a promoter regulated by the estradiol-inducible XVE transcription activator. The invention further comprises a method of expressing a gene in a plant comprising the steps of inserting the gene into the viral vector and delivering the viral vector to a plant using agroinoculation of *Agrobacterium tumefaciens*, and delivering a pER8 plasmid containing a constitutively expressed XVE transcription factor and a p19 ORF driven by another XVE-targeted promoter via a second *Agrobacterium* line. This method may further include the steps of co-agroinoculating the *Agrobacterium* cultures into a plant, preferably *Nicotiana benthamiana*, and delivering estradiol to the plant.

IV Creating Whole Transgenic Plants Containing Vectors

The invention further comprises creating transgenic whole plants using the vectors described herein. A selectable marker gene (such as the bar gene in the FBest vector of this application) would be contained within the T-DNA segment harboring the viral vector on one binary plasmid and this would need to be maintained by an *Agrobacterium* culture containing a disarmed Ti plasmid. A second binary plasmid (such as pER8/p19) containing a constitutively expressed inducible transcription factor (such as XVE), an inducibly expressed gene silencing protein (such as p19), and a second selectable marker gene would be maintained in a second *Agrobacterium* culture. The two sterile *Agrobacterium* cultures would then be centrifuged and resuspended sterilely in buffer containing magnesium and acetosyringone to stimulate the infection process. The two bacterial suspensions would be mixed and surface-sterilized leaf pieces would be dipped in these suspensions then transferred to a nutrient agar plate containing no antibiotics for 1-2 days to allow for agroinoculation to occur. The inoculated leaf pieces would then be transferred to agar medium containing the two appropriate antibiotics or herbicides for selection of transformants, an additional antibiotic to eliminate residual *Agrobacterium* (such as carbenicillin) and hormones appropriate for the production of shoots. After the appearance of shoots, the shoots would be excised and transferred to agar medium containing the double transformant-selective antibiotics and hormones appropriate for the production of roots. Upon the production of roots, rooted shoots would be transferred to soil medium and gradually acclimated to greenhouse conditions. Such whole transgenic plants would be screened for the presence of viral sequence, p19 and XVE (e.g., via PCR), screened for functionality by induction with inducer and detection of the payload gene product carried by the viral vector. Lines with good expression would be used to generate seed, and seed carrying both constructs could be selected by sprouting the seed on agar plates containing both antibiotics. Examples of the production of transgenic whole plants expressing a viral vector can be found in the literature (Zhang and Mason, 2006)

Example 1

Plants

*Panicum virgatum* cv. Blackwell (switchgrass), *Setaria viridis* (foxtail grass), *Hordeum vulgare* (barley), *Triticum aestivum* (wheat), *Avena sativa* (oat), *Zea mays* (corn), *Phaseolus vulgaris* (bean), *Lens culinaris* (lentil), *Vigna unguiculata* (cowpea) and *Medicago trunculata* (a legume model system plant) plants were germinated from seed and grown in growth pots with exposure to 24 h per day with illumination from plant-adapted spectrum fluorescent bulbs at temperatures ranging from 22 to 24° C. Plants 2-3 weeks from seed, with fully expanded leaves, were used for agroinfiltration and inoculation experiments. *Nicotiana benthamiana* was grown from seed and then transplanted and grown under 400 W metal halide lamps to 10-15 cm before inoculation.

Plasmid Constructs

All FoMV viral cDNA constructs used in this study are derivatives of a wild-type FoMV cDNA clone that was a gift from Nancy Robertson of the USDA (Robertson et al., 2000) and were constructed with standard recombinant DNA techniques. The binary vector, pJL22, provided by John Lindbo (Lindbo, 2007a), has the mini binary plasmid, pCB301, as backbone. JL22 contains multiple cloning sites (MCS) flanked by a 35S promoter and 35S polyA signal/transcription terminator.

1. pFoMV/JL22

Figure 1B:
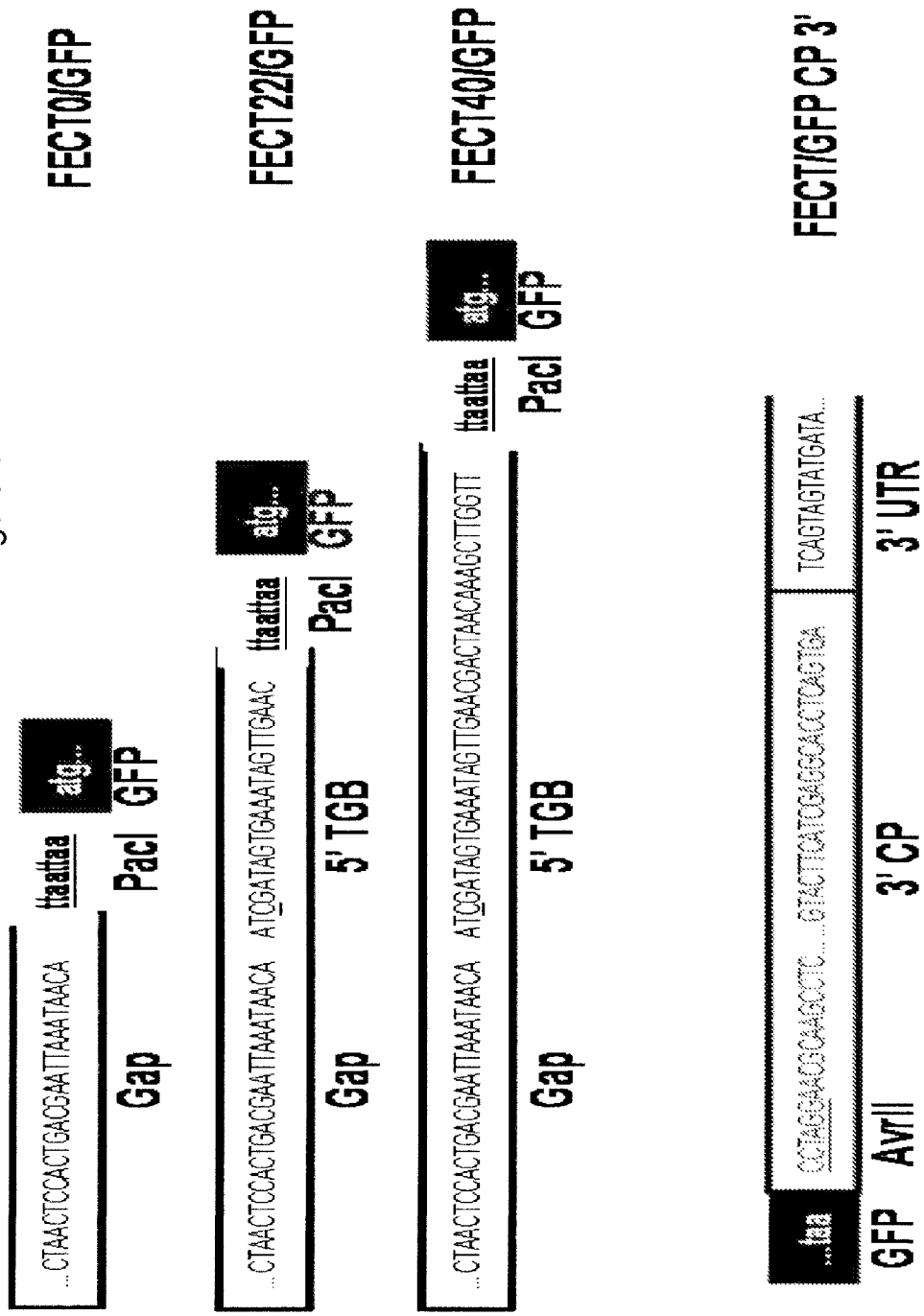

FoMV full length viral cDNA was inserted into MCS of pJL22 using standard cloning procedures. FoMV full length viral cDNA obtained from Robertson already had 70 adenosine residues at its terminus, followed by a Xba I site. The 5' end of FoMV was amplified by PCR with primers FoMV5' termUP and FoMV756NotDown and cut with NotI. The 5' end of FoMV was cloned into JL22 backbone cut with StuI and NotI to create JL22/FoMV5'. The 3' end of FoMV was prepared by restriction digest with PmlI and XbaI and then cloned into the JL22/FoMV5' backbone cut with PmlI and XbaI. JL22 contains CaMV 3' polyA signal to generate authentic FoMV 3' polyA ends. This full viral cassette including promoter, terminator is flanked with Left Border and Right Border of T-DNA (FIG. 1).

2. pFECT0, pFECT22 and pFECT40

Primers were designed to delete the TGB and CP genes and keep the subgenomic promoter of sgRNA1 and 3'-end of the CP gene in the FoMV genome. The start codon AUG of TGB1 was mutated to AUC. To ensure that the sgRNA1 promoter of FoMV constructs to drive GFP had been fully cloned, primers were created to include the first 0, 22 and 40 bases of ORF of TGB1 to create pFECT0, pFECT22 and pFECT40, respectively. Restriction enzyme sites PacI and AvrII sites were placed right after the reserved subgenomic promoter of TGB1. Primer FoMV+0sgpDown (SEQ ID NO:97) added both AvrII and PacI sites at 3' end of subgenomic promoter TGB1 and primer FoMVUp (SEQ ID NO:96) was upsteam of a unique BamHI site. With these two primers, the amplified PCR fragment was digested with BamHI and AvrII and cloned into vector backbone cut with same restriction endonucleases to create pFECT0. Subsequently, two primers FoMV+22sgp (SEQ ID NO:98) and FoMV+40sgp (SEQ ID NO:99) were pared with FoMVUP to generate two PCR fragments including 22 and 40 bases of TGB1 ORF respectively. Then, pFECT0 cut with BamHI and PacI was used as vector backbone to clone two DNA fragments to create pFECT22 and pFECT40. AvrII enzyme site presented at the 3' end of CP gene originally and was utilized as a restriction cloning site to insert foreign gene for expression. The 3' terminal part of CP FoMV gene between AvrII and 3'-UTR was reserved in the viral vector, because it is crucial for the efficient expression of viral vector. Deletion of this region dramatically reduced the viral replication and accumulation (Komarova et al., 2006).

The FECT40 vector (SEQ ID NO:34) comprises a 5' UTR (SEQ ID NO:21), a replicase (SEQ ID NO:22), 40 bp of the TGB1 ORF plus Pac I and Avr II cloning sites (SEQ ID NO: 23), the last 42 bp of the CP ORF (SEQ ID NO: 24), a 3' UTR (SEQ ID NO:25), a poly(A) tract (SEQ ID NO:26), a 35S terminator (SEQ ID NO:27), miscellaneous sequence (SEQ ID NO:28), a T-DNA right border (SEQ ID NO:29), a JL22 sequence (SEQ ID NO: 30), a T-DNA left border (SEQ ID NO:31), miscellaneous sequence 2 (SEQ ID NO: 32), and a 35S promoter (SEQ ID NO:33).

TABLE 1

Primers used for plasmid construction in FoMV study.

| Plasmid | SEQ ID NO | Primer | Oligonucleotide sequence (5'-3') | Purpose |
|---|---|---|---|---|
| pFoMV/JL22 | 92 | FoMV 5' term UP (pFoMV nt. 1-21) | P-GAAAACTCTTCCGA AACCGAA | The 5' end of FoMV was amplified by PCR with primers FoMV5'termUP and |
|  | 93 | FoMV756 NotI DOWN (pFoMV nt. 737-757) | TTTTTTGCGGCCGCTTAGCCA GTTTAGGTCCTTA | FoMV756NotDown and cut with PmlI. The 3' end of FoMV was digested with PmlI and XbaI. Both 5' and 3' end fragments of FoMV were cloned into the JL22 backbone cut with StuI and XbaI. |
| pFECT0 pFECT22 pFECT40 | 96 | FoMV Up (pFoMV nt 3044-3063) | GTGGGCATGTGCAGATGAGG | To create ΔTGB/ΔCP mutants, PacI and AvrII cloning sites were introduced by PCR amplified with two primers |
|  | 97 | FoMV + 0sgp Down (pFoMV nts.4114-4131) | AACCTACCTAGGACTTTAATT AATGTTATTTAATTCGTCAGT G | FoMVUp and FoMV + 0sgp Down). PCR with mutated start codon of TGB was cut with BamHI and AvrII and |
|  | 98 | FoMV + 22sgp Down (pFoMV nts.4124-4153) | GCTTTTAATTAAGTTCAACTA TTTCACTATCGATTGTTATT | cloned into pFoMV vector backbone to create pFECT0. Other two downstream primers (with PacI site) were used to |
|  | 99 | FoMV + 40sgp Down (pFoMV nts.4150-4169) | GTCTTTAATTAACCAAGCTTT GTTAGTCGTTC | save 22 nts and 40 nts 5' end of TGB DNA sequence. PCR fragments were cloned in pFECT0 vector backbone cut with BamHI and PacI to generate pFECT22 and pFECT40. |
| pFECT0/GFP pFECT22/GFP pFECT40/GFP | 100 | PacGFPUp | TTGTCATTAATTAAGCTAGCA AAGGAGAAGAAC | To clone the GFP ORF into the pFECT vector. Primer PacGFPUp adds a PacI |
|  | 101 | GFPAvrDown | TTTACTCCTAGGTTATTTGTA GAGCTCATCCA | site (underline) at the 5' end, and primer GFPAvrDown adds an AvrII site (underline) to the 3' end. |
| pFECT40/DsRed pFECT40/LC pFECT40/HC | 102 | PacDsRedUP | GGATGGTTAATTAAATGGCCT CCTCCGAGAACG | DsRed and anti-Langerin antibody light chain and heavy chain genes were PCR |
|  | 103 | AvrDsRedDN | TTTACTCCTAGGCTACAGGAA CAGGTGGTG | mutagenized to be flanked with PacI and AvrII restriction sites on 5'- and 3'- |
|  | 104 | PacLangLCUP | GGATGGTTAATTAAATGAAGT TGCCTGTTAGGCT | ends, correspondingly. The three gene fragments were cloned into the |
|  | 105 | AvrLangLCDN | AATACTCCTAGGCTAACACTC TCCCCTGTTG | PacI/AvrII sites of the pFECT40 to generate pFECT40/DsRed, |
|  | 106 | PacLangHCUP | ATATGGTTAATTAAATGGAAT GGAGGATC TTTCT | pFECT40/LC and pFECT40/HC constructs. |
|  | 107 | AvrLangHCDN | TTTACTCCTAGGTCAGCTAGC TTTACCCAGAG |  |

TABLE 1-continued

Primers used for plasmid construction in FoMV study.

| Plasmid | SEQ ID NO | Primer | Oligonucleotide sequence (5'-3') | Purpose |
|---|---|---|---|---|
| pFECT40/GFP/ PnosTnos | 108 | ApaI Pnos UP | ATATGAGGGCCCAACTGAAG GCGGGAAACGACAATC | To add PnosTnos in pFECT40, and create BsiWI and SpeI in between Pnos and Tnos. Inner primers PnosBsi-overlapDN and TnosSpe-overlapUP have overlap sequence and BsiWI and SpeI sites. Two inner primers pair with outer primers ApaPnosUP (ApaI at 5' end) and SbfTnosDN (SbfI at 3' end) to generate two PCR products. The two products were fused using outer primers and cloned into pFECT/GFP. |
|  | 109 | PnosBsiWI-overlapDN | GACCACTTTATGGAGGTTCGT ACGTCTAGGGGATCCGGTGC AG |  |
|  | 110 | TnosSpeI-overlapUP | AACCTCCATAAAGTGGTCACT AGTATCGTTCAAACATITGCC |  |
|  | 111 | SbfI Tnos DN | ATTATGCCTGCAGGAGCTGC ATGCAAGCTGTCGAGG |  |
| pFECT40/GFP/ p19 | 112 | BsiWI/p19 UP | TAATAACGTACGATGGAACG AGCTATACAAG | To clone the p19 ORF into pFECT40/GFP/PnosTnos vector. Primer Bsip19UP adds a BsiWI site (underline) at the 5' end and primer p19SpeDown adds a SpeI (underline) site at the 3' end of the ORF. The amplified DNA fragment was cloned into pFECT40/GFP/PnosTnos vector backbone cut with BsiWI and SpeI. |
|  | 113 | p19SpeI DOWN | TTTTTTACTAGTTTACTCG CTTTCTTTTTCGAAGG |  |
| pCB/GFP | 114 | Xba/GFP UP | TAAGCATCTAGAATGGCTAGC AAAGGAGAAGAAC | To clone the GFP ORF into pCB302 vector. Primer XbaGFPUp adds a XbaI site (underline) at the 5' end, and primer SpeGFPDown adds a SpeI (underline) site at the 3' end of the ORF |
|  | 115 | GFP/SpeI DOWN | TTTTTTACTAGTTTATTTGT AGAGCTCATCCA |  |

3. pFECT/GFP, pFECT/DsRed, pFECT/HC, pFECT/LC

The cycle 3 GFP gene was PCR mutagenized to be flanked with PacI and AvrII restriction sites on 5'- and 3'-ends, correspondingly. The GFP gene was cloned into the PacI/AvrII sites of the pFECT0, pFECT22 and pFECT40 to obtain pFECT0/GFP, pFECT22/GFP and pFECT40/GFP constructs. DsRed and anti-Langerin antibody light chain and heavy chain genes were subcloned into pFECT vector in the same manner but with only FECT40.

4. FECT/GFP/p19

Nos promoter (Pnos) and nos terminator (Tnos) were used to control the transcription of p19 gene in FECT/GFP/19 binary vector. Pnos/HygR/Tnos in pER8 plasmid was used as template to create two restriction enzyme sites (BsiWI and SpeI) in between Pnos and Tnos, which are cloning sites for p19 insertion. To fuse Pnos and Tnos together, two PCR products were generated for overlapping. The first PCR with Pnos sequence was generated using primer ApaIPnosUP (adds an ApaI site at the 5' end) and primer PnosBsiWI-overlapDN (adds a BsiWI site and overlap sequence at the 3' end). The second PCR with Tnos sequence was generated using primer TnosSpeI-overlapUP (adds overlap sequence and a SpeI site at the 5' end) and primer SbfITnosDN (adds a SbfI site at the 3' end). The two products were fused using primer ApaIPnosUP and primer SbfITnosDN by overlapping PCR to create Pnos-Tnos fragment (Apap-Pnos/(BsiWI)-(SpeI)/Tnos-(SbfI). Pnos-Tnos PCR product was digested with ApaI and SbfI restriction endonucleases, and then cloned into the FECT/GFP backbone cut with ApaI and SbfI to create FECT/GFP/Pnos-Tnos. To clone the p19 ORF into the FECT/GFP/Pnos-Tnos vector, p19 PCR product was generated using primer BsiWI/p19UP (adds a BsiWI site at the 5' end) and primer p19SpeI DOWN (adds SpeI site at the 3' end). P19 PCR product was digested by BsiWI and SpeI and cloned into the FECT/GFP/Pnos-Tnos vector backbone cut with two restriction enzymes to generate FECT/GFP/p19 binary plasmid.

Cloning and Sequencing

The high fidelity polymerase, Phusion (New England Biolabs (NEB), Beverly, Mass.), was used according to company protocols in all constructions. Recombinant clones were introduced into *Escherichia coli* NEB 10-beta electrocompetent cells by electroporation at 1.44 kV and 129Ω for 5 ms using a BTX 600 Electro Cell Manipulator (BTX Inc., San Diego, Calif., USA) and colonies were screened by PCR using NEB Taq polymerase or by restriction digests of plasmid minipreps prepared by Wizard Plus Miniprep Kit (Promega, Madison, Wis.). Sequence verification was performed using a CEQ capillary sequencer (Beckman Coulter, Fullerton, Calif.).

Agroinfection

Agroinfiltration was performed as described with modifications. *Agrobacterium tumefaciens* stain GV3101 was used for the agroinoculation of *N. benthamiana* and cereals. *A. tumefaciens* was transformed with plasmid constructs using the same conditions as for *E. coli* above. Agrobacterium transformants were selected at room temperature on Luria-Bertani plates containing 10 μg/ml rifampicin, 25 μg/ml gentamycin and 50 μg/ml kanamycin. A colony of *A. tumefaciens* was inoculated to 5 ml of L-MESA medium (LB media supplemented with 10 mM MES, 20 uM acetosyringone (Phytotechnology Labs, Shawnee Mission, Kans.), a wound response compound that elicits *Agrobacterium* virulence, and the same antibiotics), and grown overnight at room temperature. The cells of the overnight culture were harvested by centrifugation and resuspended in induction media (10 mM MES, 10 mM $MgCl_2$, 100 uM acetosyringone) for a final $OD_{600}$ of 1.0 and incubated for 2 h to overnight at room temperature. The cultures of *A. tumefaciens* were infiltrated into the underside of leaves of plants with a 3 ml syringe without needle. For agroinoculation of two or more bacterium cultures at the same time, multiple cultures of *A. tumefaciens* were mixed in equal amounts and infiltrated together. The gene expression or virus activity was tested at 6-8 days post-infiltration and one of three plant replicates were analyzed per experiment.

RT-PCR

To detect FoMV (without GFP or DsRed) in the plant, total RNA was extracted from at after seven days post-inoculation using Tri-Reagent (Sigma, St. Louis, Mo.) according to the manufacturer's protocol. RT-PCR reactions were performed using the RT-PCR kit (NEB, Beverly, Mass.) as described by the supplier. To detect the presence of virus particles, FoMV specific primers were used to amplify the partial viral genome.

GFP and DsRed Photography

Plants were examined under long-wave UV light (UVL-56, UVProducts, Upland, Calif.). For macrophotography, a Canon Digital EOS Rebel XT camera (Canon Inc., Japan) equipped with a Hoya yellow (K2) filter (Hoya Corporation, Japan) was used. For microscopic analysis, samples from infiltrated tissues were mounted with water on a glass slide. Images were obtained with a Nikon TE2000-U inverted microscope, captured using a CoolSnap cf camera (Roper Scientific, Tucson, Ariz.) and analyzed with Metavue imaging software (version 5, Molecular Devices Co, Downingtown, Pa.).

GFP Quantification Assay

GFP fluorescence was analyzed and GFP protein was quantified using a standard curve determined from a purchased GFP standard (Vector Laboratories, Inc, Burlingame, Calif.), since the amount of GFP protein is directly proportional to the fluorescence intensity (Lindbo, 2007a). Total soluble protein extracts were serially diluted in 50 mM carbonate/bicarbonate buffer, pH9.6 and loaded on the 96-well Costar black plate with clear bottom (Costar, Cambridge, Mass.). Fluorescent activities were assayed with a Fluoroskan Ascent FL (Thermo Fisher Scientific Inc., Waltham, Mass.) using a 485 nm excitation and 538 nm emission filter set.

Protein Extraction, SDS-PAGE

Proteins were extracted by grinding agroinfiltrated leaves to a fine powder in liquid nitrogen and mixing 1:2 (w/v) with reducing protein extraction buffer (50 mM Tris, pH7.5, 150 mM NaCl, 0.1% Tween 20, and 0.1% β-mercaptoethanol) or nonreducing protein extraction buffer without β-mercaptoethanol. The insoluble material was removed by centrifugation for 10 min at 16,000×g in a benchtop centrifuge. The supernatant was collected and stored at 4° C. Clarified extract of protein samples were mixed with 3×SDS-PAGE sample buffers (NEB, Beverly, Mass.) and analyzed by PAGE consisting of a 5% stacking gel and a 7.5% or 15% separation gel. Proteins in the gels were identified with Coomassie brilliant blue R-250 (Sigma, St Louis, Mo.).

Western Blot

After electrophoretic separation, the proteins were transferred to a Hybond-P PVDF membrane (Amersham Biosciences, Piscataway, N.J.) using a semi-dry transfer apparatus (Biorad, Hercules, Calif.) at 20 V for 30 min. The membranes were blocked for 1 h with TBST (150 mM NaCl, 10 mM Tris-HCl, pH 7.5, 0.05% (v/v) Tween 20) and 5% (w/v) skimmed milk. Blots were incubated for 1 h with anti-human IgG antibodies conjugated with alkaline phosphatase (Sigma, Saint Louis, Mich.), diluted 1:10000 in TBS with 1% skimmed milk to evaluate the production of the antibody in plants. The enzymatic reaction of alkaline phosphatase was developed with SIGMA FAST BCIP/NBT substrate solution (0.30 mg/ml nitroblue tetrazolium (NBT), 0.15 mg/ml 5-bromo-4-chloro-3-indolyl phosphate (BCIP), 100 mM Tris and 5 mM $MgCl_2$) (Sigma, St. Louis, Mich.). Apparent molecular weight of proteins was estimated with prestained protein molecular weight markers (NEB, Beverly, Mass.). The anti-Langerin antibody was used as a control in the antibody studies.

Enzyme-Linked Immunosorbent Assays (ELISA)

ELISA 96-well plates (Costar, Nunc, Corning, N.Y.) were coated for 1 h at 37° C. with 2 ug/mL of monoclonal anti-human IgG (Fc specific) (Sigma, St. Louis, Mo.), diluted in 50 mM sodium carbonate buffer (pH 9.6). After three washes with TBS-0.05% Tween 20, the wells were blocked for 1 h at 37° C. with 5% (w/v) skimmed milk in TBST. Plates were loaded with 50 ul of the protein extracts of two fold serial dilution and incubated for 1 h at 37° C. After three washings, the bound recombinant IgG was detected with the specific antigen conjugated with alkaline phosphatase (provided by Gerard Zurawski of the Baylor Institute for Immunology Research, Dallas, Tex.), diluted 1:3000, for 1 h at 37° C., and developed with p-nitrophenyl phosphate (Sigma, St. Louis, Mo.) as substrate. Optical densities were measured at 405 nm on a BIO-TEK ELx800 Universal Microplate Reader (Cole-Parmer, Vernon Hills, Ill.). A standard curve of serial 1:2 dilutions of antibody positive control was included in the experiments, to assess the amount of antibody present in the samples.

Results

Full Length Infectious FoMV cDNA Clone

Full-length FoMV cDNA under transcriptional control of the 35S CaMV promoter was inserted into T-DNA of binary vector JL22 to construct pFoMV (FIG. 1). *Agrobacterium* stain GV3101 containing pFoMV was agroinoculated in *Nicotiana benthamiana* to look for symptoms and evidence of viral replication. There were no symptoms of viral infection of FoMV. To detect the presence of FoMV infection, total RNA was extracted from leaves and screened by RT-PCR at 7 days post-inoculation. Systemic movement of viral RNA derived from pFoMV was demonstrated in inoculated plants, but was not seen in uninoculated controls (Data not shown). Thus agroinfection with the pFoMV construct resulted in replication, movement, and production of virions and this FoMV sequence is so mild that no symptoms were produced.

Local Infection of FECT Expression Vector

A. Construction of the Viral Vector pFECT Based on FoMV Genome

The TGB and CP genes in a full-length cDNA clone of FoMV were removed and replaced with restriction sites amenable for inserting heterologous genes. However, the subgenomic promoter of subgenomic RNA1 and the 3'-end of the CP ORF in the FoMV genome were retained to maintain the efficient viral replication in viral vectors, following the design of Komorova et al. (2006), incorporated herein by reference, for PVX, also a potexvirus. The start codon of TGB1 ORF was mutated to prevent expression of TGB1 (FIG. 1). The FoMV triple gene block (TGB) and coat protein (CP) are expressed from 3'-coterminal subgenomic RNAs (sgRNAs). The subgenomic promoters and the transcription start site of the sgRNA1 have not been mapped in FoMV. To ensure the inclusion of the entire functional region of the sgRNA1 promoter, which was expected to extend into the TGB1 ORF, the first 3 (start codon only), 22 and 40 bases of the TGB1 ORF were retained to create constructs named pFECT0, pFECT22 and pFECT40, respectively. Thus, the only difference between FECT0/GFP, FECT22/GFP and FECT40/GFP vectors is the promoter length (FIG. 1). FECT0 is the promoter length described in Komorova's paper (2006) for PVX.

To test viral replication and GFP expression of these FECT/GFP vectors, cultures of the GV3101 strain of *A. tumefaciens* carrying these constructs FECT/GFP were prepared. Leaves of 2-4 week old *N. benthamiana* were agroinfiltrated with each of the FECT/GFP cultures. At 2-4 days after agroinoculation, GFP-expressing cells could be seen faintly using a hand-held UV lamp and fluorescence microscopy. At this time, there were many faint green spots shown on inoculated leaves on leaves inoculated with FECT40/GFP, many fewer green spots shown for FECT20/GFP, but no green fluorescence could be detected on leaves inoculated with FECT0/GFP. However, the fluorescence was transient and, by eight days post-inoculation, the GFP spots on the FECT22/GFP and FECT40/GFP plants had disappeared. Apparently, the transcription of agroinfiltrated T-DNA induced posttranscriptional gene silencing (PTGS), which led to the inhibition of viral vector infection and the reduction of viral productivity.

B. Application of Gene Silencing Suppressors

It has recently been demonstrated that co-inoculation of RNA-silencing suppressor proteins enhances the expression of heterologous proteins from the viral vectors (Komarova et al. 2006; Lindbo 2007a; Lindbo 2007b). For example, tomato bushy stunt virus silencing suppressor p19 increased 100 times the expression of GFP in tobacco mosaic virus vectors (Lindbo 2007a). To test these suppressors, *N. benthamiana* plants were agroinfiltrated with a 1:1 mixture of 35S/p19 or 35S/HcPro and FECT/GFP cultures. The accumulation of GFP was followed and imaged with a hand-held UV light and fluorescence microscopy at 3-7 days post-inoculation.

When plants were co-infiltrated with the suppressor, a high level of fluorescence was observed. The fluorescence of the inoculated zones of FECT40/GFP plants was very clearly seen under the UV lamp even with the room lights turned on. Though the amount of GFP-expression was dramatically increased in FECT20/GFP and FECT40/GFP inoculated plants, no fluorescence was seen with FECT0/GFP with or without suppressor co-infiltration. By four days post-inoculation, nearly 90% of the infiltrated area was fluorescent with FECT40/GFP. Also, the leaves with FECT40/GFP displayed much stronger green color than the one with FECT20/GFP. Thus the subgenomic promoter includes at least up to 20 to 40 bases of the ORF.

The unusually high expression level led us to determine the percent of total soluble plant protein that the GFP represented in the inoculated zone. As replication of FECT/GFP replicon progressed, the amount of GFP expressed in the infiltrated leaf increased, so a time course was needed. *A. tumefaciens/*FECT40/GFP+*A. tumefaciens/*35S/p19 co-infiltrated leaves from 2 to 7 dpi were homogenized and the relative amounts of GFP in extracts of total soluble protein were measured with SDS-PAGE electrophoresis and coomassie blue protein staining. The GFP was detected from the second day after inoculation. The expression level of fluorescent protein increased gradually, and reached a peak at 7 dpi. At this time it appeared that nearly 100% of the cells in the inoculated leaves were infected with FECT40/GFP mixed with suppressors. GFP accumulated to 30% to 40% of the total soluble protein extracted.

At 7 days post-inoculation it appeared that nearly 100% of the cells in the inoculated leaves were infected with FECT40 mixed with suppressors. Green and red fluorescent cells were observed by fluorescence microscopy in plant leaves agroinoculated with FECT40/GFP or FECT40/DsRed. The FECT vector was able to replicate in the majority of plant leaf cells when delivered by agroinfection. Target protein could be expressed only as the result of this replication and the subgenomic RNA synthesis, in which cell-to-cell movement is not required.

Next compare FECT40/GFP expression was compared to expression obtained by a nonviral 35S construct, since 35S expression is the standard used in plant biotechnology. Gene silencing suppressors can also be used in tandem with 35S promoters directly driving the gene expression of the ORF, without the use of viral vectors. This results in remarkably high protein expression. To make for an exact comparison, the GFP ORF was placed into the same binary plasmid backbone (pCB302) used for FECT40, using the same 35S promoter that drives the expression of the FECT40 viral transcript. *A. tumefaciens* cultures containing p19 and FECT40/GFP binary constructs were mixed and co-infiltrated into *N. benthamiana* leaves. Control plants were co-infiltrated with a mixture of *Agrobacterium* cultures containing either the pCB302/GFP or the 35S:p19 plasmids. Total soluble protein was extracted from infiltrated leaf tissue at seven days post-infiltration. The protein yield of GFP in plants was measured by spectrofluorometry in fluorescence activity assay. The FECT40/GFP vector expressed 1.6 g/kg GFP of fresh-weight tissue, which represented up to 80 times more GFP than was obtained from co-infiltrating T-DNAs for 35S:GFP and 35S:p19 into plants. In multiple repetitions of this experiment, the FECT system consistently expressed significantly more GFP (1.58±0.13 g/kg) than the non-viral transient expression systems examined (0.02±0.002 g/kg).

Because the TGB and CP of FoMV is required for systemic and cell-to-cell movement, the FECT viral vectors were not expected to move systemically and cell-to-cell in plants. To test this, *N. benthamiana* plants were inoculated with either JL24, a full length TMV vector which expresses GFP, or FECT40/GFP by agroinfection mixed with p19. When leaves were infiltrated with higher concentration of JL24 or FECT/GFP containing *agrobacterium*, almost all plant cells in the infiltrated area expressing GFP made it difficult to separate an individual focus. Serial dilution experiment of agroinfection was performed on *N. benthamiana* plants. Plants were observed under UV illumination to visualize GFP expression and, hence, viral movement. The vector JL24 expressed GFP and all of the genes of TMV, including the MP (corresponding for TGB in FoMV) and the CP (corresponding for CP in FoMV), and was observed to move cell-to-cell at 4 dpi and systemically at about 7 dpi. As TMV replicates and viral particles move cell-to-cell from inoculated cell to adjacent cells through the help of MP, individual GFP-expressing foci enlarge it. The FECT replicon was never observed to move systemically in the agroinoculated plants in this or any other experiment, and the green fluorescent loci on the leaves never grew to larger spots by cell-to-cell movement. This effect was especially clear in comparing the sizes of individual GFP-expressing cell foci in 4 dpi images of leaves infiltrated with 1:1000 dilutions of FECT/GFP and 1:100 JL24. In this case, the spots were well separated and no cell to cell spread was observed beyond that which occurred initially.

C. FECT Expression Analysis in Monocots

It was demonstrated agroinoculation of FECT vector together with a silencing-suppressor gene dramatically increases the production level of target protein in *N. benthamiana* plants. The host range in of FECT in grasses, its natural hosts, was investigated in the same method. Switchgrass, foxtail millet, barley, wheat, oat and corn were co-agroinoculated with the mixture of two *Agrobacterium* cultures containing FECT40/GFP and p19, respectively.

Fluorescing cells were observed in corn's leaves agroinoculated with FECT/GFP by fluorescence microscopy, but not in uninoculated control leaves. In barley, clumps of cells were very occasionally seen that were not found in controls. Single fluorescent cells were present in oats and other grasses, but there were also these kinds of fluorescing cells in noninfected leaves. The low transformation efficiency in monocots via agroinoculation made it difficult to conclusively distinguish between autofluorescence in control leaves and GFP fluorescence in inoculated leaves. Successful reports of grass species agroinoculation were not found by the authors except for a single report of the infection of scattered single GUS-expressing transformed cells of agroinoculated switchgrass.

D. FECT Expression Analysis in Legumes

Expression of GFP by FECT/GFP was apparent in at least four species of legumes tested. GUS expression was visualized colorimetrically in bean and cowpea and GFP expression was visualized by fluorescent microscopy for *Medicago truncatula* and lentil, with large numbers of cells fluorescing, in clear distinction from uninoculated leaves.

E. Effect of Gene Silencing Suppressor in Cis Construct

High yield protein production in *N. benthamiana* demonstrates that specific interaction between the suppressor and FECT viral vector is absolutely required for gene silencing suppression. However, only a small fraction of cells, at best, are expected to be infected by *Agrobacterium* in the agroinoculation of grasses. As the trans construct, p19 has to be expressed in a separate binary vector and two *agrobacterium* cultures have to be mixed up before agroinoculation. Because of expected low rates of infection, co-agroinfection of the same cell with FECT and p19 was considered almost impossible in grasses. So, a combined FECT/p19 construct was built for the co-expression of p19 and FECT in the same cell. The p19 ORF was cloned into the FECT/GFP vector under the control of the nos promoter and nos terminator. GFP expression was examined under a hand-held UV lamp at 2 days post-inoculation in *N. benthamiana*. There was no significant difference between cis and trans p19 construct, with both showing strong fluorescence in the agroinoculated zone. The only difference was seen at seven days post-inoculation, when the trans treatment gained in fluorescence while the cis treatment remained at the same level.

F. Transient Antibody Expression with FECT Viral Vector

The FECT vector has been successfully used to express glucuronidase (GUS; data not shown), DsRed and GFP in *N. benthamiana*. To expand the repertoire of genes that could be expressed, a very large and multimeric protein was chosen. cDNA clones of anti-langerin mAb IgG4 HC and LC were prepared by PCR introducing restriction cloning sites for PacI and AvrII at the 5' and 3' ends, respectively. The gene fragments encoding HC and LC were cloned into viral vector FECT40, under the control of the subgenomic promoter for FoMV TGB1 mRNA, obtaining FECT40/LC and FECT40/HC. *N. benthamiana* plants were co-agroinfiltrated with three *Agrobacterium* mixtures carrying the antibody expression constructs—FECT40/LC and FECT40/HC—and gene silencing suppressor p19 driven by 35S.

Infected leaves of *N. benthamiana* were homogenized in extraction buffer, centrifuged to clear the supernatant, and directly coated onto ELISA plates. Plant-based recombinant antibody bound to the antigen was detected using the Langerin alkaline phosphatase conjugate. Extracts from plants infected with FECT40/GFP were used as negative controls. The ELISA results demonstrate that the total soluble protein from agroinfiltrated leaves contained molecules which human heavy and light antibody chains where assembled. Western blot analysis of total soluble protein extracted by non-reducing conditions indicated that the protein material from transient expression contained a 170 kDa full-length antibody protein band of similar molecular size as the positive control antibody which is expressed by mammalian expression system. The total soluble protein from leaves agroinfiltrated with *Agrobacterium tumefaciens* with FECT empty vector plasmid was negative by ELISA and western blot, as expected. The antibody yield was 10 μg/g fresh weight of agroinfiltrated leaves as calculated by ELISA using the standard antibody standard curve.

Discussion

Very high protein expression rates were demonstrated in *N. benthamiana* for the deleted viral vector, FECT. At 40% TSP for the expression of GFP, this vector expresses at rates equivalent to any plant expression system available and well beyond expression rates published for traditional plant virus vector systems. The GFP expression of the best nonviral 35S system is 270-340 ug GFP/g fresh tissue aided by p19 and 5-12 ug/g without p19. This compares to the observed expression of 1.6 mg/g. Thus, a vector system has been developed which expresses protein at close to the biological limits for plant cells.

The FECT viral vector system has many features that enhance its environmental safety when used via agroinoculation or potentially as a transgene. First, its genome is reduced by more than half, making it several crippled. Second, it does not replicate efficiently unless the plant immune system is suppressed. Thus, if it were to somehow infect another plant (e.g., via its *Agrobacterium* carrier), it would replicate poorly. Third, it lacks a coat protein and cannot form a virion, making it impossible for the virus to survive outside of a host. Finally, it is derived from a virus that in most hosts causes only mild infections. In fact, no symptoms were observed in *N. benthamiana* with the full length virus.

A novel and useful control mechanism operational with the FECT construct. In the absence of a silencing suppressor, almost no expression of GFP occurred, and what expression did occur was transient, disappearing by the seventh day after inoculation. This contrasts with the extreme expression in the presence of the silencing suppressor. This was not the case with the PVX vector of Komorova et al. (2006). Though PVX and FoMV are both potexviruses, the Komorova deletion vector performed fairly well even in the absence of suppressor. This paper states that no extra bases of ORF were used to extend the subgenomic promoter, however it was found that no expression occurred when this was emulated with FoMV. Only when extra bases of the TGB1 ORF were included was expression observed, with or without suppressor. Thus, the vectors differed in design as well as performance.

The effect of removing the coat protein of TMV (tobamovirus family) and portions of the movement protein have been examined previously by others. Complete removal of the movement protein produced only small infection points, which could be rescued by the co-agroinoculation of p19 or of various sized portions of the TMV movement protein. Thus, a similar effect was found in the tobamoviruses as was found in the current work with the FoMV potexvirus. It would not be expected that that the unrelated coat proteins and movement protein(s) of tobamoviruses and potexviruses would provide the same on/off effect with regard to the presence of suppressors. Not only are the coat proteins unrelated in sequence, but there are three triple gene block proteins responsible for movement rather than the single protein for TMV. Indeed, the work of Komorova et al. (2006) appeared at that time to clearly demonstrate that, for potexviruses, the removal of coat protein and triple gene block genes produced a vector which was quite functional in the absence of suppressor. The present results were thus unexpected, and are perhaps due to the nature of FoMV itself.

The FECT system was able to express a fully multimeric and immunological detectable IgG. The yield for this antibody was calculated to be 10 ug/g fresh tissue, which is 50-fold less than the recently published dual-virus technique of ICON Genetics, but is at least comparable to the yield obtained with nonviral systems. The low yield of multimer is probably due to less than optimal co-infection of cells with both the FECT/HC and FECT/LC viruses.

There are several uses for the use of FECT vectors. This system has the capacity for high level expression of a variety of proteins, including GFP (0.7 kb and the larger GUS (1.8 kb) and the multimeric Ds-Red (0.7 kb) proteins. At low levels, FECT was shown to express properly assembled antibody. This system, then, would be expected to be amenable to the production of vaccines or other pharmaceutical or industrial proteins via agroinoculation. The tight on/off control of this system also makes it suitable for an inducible transgenic system from the perspective of environmental safety, high yield, and the expression of proteins toxic to the plant host.

Example 2

Plants

Seeds of *Nicotiana benthamiana*, *Vigna unguiculata* (cowpea) and *Phaseolus vulgaris* (Pinto bean), *Lens culinaris* (lentils), *Pisum sativum* (peas) and *Medicago trunculata* (a model legume plant) were sown in Sunshine Mix #1 and plants were grown in 4" pots at 23° C. with 24 hour illumination. *N. benthamiana* plants were agroinoculated at the 5-10 cm stage. Legumes were agroinoculated at the two to four week stage with fully expanded primary or secondary leaves.
SHMV cDNA Constructs All SHMV clones used in this study are the derivatives of a wild-type SHMV cDNA clone (SEQ ID NO:13; Silver et al., 1996) and were constructed using standard recombinant DNA techniques. The SHMV comprises a 5' UTR (SEQ ID NO:8), a replicase ORF (SEQ ID NO:9), a movement protein ORF (SEQ ID NO:10), a virus coat protein ORF (SEQ ID NO: 11), a 3' UTR (SEQ ID NO:12). The SHMV sequence was obtained from Dr. C. M. Deom, University of Georgia, Athens, Ga., USA. The high fidelity polymerase, Phusion (NEB, Beverly, Mass.), was used according to company protocols for PCR. Recombinant DNA was introduced into *E. coli* 10-beta electrocompetent cells (NEB, Beverly, Mass.) and screened by PCR using Taq polymerase (NEB, Beverly, Mass.) or restriction digest and then sequenced using a CEQ capillary sequencer (Beckman Coulter, Fullerton, Calif.).

1. pSHMV

Figure 2A:
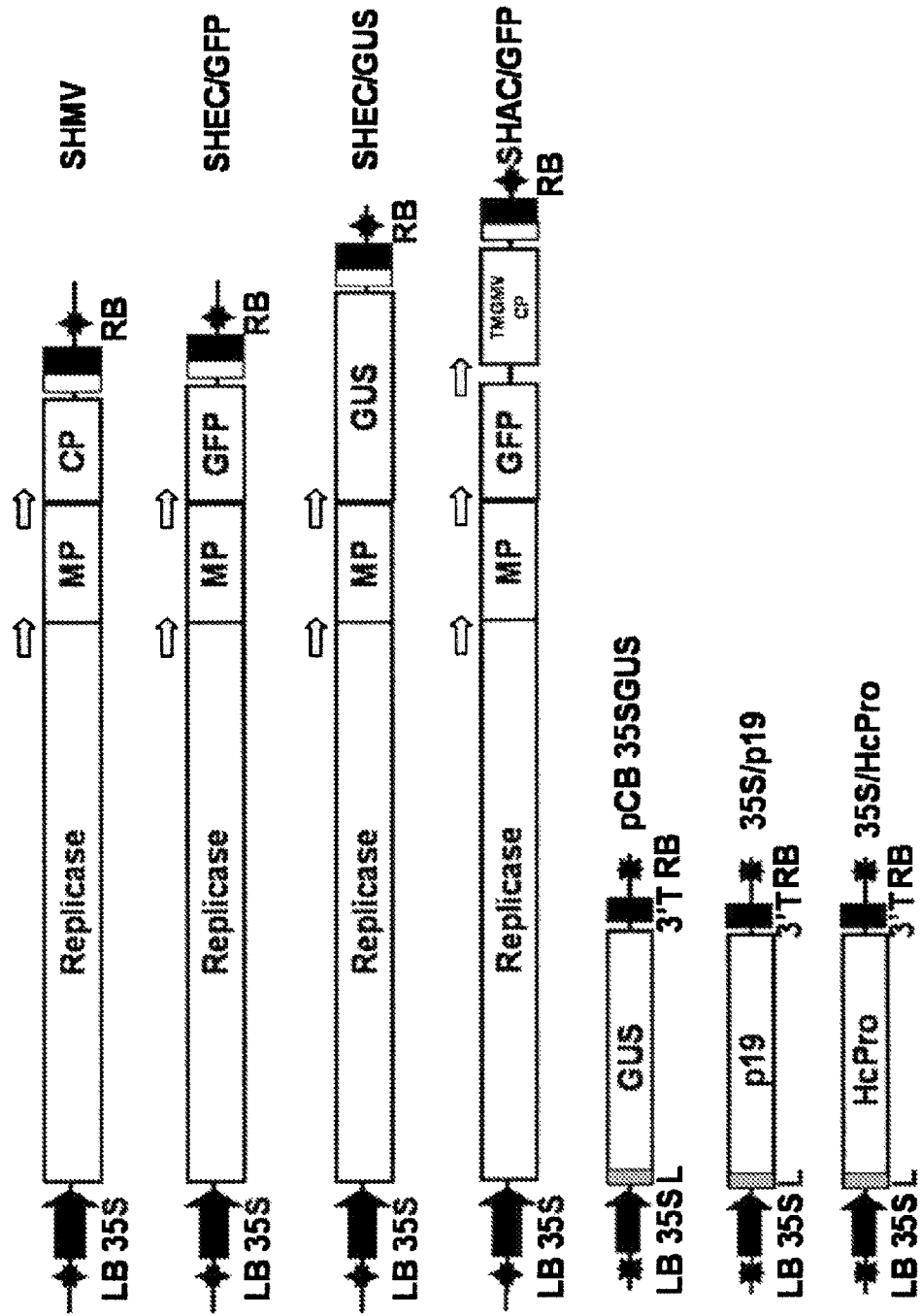
FIG. 2 shows schematic diagram of the T-DNA regions of binary plasmid used in this study (A) and the genomic organization of SHMV-based replicon (B). (A). 35S promoter-driven versions of Sunn hemp mosaic virus (SHMV) vector cDNAs and 35S driven GUS. p19 and HcPro were constructed. All plasmids were based on the binary vector pCB301 backbone. Open boxes represent open reading frames; black stars: left border and right border of T-DNA; block arrows: CaMV duplicated 35S promoter; light grey box: ribozyme; black boxes: CaMV 3' terminator sequence; gray arrows, subgenomic promoters; dark grey boxes: Tobacco etch virus 5' non-translated leader sequence (L); RB: T-DNA right border sequences; LB: T-DNA left border sequences. SHMV transcripts are processed by a ribozyme to generate authentic TMV 3' ends. (B). Shows SHEC58 (SEQ ID NO:153). SHEC74 (SEQ ID NO:154). SHEC89 (SEQ ID NO:155). SHEC/GFP-0 CP 3' (SEQ ID NO:156), SHEC/GFP-15 CP 3'(SEQ ID NO:157), and SHEC/GFP-40 CP 3' (SEQ ID NO:158). All CP deletion mutants have the root "SHEC" (Sunn Hemp Elimination of CP). In the start codon of 5'CP, two ATGs were mutated to ACGs, shown as underlined. Restriction sites PacI and BssHII were introduced at the flank of GFP ORF as cloning sites for other foreign inserts. The numbering in each construct name indicates the number of nucleotides of CP ORF retained to increase GFP expression. For example, SHEC58 retains the 5' end 58 nts of SHMV CP to lengthen the subgenomic promoter to drive the expression of GFP, and SHEC/GFP-40 CP 3' retains the 3' end 40 nts of SHMV CP to increase protein expression.
Figure 2B:
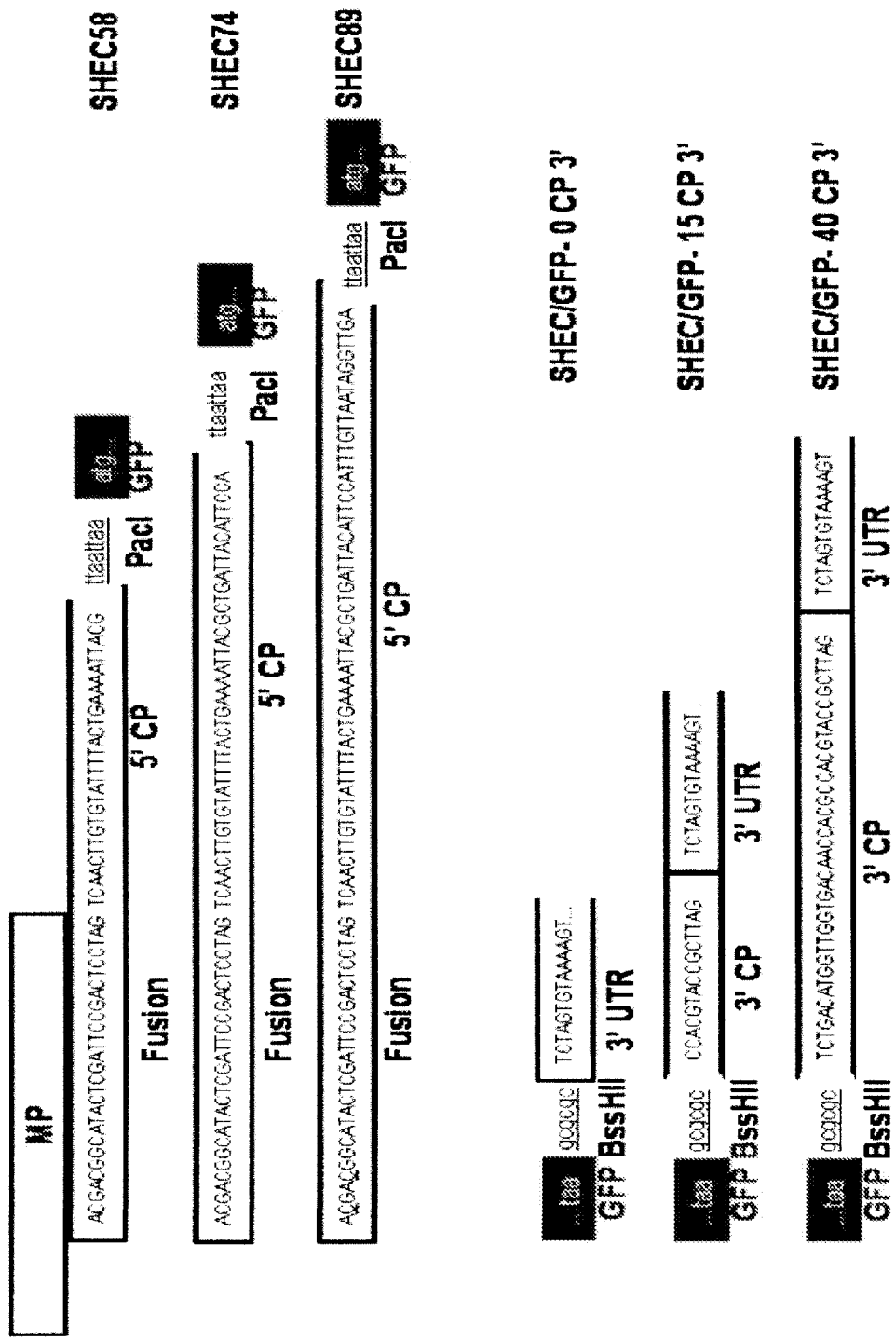

The binary vector, pJL22 (Lindbo, 2007a), has the mini binary plasmid, pCB301, as backbone. JL22 has a multiple cloning site flanked by a CaMV 35S promoter and a CaMV 3' polyA signal/transcription terminator. SHMV full length viral cDNA (Silver et al., 1996) and a ribozyme sequence from JL24 (Lindbo, 2007a) were inserted into the MCS of pJL22. SHMV in viva transcripts should be processed by the ribozyme to generate authentic SHMV 3' ends. This full viral expression cassette, including promoter and terminator, is flanked with the left and right borders of the T-DNA (FIG. 2).

2. pSHacgCP

The use of overlap PCR allowed the double start codons at the beginning of coat protein ORF in pSHMV to be functionally eliminated by mutation to a pair of ACGs. The two primers (dCP-SHMV Up and dCP-SHMV Down) in the initial PCR of the overlap strategy were used to mutate ATGATG to ACGACG without a change in protein sequence of the movement protein ORF in pSHMV. These were mated with the downstream primer, JL22 RB Down (SEQ ID NO:89), and the upstream primer, SHMV 4658 Up, respectively, in the initial PCR and were used as a pair for the second (overlap) PCR. The overlap PCR product was cloned back into KpnI/PmeI cut pSHMV to make pSHacgCP.

3. pSHEC

Mutagenic PCR was performed to delete the CP ORF and introduce PacI and BssHII cloning sites for foreign genes. These sites were introduced using two primers, SHMV PacBss3UTR Up and JL22 RB Down. The PCR product (comprising the 3' UTR and the terminator, ribozyme and T-DNA right border) was cut with PacI/PmeI and cloned into the generic cloning vector pNEB193. Next, three lengths of subgenomic promoter were retained to drive foreign genes instead of the CP gene. Specifically, three downstream primers (SHMV Pac5838 Down, SHMV Pac5854 Down and SHMV Pac5869 Down) were designed to retain 58 nts, 74 nts and 89 nts of the 5' end of the CP ORF sequence, respectively. These were each paired with the upstream primer, SHMV 4658 Up, as above and the PCR products were each cloned into the KpnI/PacI site of pNEB293 already carrying the 3'UTR and downstream elements. Finally, the KpnI/PmeI fragment was transferred from pNEB193 to pSHacgCP to create SHEC58, SHEC74 and SHEC89.

SHEC74 vector (SEQ ID NO:55) comprises a 5' UTR (SEQ ID NO:43), a replicase ORF (SEQ ID NO:44), a movement protein ORF (SEQ ID NO:45), the initial 74 bp of coat protein with first two codons mutated (ATG->ACG) (SEQ ID NO:46), PacI/Bss HII cloning site and 3' UTR (SEQ ID NO:47), 35S terminator (SEQ ID NO:48), miscellaneous sequence (SEQ ID NO:49), T-DNA right border (SEQ ID NO:50), JL22 sequence (SEQ ID NO:51), T-DNA left border (SEQ ID NO:52), miscellaneous sequence 2 (SEQ ID NO:53), and a 35S promoter (SEQ ID NO:54).

4. pSHEC/GFP and pSHEC/GUS

The Cycle 3 GFP gene was PCR amplified to add Pact and BssHII sites and cloned into the PacI/BssHII sites of pSHEC58, pSHEC74 and pSHEC89 to obtain pSHEC58/GFP, pSHEC74/GFP and pSHEC89/GFP. In the same way, GUS (the *E. coli* uidA gene) was subcloned into pSHEC74 to form pSHEC74/GUS construct.

5. pSHAC/GFP pJL24 (Lindbo, 2007) is a TMV vector with the CP subgenomic promoter, CP ORF, and 3'UTR of the Tobamovirus, Tobacco mild green mosaic virus (TMGMV) to prevent recombination with the TMV subgenomic promoter driving the foreign gene. The GFP, CP subgenomic promoter and CP ORF of pJL24 were PCR amplified and the PCR product was cloned into the PacI/BssHII sites of the pSHEC74 to generate pSHAC74/GFP construct.

SHAC74 vector (SEQ ID NO:72) comprises a 5' UTR (SEQ ID NO:56), a replicase ORF (SEQ ID NO:57), a movement protein (SEQ ID NO:58), the initial 74 bp of coat protein ORF with the first two codons mutated (ATG->ACG) (SEQ ID NO:59), PacI and AvrII cloning sites (SEQ ID NO:60), a TMV-UI 3' UTR (SEQ ID NO:61), a Tobacco mild green mottle virus subgenomic promoter (SEQ ID NO:62), a Tobacco mild green mottle virus CP ORF (SEQ ID NO:63), a SHMV 3' UTR (SEQ ID NO:64), a 35S terminator (SEQ ID NO:65), a miscellaneous sequence (SEQ ID NO:66), a T-DNA right border (SEQ ID NO:67), JL22 sequence (SEQ ID NO:68), T-DNA left border (SEQ ID NO:69), miscellaneous sequence 2 (SEQ ID NO:70), and a 35S promoter (SEQ ID NO:71).

6. 35S/GUS

To clone the GUS ORF into the generic binary vector, pCB302 (Xiang et al., 1999), primer XbaGUSUp was used to add aXbaI site at the 5' end, and primer SpeGUSDown was used to add a SpeI site to the 3' end of the GUS ORF. The PCR product was cloned into the XbaI/SpeI sites of the pCB302 to generate pCB/GUS.

7. pSHEC74/GFP 15CP3' and pSHEC74/GFP 40CP3'

In these constructs, 15 or 40 bp of the 3' end of the ORF of CP were reintroduced in an attempt to improve translation, following the design of the TMV TRBO vector (Lindbo, 2007b). A PCR product was generated using upstream primer BssSHMVUp15 or BssSHMVUp40 and downstream primer JL22 RB Down. The amplified DNA was cloned into pSHEC74/GFP cut with BssHII and PmeI.

TABLE 2

Primers used for plasmid construction

| Plasmid | Primer | SEQ ID NO | Oligonucleotide sequence (5'-3') | Purpose |
|---|---|---|---|---|
| pSHacgCP | SHMV 4658 Up (pSHMV nt. 4597-4621) | 116 | CAGATATCCAATCGGTCTCCAACAA | To generate a mutation in the initiation codon of the CP cDNA and eliminate the double ATG's |
|  | dCP-SHMV Down (pSHMV nt. 5769-5801) | 117 | TCGGAATCGAGTATGCCGTCGTCAAATACAGAC | start codon within pSHMV. The mutation is in underlined. |
|  | dCP-SHMV Up (pSHMV nt. 5769-5801) | 118 | GTCTGTATTTGACGACGGCATACTCGATTCCGA |  |
|  | JL22 RB Down (pSHMV nt. 6874-6901) | 119 | TCTAATAAACGCTCTTTTCTTCTTAGGTT |  |
| pSHEC58 pSHEC74 pSHEC89 | SHMV Pac5838 Down (pSHMV nts.5851-5822) | 120 | TGGAATTTAATTAACGTAATTTTCAGTAAA | Three downstream primers (containing the rare-cutting PacI) were paired with the primer - |
|  | SHMV Pac5854 Down (pSHMV nts.5865-5836) | 121 | AACCTATTAATTAATGGAATGTAATCAGCG | SHMV 4658 Up - as above to save 58 nts, 74 nts and 89 nts 5' end of CP DNA sequence from mutated |
|  | SHMV Pac5869 Down (pSHMV nts.5880-5850) | 122 | CTGCGTTAATTAATCAACCTATTAACAAATG | start codon of coat protein respectively. PacI and BssHII cloning sites were introduced by |
|  | SHMV PacBss3UTR Up (pSHMV nts 6275-6292) | 123 | TGCTCGTTAATTAAACTGCGCGCTCTAGTGTAAAAGTTTGGTC | PCR amplified with two primers (SHMV PacBss3UTR Up and JL22 RB Down). Once each pair of PCRs is completed, they are cut with KpnI/PacI or PacI/PmeI and cloned into pSHacgCP vector backbone cut with KpnI and PmeI to create pSHEC58, pSHEC74 and pSHEC89. |
| pSHEC58/GFP pSHEC74/GFP pSHEC89/GFP | PacGFPUp | 141 | TTGTCATTAATTAAGCTAGCAAAGGAGAAGAAC | To clone the GFP ORF into the pSHEC vector. Primer PacGFPUp adds a PacI |
|  | GFPBssDown | 124 | TTTACTCCTAGGTTATTTGTAGAGCTCATCCA | site (underline) at the 5' end, and primer GFPBssDown adds an BssHII site (underline) to the 3' end. |
| pSHEC74/GUS | PacGUSUp | 125 | GGATGGTTAATTAAATGTTACGTCCTGTAGAAG | To clone the GUS ORF into pSHEC vector. Primer PacGUSUp adds an |
|  | GUSBssDown | 126 | TTTACTGCGCGCTCATTGTTTGCCTCCCTGC | PacI site (underline) at the 5' end, and primer BssGUSDown adds an BssHII (underline) site at the 3' end of the ORF. |
| pSHAC/GFP | PacGFPUp | 141 | TTGTCATTAATTAAGCTAGCAAAGGAGAAGAAC | GFP gene and coat protein (CP) gene of Tobacco Mild Green |
|  | TMGMVCPBssDown | 127 | TTTACTGCGCGCCTAAGTAGCCGGAGTTGTG | Mosaic Virus (TMGMV) were amplified together with JL24 as the template. The amplified DNA fragment was cloned into the PacI/BssHII sites of the pSHEC74 to generate pSHAC74/GFP constructs. |

TABLE 2-continued

Primers used for plasmid construction

| Plasmid | Primer | SEQ ID NO | Oligonucleotide sequence (5'-3') | Purpose |
|---|---|---|---|---|
| pSHEC74/GFP 15CP3' | BssSHMVUp15 (pSHMV nts 6235-6255) | 128 | TTTACT<u>GCGCGC</u>CCACGTA CGCTTAGTCTAG | To add a 15 bp or 40 bp more to the 3' end of CP in pSHEC74 vector. The PCR product was generated using primer BssSHMVUp15 or BssSHMVUp40 with a BssHII site (underline) at the 5' end and primer JL22 RB Down at downstream of PmeI site in T-DNA right border of pSHMV. The amplified DNA fragment was cloned into pSHEC74/GFP vector backbone cut with BssHII and PmeI. |
| pSHEC74/GFP 40CP3' | BssSHMVUp40 (pSHMV nts 6235-6255) | 129 | TTTACT<u>GCGCGC</u>TCTGACA GGTTGGTGACAAC | |
| pCB/GUS | XbaGUSUp | 130 | GGATGG<u>TCTAGA</u>ATGTTACG TCCTGTAGAAAC | To clone the GUS ORF into pCB302 vector. Primer XbaGUSUp adds a XbaI site (underline) at the 5' end, and primer SpeGUSDown adds a SpeI (underline) site at the 3' end of the ORF. |
| | SpeGUSDown | 131 | TTTACT<u>ACTAGT</u>TCATTGTT GCTGCCTCCCT | |

Agroinoculation of Plants

Binary constructs were transformed into *A. tumefaciens* EHA105 by electroporation at 1.44 kV and 129Ω for 5 ms using a BTX 600 Electro Cell Manipulator (BTX Inc., San Diego, Calif., USA). *A. tumefaciens* transformants were selected with 10 μg/ml rifampicin and 50 μg/ml kanamycin (Phytotechnology lab, Shawnee Mission, Kans.). Initially, three transformants per binary vector construct were tested for agroinoculation of plant leaves. The gene expression or virus activity was tested at 6 and 8 days post-inoculation and one of three transformants was used for further experimentation.

Agroinoculation was carried out according to standard procedures. A two-day colony of *A. tumefaciens* was transferred to 5 ml LB media supplemented with 10 mM MES (Fisher Biotech,), 20 uM acetosyringone (Phytotechnology lab, Shawnee Mission, Kans.), 10 ug/ml rifampicin and 50 ug/mL kanamycin, and grown overnight at 24° C. The cells of the overnight culture were collected by centrifugation, resuspended in induction media (10 mM MES, 10 mM $MgCl_2$, 150 uM acetosyringone) for a final $OD_{600}$ of 1.0 and incubated for 2 h to overnight at room temperature. The cultures of *A. tumefaciens* were infiltrated with a 3 ml syringe without needle at the abaxial leaf surface.

RT-PCR

Total RNA was extracted from leaves after seven days post-inoculation using Tri-reagent (Sigma, St. Louis, Mo.) according to the manufacturer's protocol. RT-PCR reactions were performed using an RT-PCR kit (NEB, Beverly, Mass.), as described by the supplier, using SHMV-specific primers.

Electron Microscopy

Virus samples were prepared for transmission electron microscopy using a leaf dip method. Hexagonal 300 mesh copper grids (Electron Microscopy Sciences, Hatfield, Pa.) were coated with a film made from a 1% (w/v) aqueous formvar solution. A drop of a saturated aqueous uranyl acetate stain was placed on the coated grid. The cut edge of the leaf was pulled through the drop of stain several times to release virus particles. After 1 minute, the stain was removed with filter paper and the grid was allowed to dry. Samples were viewed using a JEOL JEM 1010 Transmission Electron Microscope (JEOL Ltd., Tokyo, Japan) operated at 60 kV.

Protein Extraction and SDS-PAGE

Inoculated *N. benthamiana* leaf tissue (1 g) was ground to a fine powder in liquid nitrogen using a pestle and mortar. The powder was resuspended by vigorous mixing in 2 ml of protein extraction buffer (50 mM Tris, pH7.5, 150 mM NaCl, 0.1% Tween 20, and 0.1% 3-mercaptoethanol). Extracts were centrifuged for 15 min at 13,000×g at 4° C. Clarified supernatant was stored at 4° C. Clarified extracts of protein samples were mixed with 3×SDS-PAGE sample buffer (NEB, Beverly, Mass.) and PAGE analyzed on a 5% stacking gel and 15% separation gel. Gels were stained with Coomassie brilliant blue R-250 (Sigma, St Louis, Mo.) to visualize proteins.

Detection of GFP Fluorescence

Plants were examined under long-wave UV light using a hand-held UV device (UVL-56, UV Products, Upland, Calif.) and photographs were taken with Canon digital EOS Rebel camera equipped with a Hoya yellow (K2) filter (Hoya Corporation, Japan). For GFP-positive plants, samples from infiltrated tissues were mounted with water on a glass slide. Images were obtained with a Nikon TE2000-U inverted microscope, captured using a CoolSnap cf camera (Roper Scientific, Tucson, Ariz.) and analyzed with Metavue imaging software (version 5, Molecular Devices Co, Downingtown, Pa.).

Histochemical GUS Assay

X-Gluc substrate solution was made with 1 mM X-Gluc (5-bromo-4-chloro-3-indolyl-β-D-glucuronic acid, Gold Biotechnology, St. Louis, Mo.), 100 mM sodium phosphate buffer, pH 7.0, and 0.5 mM potassium ferrocyanide (Acros Organics, Morris Plains, N.J.). Seven dpi leaves were placed in X-Gluc solution and were subjected to a 700-mm Hg (93 kPa) vacuum for 5 min to improve the penetration of the substrate. The samples were incubated in the dark at 37° C. from 1 h to overnight until the staining was satisfactory. After staining, the leaves were cleared with 70% ethanol to improve contrast by removing photosynthetic pigments. GUS-stained leaves were viewed under a light microscope. Micro and macrophotography was performed as above but without UV light.

Spectrophotometric GUS-Assay

Transient GUS activity was determined using the spectrophotometric GUS assay. Inoculated leaves were harvested and grinded as frozen tissue in liquid nitrogen. Freshly prepared 1 ml of GUS lysis buffer (50 mM NaPO$_4$ pH 7.0, 10 mM β-mercaptoethanol, 0.1% Triron X-100) was added to ground tissue powder. Crude extracted homogenate was centrifuged in a microcentrifuge at 12,000×g for 5 min and the extract supernatant was collected. Lysis buffer (100 ul of 10 mM p-nitrophenyl beta-D-glucuronide (PNPG, Sigma)) was added and the reaction was allowed to proceed at 37° C. for 15 h. The reaction was terminated by the addition of 0.4 ml 2.5 M 2-amino-2-methyl propanediol (Sigma), followed by measurement of the absorbance at 415 nm.

Results

Full Length Infectious SHMV cDNA Clone

Full-length SHMV cDNA under transcriptional control of the 35S promoter was inserted into the T-DNA of binary vector JL22 to construct pSHMV (FIG. 2). *Agrobacterium* stain EHA105 containing pSHMV were agroinoculated in *Nicotiana benthamiana* and various legumes to verify host range. Systemic symptoms were visible as mild leaf distortion and mottling in cowpea, and some necrotic spots in Pinto bean and strong mosaic and distortion in *N. benthamiana* similar to TMV infection, while later symptoms involved more severe leaf distortion in systemically-infected leaves in cowpea and bean. SHMV RNA was detected in the inoculated and systemic leaves of these legumes by RT-PCR. As confirmation, SHMV virions were seen in systemic leaves with a transmission electron microscopy, which showed an abundance of rod-shaped virions typical of tobamovirus infections.

Infection of *N. benthamiana* by SHEC Variants

1. Construction of pSHEC

A CP-deletion vector was constructed to allow the environmentally safe expression of protein via agroinoculation or in transgenic plants. The coat protein (CP) subgenomic promoter would be used to drive foreign gene expression and it was expected to comprise sequence both upstream and downstream of the start codon of CP ORF. Since there was an additional AUG next to the start codon, both of the codons were mutated to ACGs (SHacgCP construct) so that the start codon of the foreign gene would be used. Next, constructs with varying lengths of putative subgenomic promoter were created, including 58, 74 and 89 nts of CP ORF in constructs SHEC58, SHEC74 and SHEC89, respectively. Thus, these vectors differed from pSHMV only in the mutated AUGs, a PacI/BssHII cloning site, and the elimination of the CP ORF except for the upstream bases noted. GPF was inserted into the cloning site of each construct to create the SHEC/GFP series.

To test the expression of the SHEC/GFP vectors, cultures of the EHA105 strain of *A. tumefaciens* with SHEC/GFP were prepared and *N. bethamiana* plants were agroinoculated. Four days post-inoculation (dpi), GFP-expressing cells could be seen using a hand-held UV lamp and fluorescence microscopy. There are many green spots shown on inoculated leaves and no significant differences of GFP expression between these SHEC/GFPs.

2. Co-Inoculation with Gene Silencing Suppressors P19 and HcPro

Co-inoculation of RNA-silencing suppressor proteins has enhanced the expression of heterologous proteins from the vectors (Komarova et al. 2006; Lindbo 2007a; Lindbo 2007b). Tomato bushy stunt virus silencing suppressor p19 increased 100 times the expression of GFP in TMV vectors (Lindbo 2007a). HC-Pro, from Tobacco etch virus, serves a similar function in suppressing gene silencing. To test two gene silencing suppressors, *N. benthamiana* plants were agroinoculated with a 1:1 mixture of 35S/p19 or 35S/HcPro and pSHEC/GFP cultures. The accumulation of GFP was followed and imaged by hand-hold UV light and fluorescence microscopy at 3-7 days post-inoculation. When plants were infiltrated with virus and either of these two gene silencing suppressors, the amount of GFP-expression was dramatically increased. At 7 dpi the great majority of the cells fluoresced strongly.

3. Determining Protein Yield of SHEC

*A. tumefaciens*/pSHEC78/GFP+*A. tumefaciens*/35S:p19 co-infiltrated leaves from 3-7 dpi were extracted and the relative GFP expressions were examined by SDS-PAGE electrophoresis and coomassie blue staining. Recombinant GFP expression in infiltrated leaves increased up to the maximal GFP expression level at 7 dpi, to 25% total soluble protein as measured in comparison to a known quantity of GFP protein standard and the determined total protein content of the sample.

4. 3'-Terminal Sequences of Coat Protein Gene

The 3'-terminal 22 nt of the TMV CP ORF as a UTR downstream of the GFP ORF have a positive effect on GFP accumulation (Lindo 2007b). However, with the last 3'-terminal 50 nt of the CP ORF as a UTR downstream of the GFP ORF, GFP accumulation decreased by 70%. To further elucidate possible up-regulatory roles of specific sequences from the 3' end of CP ORF, constructs were made adding either 15 nt or 40 nt sequences derived from the 3' termini of the CP ORF of SHEC74/GFP, creating 5' GFP-15 3' or 5' GFP-40 3' constructs respectively. However, these 3' ORF additions did not significantly increase the GFP accumulation level in *N. benthamiana* compared with SHEC74, which lacked any 3' CP ORF sequence.

5. Cell-to-Cell Movement of SHEC Expression Vector

When the CP genes of TMV, PVX, Brome mosaic virus (BMV), and Cowpea mosaic virus (CPMV) were replaced with the GFP encoding sequence, the chimeric viruses were restricted to local GFP expression (Lindbo 2007b; Komarova et al. 2006). With the SHEC vectors, lacking a CP ORF, no green spots were found in systemic leaves, only in the inoculated leaves. Fluorescence was seen to move into the petioles and stems over several weeks, presumably by cell-to-cell movement through the parenchyma rather than through the phloem since no vein banding patterns typically seen with systemic infections were ever seen in SHEC/GFP infected plants.

SHEC Expression in Legumes

Pinto bean and cowpea were co-inoculated with a mixture culture of *agrobacterium* containing SHEC74:GFP and 35S: p19 and examined by fluorescence microscopy. Though no fluorescence was seen macroscopically, inoculated Pinto bean leaves showed unique and bright fluorescent cells under the fluorescence microscope, in contrast to uninoculated Pinto bean leaves, which were uniformly dark. Unfortunately, uninoculated control cowpea leaves had many autofluorescent cells, but it appeared that inoculated leaves had some unique fluorescent cells not present in uninoculated controls.

SHEC containing the β-glucuronidase (GUS) gene, in co-agroinoculation with 35::p19, yielded legume infections that showed strong GUS expression macroscopically for Pinto bean and cowpea as well as for *N. benthamiana* and also for *Medicago* trunculata, showing large patches of blue pigment, the product of the GUS enzyme reacting with the X-gluc substrate. These blue patches were somewhat less prominent for pea and lentil. When Pinto bean, cowpea and *N. benthamiana* infections were examined microscopically, all showed large numbers of dark blue cells. To verify the absence of endogenous GUS activity, *A. tumefaciens*/pSHEC78/GFP was used as the negative control. To compare SHMV expression vector with other transient expression systems, *A. tumefaciens* cultures with plasmids pCB/GUS or 35S/p19 were mixed and co-infiltrated into *N. benthamiana* leaves. The activity levels of GUS in extracts were determined by a spectrophotometric GUS assay. SHEC/GUS expression was five times that of the 35S::GUS in the pCB/GUS construct co-infiltrated with the 35S::p19 gene in both *N. benthamiana* and legume. GUS expression was very low when legumes were agroinoculated with SHEC/GUS in the absence of 35S::p19. As a negative control, agrobacterial cultures carrying SHEC/GUS did not by themselves produce any blue color by the GUS assay in the absence of inoculation onto plants.

The Full Length Vector, SHAC/GFP

To rescue SHEC vector for systemic movement, the pSHAC78/GFP was constructed. The CP gene of the TMV and SHMV relative, TMGMV, together with its subgenomic promoter, was inserted upstream of the 3' untranslated region (UTR) of pSHEC74/GFP to compensate the function of SHMV CP. The additional sequences of 5' end of SHMV CP ORF were reserved as the subgenomic promoter to drive GFP expression as in SHEC74. Using a different tobamoviral CP subgenomic promoter was expected to prevent homologous recombination between duplicated homologous subgenomic promoters which would lead to deletion of the foreign gene. The SHAC vector expressed GFP plus all of genes for viral functions, including the MP, CP and replicase. Green fluorescent spots were observed in locally inoculated leaves at three dpi, and moved systemically to uninoculated leaves at about seven days post-inoculation. To monitor the stability of foreign gene expression in the recombinant viral vector, vSHAC74/GFP was serially passaged in *N. benthamiana* every 20-30 days intervals using sap inoculation. This chimeric SHMV had no disease symptoms during the infection of plants and the GFP expression was stable for three months over four serials passages using sap inoculation.

However, SHAC/GFP did not move and express GFP systemically in legumes. When Pinto bean was co-inoculated with the mixture culture of *agrobacterium* containing SHAC/GFP and 35S:p19, green fluorescence was observed only in the inoculated leaves of the plant by fluorescent microscopy. GFP expression was not able to be found in upper leaves of legumes, and the genomic RNA of SHMV was not detected in systemic leaves by RT-PCR. SHAC/GUS was not constructed.

Discussion

Currently, vectors derived from the type virus of the Tobamovirus family, TMV, using the host *N. benthamiana*, dominate the commercial use of plant virus vectors for the production of pharmaceutically relevant proteins. A TMV vector which has been heavily modified with added introns to increase nuclear export of the viral transcript has been developed, resulting in foreign protein expression yields of up to 25% total soluble protein (Gleba et al., 2005). Fraunhofer does not use added introns in their TMV vectors, but have made other modifications. Previous to this, many modifications were made to create an earlier generation TMV vector. Thus, the current commercial TMV vectors represent a series of improvements over the original vector.

Herein, the use of the Tobamovirus, SHMV, as a plant expression vector for use in *N. benthamiana* and legumes has been initiated. An infectious clone was obtained from Mike Deom of the University of Georgia (unpublished) which was from the virus used in determining the SHMV 5' sequence (Silver et al., 1996). Realizing that the production of an excellent full length vector will be a long term process, as it was for TMV, a vector suitable for agroinoculation and for use in stable transgenics was developed. For these purposes, the coat protein gene is not necessary, freeing up a subgenomic promoter for expression of a foreign gene and simplifying the vector development process.

The effect of additional bases from the 5' and 3' ends of the CP ORF on expression of GFP was examined. It was established that a subgenomic promoter comprising 58 bases of CP 5' ORF was as effective as longer promoter constructs in the expression of GFP. This is in accordance with previous studies on TMV. The minimal TMV CP subgenomic promoter was mapped between −69 and +12, whereas the boundaries of the fully active promoter were between −157 and +54. Also, it was found that the addition of 15 or 40 bases from the 3' end of the CP ORF did not improve GFP expression, in contrast to the report for the TMV-based TRBO vector (Lindbo, 2007b).

The use of gene silencing suppressors provides a strong on/off effect with the entire SHEC vector series. In *N. benthamiana*, GFP expression was very weak in the absence of suppressors, but strong in the presence of either p19 or HcPro. In both *N. benthamiana* and in legumes, there is little GUS expression in the absence of p19, but in the presence of p19, GUS production was very strong. This on/off property would be useful in an inducible transgenic system. The control of both the suppressor gene and the viral construct by inducible promoters would be expected to provide less leakiness than control of the viral construct alone. In addition, the inherent weakness of the viral construct in the absence of suppressor adds an extra layer of environmental safety to the system.

The effect of removing the coat protein of TMV and portions of the movement protein has been examined. It was found that complete removal of the movement protein produced only small infection points, which could be rescued by the co-agroinoculation of p19 or of various sized portions of the TMV movement protein. Thus, an on/off effect similar to the one described here has been previously described. However, the effect was created with the removal of both the CP and MP genes, whereas here the MP of SHMV has been preserved. The MP gene is useful in agroinoculation in that it allows for viral movement and creates a stronger infection. If fewer cells than the optimal 100% support a viral infection, as is often true with tobamoviral infections compared to potexviral infections, the presence of the MP gene is useful.

SHEC has been shown herein to strongly infect a variety of legumes in the presence of silencing suppressor, a property lacking with any of the TMV vectors. Thus, SHEC could be used to test a candidate for correct protein folding and function in legumes before performing a long term project in the creation of transgenic legumes. SHEC would also be useful as an overexpression agroinoculation screen for an array of unknown genes. Its use as a VIGS vector would be precluded by the need for silencing suppressor coexpression. SHEC would be useful in an inducible transgenic system to replace 35S or other promoters. It has been shown in legumes that the SHEC induces much greater expression of GUS than a comparable 35S-driven nonviral vector.

The SHAC/GFP vector constructed demonstrated that a full length vector of SHMV could be constructed. This SHAC vector was unusual in that it moved more slowly through the plant than the TMV/GFP JL24, it caused almost no symptoms, and it was very stable in terms of retaining the GFP over long term passaging. In this respect, it might serve as a good VIGS vector, due to its low impact on the plant host. Many variations of SHAC could be made, such as using other tobamovirus CP genes, or simply replacing the subgenomic region without replacing the CP ORF, that would hopefully restore infectivity in legumes.

There are other three other viral vectors that are able to infect legumes. Clover yellow vein virus (Potyvirus group) was made into an expression vector with the viral transcript created by 35S. However, the plasmid DNA was introduced to the plant by biolistics rather than by agroinoculation. GFP fluorescence was imaged by UV microscopy in bean. Bean pod mottle virus is a comovirus which has been made into a vector which infects soybeans. It was shown to express GFP when viewed macroscopically, and its ability as a VIGS vector was demonstrated. Rather than agroinoculation, infection was achieved by in vitro transcription. Pea early browning virus (PEBV) is tobravirus which was developed into a VIGS vector for legumes. PEBV is able to enter the meristematic tissue and affect the development of the plant by silencing the gene corresponding to the foreign gene fragment expressed by the virus. The PEBV vector was used via agroinoculation.

Example 3

Plants

*Nicotiana benthamiana* was grown from seed and then transplanted and grown in 4" plastic azalea pots in Sunshine Mix #1 under 400 W metal halide lamps to 10-15 cm before inoculation. GFP fluorescence in whole plants was examined under long-wave UV light (UVL-56, UVProducts, Upland, Calif.) and photographs with a Canon Digital EOS Rebel XT camera (Canon Inc., Japan) equipped with a Hoya yellow (K2) filter (Hoya Corporation, Japan) was used.

General Methods

The high fidelity polymerase, Phusion (New England Biolabs (NEB), Beverly, Mass.), was used according to company protocols in all constructions. Recombinant clones were introduced into *Escherichia coli* NEB 10-beta electrocompetent cells by electroporation at 1.44 kV and 129Ω for 5 ms using a BTX 600 Electro Cell Manipulator (BTX Inc., San Diego, Calif., USA) and colonies were screened by PCR using NEB Taq polymerase or by restriction digests of plasmid minipreps prepared by Wizard Plus Miniprep Kit (Promega, Madison, Wis.).

Construction of JBest

The bialaphos resistance gene (bar) flanked by the promoter and terminator from the nopaline synthase gene of *A. tumefaciens* was transferred from the binary vector, pCB302, to the binary vector, JL22 (Lindbo, 2000a), via flanking HindIII and EcoRI sites to create pJL22/bar. Next, the 35S transcription start site of JL22, which allows an exact start of any virus blunt-end ligated into the StuI site (FIG. 3), was combined with the XVE/estradiol activated promoter of pER8 by overlap PCR. The pER promoter was amplified with primers EcoLexUp (SEQ ID NO:86) and 35termAS Down (SEQ ID NO:88) (FIG. 4) and the JL22 start site was amplified with 35StermUp and JL22RB Down; the two products were gel purified and then amplified for 5 cycles, after which the flanking EcoLexUp and JL22RB Down primers were used to complete the overlap PCR. The final product was inserted into JL22/bar at the EcoRI and PmeI (in RB) sites to create JBest (FIG. 3).

Construction of the TBest Series

An upstream phosphorylated PCR product of the 5' 1027 nts of TMV was created using primers TMVp1-21Up (SEQ ID NO:90) and TMV1008NotDN(SEQ ID NO:91). This was inserted into the StuI blunt site and the NotI site of JBest. The various versions of TBest were created by inserting almost the entire TMV sequence from a previously made noninducible vector carried by the JL22 vector expressing a gene of interest. Specifically, the XmaI site at TMV nt256 and the PmeI site in the RB were used to transport the TMV sequence into JBest carrying the 5' end of TMV to create each TBest vector (FIG. 3).

Construction of the FBest Series

As for the construction of the TBest series, an upstream phosphorylated PCR product of the 5' 756 nts of FoMV was created using primers FoMV 5' termUp (SEQ ID NO:92) and FoMV756NotIDown (SEQ ID NO:93). This was inserted into the StuI blunt site and the NotI site of JBest. The various versions of FBest were created as with TBest, but at different sites. Specifically, the PmlI site at FECT nt411 and the XbaI site at FECT nt4446 (after the poly(A) tail) were used to transport the FECT sequence into JBest carrying the 5' end of FECT to create each FBest vector (FIG. 3).

The FBest vector (SEQ ID NO:42) comprises a T-DNA left border (SEQ ID NO:35), miscellaneous sequence (SEQ ID NO:36), a Nos promoter (SEQ ID NO:37), a bar gene (SEQ ID NO: 38), a Nos terminator (SEQ ID NO:39), a Lex operator (SEQ ID NO:40), and a 35S core promoter segment (SEQ ID NO:41).

Construction of pER8/p19 pER8/p19 was created by adding XhoI and SpeI sites to p19 by mutagenic PCR using primers p19XhoIUp (SEQ ID NO:94) and p19SpeIDown (SEQ ID NO:95). These sites were used for insertion of p19 into pER8 between the 35S promoter and pea3A terminator (FIG. 3).

Agroinoculation

Agroinfiltration was performed using standard procedures. *Agrobacterium tumefaciens* stain GV3101 was used for the agroinoculation of *N. benthamiana*. *A. tumefaciens* was transformed with plasmid constructs using the same conditions as for *E. coli* above. *Agrobacterium* transformants were selected at room temperature on Luria-Bertani plates containing 50 μg/ml kanamycin. A colony of *A. tumefaciens* was inoculated to 5 ml of L-MESA medium (LB media supplemented with 10 mM MES, 20 uM acetosyringone (Phytotechnology Labs, Shawnee Mission, Kans.), a wound response compound that elicits *Agrobacterium* virulence, and the same antibiotics), and grown overnight at room temperature. The cells of the overnight culture were harvested by centrifugation and resuspended in induction media (10 mM MES, 10 mM $MgCl_2$, 100 uM acetosyringone) for a final $OD_{600}$ of 1.0 and incubated for 2 h to overnight at room temperature. The cultures of *A. tumefaciens* were infiltrated into the underside of leaves of plants with a 3 ml syringe without needle. For agroinoculation of two or more bacterium cultures at the same time, multiple cultures of *A. tumefaciens* were mixed in equal amounts and infiltrated together.

Induction with Estradiol Estradiol was prepared as a 10 mM stock in DMSO and diluted to 10 µM in deionized water. Plants were agroinoculated and then, 1-2 days later, the estradiol was administered by syringe injection or root drench (40 ml of 10 µM estradiol used to water one 4" pot).

Results

Induction of TBest

TBest carrying various genes of interest was inoculated onto *N. benthamiana* as a control experiment to determine the leakiness of the estradiol system when teamed with TMV, the most commonly used commercial vector of whole plants. Two days after inoculation, estradiol was applied to the plants either as a root drench or via syringe inoculation into the inoculated leaves. pER8/p19, expressing the silencing suppressor, p19, under the control of the estradiol inducible promoter, was co-inoculated in its own *Agrobacterium* culture along with an *Agrobacterium* culture containing an estradiol-inducible TBest construct (FIG. 3). TBest/GFP at four days post-estradiol (dpe) showed strong fluorescence in the inoculated zone in all plants, regardless of treatment: estradiol by syringe or by root drench or no estradiol at all. By 11 dpe, all of these plants also showed systemically moving fluorescence due to the mobility of the full length TMV vector.

To further test whether this system could be used to disrupt cell wall structures in order to produce plant material amenable to the production of bioethanol, two different cell wall modifying genes were transferred to TBest vectors. EngD, a cellulase from *Clostridium cellulovorans*, gave no necrosis when carried in the TBest vector, regardless of induction, even though it did produce some necrotic specks when expressed in the noninducible JL24 vector with constitutively expressed p19. On the other hand, lipid transfer protein (LTP-2 from tobacco) caused severe necrosis in all plants by 11 dpe, but the fastest development (1 to 4 dpe) was with either estradiol application. Thus, TBest suggested that difficulties with leakiness would make the use of full length TMV in an inducible form an unworkable approach.

Induction of FBest

FBest was used as a deleted virus vector alternative to TBest. FBest carrying either GFP or maize anther xylanase (mxyl) was inoculated to *N. benthamiana* plants along with estradiol inducible p19 carried in the pER8 binary vector and estradiol was applied by both syringe and root drench the next day. FBest/GFP, in the presence of induced p19, showed good fluorescence the day after estradiol induction, becoming very strong at 3 dpe, which is maintained afterwards. However, with no estradiol induction, very little fluorescence was detected at any time. FECT/GFP could substitute for FBest and achieve the same inducible on/off results in conjunction with inducible p19, with little or no fluorescence in the presence or absence of estradiol when p19 was absent or when 19 was present and estradiol was absent, but with strong fluorescence in the presence of estradiol and p19. No effects or symptoms, other than mechanical damage, were seen on pER8/p19/estradiol control plants. FBest/mxyl plants induced by estradiol showed confluent necrotic spots in the inoculated zones at 3 dpe but no symptoms at 1 dpe. Necrosis grew more severe by 6 dpe. In contrast, noninduced leaves showed scattered necrotic spots.

The necrosis obtained with EngD, LTP and mxyl cell wall-modifying enzymes was also observed with other enzymes expressed by the noninducible JL24. In order to determine whether this necrosis was due to a hypersensitive response to the pathogens involved (TMV and *Agrobacterium*) or to cell wall damage by the enzymes, *N. bethamiana* leaves were agroinoculated with various JL24/glycanase constructs and infiltrated with 0.5 M mannitol (allowing osmotic equilibrium between cytoplasm and surrounding medium) or water the next day. The inoculum consisted of 35S::p19 in a binary vector plus JL24 constructs expressing EngD, LTP-2, Jun a 1 (a pectinase) and XynA (a xylanase). After five days in their respective media, only the mannitol floated leaves were green. In contrast, inoculated leaves floated on water showed conspicuous necrosis in the inoculated zones.

In a control experiment, *Nicotiana glutinosa*, which is hypersensitive to TMV, was inoculated with TMV virions from the sap of an infected *Nicotiana tabacum* plant, a systemic host. The next day, the infected leaves were infiltrated and floated on 0.5 M mannitol or water. Both the mannitol and water treated leaves developed characteristic necrotic lesions.

Discussion

Inducible viral vector systems promise higher yields of target protein in replacing traditional inducible and noninducible promoters in agroinoculation (e.g., Sudarshana et al., 2006) and stable transgenic (e.g. Zhang and Mason, 2006) applications. UV macroscopic observations, both the FBest/GFP and the FECT/GFP) fluorescence with p19) had the fairly unique capacity to be not be washed out by indoor lighting and did not require darkness to be seen. FECT/GFP with p19 gave yields of GFP of 40% TSP, which is matched only by some recently developed TMV vectors (Lindo, 2007bGleba et al., 2005) and is 4-8-fold greater than the next more expressive viral vectors.

The leakiness of the TBest system was not seen in the FBest system. JL24, the noninducible TMV/GFP vector that TBest system is built upon, gives good fluorescence even without p19, while FECT, the noninducible version of FBest, yields very poor fluorescence. This concept of using an inducible version of a functionally crippled virus coupled with an inducible silencing suppressor to rescue the virus appears to be the reason for the low amount of leakiness with this system. Even a small amount of virus leaking into the cytoplasm will not be able to sustain a strong infection if only a small amount of silencing suppressor, insufficient to elicit silencing, is produced.

The use of a functionally crippled virus also enhances the environmental safety of this construct if used in agroinoculation or, as has been done for other published inducible viral vectors, if used as a stable transgenic expression cassette. FoMV is the parent virus of FBest and is noteworthy for its mild infections. FBest has 29% of its viral genome deleted and expresses GFP very poorly in the absence of a silencing suppressor. Thus, if carried as a cassette in a transgenic plant in the field, very little or no viral RNA would be available for translation to target protein or available for RNA recombination with wild viruses. The viral RNA would be expected to be noninfectious under normal situations, since it is unprotected by a virion coat. If infection did occur, however, the resulting infection would be expected to be fairly nonproductive in the presence of the silencing machinery of a normal plant.

One use for this system would be the production of target proteins, such as vaccines, that are toxic to plants. Liu and Kearney (unpublished data), for example, have expressed the allergen, Jun a 1, in tobacco by agroinoculation using a standard TMV vector. If this were to be used as a vaccine for large scale production in the field, a transgenic version would need to be produced. An inducible viral vector would be needed for this step since they allow for transgenic plants to be produced from tissue culture without the injury or silencing seen in noninducible vectors. FBest would allow for yields perhaps as high as presently possible in plants and would maintain an unusually high level of environmental safety during the process of field bulk up. The transgenic seed could be used to produce seedlings which could then be fed to livestock or poultry as an edible vaccine after induction.

Example 4

Plants

*Nicotiana benthamiana* was grown from seed and then transplanted and grown in 4" plastic azalea pots in Sunshine Mix #1 under 400 W metal halide lamps to 10-15 cm before inoculation. GFP fluorescence in whole plants was examined under long-wave UV light (UVL-56, UVProducts, Upland, Calif.) and photographs with a Canon Digital EOS Rebel XT camera (Canon Inc., Japan) equipped with a Hoya yellow (K2) filter (Hoya Corporation, Japan) was used.

General Methods

The high fidelity polymerase, Phusion (New England Biolabs (NEB), Beverly, Mass.), was used according to company protocols in all constructions. Recombinant clones were introduced into *Escherichia coli* NEB 10-beta electrocompetent cells by electroporation at 1.44 kV and 129 n for 5 ms using a BTX 600 Electro Cell Manipulator (BTX Inc., San Diego, Calif., USA) and colonies were screened by PCR using NEB Taq polymerase or by restriction digests of plasmid minipreps prepared by Wizard Plus Miniprep Kit (Promega, Madison, Wis.).

Construction of JL22/WClMV

Figure 5:
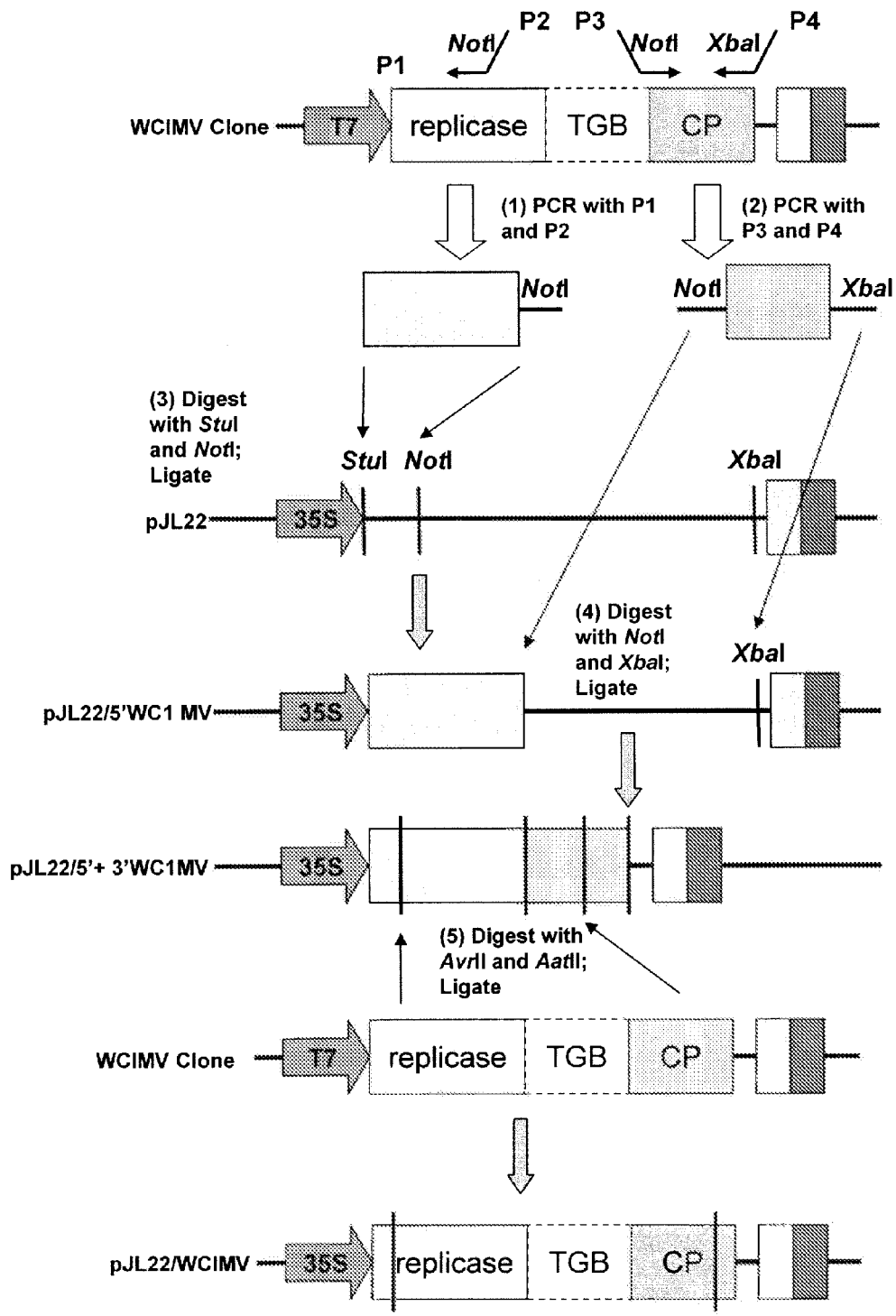
FIG. 5 shows the construction of pJL22/WClMV. The white clover mosaic virus cDNA sequence was transferred from an in vitro transcription vector background to a binary vector background. The 5' portion of the viral cDNA was transferred to the binary vector, JL22, followed by transfer of the 3' portion. The middle section was added via native AvrII and AatII sites to create pJL22/WClMV.

A clone was obtained from the New Zealand government agency, HortScience, and this construct contained the full length white clover mosaic virus (WClMV) (SEQ ID NO:20) sequence driven by a T7 RNA polymerase promoter in a standard *E. coli* cloning vector, and fully described by Beck et al. (1990). The WClMV comprises a 5' UTR (SEQ ID NO:14), a replicase ORF (SEQ ID NO:15), a TGB1 ORF (SEQ ID NO:16), TGB2 and TGB3 ORFs (SEQ ID NO:17), a CP ORF (SEQ ID NO:18), and a 3' UTR (SEQ ID NO:19). Steps were then taken to transfer the sequence to a binary vector. First, two PCRs were performed to amplify the 5' and 3' sections of the virus. This is diagramed in FIG. 5, using primers listed in Table 2. The 5' section was than cloned into binary vector, JL22, followed by the 3' section. The remaining middle section of the viral sequence was retrieved from the original full length clone and inserted into the partial sequence in the binary vector using native restriction sites.

TABLE 3

Plasmids used in construction of the WECT vectors.

| Plasmid | Primer (P) | SEQ ID NO | Oligonucleotide sequence (5' → 3') |
|---|---|---|---|
| pJL22/WClMV | 1. WClMV 5' term UP (pWClMV nt. 1-21) | 132 | 1. P-GAAAACAAGACGAGACGAACC |
|  | 2. WClMV1089 NotI DN (pWClMV nt. 1070-1089) | 133 | 2. AAAAAAGCGGCCGCGATAATCAGATAGCTCAGAA |
|  | 3. WClMV4822 NotI UP (pWClMV nt. 4822-4841) | 134 | 3. TATTATGCGGCCGCTTGGAGGTGAATACAAAGAC |
|  | 4. WClMV5846 XbaI DN (pWClMV nt. 5846-5827) | 135 | 4. AATGAATCTAGACTGAAATTTTATTAAACAGA |
| pWECT26atg pWECT40atg | 5. WClMV2608XmaUP (pWClMV nt. 2599-2618) | 136 | 5. AGAGTACCCGGGAGATCATCGCTGCTGAAGAA |
|  | 6. WClMVsg26PacDN (pWClMV nt. 4020-4000) | 137 | 6. GAAGTCTTAATTAACTGAGGAGGTGGTGAATGTGA |
|  | 7. WCMVsg40PacDN (pWClMV nt. 4034-4014) | 138 | 7. GAAGTCTTAATTAATAAAACCGTGGGAGCTGAGGA |
|  | 8. WCMVPacI MluI 3'CP UP | 139 | 8. AAGTTGTTAATTAA ACGCGT GTTGAAATCACTAACGGTC |
|  | 9. JL22RB DN (pJL22 nt. 827-800) | 140 | 9. TCTAATAAACGCTCTTTTCTCTTAGGTT |
| pWECT26atg/GFP | 10. PacGFP UP | 141 | 10. TTGTCATTAATTAAGCTAGCAAAGGAGAAGAAC |
| pWECT40atg/GFP | 11. GFP Bss DN | 142 | 11. TTTACTGCGCGCTTATTTGTAGAGCTCATCCA |
|  | 12. WCMV2590 XmaI UP (pWClMV nt. 2590-2611) | 143 | 12. TGCGTACCCGGGAAATGAATGAGATCATCGCTGC |
| pWECT25 pWECT40 | 13. WECT + 22ORF PacDN (pWClMV nt. 4016-3988) | 144 | 13. GTACTATTAATTAA GGAGGTGGTGAATGTGATCGATCGCTACT |
|  | 14. WECT + 40ORF PacDN (pWClMV nt. 4031-3999) | 145 | 14. GACTACTTAATTAA AACCGTGGGAGCTGAGGAGGTGGTGAATGTGAT |

TABLE 3-continued

Plasmids used in construction of the WECT vectors.

| Plasmid | Primer (P) | SEQ ID NO | Oligonucleotide sequence (5' → 3') |
|---|---|---|---|
| pWECT25[2] pWECT40[2] | 15. WECT UPscreen (pWClMV nt. 2594-2611) | 146 | 15. GAATGAGATCATCGCTGC |
| | 16. WECTscreen AUC (pWClMV nt. 3997-4014) | 147 | 16. AGGTGGTGAATGTGATCG |
| | 17. WECT40screen (pWClMV nt. 4017-4034) | 148 | 17. TAAAACCGTGGGAGCTGA |

Construction of WECTatg

Figure 6:
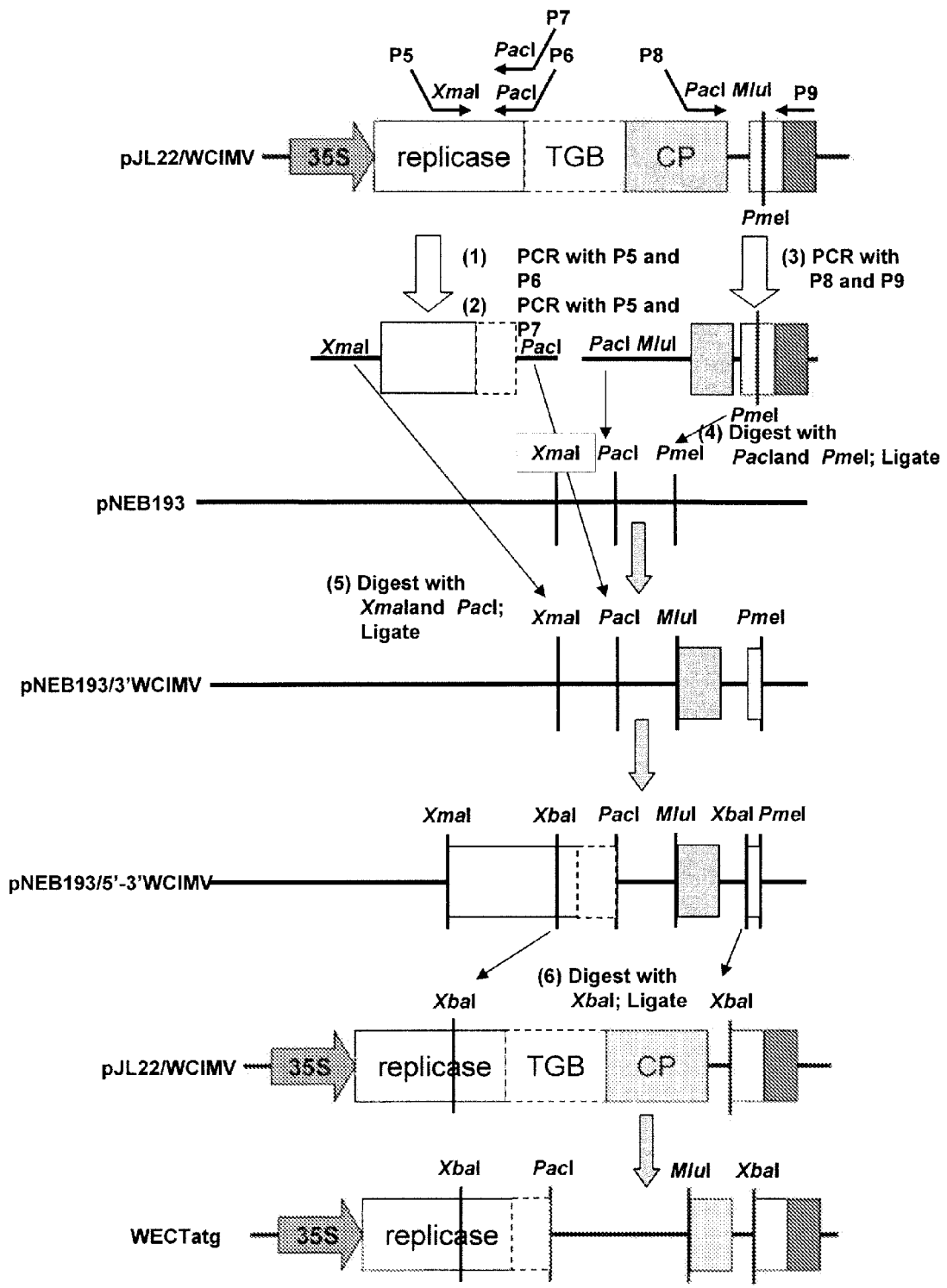
FIG. 6 shows construction of the WECTatg vector from JL22WClMV. The triple gene block (TGB) and coat protein (CP) genes were removed, wholly or partially, by subcloning the 3' viral sequence to cloning vector pNEB193 and then adding the 5' viral sequence upstream of this. The combined structure, with the deletion in the center, was subcloned back into JL22WClMV to create WECTatg. Primer numbers as in Table 3.
Figure 7:
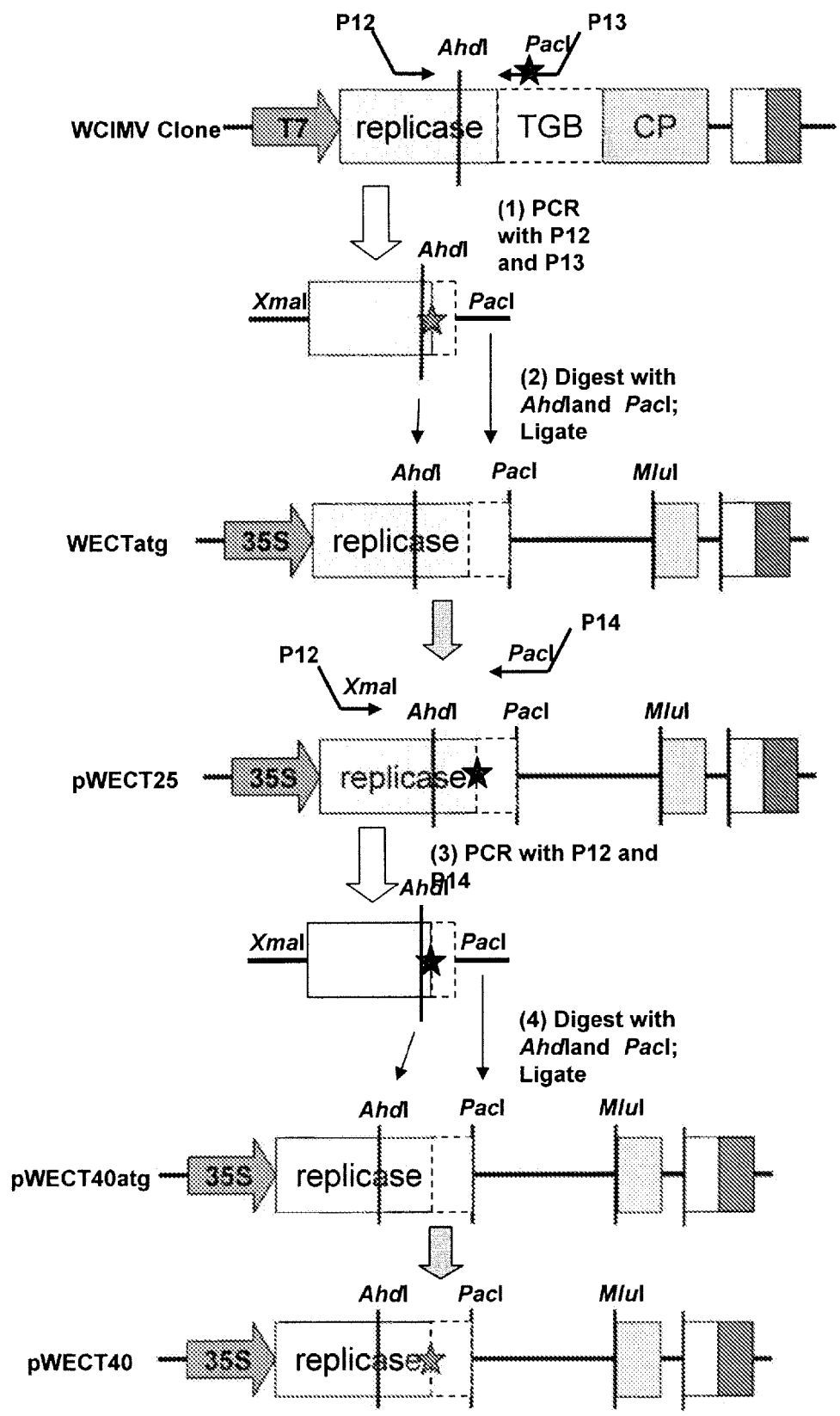
FIG. 7 shows removal of the start codon of the residual TGB1 open reading frame from WECTatg to create WECT25 and WECT40. A primer containing the sequence ATC (replacing the ATG start codon) was used to create a PCR product which was then inserted back into WECTatg to create WECT25. WECT 25 served as the template to create WECT40. Primer numbers as in Table 3.

The TGB and CP genes were wholly or partially removed by two PCRs of the viral sections flanking the deletion site (FIG. 6). Primers binding to either side of the deletion site were created which also contained PacI and MluI sites that would constitute the multiple cloning site of WECT. The PCR product of the 3' viral sequence was placed into the cloning vector, pNEB193, and then the 5' viral sequence was placed upstream of it in the same vector. This combined sequence, which lacks the TGB2 and TGB3 genes and most of the TGB1 and CP genes, was placed back into the JL22/WClMV clone via native WClMV Xba I sites. Differing amounts of TGB1 ORF sequence were removed to determine how much of this sequence had a role as part of the subgenomic promoter. Two different length were created using primers P6 and P7 (FIG. 6). In a preferred embodiment, approximately 30% or less of the initial sequence of the TGB1 ORF would be retained, preferably approximately 20% or less of the initial sequence of the TGB1 ORF would be retained, most preferably approximately 6% or less of the initial sequence of the TGB2 ORF comprising the initial 40 bp of the 688 bp sequence would be retained. In a preferred embodiment, approximately 30% or less of the final sequence of the CP ORF would be retained, preferably approximately 20% or less of the final sequence of the CP ORF would be retained, most preferably approximately 10% or less of the final sequence of the TGB2 ORF comprising the final 60 bp of the 627 bp sequence would be retained.

Construction of WECT

In order to change the TGB1 start codon to ATC, a mutagenic primer (P13) was used in a PCR (FIG. 7). This PCR product was inserted back into WECTatg to create WECT25. The middle section of WECT40, which has a longer subgenomic promoter (40 bases of TGB1 ORF rather than 25 bases), was created by PCR with primer P14 using WECT25 as a template. WECT40 was created by inserting this PCR product into WECT40atg using the Ahd I and Pac I sites.

WECT40 vector (SEQ ID NO:85) comprises a 5' UTR (SEQ ID NO:73), a replicase ORF (SEQ ID NO:74), 40 bp of TGB1 ORF (SEQ ID NO:75), PacI and MluI cloning sites followed by the last 60 bp of CP ORF (SEQ ID NO:76), a 3' UTR (SEQ ID NO:77), a 35S terminator (SEQ ID NO:78), miscellaneous sequence (SEQ ID NO:79), a T-DNA right border (SEQ ID NO:80), a JL22 sequence (SEQ ID NO:81), a T-DNA left border (SEQ ID NO:82), miscellaneous sequence 2 (SEQ ID NO:83), and a 35S promoter (SEQ ID NO:84).

Agroinoculation

Agroinfiltration was performed as described (Kapila et al., 1997) with modifications. *Agrobacterium tumefaciens* stain GV3101 was used for the agroinoculation of *N. benthamiana*. *A. tumefaciens* was transformed with plasmid constructs using the same conditions as for *E. coli* above. *Agrobacterium* transformants were selected at room temperature on Luria-Bertani plates containing 50 μg/ml kanamycin. A colony of *A. tumefaciens* was inoculated to 5 ml of L-MESA medium (LB media supplemented with 10 mM MES, 20 uM acetosyringone (Phytotechnology Labs, Shawnee Mission, Kans.), a wound response compound that elicits *Agrobacterium* virulence, and the same antibiotics), and grown overnight at room temperature. The cells of the overnight culture were harvested by centrifugation and resuspended in induction media (10 mM MES, 10 mM $MgCl_2$, 100 uM acetosyringone) for a final $OD_{600}$ of 1.0 and incubated for 2 h to overnight at room temperature. The cultures of *A. tumefaciens* were infiltrated into the underside of leaves of plants with a 3 ml syringe without needle. For agroinoculation of two or more bacterium cultures at the same time, multiple cultures of *A. tumefaciens* were mixed in equal amounts and infiltrated together.

Results

Expression of GFP by WECT in *Nicotiana benthamiana*

The subgenomic promoter length affected the expression of GFP in WECT. WECT25/GFP expressed GFP less well than FECT40/GFP but WECT40/GFP was indistinguishable from FECT40/GFP. When plants were agroinoculated and infection was allowed to proceed for four days, WECT25/GFP agroinoculated plants were seen by UV light to have moderate fluorescence in the inoculated zones, whereas plants agroinoculated with WECT40/GFP or FECT40/GFP had very strongly fluorescent zones. Similar to FECT40, there was little of no expression of GFP in the absence of the p19 silencing suppressor.

Expression of GFP by WECT in Legumes

Expression of GFP by WECT40/GFP in legumes was not robust as in *N. benthamiana*. However, infection was readily seen in pea and especially in chickpea and lentil as multitudes of clearly fluorescent cells under UV fluorescence microscopy. In contrast, few or no fluorescent cells were seen in uninoculated controls of these plants.

Discussion

The performance of the WECT vectors remarkably paralleled that of the FECT vectors. The optimal size of the TGB1 subgenomic promoter for driving GFP expression was found to include at least 40 bases or TGB1 ORF for both WECT and FECT. There was little or no expression of GFP from the WECT vectors in the absence of p19 silencing suppressor. In side by side comparison, the GFP expression level appeared to be equivalent, by eye, to that of FECT, though SDS-PAGE analysis of actual protein levels has not yet been conducted. It is also notable that WECT infected legume species that FECT infected poorly or not at all, namely, chickpea and pea, as well as infecting lentil well, which FECT also infected.

Perhaps most interesting is the contrast between FECT and WECT vectors to a vector constructed from another potexvirus, PVX. Komarova et al. (2006), removed the TGB2 and TGB3 genes plus most of the TGB1 ORF, leaving only the first 5% of the TGB1 ORF (thought to be functionally a part of the TGB1 subgenomic promoter and needed to drive foreign gene expression). In the PVX vector, the entire CP ORF was removed, but, since this gave no GFP expression in the FECT vector, the final 42 bases of CP ORF were included in the WECT construction, just as was done for FECT. Though the PVX vector was nearly identical, it was quite a capable vector in the absence of p19. This is in complete contrast to the FECT and WECT vectors, which are almost entirely dependent on p19 for any foreign gene expression.

It is reasonable to conclude, then, that some potexviruses can be made into vectors with the silencing supressor-dependent "on/off" switch herein described, and others cannot. The value of this switch is two-fold. First, the virus is essentially crippled in a plant with a normal RNA silencing system. Even if the virus were to survive in the environment and infect a plant (which would be unlikely due to the lack of a CP gene), the infection would be nonproductive. Only when the silencing suppressor is supplied does the virus replicate significantly. Second, an inducible system should be able to be made, similar to that of the FECT vector, in which viral replication is dependent on the presence of high p19 levels and therefore "nonleaky" when not induced. In contrast, other "noncrippled" viruses need only have one viral RNA exported to the cytoplasm for to process towards full viral replication levels to commence.

REFERENCES CITED

The following references, to the extent that they provide exemplary procedural or other details supplementary to those set forth herein, are specifically incorporated herein by reference.

Beck L B, Forster R L S, Bevan M W, Boxen K A, Lowe S C (1990) Infectious transcripts and nucleotide sequence of cloned cDNA of the potexvirus white clover mosaic virus. Virology 177: 152-158.

Bruun-Rasmussen M, Madsen C T, Johansen E, Albrechtsen M. (2008) Revised sequence of foxtail mosaic virus reveals a triple gene block structure similar to potato virus X. Arch Virol 153: 223-226.

Gleba Y, Klimyuk V, Marillonnet S. (2005) Magnifection—a new platform for expressing recombinant vaccines in plants. Vaccine. 23(17-18):2042-8.

Komarova T V, Skulachev M V, Zvera A S, Schwartz A M, Dorokhov Y L & Atabekov J G (2006). New viral vector for efficient production of target proteins in plants. Biochemistry (Moscow) 71, 846-850.

Lindbo J A (2007a) High-efficiency protein expression in plants from agroinfection-compatible Tobacco mosaic virus expression vectors. BMC Biotechnol 7: 52.

Lindbo J A (2007b) TRBO: a high-efficiency tobacco mosaic virus RNA-Based overexpression vector. Plant Physiol 145: 1232-1240.

Silver S, Quan S, Deom C M. (1996) Completion of the nucleotide sequence of sunn-hemp mosaic virus: a tobamovirus pathogenic to legumes. Virus Genes. 13:83-85.

Sudarshana M R, Plesha M A, Uratsu S L, Falk B W, Dandekar A M, Huang T K, McDonald K A. (2006) A chemically inducible cucumber mosaic virus amplicon system for expression of heterologous proteins in plant tissues. Plant Biotechnol J. 4(5):551-9.

Zhang, X. R. and Mason, H. (2006) Bean Yellow Dwarf Virus replicons for high-level transgene expression in transgenic plants and cell cultures. Biotechnol. Bioeng. 93, 271-279.

Zuo J, Niu Q W, Chua N H (2000) An estrogen receptor-based transactivator XVE mediates highly inducible gene expression in transgenic plants. Plant J. 2000 October; 24(2):265-273.

What is claimed:

1. A viral vector system comprising:

1) a functionally crippled viral vector carried on a binary vector, wherein the viral vector is expressed via a constitutively expressed or inducible viral vector promoter, with expression terminating via a viral vector polyA signal/transcription terminator at the 3' end of the viral vector, and the viral vector comprises a modified foxtail mosaic virus (FoMV) full length cDNA and a heterologous gene;

wherein the modified FoMV full length cDNA is a modified wildtype FoMV full length cDNA such that the triple gene block 2 (TGB2) and triple gene block 3 (TGB3) genes are deleted, all bases except the beginning of the triple gene block 1 (TGB1) gene are deleted, all bases except the 3' end of the coat protein (CP) gene are deleted, the subgenomic promoter of subgenomic RNA 1 is retained, and the start codon of the TGB1 open reading frame has been mutated to be non-functional;

wherein the beginning of the TGB1 gene open reading frame is 30% or less of the initial sequence of the open reading frame of TGB 1; and wherein the 3' end of the CP gene is 30% or less of the 3' terminal sequence of the CP FoMV gene; and wherein the heterologous gene is inserted into restriction sites at the 3' end of the subgenomic promoter of subgenomic RNA 1; and 2) a second binary vector carrying a gene for a p19 or a helper-component proteinase (HcPro) silencing suppressor, driven by a constitutively expressed or inducible silencing suppressor promoter;

wherein expression of the heterologous gene is dependent on the presence of the p19 or the HcPro silencing suppressor.

2. The viral vector system of claim 1, wherein the silencing suppressor promoter is a CaMV 35S promoter (35S).

3. The viral vector system of claim 1, wherein the viral vector promoter is an XVE/estradiol activated promoter of pER8 or a constitutive promoter, and the second binary vector comprises an XVE transcription factor gene and the silencing suppressor promoter is an XVE/estradiol activated promoter.

4. A process for expressing genes in a plant, comprising: agroinoculating the plant with the viral vector system of claim 1.

5. The process of claim 4, wherein the plant is *Nicotiana benthamiana*, lentil, *Meclicago trunculata*, barley, wheat or switchgrass.

6. The process of claim 4, wherein the plant is classified in the taxonomic family of Fabaceae or Poaceae.

7. A process for expressing genes in a plant, comprising: agroinoculating the plant with the viral vector system of claim 3 with the two binary vectors each in a separate *Agrobacterium* line.

8. The process of claim 7, further comprising induction of the XVE/estradiol activated promoter with estradiol.

9. The process of claim 8, wherein the induction is carried out by either root drench or syringe injection of estradiol.

10. A viral vector system comprising:
1) a functionally crippled viral vector carried on a binary vector,
    wherein the viral vector is expressed via a constitutively expressed or inducible viral vector promoter system, with expression terminating via a viral vector polyA signal/transcription terminator at the 3' end of the viral vector, and the viral vector comprises a modified white clover mosaic virus (WCIMV) full length cDNA and a heterologous gene;
    wherein the modified WCIMV full length cDNA is a modified wildtype WCIMV full length cDNA such that the TGB2 and TGB3 genes are deleted, all bases except the beginning of the TGB1 gene are deleted, all bases except the 3' end of the CP gene are deleted, the subgenomic promoter of subgenomic RNA1 is retained, and the start codon of the TGB1 open reading frame has been mutated to be non-functional;
    wherein the beginning of the TGB1 gene open reading frame is 30% or less of the initial sequence of the open reading frame of TGB1; and
    wherein the 3' end of the CP gene is 30% or less of the 3' terminal sequence of the CP WCIMV gene; and
    wherein the heterologous gene is inserted into restriction sites at the 3' end of the subgenomic promoter of subgenomic RNA1; and
2) a second binary vector carrying a gene for a p19 silencing suppressor, driven by a constitutively expressed or inducible silencing suppressor promoter;
   wherein expression of the heterologous gene is dependent on the presence of the p19 silencing suppressor.

11. The viral vector system of claim 10, wherein the silencing suppressor promoter is 35S.

12. A process for expressing genes in a plant, comprising: agroinoculating the plant with the viral vector of claim 10.

13. The process of claim 12 wherein the plant is *Nicotiana benthamiana*, chickpea, lentil, or pea.

14. A process for expressing genes in a plant, comprising: agroinoculating the plant with the viral vector system of claim 12.

15. The process of claim 14, further comprising induction of the XVE/estradiol activated promoter with estradiol.

16. The process of claim 15, wherein the induction is carried out by either root drench or syringe injection of estradiol.

17. A method of expressing a gene in a plant comprising the steps of:

(a) delivering a viral vector to the plant;
   wherein the vector is carried by a viral binary vector and the viral vector is expressed via a viral vector promoter, with expression terminating via a viral vector polyA signal/transcription terminator at the 3' end of the viral vector, and the viral vector comprises a modified FoMV full length cDNA and a heterologous gene;
   wherein the modified FoMV full length cDNA is a modified wildtype FoMV full length cDNA such that the TGB2 and TGB3 genes are deleted, all bases except the beginning of the TGB1 gene are deleted, all bases except the 3' end of the CP gene are deleted, the subgenomic promoter of the subgenomic RNA1 is retained, and the start codon of the TGB1 open reading frame has been mutated to be non-functional;
   wherein the beginning of the TGB1 open reading frame is 30% or less of the initial sequence of the open reading frame of TGB1; and
   wherein the 3' end of the CP gene is 30% or less of the terminal sequence of the FoMV CP gene; and
   wherein the heterologous gene is inserted into restriction sites at the 3' end of the subgenomic promoter of subgenomic RNA1; and
(b) delivering a p19 or a helper-component proteinase (HcPro) silencing suppressor
   wherein the p19 or the HcPro silencing suppressor is delivered via a p19 or HcPro silencing suppressor vector comprising a p19 or HcPro silencing suppressor open reading frame, and wherein the expression of the p19 or the HcPro silencing suppressor open reading frame is driven by a silencing suppressor promoter and terminated by a silencing suppressor polyA signal/transcription terminator;
   wherein the viral vector may be constitutively or inducibly expressed; and
   wherein the p19 or the HcPro silencing suppressor vector may be constitutively or inducibly expressed; and
   wherein expression of the heterologous gene is dependent on the presence of the p19 or the HcPro silencing suppressor.

18. A method of expressing a gene in a plant comprising the steps of:

(a) delivering a viral vector to the plant;
   wherein the vector is carried by a viral binary vector and the viral vector is expressed via a viral vector promoter system, with expression terminating via a viral vector polyA signal/transcription terminator at the 3' end of the viral vector, and the viral vector comprises a modified WClMV full length cDNA and a heterologous gene;
   wherein the modified WClMV full length cDNA is a modified wildtype WClMV full length cDNA such that the TGB2 and TGB3 genes are deleted, all bases except the initial portion of the TGB1 gene are deleted, all bases except the 3' end of the CP gene are deleted, the subgenomic promoter of the subgenomic RNA1 is retained, and the start codon of the TGB1 open reading frame has been mutated to be non-functional;

wherein the beginning of the TGB1 open reading frame is the initial 30% or less of the open reading frame of TGB1; and wherein the 3' end of the CP gene is terminal 30% or less of the 3' terminal sequence of the CP WCIMV gene; and wherein the heterologous gene is inserted into restriction sites at the 3' end of the subgenomic promoter of subgenomic RNA1; and (b) delivering a p19 silencing suppressor wherein the p19 silencing suppressor is delivered via a p19 silencing suppressor vector comprising a p19 silencing suppressor open reading frame, and wherein the expression of the p19 silencing suppressor open reading frame is driven by a silencing suppressor promoter system and terminated by a silencing suppressor polyA signal/transcription terminator;

wherein the viral vector may be constitutively or inducibly expressed; and wherein the p19 silencing suppressor vector may be constitutively or inducibly expressed; and wherein expression of the heterologous gene is dependent on the presence of the p19 silencing suppressor.

19. The viral vector system of claim 10, wherein the viral vector promoter is an XVE/estradiol activated promoter of pER8 or a constitutive promoter, and the second binary vector comprises an XVE transcription factor gene and the silencing suppressor promoter is an XVE/estradiol activated promoter.

20. The viral vector system of claim 1, wherein the viral vector promoter is a 35S promoter, and the second binary vector promoter is a 35S promoter.

* * * * *

SEQUENCE LISTING

```
<160> NUMBER OF SEQ ID NOS: 148

<210> SEQ ID NO 1
<211> LENGTH: 80
<212> TYPE: DNA
<213> ORGANISM: Artificial Sequence
<220> FEATURE:
<223> OTHER INFORMATION: Foxtail mosaic virus: 5' UTR

<400> SEQUENCE: 1
gaaaactctt ccgaaaccga aactgactga aactacctcg accgacctta gaacccaaga     60
acccaacggg tgcggccact                                                 80

<210> SEQ ID NO 2
<211> LENGTH: 4051
<212> TYPE: DNA
<213> ORGANISM: Artificial Sequence
<220> FEATURE:
<223> OTHER INFORMATION: Foxtail mosaic virus: replicase

<400> SEQUENCE: 2
atgtctatcg aggcagtttt cgaccaggtt acagacccat cgctccgcgc tgtgattcag     60
gaggaagcgc acaaacagat caaagatttg tttaaggaaa cgacgcgctg caatccctac    120
```

```
tccataccgc aagctgggcg caaggttttg gaaaagtacg ccatccccta caacccgtac    180
tctctcaaac tacaccctca cgcagcctca aaagcgtttg aagtgtcgct ctacgaggct    240
gcgtctaact acctcccctc cacctcctca actcctgtca cattcatgtt cacaaaaccg    300
ggcaagctca gattctttag gcgccgaggt cacgtgtgaca aattcgttaa tgctgacata    360
```
*(Note: line 4 reading — reproduced as seen)*
```
gttccaagag acttggctag atacccacgc gacacagtct acagttatct gcccgagatc    420
accaccacac acgctttcat tggcgacacc ctacatcact tcggtgagga ctttctcgtc    480
gaggttttct ccaggtcacc gaaactagaa gtgcttctag ccaccatggt attaccaccc    540
gaagcctttt acagaatgga gtcccttcat ccctcggttt acactctcct ctacagggac    600
gaccgattcc tatacctgcc tggtggcctg tctggcggtg agtacgaaca tcgctataag    660
gacctaaact ggctaacatt tggcacagtt acgcacggcg ggatcactat cacaggagaa    720
cgcattgaga ctaaggccgc gaatcatctt ttcctcttca gacgagggcg actagcgaca    780
ccaaaattcc gctcattcga catgcccgag cctatggtcc tgcttcccaa ggttttccgc    840
cccgcaaagt acaatgtaca aagccaatt ccccgggaga aagcaaacaa atggttgatg    900
tacgttaaat ccatcggcaa tgccaccatt cgtgacgtat gggctaagct gaggcaaacc    960
atagccaatg cagacattgg actcttctcg cccactgagc tcgtgcatct cacgaattac   1020
ttcctgctcc tgggccggct tgactcacac aattccttcg accaagtact ggccgacagt   1080
gtgctgaaag catggttcag accaatggtc gcaaagcttc aggagattaa gcacaaactc   1140
atggggcaga cccaattcat gcaactctgc caagcgctag agatgacgga ggtgacctc    1200 gtctttgagg tccgggactc caagactccc cacaaacaag ctgtgccgtt ggaccgtgaa   1260
attgaaaacg ttttgttgga aggagtctca tcggagccaa cttacactga aaccgaaggc   1320
gttgctgatg gtccacttcc ccccccaatg caaactgcag ccgagccgtc cgcgacctca   1380
gacgagcccg agagctctag ctcgcgtgaa attgagcatc aaccggcgcc tgagatcacg   1440
cttgacgagg aagaacctca gcgagacgat ctgccttggg acgcttggag aacacaatta   1500
agggcgcttg gctttgaggc ctccgaaagg cagtatgacc cggacggtga actgatctct   1560
cctatcctga gcacccgaag gttgcctaaa actcccatag acacaacact ctacgccacg   1620
ctagacaaga ttgcacgctg cccaactttc tacaagcctg acacagatcg cgcgcagact   1680
tacgctcgcg atgtcatggc ggggaaaacc ggtgccattc tcaagcaaca ccctttgag    1740 tggaaaacca cgctcaagcg caagactaaa gaggaaccga aggaaattca ccttgcggtg   1800
ttgcatggtg cgggcgggtc gggcaaatcc tacgcactgc aggaatttat gcggaacaac   1860
tctgacacac cgattacggt catcctgccg actaacgagc tcagggccga ctggaagaaa   1920
aaattgcccg cccacgacaa agacacattt atgacatacg aaaacgcgct cttgtgccct   1980
cgtggagaca tcttcattat ggacgattac acaaaattgc ccagggcta cattgaggct   2040 ttcgtgcaga atgcacctgc cctctcactt ctgatactca ccggtgaccc caaccaagcc   2100
gaacactttg agaccactga ggacaatgaa attaacagcc tcgccccgc ctcagtggtc   2160 ttcggcaagt tctctaggta ccacataaat gccacacacc gcaacccag aaacttggca   2220 aacgccctcg gtgtttactc cgagacgccc ggggaggtta agtgcttta cacgaggaac   2280 atcaagaccg gttatcacaa tctcgtgccc tcacaaatga gatgagaaa ttacgcctca   2340 ctcgggcagc gagcgtccac ctatgcgggt tgtcagggga tcaccgcgcc ccgcgttcaa   2400
atcatcctag actccgacac accccggtgc accaggcaag tcatgtacac tgcactctca   2460
agggccacga cggaagtggt gctctgcaac acgatgccgg atgagaaaag ctttttccag   2520
```

```
aaggttgaag caacaccgta cctcaaagcc atcctcaacc tcaacaaaga gattaaagtc      2580
actgagggcg acttgacaga agaaccgccg agggagcccg ctcctcccac cacacacctg      2640
cctgttgaaa acagaatcat tcttaatgag gccctagtcg aaccgctgcc cgacaaacat      2700
gaccgcgaga tctactccaa ctccactggc ttttcaaact gcatacagac tcaagacccg      2760
tacatccaag ccttccaaca tcagcaagcc aaggacgaga cattgttctg ggcaaccgtc      2820
gagaagaggc tcgcagcatc tacgccgaag acaactggac agaattcaa gaccaagaga       2880 cctctgggtg acgtgctttg gctcgcgtac aagcgggcga tggtgctccc agatgagccc      2940
atcaaattta acccagagct ctggtgggca tgtgcagatg aggtgcaaaa gacctacctc      3000
tccaagccca tacacgcgct caagaacgga attcttcggc aatcacccga ctttgactgg      3060
aacaaactgc agattttcct caagtcacag tgggttaaga aaattgacaa aatcgggaaa      3120
attgacgtca acgctggaca gacaattgcc gccttttacc aaccaactgt tatgctgttt      3180
ggaaccatgg cgagatacat gcgccgcatc cgcgacactt atcaacccgg cgaaatactc      3240
atcaattgcg agaagaacca gaagcacatt tcgaagtggg tcgagagcaa ttggaaccac      3300
cgcctacctg cttacaccaa tgacttcact gcttacgacc aaagccaaga cggggctatg      3360
ttacagtttg aggtactgaa agccctgcac catgatatcc ctcatgaggt tgtggaagct      3420
tacgtagccc ttaaactcaa ctcaaaaatg tttctgggca cactggcgat tatgagatta      3480
actggtgagg gacccacctt cgacgctaac acagagtgca acattgctta cacacacgcc      3540
cggttcgaga tcccaaagaa tgtggcgcaa atgtacgcgg gtgacgactg tgcgctcaac      3600
tgcaggcccg ttgaacggca gtccttcctg cctcttgtgg agaaattcac cctgaaatca      3660
aaacctaaag tatttgagca aaaagttggg tcatggcctg agttctgcgg caatctgatc      3720
accccacggg gctacctcaa ggatcccatg aagctacaac actgcctgca actggcacag      3780
aggaagaaac catccgaacc tgggtcgctt aaagacgttg ctgagaacta cgctatggac      3840
ttgctaccca catacgagct aggtgatgca ctctacgaaa tcttcgacga gagacaaatg      3900
aacgcgcact atcagtcggt caggacgctt atcacatgcg cccacaccaa agtcctccga      3960
gttgcacagg cacttcagga agactgcacc ttctttagct ccatctaaca ggttttgagt      4020
taggctaact ccactgacga attaaataac a                                    4051

<210> SEQ ID NO 3
<211> LENGTH: 711
<212> TYPE: DNA
<213> ORGANISM: Artificial Sequence
<220> FEATURE:
<223> OTHER INFORMATION: Foxtail mosaic virus: TGB1 ORF

<400> SEQUENCE: 3
atggatagtg aaatagttga acgactaaca aagcttggtt tcgtcaagac ttcacacacg       60
cacatcgctg gcgagcccct cgtgattcac gccgttgctg ggccggtaa aaccaccctc       120 cttcggtcct tacttgaatt accgggagtg gaagtcttca caggcgggga gcacgatcct      180
ccaaatttgt cagggaaata tatccgctgc gctgcacccc ctgtggccgg tgcatacaac      240
attcttgacg agtaccccgc gtacccaaat tggcgatcgc aaccctggaa cgtcctaatc      300
gccgacaacc tacaatacaa agaacccaca cgtcgcgccc actacacatg caatcgcact      360
caccgcctgg ggcagctcac tgtcgacgct ttgcgtaggg ttggtttcga catcaccttt      420
gccggcacgc agactgaaga ctacggattc caggaaggcc atctctacac tagtcaattt      480
tacggacagg tcatttcact tgacacgcag gcccataaga tcgctgtgcg ccacggactc      540
```

-continued

```
gcacccctgt ccgctttaga aacccggggg ctggaatttg atgagaccac tgtgataacg    600
actaaaacct cgctggagga agtgaaggac aggcacatgg tctatgtcgc tctcacaagg    660
cacaggcgca cctgccatct ctacaccgct cactttgcgc cctccgcctg a             711
```

<210> SEQ ID NO 4
<211> LENGTH: 455
<212> TYPE: DNA
<213> ORGANISM: Artificial Sequence
<220> FEATURE:
<223> OTHER INFORMATION: Foxtail mosaic virus: TGB2 and TGB3 genes

<400> SEQUENCE: 4

```
caacacgaaa gccatactaa ctgtagctat aggtatagcc gcctccctcg tcttttcat     60 gctcacacgc aacaatctgc cacacgtcgg tgataacatc cactcactac cccacggagg   120
aagttacatt gacggtacca agtccatcaa ctaccgccca cctgcgtcac gctacccctc   180
atctaactta ctcgtttcgc tccaccaata ctcgccgcag tactctttt cctcacacag   240 ccatatctag ctaccagacg atccaggtgc gttcggtgct tcgttgtcca cggggcatgc   300
acgaatcaca cctagttgtt atattagcgc tgttacttat agctctgtgg tgtctaagca   360
ctcgacccgt tcaaccatcg tgccatgtcg aaatcaacgg ccactccatc atcgtcaccg   420
gaaactgctg gcactccact caacgaccgc attga                              455
```

<210> SEQ ID NO 5
<211> LENGTH: 721
<212> TYPE: DNA
<213> ORGANISM: Artificial Sequence
<220> FEATURE:
<223> OTHER INFORMATION: Foxtail mosaic virus: CP gene

<400> SEQUENCE: 5

```
gggtgttagg gtaaccaaca tcagtgaaga gaaacaaccc acctcaagtg tgacctcatc    60
atttcaggac acaatggcaa cacaaaatgc cgacgtcact gatgcgacgg actacaagaa   120
accgcctgct gaaactgagc agaaggcact caccattcaa ccacggtcaa acaaggcgcc   180
cagtgacgag gagttggtac gcatcatcaa cgcggcgcag aagcgaggcc tcacacccgc   240
ggcctttgtt caagcagcta tagtcttcac catggacaag ggcgccaccg actccacgat   300
tttcacggga aaatacaaca ctttcccaat gaaaagtctg cgcgctacgt tgcaaagatgc   360 tggcgtgccc gtgcacaaac tttgctactt ctataccaag ccggcttacg cgaaccgtag   420
ggtcgccaac cagccgcctg ctcgctggac caacgagaat gtgcccaaag ctaacaagtg   480
ggcggctttc gacaccttcg acgcacttct cgacccatac gtagtcccat cctctgtacc   540
gtacgatgag cccacgccag aggatcgcca agtcaatgag attttcaaga aggacaattt   600
gagtcaggca gcatccagaa accaactcct aggaacgcaa gcctccatca cgcgcgggag   660
actcaacggc gcaccagcac taccaaacaa cgggcagtac ttcatcgagg cacctcagtg   720
a                                                                   721
```

<210> SEQ ID NO 6
<211> LENGTH: 133
<212> TYPE: DNA
<213> ORGANISM: Artificial Sequence
<220> FEATURE:
<223> OTHER INFORMATION: Foxtail mosaic virus: 3' UTR

<400> SEQUENCE: 6

```
tcagtagtat gataccaata aataaatcgg gcgaatccgc gcctcctgac tatgggcagg    60
```

| | |
|---|---|
| tttacggacc aagctgtatc gagatacgac ctaacagtaa cgcagctaag gggtgaatgc | 120 |
| acacatcgct tat | 133 |

<210> SEQ ID NO 7
<211> LENGTH: 6151
<212> TYPE: DNA
<213> ORGANISM: Artificial Sequence
<220> FEATURE:
<223> OTHER INFORMATION: Foxtail mosaic virus: full sequence

<400> SEQUENCE: 7

| | |
|---|---|
| gaaaactctt ccgaaaccga aactgactga aactacctcg accgacctta gaacccaaga | 60 |
| acccaacggg tgcggccact atgtctatcg aggcagtttt cgaccaggtt acagacccat | 120 |
| cgctccgcgc tgtgattcag gaggaagcgc acaaacagat caaagatttg tttaaggaaa | 180 |
| cgacgcgctg caatccctac tccataccgc aagctgggcg caaggttttg gaaaagtacg | 240 |
| ccatccccta caacccgtac tctctcaaac tacaccctca cgcagcctca aaagcgtttg | 300 |
| aagtgtcgct ctacgaggct gcgtctaact acctcccctc cacctcctca actcctgtca | 360 |
| cattcatgtt cacaaaaccg ggcaagctca gattctttag gcgccgaggt cacgtggaca | 420 |
| aattcgttaa tgctgacata gttccaagag acttggctag atacccacgc gacacagtct | 480 |
| acagttatct gcccgagatc accaccacac acgctttcat tggcgacacc ctacatcact | 540 |
| tcggtgagga ctttctcgtc gaggttttct ccaggtcacc gaaactagaa gtgcttctag | 600 |
| ccaccatggt attaccaccc gaagcctttt acagaatgga gtcccttcat ccctcggttt | 660 |
| acactctcct ctacagggac gaccgattcc tatacctgcc tggtggcctg tctggcggtg | 720 |
| agtacgaaca tcgctataag gacctaaact ggctaacatt tggcacagtt acgcacggcg | 780 |
| ggatcactat cacaggagaa cgcattgaga ctaaggccgc gaatcatctt ttcctcttca | 840 |
| gacgagggcg actagcgaca ccaaaattcc gctcattcga catgcccgag cctatggtcc | 900 |
| tgcttcccaa ggttttccgc cccgcaaagt acaatgtaca aagccaatt ccccgggaga | 960 |
| aagcaaacaa atggttgatg tacgttaaat ccatcggcaa tgccaccatt cgtgacgtat | 1020 |
| gggctaagct gaggcaaacc atagccaatg cagacattgg actcttctcg cccactgagc | 1080 |
| tcgtgcatct cacgaattac ttcctgctcc tgggccggct tgactcacac aattccttcg | 1140 |
| accaagtact ggccgacagt gtgctgaaag catggttcag accaatggtc gcaaagcttc | 1200 |
| aggagattaa gcacaaactc atggggcaga cccaattcat gcaactctgc caagcgctag | 1260 |
| agatgacgga ggtggacctc gtcttttgagg tccgggactc caagactccc cacaaacaag | 1320 |
| ctgtgccgtt ggaccgtgaa attgaaaacg ttttgttgga aggagtctca tcggagccaa | 1380 |
| cttacactga aaccgaaggc gttgctgatg gtccacttcc cccccaatg caaactgcag | 1440 |
| ccgagccgtc cgcgacctca gacgagcccg agagctctag ctcgcgtgaa attgagcatc | 1500 |
| aaccggcgcc tgagatcacg cttgacgagg aagaacctca gcgagacgat ctgccttggg | 1560 |
| acgcttggag aacacaatta agggcgcttg gctttgaggc ctccgaaagg cagtatgacc | 1620 |
| cggacggtga actgatctct cctatcctga gcacccgaag gttgcctaaa actcccatag | 1680 |
| acacaacact ctacgccacg ctagacaaga ttgcacgctg cccaactttc tacaagcctg | 1740 |
| acacagatcg cgcgcagact tacgctcgcg atgtcatggc ggggaaaacc ggtgccattc | 1800 |
| tcaagcaaca acccttgag tggaaaacca cgctcaagcg caagactaaa gaggaaccga | 1860 |
| aggaaattca ccttgcggtg ttgcatggtg cgggcgggtc gggcaaatcc tacgcactgc | 1920 |
| aggaatttat gcggaacaac tctgacacac cgattacggt catcctgccg actaacgagc | 1980 |

```
tcagggccga ctggaagaaa aaattgcccg cccacgacaa agacacattt atgacatacg   2040
aaaacgcgct cttgtgccct cgtggagaca tcttcattat ggacgattac acaaaattgc   2100
ccaggggcta cattgaggct ttcgtgcaga atgcacctgc cctctcactt ctgatactca   2160
ccggtgaccc caaccaagcc gaacactttg agaccactga ggacaatgaa attaacagcc   2220
tcgcccccgc ctcagtggtc ttcggcaagt tctctaggta ccacataaat gccacacacc   2280
gcaaccccag aaacttggca aacgccctcg gtgtttactc cgagacgccc ggggaggtta   2340
aagtgcttta cacgaggaac atcaagaccg ttatcacaa tctcgtgccc tcacaaatga    2400
agatgagaaa ttacgcctca ctcgggcagc gagcgtccac ctatgcgggt tgtcagggga   2460
tcaccgcgcc ccgcgttcaa atcatcctag actccgacac accccggtgc accaggcaag   2520
tcatgtacac tgcactctca agggccacga cggaagtggt gctctgcaac acgatgccgg   2580
atgagaaaag cttttccag aaggttgaag caacaccgta cctcaaagcc atcctcaacc    2640
tcaacaaaga gattaaagtc actgagggcg acttgacaga agaaccgccg agggagcccg   2700
ctcctcccac cacacacctg cctgttgaaa acagaatcat tcttaatgag gccctagtcg   2760
aaccgctgcc cgacaaacat gaccgcgaga tctactccaa ctccactggc ttttcaaact   2820
gcatacagac tcaagacccg tacatccaag ccttccaaca tcagcaagcc aaggacgaga   2880
cattgttctg ggcaaccgtc gagaagaggc tcgcagcatc tacgccgaag gacaactgga   2940
cagaattcaa gaccaagaga cctctgggtg acgtgctttg gctcgcgtac aagcgggcga   3000
tggtgctccc agatgagccc atcaaattta cccagagct ctggtgggca tgtgcagatg    3060
aggtgcaaaa gacctacctc tccaagccca tacacgcgct caagaacgga attcttcggc   3120
aatcacccga ctttgactgg aacaaactgc agattttcct caagtcacag tgggttaaga   3180
aaattgacaa aatcgggaaa attgacgtca acgctggaca gacaattgcc gccttttacc   3240
aaccaactgt tatgctgttt ggaaccatgg cgagatacat gcgccgcatc cgcgacactt   3300
atcaacccgg cgaaatactc atcaattgcg agaagaacca gaagcacatt tcgaagtggg   3360
tcgagagcaa ttggaaccac cgcctacctg cttacaccaa tgacttcact gcttacgacc   3420
aaagccaaga cggggctatg ttacagtttg aggtactgaa agccctgcac catgatatcc   3480
ctcatgaggt tgtggaagct tacgtagccc ttaaactcaa ctcaaaaatg tttctgggca   3540
cactggcgat tatgagatta actggtgagg gacccacctt cgacgctaac acagagtgca   3600
acattgctta cacacacgcc cggttcgaga tcccaaagaa tgtggcgcaa atgtacgcgg   3660
gtgacgactg tgcgctcaac tgcaggcccg ttgaacggga gtccttcctg cctcttgtgg   3720
agaaattcac cctgaaatca aaacctaaag tatttgagca aaaagttggg tcatggcctg   3780
agttctgcgg caatctgatc accccacggg gctacctcaa ggatcccatg aagctacaac   3840
actgcctgca actggcacag aggaagaaac catccgaacc tgggtcgctt aaagacgttg   3900
ctgagaacta cgctatggac ttgctaccca catacgagct aggtgatgca ctctacgaaa   3960
tcttcgacga gagacaaatg aacgcgcact atcagtcggt caggacgctt atcacatgcg   4020
cccacaccaa agtcctccga gttgcacagg cacttcagga agactgcacc ttctttagct   4080
ccatctaaca ggttttgagt taggctaact ccactgacga attaaataac aatggatagt   4140
gaaatagttg aacgactaac aaagcttggt ttcgtcaaga cttcacacac gcacatcgct   4200
ggcgagcccc tcgtgattca cgccgttgct ggggccggta aaaccaccct ccttcggtcc   4260
ttacttgaat taccgggagt ggaagtcttc acaggcgggg agcacgatcc tccaaatttg   4320
tcagggaaat atatccgctg cgctgcaccc cctgtggccg gtgcatacaa cattcttgac   4380
```

```
gagtacccoc cgtacccaaa ttggcgatcg caaccctgga acgtcctaat cgccgacaac    4440
ctacaataca aagaacccac acgtcgcgcc cactacacat gcaatcgcac tcaccgcctg    4500
gggcagctca ctgtcgacgc tttgcgtagg gttggtttcg acatcacctt tgccggcacg    4560
cagactgaag actacggatt ccaggaaggc catctctaca ctagtcaatt ttacggacag    4620
gtcatttcac ttgacacgca ggcccataag atcgctgtgc gccacggact cgcacccctg    4680
tccgctttag aaacccgggg gctggaattt gatgagacca ctgtgataac gactaaaacc    4740
tcgctggagg aagtgaagga caggcacatg gtctatgtcg ctctcacaag gcacaggcgc    4800
acctgccatc tctacaccgc tcactttgcg ccctccgcct gacaacacga aagccatact    4860
aactgtagct ataggtatag ccgcctccct cgtcttttc atgctcacac gcaacaatct     4920
gccacacgtc ggtgataaca tccactcact accccacgga ggaagttaca ttgacggtac    4980
caagtccatc aactaccgcc cacctgcgtc acgctacccc tcatctaact tactcgtttc    5040
gctccaccaa tactcgccgc agtactcttt ttcctcacac agccatatct agctaccaga    5100
cgatccaggt gcgttcggtg cttcgttgtc cacggggcat gcacgaatca cacctagttg    5160
ttatattagc gctgttactt atagctctgt ggtgtctaag cactcgaccc gttcaaccat    5220
cgtgccatgt cgaaatcaac ggccactcca tcatcgtcac cggaaactgc tggcactcca    5280
ctcaacgacc gcattgaggg tgttagggta accaacatca gtgaagagaa acaacccacc    5340
tcaagtgtga cctcatcatt tcaggacaca atggcaacac aaaatgccga cgtcactgat    5400
gcgacggact acaagaaacc gcctgctgaa actgagcaga aggcactcac cattcaacca    5460
cggtcaaaca aggcgcccag tgacgaggag ttggtacgca tcatcaacgc ggcgcagaag    5520
cgaggcctca caccgcggc cttttgttcaa gcagctatag tcttcaccat ggacaagggc    5580
gccaccgact ccacgatttt cacgggaaaa tacaacactt cccaatgaa aagtctggcg     5640 ctacgttgca aagatgctgg cgtgcccgtg cacaaacttt gctacttcta taccaagccg    5700
gcttacgcga accgtagggt cgccaaccag ccgcctgctc gctggaccaa cgagaatgtg    5760
cccaaagcta acaagtgggc ggctttcgac accttcgacg cacttctcga cccatacgta    5820
gtcccatcct ctgtaccgta cgatgagccc acgccagagg atcgccaagt caatgagatt    5880
ttcaagaagg acaatttgag tcaggcagca tccagaaacc aactcctagg aacgcaagcc    5940
tccatcacgc gcgggagact caacggcgca ccagcactac caaacaacgg gcagtacttc    6000
atcgaggcac ctcagtgatc agtagtatga taccaataaa taaatcgggc gaatccgcgc    6060
ctcctgacta tgggcaggtt tacgaccaa gctgtatcga gatacgacct aacagtaacg     6120
cagctaaggg gtgaatgcac acatcgctta t                                  6151

<210> SEQ ID NO 8
<211> LENGTH: 74
<212> TYPE: DNA
<213> ORGANISM: Artificial Sequence
<220> FEATURE:
<223> OTHER INFORMATION: Sunn hemp mosaic virus: 5' UTR

<400> SEQUENCE: 8
gtatgattaa cttcacaaca cggttgaagt tataagacca acatttacat ttacatttac      60
aacaaacatt caca                                                       74

<210> SEQ ID NO 9
<211> LENGTH: 4882
<212> TYPE: DNA
<213> ORGANISM: Artificial Sequence
<220> FEATURE:
```

-continued

<223> OTHER INFORMATION: Sunn hemp mosaic virus: replicase ORF

<400> SEQUENCE: 9

```
atgtctacat ctacactcat taacaaagca caaactaact cctgcggtga cgttggcgtt     60
gtggaccttc tgaaaagaaa ggtctacgat gacactgtca aaaccatgca ggggttagat    120
cgcagggcca agtaccggtt aaaccaatgc ttgggacctg aacagtgtag gactgtcaga    180
ggtggctacc ctgaatttca aattgaattc acaggagcat cgaacacgtc gcatgcaatg    240
gcggcgggtt tgagaggact tgaactcgag tatctttata ctcttgttcc gtacggggcc    300
gtgtcttacg acattggtgg aaacttcccc gcacacatga tgaagggtcg ttcgtacgtt    360
cattgctgca atccggcttt agacgcccgc gacctagcca gaaacgagaa ctacagaatc    420
tccattgaga actatttgtc acgcttcgag gacaaatccg gtgattattg tcaatggcaa    480
cggaaaaaac caaaggtttc aaaaccgtta ccaaggtatc aaaaggcctg tttcgacagg    540
tacaatgaag atccggaaca tgttacttgt agcgaaacat ttgagaaatg taggatctcg    600
ccacctgctg aaagggatga tatctacgcc acgagtttac actcgttata cgatatccct    660
taccaaaacc tcggtcctgc tttagccagg aagaggatca aagttcttca cgctgcattt    720
cattttagtg aagatctact actcggtgcc tctgaagggt tgttgaccca gattggtggt    780
actttccaac ggaacggtga tgttctcacc ttttcgtttt tggatgagtc ttctttaatt    840
tacacccata gtttccgtaa tgtgtttgag tatgttacca gaactttctt cgtggcgtgc    900
aataggtacg cctacatgaa ggaatttcgt agtagacgcg tggatactgt tttctgtagc    960
tttattagga tagacactta ttgtctgtac agaagtgtgt tcaaagactg cgacgaacat   1020
gtgttcgcgg ccatggacga tgcatgggag tttaaaaaga aaagagtgat gttggaagct   1080
tcaagaccca tctttaacga cgtcgcacaa ttcaacgtct acttcccgaa tgcaaaggac   1140
aaggtttgct tacccatttt cgcagtcaaa tctgtttctg gtgcacctgt taccacgcgc   1200
cacatacttg ttgagaagga cttctactgg acggctttga accatatctt aacatatcct   1260
gatggaaaag ccgatttcag aggagtgatg agcttcttgg agagcatcag gtcaagggtt   1320
gttatcaatg gtacaaccac agcatctcaa tgggaggtgg ataagagtca acttaaggac   1380
attgccttga gtttactgct gattgcaaaa ctcgaaaagc tgaagatctc agtgatcgag   1440
aagcggatca aaattgaaag acagggtttg gtatcgttac tcaaagagtt ccttcatggc   1500
ctcctggacg agtacacgca gacaatggcc gagtgggttg tagagaaggg ttgggtgaag   1560
tctgtagacc aagttctaca ggtgacaatt cctgacctgg ttctgaactt tagggatcac   1620
ttcagatgtg agttccgtac ttccgctaac gtctccgagg tgaatgtctc cgagcatctt   1680
gttgcaacga atgagtatta cgctaaggtc agtgatctcg ttgaccgtaa cccgaccctg   1740
gcttttgatt ttgaaaagtt tcaagactac tgtgagaaac tcggtgttga tatcgacacc   1800
gtcacagaac tgatcgacgc tatatcgaca gggcgtgccg gtatcacgct ggaccacaca   1860
gatgataaag aagagcaatt gccaagaaca ctcgcaggta gcagttctta tcttgaggaa   1920
gaaccatcag acgatttggt ttgtctgtct gataaggcca ttgtaaaccg atcaaccatt   1980
ctgggcgagc tgaaaaacaa tgtagttatc ttcgaaggca cactcccaaa gaacagtgtc   2040
ttcgtgagcg cccctgacga cccgtcagta acaatagagt tatctgaatt acacgcccgt   2100
cccgtctcag actttttgag tatgcaaaag cccgtcaaca ttgtttacac gggcgaagta   2160
caaatttgtc aaatgcagaa ctacctggac tatttgtccg cttctctggt agcatgcata   2220
agcaatctca agaagtatct gcaggaccaa tggttgaacc ctggtgaaaa gttccagaag   2280
```

```
attggtgtct gggacaatct taacaacaag tggatcgttg tcccccaaaa gaagaaatat    2340
gcctggggac tcgcggctga tgtcgacggc aaccaaaaga ccgtcatact gaactacgac    2400
gaacacggga tgccgattct cgaaaagtcg tatgtgaggt tggttgtctc gacagacaca    2460
tacctcttta cggtcgtctc gatgcttggg tatctcaggc atctcgacca aaaaaaaccc    2520
accgccacta taacactagt tgacggggtc cctgggtgtg aaagactca agaaatattg     2580
agtcgtttcg acgctaacag tgacctcata ctagtacagg gtaggaggc atgtgaaatg     2640
atcagacgca gagctaatga taacgtaccc ggttccgcca caaggaaaa cgttagaacg     2700
ttcgattctt tcgttatgaa cagaaaacca ggaaagttta aaactctgtg ggttgatgag    2760
gggttgatgg tgcaccccgg attaatcaat ttttgtataa acatttcgtg tgtttcctct    2820
gtatatattt ttggtgatag aaaacagatt ccctttatta atagagtaat gaattttttca   2880
attcccgata acctagcaaa actgtattac gatgagattg tctcccgtga tacaacaaaa    2940
agatgtccgt tagatgtgac acatttcttg aacagtgtct atgaaaagag ggttatgtcg    3000
tacagcaatg tacaacgttc cctcgagtgc aaaatgataa gtggtaaggc caaaatcaac    3060
gactatcgta gtatcttggc agaagggaag ttgttgacgt ttacccagga agataaagaa    3120
tatcttttga aggccgggtt taaagatgtc aacaccgttc atgaagcgca gggtgaaact    3180
tatcgggatg tgaatctcat aagagtcacc gccacgccct taaccattgt cagtgctggg    3240
tcacctcatg tgacggttgc actctcaaga cacacgaata gatttgtgta ctatacagta    3300
gtacctgatg tagttatgac aactgtacag aagactcagt gtgtaagtaa cttccttctg    3360
gatatgtacg ccgtggcgta caccaaaaa tagcaattac agatctcgcc cttctacacc     3420
catgatatac catttgtgga gacgaacaag gtaggtcaaa tctctgattt acaatatttc    3480
tatgacagtt ggctaccagg gaactcattt gtccagaaca ccacgatca atggtcgatc     3540
atttcatcgg acattaatct tcattccgaa gccgtccgtt tggatatgaa caaacgccat    3600
attcctagga caaaaggtga gtttctgagg ccgttgttga acacggctgt cgaacctcca    3660
agaataccgg gtttattgga aaatctgctg gcgttgatta aagaaattt taatgcgccg     3720
gatctagccg gtcaattgga ttacgacttt ctctccagaa aggtttgtga tgggtttttc    3780
gggaagctct tgcccccgga tgtagaagcg agcgaactgt tgaggttacc ggtcgatcac    3840
atgtattcgg tgcaaaactt tgatgactgg ttgaacaagc aggaacctgg agtcgtaggg    3900
caattagcga actgggacca catcggtatg cccgcggccg accaatacag gcatatgatt    3960
aaaaggactc ctaaggccaa attagatttg tccatacaga gcgaataccc cgctctgcaa    4020
acgattgtgt atcacagcaa gcatgtgaac gcagttttg gaccgatctt ttcatgtctg     4080
acggaacgat tactgtctgt ggtcgatcct ttgaggttca aattcttcac aagaactacc    4140
cctgcagatc ttgaatttt ttttagggat atggttgtcg gtgacatgga gatcctagaa     4200
ctcgacatct cgaagtacga caaaagtcaa aacaagtttc attttgaagt cgagatgaga    4260
atatgggaga tgctgggcat cgacaagtat atagaaaagg tgtgggaaaa cggtcaccgg    4320
aaaacgcatt tgcgtgacta tacagctggt attaagacgg tgatcgagta ccagagaaag    4380
agtggcgacg taacaacgtt cattgggaac actatcatta tcgccgcctg tctctgcagt    4440
attctaccaa tggagaaggt gtttaaagct gggttctgtg gtgatgactc gataatttac    4500
ttgccgagaa atcttctcta cccagatatc caatcggtct ccaacaacat gtggaatttt    4560
gaggcaaagc ttttcaagaa gctgcacggt tacttctgtg gtaggtatat tctacgcaac    4620
ggaaggtacc tgaggctttt accagacccc ctcaaaatta tcacaaaact gggttgtaaa    4680
```

```
gccatcaagg actgggatca cctggaggaa ttcaggatat ctatgttcga catggcatgt    4740
gaatataaaa attgttttgg ttttgatgtt ttggagtcgg cagttaagga atcttttcca    4800
aaagctgaag gctgcaacgt tgcttttgt gctatttata aattttaag taataaatat     4860 ttgtttagaa ctttatttag tg                                             4882
```

<210> SEQ ID NO 10
<211> LENGTH: 823
<212> TYPE: DNA
<213> ORGANISM: Artificial Sequence
<220> FEATURE:
<223> OTHER INFORMATION: Sunn hemp mosaic virus movement protein ORF

<400> SEQUENCE: 10

```
atgtctgagg tgtctaaaat ctccactttg ttggctccgg aaaagtttgt aaaactttcc     60
gtttccgaca agtttaaatg gaaggcacct tcgagagttt gtagtatagt acagagtgat    120
accatatcta tgactgcgaa cggaagatca ttgtttacgt ttgatgtttt gaaggacgtg    180
ttaaaacacg cagaggagta cacatatgtc gatgttcttg gcgttgtgtt atctggacag    240
tggttgctcc cgaaagggac gcccggttcg gcagagatca ttctcttaga ctcgcgcctt    300
aagggaaagg cttctgtcct cgcggttttt aactgtagag ctgccacgca agaatttcag    360
ttcctgattt caccagggta ctctctgact tgtgcgacg ctcttaagaa acccttcgaa     420
atatcatgta atgtgatcga cctgccggtc aaagatggtt tcactccttt gtctgtcgag    480
attgcgtgtt tagtgcagtt ttctaattgt gttataacaa ggtctttgac catgaaatta    540
aaagaaaacc cagcgaccag acattctct gctgaagagg tcgacgaact tttgggttcg    600
atgactactt tacggagtat cgaggggttg cgaaaaaaga agaacccaa cgacgttgta    660 caaggacatc tgagtgccga gtacgatgtg aaaaggagtg ttaaaggac aaaatctgaa    720 aacactccgg gaaaagaag ggtgaatgtt gatagtgtga gtttgggatt aggaaaggga    780
aagagtgtgt ctgctaaaaa cgaagacaca gagtctgtat ttg                      823
```

<210> SEQ ID NO 11
<211> LENGTH: 495
<212> TYPE: DNA
<213> ORGANISM: Artificial Sequence
<220> FEATURE:
<223> OTHER INFORMATION: Sunn hemp mosaic virus coat protein ORF

<400> SEQUENCE: 11

```
atgatggcat actcgattcc gactcctagt caacttgtgt attttactga aaattacgct     60
gattacattc catttgttaa taggttgatc aatgctcgca gtaattcgtt tcagacccaa    120
tcgggtaggg atgaattacg tgagatactg atcaagtcgc aggtttctgt tgtttcacct    180
atttctaggt ttccggcgga acctgcatat tatatatatt tacgggatcc ttcgatctcc    240
acagtttaca ctgctttgct acagtctaca gacacacgta atagagtcat cgaggttgag    300
aactctacga atgtgactac tgcagagcag ctgaacgctg tgaggaggac ggatgatgcg    360
tctactgcta tacataataa tttagagcag ttgttgagtc ttttgacgaa cggtactggt    420
gtgtttaacc gtacgtcttt tgagtcggct agtggtctga catggttggt gacaaccacg    480
ccacgtaccg cttag                                                     495
```

<210> SEQ ID NO 12
<211> LENGTH: 209
<212> TYPE: DNA
<213> ORGANISM: Artificial Sequence
<220> FEATURE:

<223> OTHER INFORMATION: Sunn hemp mosaic virus 3' UTR

<400> SEQUENCE: 12

```
tctagtgtaa aagtttggtc gtacttaacg acctaggggc ttaccgaaat aagccgtgtt      60
taagagtcca cgcaaatcga actctagaac ttatgaacag tcatggtttc catgccgtaa     120
agttcataac cgcgaagtcg cggcgccgtc aagacacgac ggtgagtggg gagcattacc     180
cccccaaaac cctggggata cagggccca                                       209
```

<210> SEQ ID NO 13
<211> LENGTH: 6483
<212> TYPE: DNA
<213> ORGANISM: Artificial Sequence
<220> FEATURE:
<223> OTHER INFORMATION: Sunn hemp mosaic virus full sequence

<400> SEQUENCE: 13

```
gtatgattaa cttcacaaca cggttgaagt tataagacca acatttacat ttacatttac      60
aacaaacatt cacaatgtct acatctacac tcattaacaa agcacaaact aactcctgcg     120
gtgacgttgg cgttgtggac cttctgaaaa gaaaggtcta cgatgacact gtcaaaacca     180
tgcaggggtt agatcgcagg gccaagtacc ggttaaacca atgcttggga cctgaacagt     240
gtaggactgt cagaggtggc taccctgaat tcaaattga attcacagga gcatcgaaca     300
cgtcgcatgc aatggcggcg ggtttgagag gacttgaact cgagtatctt tatactcttg     360
ttccgtacgg ggccgtgtct tacgacattg tggaaaactt ccccgcacac atgatgaagg     420
gtcgttcgta cgttcattgc tgcaatccgg ctttagacgc ccgcgaccta gccagaaacg     480
agaactacag aatctccatt gagaactatt tgtcacgctt cgaggacaaa tccggtgatt     540
attgtcaatg gcaacggaaa aaaccaaagg tttcaaaacc gttaccaagg tatcaaaagg     600
cctgtttcga caggtacaat gaagatccgg aacatgttac ttgtagcgaa acatttgaga     660
aatgtaggat ctcgccacct gctgaaaggg atgatatcta cgccacgagt ttacactcgt     720
tatacgatat cccttaccaa aacctcggtc ctgctttagc caggaagagg atcaaagttc     780
ttcacgctgc atttcatttt agtgaagatc tactactcgg tgcctctgaa gggttgttga     840
cccagattgg tggtactttc caacggaacg gtgatgttct cacctttcg tttttggatg     900
agtcttcttt aatttacacc catagtttcc gtaatgtgtt tgagtatgtt accagaactt     960
tcttcgtggc gtgcaatagg tacgcctaca tgaaggaatt tcgtagtaga cgcgtggata    1020
ctgttttctg tagcttatatt aggatagaca cttattgtct gtacagaagt gtgttcaaag    1080
actgcgacga acatgtgttc gcggccatgg acgatgcatg ggagtttaaa agaaaagag    1140
tgatgttgga agcttcaaga cccatcttta acgacgtcgc acaattcaac gtctacttcc    1200
cgaatgcaaa ggacaaggtt tgcttaccca ttttcgcagt caaatctgtt tctggtgcac    1260
ctgttaccac gcgccacata cttgttgaga aggacttcta ctggacggct ttgaaccata    1320
tcttaacata tcctgatgga aaagccgatt tcagaggagt gatgagcttc ttggagagca    1380
tcaggtcaag ggttgttatc aatggtacaa ccacagcatc tcaatgggag gtggataaga    1440
gtcaacttaa ggacattgcc ttgagtttac tgctgattgc aaaactcgaa aagctgaaga    1500
tctcagtgat cgagaagcgg atcaaaaattg aaagacaggg tttggtatcg ttactcaaag    1560
agttccttca tggcctcctg gacgagtaca cgcagacaat ggccgagtgg gttgtagaga    1620
agggttgggt gaagtctgta gaccaagttc tacaggtgac aattcctgac ctggttctga    1680
actttaggga tcacttcaga tgtgagttcc gtacttccgc taacgtctcc gaggtgaatg    1740
```

-continued

```
tctccgagca tcttgttgca acgaatgagt attacgctaa ggtcagtgat ctcgttgacc    1800
gtaacccgac cctggctttt gatttttgaaa agtttcaaga ctactgtgag aaactcggtg   1860
ttgatatcga caccgtcaca gaactgatcg acgctatatc gacagggcgt gccggtatca    1920
cgctggacca cacagatgat aaagaagagc aattgccaag aacactcgca ggtagcagtt    1980
cttatcttga ggaagaacca tcagacgatt tggtttgtct gtctgataag gccattgtaa    2040
accgatcaac cattctgggc gagctgaaaa acaatgtagt tatcttcgaa ggcacactcc    2100
caaagaacag tgtcttcgtg agcgcccctg acgacccgtc agtaacaata gagttatctg    2160
aattacacgc ccgtcccgtc tcagactttt tgagtatgca aaagcccgtc aacattgttt    2220
acacgggcga agtacaaatt tgtcaaatgc agaactacct ggactatttg tccgcttctc    2280
tggtagcatg cataagcaat ctcaagaagt atctgcagga ccaatggttg aaccctggtg    2340
aaaagttcca gaagattggt gtctgggaca atcttaacaa caagtggatc gttgtccccc    2400
aaaagaagaa atatgcctgg ggactcgcgg ctgatgtcga cggcaaccaa aagaccgtca    2460
tactgaacta cgacgaacac gggatgccga ttctcgaaaa gtcgtatgtg aggttggttg    2520
tctcgacaga cacatacctc tttacggtcg tctcgatgct tgggtatctc aggcatctcg    2580
accaaaaaaa acccaccgcc actataacac tagttgacgg ggtccctggg tgtggaaaga    2640
ctcaagaaat attgagtcgt ttcgacgcta acagtgacct catactagta cagggtaggg    2700
aggcatgtga aatgatcaga cgcagagcta atgataacgt acccggttcc gccacaaagg    2760
aaaacgttag aacgttcgat tctttcgtta tgaacagaaa accaggaaag tttaaaactc    2820
tgtgggttga tgagggggttg atggtgcacc ccggattaat caattttttgt ataaacattt   2880
cgtgtgtttc ctctgtatat attttttggtg atagaaaaca gattccctttt attaatagag   2940
taatgaattt ttcaattccc gataacctag caaaactgta ttacgatgag attgtctccc    3000
gtgatacaac aaaaagatgt ccgttagatg tgacacattt cttgaacagt gtctatgaaa    3060
agagggttat gtcgtacagc aatgtacaac gttccctcga gtgcaaaatg ataagtggta    3120
aggccaaaat caacgactat cgtagtatct tggcagaagg gaagttgttg acgtttaccc    3180
aggaagataa agaatatctt ttgaaggccg ggtttaaaga tgtcaacacc gttcatgaag    3240
cgcagggtga aacttatcgg gatgtgaatc tcataagagt caccgccacg cccttaacca    3300
ttgtcagtgc tgggtcacct catgtgacgg ttgcactctc aagacacacg aatagatttg    3360
tgtactatac agtagtacct gatgtagtta tgacaactgt acagaagact cagtgtgtaa    3420
gtaacttcct tctggatatg tacgccgtgg cgtacaccca aaaatagcaa ttacagatct    3480
cgcccttcta cacccatgat ataccatttg tggagacgaa caaggtaggt caaatctctg    3540
atttacaata tttctatgac agttggctac cagggaactc atttgtccag aacaaccacg    3600
atcaatggtc gatcatttca tcggacatta atcttcattc cgaagccgtc cgtttggata    3660
tgaacaaacg ccatattcct aggacaaaag gtgagtttct gaggccgttg ttgaacacgg    3720
ctgtcgaacc tccaagaata ccgggtttat tggaaaatct gctggcgttg attaaaagaa    3780
atttttaatgc gccggatcta gccggtcaat tggattacga ctttctctcc agaaaggttt    3840
gtgatgggtt tttcgggaag ctcttgcccc cggatgtaga agcgagcgaa ctgttgaggt    3900
taccggtcga tcacatgtat tcggtgcaaa actttgatga ctggttgaac aagcaggaac    3960
ctggagtcgt agggcaatta gcgaactggg accacatcgg tatgcccgcg ccgaccaat     4020
acaggcatat gattaaaagg actcctaagg ccaaattaga tttgtccata cagagcgaat    4080
accccgctct gcaaacgatt gtgtatcaca gcaagcatgt gaacgcagtt tttgaccga    4140
```

```
tcttttcatg tctgacggaa cgattactgt ctgtggtcga tcctttgagg ttcaaattct   4200
tcacaagaac taccccctgca gatcttgaat tttttttag ggatatggtt gtcggtgaca   4260
tggagatcct agaactcgac atctcgaagt acgacaaaag tcaaacaag tttcattttg   4320
aagtcgagat gagaatatgg gagatgctgg gcatcgacaa gtatatagaa aaggtgtggg   4380
aaaacggtca ccggaaaacg catttgcgtg actatacagc tggtattaag acggtgatcg   4440
agtaccagag aaagagtggc gacgtaacaa cgttcattgg gaacactatc attatcgccg   4500
cctgtctctg cagtattcta ccaatggaga aggtgtttaa agctgggttc tgtggtgatg   4560
actcgataat ttacttgccg agaaatcttc tctacccaga tatccaatcg gtctccaaca   4620
acatgtggaa ttttgaggca agcttttca agaagctgca cggttacttc tgtggtaggt   4680
atattctacg caacggaagg tacctgaggc ttttaccaga cccccctcaaa attatcacaa   4740
aactgggttg taaagccatc aaggactggg atcacctgga ggaattcagg atatctatgt   4800
tcgacatggc atgtgaatat aaaaattgtt ttggttttga tgttttggag tcggcagtta   4860
aggaatcttt tccaaaagct gaaggctgca acgttgcttt ttgtgctatt tataaatttt   4920
taagtaataa atatttgttt agaactttat ttagtgatgt ctgaggtgtc taaaatctcc   4980
actttgttgg ctccggaaaa gtttgtaaaa ctttccgttt ccgacaagtt taaatggaag   5040
gcaccttcga gagtttgtag tatagtacag agtgatacca tatctatgac tgcgaacgga   5100
agatcattgt ttacgtttga tgttttgaag gacgtgttaa aacacgcaga ggagtacaca   5160
tatgtcgatg ttcttggcgt tgtgttatct ggacagtggt tgctcccgaa agggacgccc   5220
ggttcggcag agatcattct cttagactcg cgccttaagg gaaaggcttc tgtcctcgcg   5280
gtttttaact gtagagctgc cacgcaagaa tttcagttcc tgatttcacc agggtactct   5340
ctgacttgtg cggacgctct taagaaaccc ttcgaaatat catgtaatgt gatcgacctg   5400
ccggtcaaag atggtttcac tcctttgtct gtcgagattg cgtgtttagt gcagttttct   5460
aattgtgtta taacaaggtc tttgaccatg aaattaaaag aaaacccagc gaccaggaca   5520
ttctctgctg aagaggtcga cgaacttttg ggttcgatga ctactttacg gagtatcgag   5580
gggttgcgaa aaagaaaga acccaacgac gttgtacaag gacatctgag tgccgagtac   5640
gatgtgaaaa ggagtgttaa aaggacaaaa tctgaaaaca ctccgggaaa agaagggtg   5700
aatgttgata gtgtgagttt gggattagga aagggaaaga gtgtgtctgc taaaaacgaa   5760
gacacagagt ctgtatttga tgatggcata ctcgattccg actcctagtc aacttgtgta   5820
ttttactgaa aattacgctg attacattcc atttgttaat aggttgatca atgctcgcag   5880
taattcgttt cagacccaat cgggtaggga tgaattacgt gagatactga tcaagtcgca   5940
ggtttctgtt gtttcaccta tttctaggtt tccggcggaa cctgcatatt atatatattt   6000
acgggatcct tcgatctcca cagtttacac tgctttgcta cagtctacag acacacgtaa   6060
tagagtcatc gaggttgaga actctacgaa tgtgactact gcagagcagc tgaacgctgt   6120
gaggaggacg gatgatgcgt ctactgctat acataataat ttagagcagt tgttgagtct   6180
tttgacgaac ggtactggtg tgtttaaccg tacgtctttt gagtcggcta gtggtctgac   6240
atggttggtg acaaccacgc cacgtaccgc ttagtctagt gtaaagtttt ggtcgtactt   6300
aacgacctag gggcttaccg aaataagccg tgtttaagag tccacgcaaa tcgaactcta   6360
gaacttatga acagtcatgg tttccatgcc gtaaagttca taaccgcgaa gtcgcggcgc   6420
cgtcaagaca cgacggtgag tggggagcat tacccccca aaaccctggg gatacagggc   6480
cca                                                                 6483
```

```
<210> SEQ ID NO 14
<211> LENGTH: 107
<212> TYPE: DNA
<213> ORGANISM: Artificial Sequence
<220> FEATURE:
<223> OTHER INFORMATION: White clover mosaic virus: 5' UTR

<400> SEQUENCE: 14
gaaaacaaga cgagacgaac ccaaacagaa cgagccatcc gcagaaaaac taaaccatcc      60 caggtttct ttgaacataa ccaatccgta gtttgacaaa ggctgcc                    107

<210> SEQ ID NO 15
<211> LENGTH: 3887
<212> TYPE: DNA
<213> ORGANISM: Artificial Sequence
<220> FEATURE:
<223> OTHER INFORMATION: White clover mosaic virus replicase ORF

<400> SEQUENCE: 15
atggctaaag ttcgtgccgc tcttgacaga atcactgatc catcggttaa agctgtactc      60
aatgaagagg catacagcca catccgaccg gttcttcgtg aatccctaac caacaacccc     120
tacgccatcg cacccgatgc tgctgatacg ctagaaaagt atggaattgc tactaatcca     180
ttcgcagtga agtacattc ccatggagca gttaaagta ttgaaaacac cctacttgag       240
agagttgggt ttaacttgcc gaaagagcca tgtaccttcc tcttcctcaa aagaagtaag    300
ctgcgttacc tcagacgtgg acctagcaac aatgacatct ttatcaatct agcgatcgaa    360
ccccgcgacc tccaaagata cgaggaagac actcttgttg agagttggac acgtatcacc    420
actaggtatg catatattag tgacactttc cacttcttca ctaggaagat gttggctgac    480
cttttctttc ataatccggc cttagatgta ttatatgcca ctttagtact tccacccgaa    540
gccctccaca acatcctag catagaacct gacttataca ctattaacta aactttaat     600 ggtttccaat acatcccagg caatcatggt ggtggttcct actcccatga attcaaacaa    660
ctggagtggc tcaaagttgg acatctcaaa tctccagaac tatgcctcac tttccagatg    720
atcgaatcca ttggtgccaa ccacctttc atgattaccc gcggtattaa ataaccccct     780
agggtcagga ctttcaccaa agactcttac gtgctctttc cccaaatctt ccaccctcga    840
aacctcaatc cctcaaaacc attcccgaaa gtcaaagcaa tgcaactatt cacttatgtg    900
aagtctgtca gaatccaac tgaacgagac atctatgcca aaattcgaca gctaatcaag    960
acttctgagc tatctgatta tcatccagat gaaattgtgc acattgtaaa ttactttgtg   1020
ttcatctcca gttagatag catcaactct tattctgaca tactctcgct acccatctgg   1080
tctaaagcat tgctacccat caaaaccaaa attacacaac tttgggaaaa gctcaccggc   1140
gcaagagcct tcaatcaact cttagatgca ctccaatgga aaacattcac ttatcctta    1200 gaggtagttg attctccaca gccccttcag acccgagatt gcttcattga agacgagaga   1260
ttagagattg acacacttga ggatgaaatc ccaccaaatc cgaacgacaa cacttcaatg   1320
agtccacaga gcattgagga ggctgttaaa acaaccctg atttaccctg gcaccatgg     1380 ttactcatct tgcaggctca taatgctgac tgcactgaaa agcagtatga ccctgagaat   1440
aacctcattc ttcctataca agagatcaac ccctcccca gcaccaaca ccctgacatc     1500 ccaactgacc ttctaacact cctaaccaaa ttacacagag agccaactac agtctcactt   1560
gacaaccatc gagctcgtgc ctatggttct gacgttaaga atctgcgaat aggcgctcta   1620
ctcaaaaaac aaagcaaaga ttggttagct agtttcgctc tcaaaacgga aaatattgaa   1680
```

```
cgtgaagttt tgatgtctgt catccatggt gccggcggct ctgggaaatc acatgccatt    1740
caaacttgga tgcgctccct gaaccgaaga gaccgtcatg tcacaatcat tttaccaacg    1800
acagacttgc ggaatgactg gaccaacaaa gtgcccaatc tggagcaagc aaatttcaaa    1860
acttttgaga aagctctttg tcaaccttgt ggtaaaatta tcgtatttga tgactactcc    1920
aagcttcctc aaggctacat cgaagcattc cttgctatca accaaaatgt catttttagcc   1980 attcttaccg gagattctaa gcagagcttt catcatgaat ccaatgagga tgcctacact    2040
gccaccctag aacccagcat tatcacatac aacccttct gccgctacta cctaaacata     2100
acccatagaa acaaaccaga cctagctaac aaactgggtg tttactcctg ttctagtggc    2160
accacctcct tcacaatgtc atcccaagct ctcaagggta tgccaattct ctcccccagt    2220
ataatgaaga aaactgctct tggagaaatg ggccaaaaaa gcatgacata cgctggctgc    2280
caaggtctca aactaaagc tgtccaaatt ctcttggata ccaataccc tttgtgcagt      2340 tccaacgtca tatacactgc tctcagccgt gctgttgacc acatacattt tattaacact    2400
ggacccaact caacagactt ctgggagaaa cttgattcca cccctacct caaaactttc     2460 ttggactgtg ttcgagaaga aaaatgaat gagatcatcg ctgctgaaga accacctact     2520
cctgtgcagg ctcctaccac ccacttccca aaagtgaacc ccaccacagt gattgaatca    2580
tatgtccacg atcttcccga aaaacatgat cgtgaaatct tttcagagac tcatggtcac    2640
tcaaatgcaa ttcaaactga caatcctgtg gttcaactct ttccccacca acaagccaaa    2700
gatgaaactc tttattgggc taccatcgaa gctagactac aatgcacttc atctgaagaa    2760
aaccttaaag aatttcatct caaacatgat attggtgaca ttctcttcct taattacaaa    2820
caagccatga accttcctca agaccccata ccatttaacc cagacctatg gacccctttgc   2880 agacaggaaa ttgagaacac atacctcaag aaaagtgctg ctgcccttgt taatgctgcc    2940
acccgccaat cacctgattt tgactcacat gcgatagcac tctttctcaa atcacaatgg    3000
gtcaagaaaa ctgaaaaaat tggttgcctt aaaatcaaag ctggcaaaac tattgctgcc    3060
ttcatgcaac aaactgtcat gatttatggc acaatggctc gatacatgag aaaatttaga    3120
aaccaatatt gccccaggaa aatctttgtg aactgtgaaa ccacaccagc cgacttcaac    3180 tcttttcatcc tcgacgagtg gaattttaat agaacttgct tttcaaatga cttcactgca    3240
tttgatcaaa gtcaagatgg ctccatcctc caattcgaag tcattaaagc aaagtttcac    3300
aacatacccg aggatgttat tgaaggctat atccaaatca aaacacatgc caagatcttc    3360
ctgggcaccc ttagtatcat gagactctct ggtgaaggtc ccacttttga tgctaacact    3420
gaagcaaaca ttgcttatac acacaccaag tttaacatac cctgcgatgc tgcacaggtg    3480
tacgctggtg atgatatgtc cattgactac gtggcttcag tcaagcccag tttcaacatg    3540
attgaacatc tgatgaaact caaaggtaaa ccagttttta acacacaaac tcagggagac    3600
ttcgctgaat tttgcgggtg acaatctca ccaaaaggca ttatcaagaa accagaaaaa     3660
atgaacatga gcattgaact ccaaaagaac atcaacaagt ttcatgaagt caaaagaagt    3720
tatgctctag accatgcctt cgcataccaa cttggtgatg aattacatga gctatacaat    3780
gagaatgaag cagaacacca ccaacttgct acaaggtcac tcattctcgc tggtcaagcc    3840
accgccctag acatacttga ttacgggtta agagacctaa agtagcg                  3887
```

<210> SEQ ID NO 16
<211> LENGTH: 688
<212> TYPE: DNA
<213> ORGANISM: Artificial Sequence
<220> FEATURE:

<223> OTHER INFORMATION: White clover mosaic virus: TGB1 ORF

<400> SEQUENCE: 16

```
atggatcaca ttcaccacct cctcagctcc cacggtttta cccgcaccag actcgccaaa        60
tccaaaccta tcgttgtcca tgctattgca ggctccggta atctactgt gatcaggaaa        120
attctctcag acctacccaa cgctagagcc tacacattag gtaaaccaga cccctattct      180
ctctccaacc ccacaattaa agctttcgcc caattcaaaa gaggtacact cgacattttg      240
gatgagtacg gccaactccc gttcgccgac ttagattcat ctttcgagtt tatcttcact      300
gaccccttacc aagcaccaac tgacaatctc tttgaacctc actacacact agaaatcacc     360
tacagatttg gccctaacac ttgtaaccttc tcaatcaag cattccaatc taacatcaca      420
agccttgtca cccaggacaa catttcattt ggttcaccct acttagttga cccagtaggt      480
accatcctcg cgtttcaacc tgacacctac cttatccttt gcttacatca gccccttttc      540
ttcaaagttt cagaagtgat tggttatcag tggcctactg taacgttgta cctagcctgc      600
aaaatttctg agattcctga agaagaacgt cacctcctct tcattggcct gactagacac     660
acagaatccc tccttatttt aggtcctg                                       688
```

<210> SEQ ID NO 17
<211> LENGTH: 484
<212> TYPE: DNA
<213> ORGANISM: Artificial Sequence
<220> FEATURE:
<223> OTHER INFORMATION: White clover mosaic virus TGB2 and TGB3 ORFs

<400> SEQUENCE: 17

```
atgcctttga ttcctccccc taatcccag aaaacttacc aaattgccgt acttgcttta        60
ggattagtgc tacttcttgc cttgttcta atttctgatc actctcccaa agtaggtgat      120
catctgcaca atcttccttt tggaggtgaa tacaaagacg gtactaaaac tatcaagtat      180
ttccaaagac ccaaccaaca ttcccttttcc aaaactcttg ccaaatctca caacaccacc     240
attttcctga tcatcttagg tttaattggt accttgcatg gacttcacta ctttagtaat    300
aataggcgta tcttctctag tcttcattgt gtactttgcc aaaataaaca ctagcatgtg    360
tactattagt atatcaggag cttctgttga aatctcaggt tgcgacaacc cggctctctt     420
cgaaatcctc ccaaatctca aaccctttga ccacggggtta agtgtgccat ctatttgaaa     480
tcca                                                                  484
```

<210> SEQ ID NO 18
<211> LENGTH: 627
<212> TYPE: DNA
<213> ORGANISM: Artificial Sequence
<220> FEATURE:
<223> OTHER INFORMATION: White clover mosaic virus: CP ORF

<400> SEQUENCE: 18

```
atggcaacca ccacagcaac cactcctcca tccttgacag acatccgagc cctaaaatac        60
acttcctcca ccgtctcagt cgcctcacct gctgaaattg aagctatcac taaaacctgg      120
gcagaaacat tcaaaattcc aaatgacgtc ttgcctctcg cttgttggga tctggctcgt      180
gctttcgctg atgttggcgc ttcttctaag tctgaactta ctggtgactc tgctgctctt      240
gcgggtgttt cacggaaaca actggctcaa gctatcaaaa tccattgcac cattcgccag     300
ttctgcatgt acttcgccaa tgttgtgtgg aacatcatgt tagataccaa acaccgcca     360
gcatcctggt ctaaactcgg ctataaagaa gagagcaaat tcgctggctt tgacttcttt     420
```

| | |
|---|---|
| gatggtgtca atcatcctgc tgcactcatg cctgcagacg gcctcatccg tggtccttcc | 480 |
| gaagctgaac tcttagccca tcaaaccgca aaacaagtag ccctccatcg cgacgcaaaa | 540 |
| cgccgtggca ccaacgttgt caactctgtt gaaatcacta acggtcgctc cgaccctatt | 600 |
| ggtcccctta ttacctatcc ccagtaa | 627 |

<210> SEQ ID NO 19
<211> LENGTH: 53
<212> TYPE: DNA
<213> ORGANISM: Artificial Sequence
<220> FEATURE:
<223> OTHER INFORMATION: White clover mosaic virus: 3' UTR

<400> SEQUENCE: 19

| | |
|---|---|
| ttgccttatc acttcactta atatgtgtgg ctttctgttt aataaatttt cag | 53 |

<210> SEQ ID NO 20
<211> LENGTH: 5846
<212> TYPE: DNA
<213> ORGANISM: Artificial Sequence
<220> FEATURE:
<223> OTHER INFORMATION: White clover mosaic virus full sequence

<400> SEQUENCE: 20

| | |
|---|---|
| gaaaacaaga cgagacgaac ccaaacagaa cgagccatcc gcagaaaaac taaaccatcc | 60 |
| caggttttct ttgaacataa ccaatccgta gtttgacaaa ggctgccatg ctaaagttc | 120 |
| gtgccgctct tgacagaatc actgatccat cggttaaagc tgtactcaat gaagaggcat | 180 |
| acagccacat ccgaccggtt cttcgtgaat ccctaaccaa caaccccctac gccatcgcac | 240 |
| ccgatgctgc tgatacgcta gaaaagtatg gaattgctac taatccattc gcagtgaaag | 300 |
| tacattccca tggagcagtt aaaagtattg aaaacaccct acttgagaga gttgggttta | 360 |
| acttgccgaa agagccatgt accttcctct tcctcaaaag aagtaagctg cgttacctca | 420 |
| gacgtggacc tagcaacaat gacatcttta tcaatctagc gatcgaaccc cgcgacctcc | 480 |
| aaagatacga ggaagacact cttgttgaga gttggacacg tatcaccact aggtatgcat | 540 |
| atattagtga cactttccac ttcttcacta ggaagatgtt ggctgacctt ttctttcata | 600 |
| atccggcctt agatgtatta tatgccactt tagtacttcc acccgaagcc ctccacaaac | 660 |
| atcctagcat agaacctgac ttatacacta ttaactataa cttttaatggt ttccaataca | 720 |
| tcccaggcaa tcatggtggt ggttcctact cccatgaatt caaacaactg gagtggctca | 780 |
| aagttggaca tctcaaatct ccagaactat gcctcacttt ccagatgatc gaatccattg | 840 |
| gtgccaacca ccttttcatg attacccgcg gtattaaaat aaccccctagg gtcaggactt | 900 |
| tcaccaaaga ctcttacgtg ctcttttccc aaatcttcca ccctcgaaac ctcaatccct | 960 |
| caaaaccatt cccgaaagtc aaagcaatgc aactattcac ttatgtgaag tctgtcaaga | 1020 |
| atccaactga acgagacatc tatgccaaaa ttcgacagct aatcaagact tctgagctat | 1080 |
| ctgattatca tccagatgaa attgtgcaca ttgtaaatta ctttgtgttc atctccaagt | 1140 |
| tagatagcat caactcttat tctgacatac tctcgctacc catctggtct aaagcattgc | 1200 |
| tacccatcaa aaccaaaatt acacaacttt gggaaaagct caccggcgca agagccttca | 1260 |
| atcaactctt agatgcactc caatggaaaa cattcactta tcctttagag gtagttgatt | 1320 |
| ctccacagcc ccttcagacc cgagattgct tcattgaaga cgagagatta gagattgaca | 1380 |
| cacttgagga tgaaatccca ccaaatccga acgacaacac ttcaatgagt ccacagagca | 1440 |
| ttgaggaggc tgttaaaaac aaccctgatt taccctgggc accatggtta ctcatcttgc | 1500 |

```
aggctcataa tgctgactgc actgaaaagc agtatgaccc tgagaataac ctcattcttc    1560
ctatacaaga gatcaacacc ctccccaagc accaacaccc tgcatcccca actgaccttc    1620
taacactcct aaccaaatta cacagagagc caactacagt ctcacttgac aaccatcgag    1680
ctcgtgccta tggttctgac gttaagaatc tgcgaatagg cgctctactc aaaaaacaaa    1740
gcaaagattg gttagctagt ttcgctctca aaacggaaaa tattgaacgt gaagttttga    1800
tgtctgtcat ccatggtgcc ggcggctctg ggaaatcaca tgccattcaa acttggatgc    1860
gctccctgaa ccgaagagac cgtcatgtca caatcatttt accaacgaca gacttgcgga    1920
atgactggac caacaaagtg cccaatctgg agcaagcaaa tttcaaaact tttgagaaag    1980
ctctttgtca accttgtggt aaaattatcg tatttgatga ctactccaag cttcctcaag    2040
gctacatcga agcattcctt gctatcaacc aaaatgtcat tttagccatt cttaccggag    2100
attctaagca gagctttcat catgaatcca atgaggatgc ctacactgcc accctagaac    2160
ccagcattat cacataccaa cccttctgcc gctactacct aaacataacc catagaaaca    2220
aaccagacct agctaacaaa ctgggtgttt actcctgttc tagtggcacc acctccttca    2280
caatgtcatc ccaagctctc aagggtatgc caattctctc ccccagtata atgaagaaaa    2340
ctgctcttgg agaaatgggc caaaaaagca tgacatacgc tggctgccaa ggtctcacaa    2400
ctaaagctgt ccaaattctc ttggatacca ataccccttt gtgcagttcc aacgtcatat    2460
acactgctct cagccgtgct gttgaccaca tacattttat taacactgga cccaactcaa    2520
cagacttctg ggagaaactt gattccacac cctacctcaa aactttcttg gactgtgttc    2580
gagaagaaaa aatgaatgag atcatcgctg ctgaagaacc acctactcct gtgcaggctc    2640
ctaccaccca cttcccaaaa gtgaacccca ccacagtgat tgaatcatat gtccacgatc    2700
ttcccgaaaa acatgatcgt gaaatctttt cagagactca tggtcactca aatgcaattc    2760
aaactgacaa tcctgtggtt caactctttc cccaccaaca agccaaagat gaaactcttt    2820
attgggctac catcgaagct agactacaat gcacttcatc tgaagaaaac cttaaagaat    2880
ttcatctcaa acatgatatt ggtgacattc tcttccttaa ttacaaacaa gccatgaacc    2940
ttcctcaaga ccccatacca tttaacccag acctatggac cctttgcaga caggaaattg    3000
agaacacata cctcaagaaa agtgctgctg ccccttgtta atgctgccac cgccaatcac    3060
ctgattttga ctcacatgcg atagcactct ttctcaaatc acaatgggtc aagaaaactg    3120
aaaaaattgg ttgccttaaa atcaaagctg ccaaactat tgctgccttc atgcaacaaa    3180
ctgtcatgat ttatggcaca atggctcgat acatgagaaa atttagaaac caatattgcc    3240
ccaggaaaat ctttgtgaac tgtgaaacca caccagccga cttcaactct ttcatcctcg    3300
acgagtggaa ttttaataga acttgctttt caaatgactt cactgcattt gatcaaagtc    3360
aagatggctc catcctccaa ttcgaagtca ttaaagcaaa gtttcacaac atacccgagg    3420
atgttattga aggctatatc caaatcaaaa cacatgccaa gatcttcctg gcacccttta    3480
gtatcatgag actctctggt gaaggtccca cttttgatgc taacactgaa gcaaacattg    3540
cttatacaca caccaagttt aacatacccct gcgatgctgc acaggtgtac gctggtgatg    3600
atatgtccat tgactacgtg gcttcagtca agcccagttt caacatgatt gaacatctga    3660
tgaaactcaa aggtaaacca gttttttaaca cacaaactca gggagacttc gctgaatttt    3720
gcgggtggac aatctcacca aaaggcatta tcaagaaacc agaaaaaatg aacatgagca    3780
ttgaactcca aaagaacatc aacaagtttc atgaagtcaa aagaagttat gctctagacc    3840
atgccttcgc ataccaactt ggtgatgaat tacatgagct atacaatgag aatgaagcag    3900
```

| | |
|---|---|
| aacaccacca acttgctaca aggtcactca ttctcgctgg tcaagccacc gccctagaca | 3960 |
| tacttgatta cgggttaaga gacctaaagt agcgatggat cacattcacc acctcctcag | 4020 |
| ctcccacggt tttacccgca ccagactcgc caaatccaaa cctatcgttg tccatgctat | 4080 |
| tgcaggctcc ggtaaatcta ctgtgatcag gaaaattctc tcagacctac caacgctag | 4140 |
| agcctacaca ttaggtaaac cagaccccta ttctctctcc aaccccacaa ttaaagcttt | 4200 |
| cgcccaattc aaaagaggta cactcgacat tttggatgag tacggccaac tcccgttcgc | 4260 |
| cgacttagat tcatctttcg agtttatctt cactgaccct taccaagcac caactgacaa | 4320 |
| tctctttgaa cctcactaca cactagaaat cacctacaga tttggcccta acacttgtaa | 4380 |
| ccttctcaat caagcattcc aatctaacat cacaagcctt gtcacccagg acaacatttc | 4440 |
| atttggttca ccctacttag ttgacccagt aggtaccatc ctcgcgtttc aacctgacac | 4500 |
| ctaccttatc ctttgcttac atcaagcccc tttcttcaaa gtttcagaag tgattggtta | 4560 |
| tcagtggcct actgtaacgt tgtacctagc ctgcaaaatt tctgagattc ctgaagaaga | 4620 |
| acgtcacctc ctcttcattg gcctgactag acacacagaa tccctcctta ttttaggtcc | 4680 |
| tgatgccttt gattcctccc cctaatcccc agaaaactta ccaaattgcc gtacttgctt | 4740 |
| taggattagt gctacttctt gcctttgttc taatttctga tcactctccc aaagtaggtg | 4800 |
| atcatctgca caatcttcct tttggaggtg aatacaaaga cggtactaaa actatcaagt | 4860 |
| atttccaaag acccaaccaa cattcccttt ccaaaactct tgccaaatct cacaacacca | 4920 |
| ccattttcct gatcatctta ggtttaattg gtaccttgca tggacttcac tactttagta | 4980 |
| ataataggcg tatatcttct agtcttcatt gtgtactttg ccaaaataaa cactagcatg | 5040 |
| tgtactatta gtatatcagg agcttctgtt gaaatctcag gttgcgacaa cccggctctc | 5100 |
| ttcgaaatcc tcccaaatct caaacccttt gaccacgggt taagtgtgcc atctatttga | 5160 |
| aatccaatgg caaccaccac agcaaccact cctccatcct tgacagacat ccgagcccta | 5220 |
| aaatacactt cctccaccgt ctcagtcgcc tcacctgctg aaattgaagc tatcactaaa | 5280 |
| acctgggcag aaacattcaa aattccaaat gacgtcttgc ctctcgcttg ttgggatctg | 5340 |
| gctcgtgctt tcgctgatgt tggcgcttct tctaagtctg aacttactgg tgactctgct | 5400 |
| gctcttgcgg gtgtttcacg gaaacaactg gctcaagcta tcaaaatcca ttgcaccatt | 5460 |
| cgccagttct gcatgtactt cgccaatgtt gtgtggaaca tcatgttaga taccaaaaca | 5520 |
| ccgccagcat cctggtctaa actcggctat aaagaagaga gcaaattcgc tggctttgac | 5580 |
| ttctttgatg gtgtcaatca tcctgctgca ctcatgcctg cagacggcct catccgtggt | 5640 |
| ccttccgaag ctgaactctt agcccatcaa accgcaaaac aagtagccct ccatcgcgac | 5700 |
| gcaaaacgcc gtggcaccaa cgttgtcaac tctgttgaaa tcactaacgg tcgctccgac | 5760 |
| cctattggtc cccttattac ctatccccag taattgcctt atcacttcac ttaatatgtg | 5820 |
| tggctttctg tttaataaaa tttcag | 5846 |

<210> SEQ ID NO 21
<211> LENGTH: 80
<212> TYPE: DNA
<213> ORGANISM: Artificial Sequence
<220> FEATURE:
<223> OTHER INFORMATION: FECT40 vector: 5' UTR

<400> SEQUENCE: 21

| | |
|---|---|
| gaaaactctt ccgaaaccga aactgactga aactacctcg accgaccttga gaacccaaga | 60 |
| acccaacggg tgcggccact | 80 |

<210> SEQ ID NO 22
<211> LENGTH: 4051
<212> TYPE: DNA
<213> ORGANISM: Artificial Sequence
<220> FEATURE:
<223> OTHER INFORMATION: FECT40 vector: replicase

<400> SEQUENCE: 22

| | | | | | | |
|---|---|---|---|---|---|---|
| atgtctatcg | aggcagtttt | cgaccaggtt | acagacccat | cgctccgcgc | tgtgattcag | 60 |
| gaggaagcgc | acaaacagat | caaagatttg | tttaaggaaa | cgacgcgctg | caatccctac | 120 |
| tccataccgc | aagctgggcg | caaggttttg | gaaaagtacg | ccatcccta | caacccgtac | 180 |
| tctctcaaac | tacaccctca | cgcagcctca | aaagcgtttg | aagtgtcgct | ctacgaggct | 240 |
| gcgtctaact | acctcccctc | cacctcctca | actcctgtca | cattcatgtt | cacaaaaccg | 300 |
| ggcaagctca | gattctttag | gcgccgaggt | cacgtggaca | aattcgttaa | tgctgacata | 360 |
| gttccaagag | acttggctag | atacccacgc | gacacagtct | acagttatct | gcccgagatc | 420 |
| accaccacac | acgctttcat | ggcgacacc | ctacatcact | tcggtgagga | ctttctcgtc | 480 |
| gaggttttct | ccaggtcacc | gaaactagaa | gtgcttctag | ccaccatggt | attaccaccc | 540 |
| gaagcctttt | acagaatgga | gtcccttcat | ccctcggttt | acactctcct | ctacagggac | 600 |
| gaccgattcc | tatacctgcc | tggtggcctg | tctggcggtg | agtacgaaca | tcgctataag | 660 |
| gacctaaact | ggctaacatt | tggcacagtt | acgcacggcg | ggatcactat | cacaggagaa | 720 |
| cgcattgaga | ctaaggccgc | gaatcatctt | ttcctcttca | gacgagggcg | actagcgaca | 780 |
| ccaaaattcc | gctcattcga | catgcccgag | cctatggtcc | tgcttcccaa | ggttttccgc | 840 |
| cccgcaaagt | acaatgtaca | gaagccaatt | ccccgggaga | agcaaacaa | atggttgatg | 900 |
| tacgttaaat | ccatcggcaa | tgccaccatt | cgtgacgtat | gggctaagct | gaggcaaacc | 960 |
| atagccaatg | cagacattgg | actcttctcg | cccactgagc | tcgtgcatct | cacgaattac | 1020 |
| ttcctgctcc | tgggccggct | tgactcacac | aattccttcg | accaagtact | ggccgacagt | 1080 |
| gtgctgaaag | catggttcag | accaatggtc | gcaaagcttc | aggagattaa | gcacaaactc | 1140 |
| atggggcaga | cccaattcat | gcaactctgc | caagcgctag | atgacggaa | ggtggaccct | 1200 |
| gtctttgagg | tccgggactc | caagactccc | cacaaacaag | ctgtgccgtt | ggaccgtgaa | 1260 |
| attgaaaacg | ttttgttgga | aggagtctca | tcggagccaa | cttacactga | aaccgaaggc | 1320 |
| gttgctgatg | gtccacttcc | cccccaatg | caaactgcag | ccgagccgtc | cgcgacctca | 1380 |
| gacgagcccg | agagctctag | ctcgcgtgaa | attgagcatc | aaccggcgcc | tgagatcacg | 1440 |
| cttgacgagg | aagaacctca | gcgagacgat | ctgccttggg | acgcttggag | aacacaatta | 1500 |
| agggcgcttg | gctttgaggc | ctccgaaagg | cagtatgacc | cggacggtga | actgatctct | 1560 |
| cctatcctga | gcacccgaag | gttgcctaaa | actcccatag | acacaacact | ctacgccacg | 1620 |
| ctagacaaga | ttgcacgctg | cccaactttc | tacaagcctg | acacagatcg | cgcgcagact | 1680 |
| tacgctcgcg | atgtcatggc | ggggaaaacc | ggtgccattc | tcaagcaaca | acccttgag | 1740 |
| tggaaaacca | cgctcaagcg | caagactaaa | gaggaaccga | aggaaattca | ccttgcggtg | 1800 |
| ttgcatggtg | cgggcgggtc | gggcaaatcc | tacgcactgc | aggaatttat | gcggaacaac | 1860 |
| tctgacacac | cgattacggt | catcctgccg | actaacgagc | tcagggccga | ctggaagaaa | 1920 |
| aaattgcccg | cccacgacaa | agacacattt | atgacatacg | aaaacgcgct | cttgtgccct | 1980 |
| cgtggagaca | tcttcattat | ggacgattac | acaaaattgc | caggggcta | cattgaggct | 2040 |
| ttcgtgcaga | atgcacctgc | cctctcactt | ctgatactca | ccggtgaccc | caaccaagcc | 2100 |

```
gaacactttg agaccactga ggacaatgaa attaacagcc tcgcccccgc ctcagtggtc    2160
ttcggcaagt tctctaggta ccacataaat gccacacacc gcaacccag aaacttggca    2220 aacgccctcg gtgtttactc cgagacgccc ggggaggtta aagtgcttta cacgaggaac    2280
atcaagaccg gttatcacaa tctcgtgccc tcacaaatga agatgagaaa ttacgcctca    2340
ctcgggcagc gagcgtccac ctatgcgggt tgtcagggga tcaccgcgcc ccgcgttcaa    2400
atcatcctag actccgacac accccggtgc accaggcaag tcatgtacac tgcactctca    2460
agggccacga cggaagtggt gctctgcaac acgatgccgg atgagaaaag cttttttccag   2520 aaggttgaag caacaccgta cctcaaagcc atcctcaacc tcaacaaaga gattaaagtc    2580
actgagggcg acttgacaga agaaccgccg agggagcccg ctcctcccac cacacacctg    2640
cctgttgaaa acagaatcat tcttaatgag gccctagtcg aaccgctgcc cgacaaacat    2700
gaccgcgaga tctactccaa ctccactggc ttttcaaact gcatacagac tcaagacccg    2760
tacatccaag ccttccaaca tcagcaagcc aaggacgaga cattgttctg ggcaaccgtc    2820
gagaagaggc tcgcagcatc tacgccgaag gacaactgga cagaattcaa gaccaagaga    2880
cctctgggtg acgtgctttg gctcgcgtac aagcgggcga tggtgctccc agatgagccc    2940
atcaaattta acccagagct ctggtgggca tgtgcagatg aggtgcaaaa gacctacctc    3000
tccaagccca tacacgcgct caagaacgga attcttcggc aatcacccga ctttgactgg    3060
aacaaactgc agattttcct caagtcacag tgggttaaga aaattgacaa aatcgggaaa    3120
attgacgtca acgctggaca gacaattgcc gcctttacc aaccaactgt tatgctgttt    3180
ggaaccatgg cgagatacat gcgccgcatc cgcgacactt atcaacccgg cgaaatactc    3240
atcaattgcg agaagaacca gaagcacatt tcgaagtggg tcgagagcaa ttggaaccac    3300
cgcctacctg cttacaccaa tgacttcact gcttacgacc aaagccaaga cggggctatg    3360
ttacagtttg aggtactgaa agccctgcac catgatatcc ctcatgaggt tgtgaagct    3420 tacgtagccc ttaaactcaa ctcaaaaatg tttctgggca cactggcgat tatgagatta    3480
actggtgagg gacccacctt cgacgctaac acagagtgca acattgctta cacacacgcc    3540
cggttcgaga tcccaaagaa tgtggcgcaa atgtacgcgg gtgacgactg tgcgctcaac    3600
tgcaggcccg ttgaacggca gtccttcctg cctcttgtgg agaaattcac cctgaaatca    3660
aaacctaaag tatttgagca aaaagttggg tcatggcctg agttctgcgg caatctgatc    3720
accccacggg gctacctcaa ggatcccatg aagctacaac actgcctgca actggcacag    3780
aggaagaaac catccgaacc tgggtcgctt aaagacgttg ctgagaacta cgctatggac    3840
ttgctaccca catacgagct aggtgatgca ctctacgaaa tcttcgacga gagacaaatg    3900
aacgcgcact atcagtcggt caggacgctt atcacatgcg cccacaccaa agtcctccga    3960
gttgcacagg cacttcagga agactgcacc ttctttagct ccatctaaca ggttttgagt    4020
taggctaact ccactgacga attaaataac a                                  4051
```

<210> SEQ ID NO 23
<211> LENGTH: 55
<212> TYPE: DNA
<213> ORGANISM: Artificial sequence
<220> FEATURE:
<223> OTHER INFORMATION: FECT40 vector: 40 bp of TGB1 ORF plus Pac I and Avr II cloning sites

<400> SEQUENCE: 23

```
atggatagtg aaatagttga acgactaaca aagcttggtt aattaaagtc ctagg        55
```

```
<210> SEQ ID NO 24
<211> LENGTH: 42
<212> TYPE: DNA
<213> ORGANISM: Artificial Sequence
<220> FEATURE:
<223> OTHER INFORMATION: FECT40 vector: last 42 bp of CP ORF

<400> SEQUENCE: 24
ctaccaaaca acgggcagta cttcatcgag gcacctcagt ga                           42

<210> SEQ ID NO 25
<211> LENGTH: 133
<212> TYPE: DNA
<213> ORGANISM: Artificial Sequence
<220> FEATURE:
<223> OTHER INFORMATION: FECT40 vector: 3' UTR

<400> SEQUENCE: 25
tcagtagtat gataccaata aataaatcgg gcgaatccgc gcctcctgac tatgggcagg        60
tttacggacc aagctgtatc gagatacgac ctaacagtaa cgcagctaag gggtgaatgc      120
acacatcgct tat                                                         133

<210> SEQ ID NO 26
<211> LENGTH: 85
<212> TYPE: DNA
<213> ORGANISM: Artificial sequence
<220> FEATURE:
<223> OTHER INFORMATION: FECT40 vector: poly(A) tract

<400> SEQUENCE: 26
aaaaaaaaaa aaaaaaaaaa aaaaaaaaaa aaaaaaaaaa aaaaaaaaaa aaaaaaaaaa        60
aaaaaaaaaa aaaaaaaaaa tctag                                             85

<210> SEQ ID NO 27
<211> LENGTH: 208
<212> TYPE: DNA
<213> ORGANISM: Artificial sequence
<220> FEATURE:
<223> OTHER INFORMATION: FECT40 vector: 35S terminator

<400> SEQUENCE: 27
agtccgcaaa tcaccagtct ctctctacaa atctatctct ctctattttc tccagaataa        60
tgtgtgagta gttcccagat aagggaatta gggttcttat agggtttcgc tcatgtgttg      120
agcatataag aaacccttag tatgtatttg tatttgtaaa atacttctat caataaaatt      180
tctaattcct aaaaccaaaa tccagtga                                         208

<210> SEQ ID NO 28
<211> LENGTH: 69
<212> TYPE: DNA
<213> ORGANISM: Artificial sequence
<220> FEATURE:
<223> OTHER INFORMATION: FECT40 vector: miscellaneous sequence

<400> SEQUENCE: 28
cctgcagccc ggccggggga tccactagca gattgtcgtt tcccgccttc agtttaaact        60
atcagtgtt                                                               69

<210> SEQ ID NO 29
<211> LENGTH: 25
<212> TYPE: DNA
<213> ORGANISM: Artificial sequence
<220> FEATURE:
<223> OTHER INFORMATION: FECT40 vector: T-DNA right border
```

-continued

<400> SEQUENCE: 29
tgacaggata tattggcggg taaac                                          25

<210> SEQ ID NO 30
<211> LENGTH: 3316
<212> TYPE: DNA
<213> ORGANISM: Artificial sequence
<220> FEATURE:
<223> OTHER INFORMATION: FECT40 vector: JL22 sequence

<400> SEQUENCE: 30
ctaagagaaa agagcgttta ttagaataat cggatattta aaagggcgtg aaaaggttta     60
tccgttcgtc catttgtatg tgcatgccaa ccacaggaga tctcagtaaa gcgctggctg    120 aaccccagc cggaactgac cccacaaggc cctagcgttt gcaatgcacc aggtcatcat     180
tgacccaggc gtgttccacc aggccgctgc ctcgcaactc ttcgcaggct tcgccgacct    240
gctcgcgcca cttcttcacg cggggtggaat ccgatccgca catgaggcgg aaggtttcca   300
gcttgagcgg gtacggctcc cggtgcgagc tgaaatagtc gaacatccgt cgggccgtcg    360
gcgacagctt gcggtacttc tcccatatga atttcgtgta gtggtcgcca gcaaacagca    420
cgacgatttc ctcgtcgatc aggacctggc aacgggacgt tttcttgcca cggtccagga    480
cgcggaagcg gtgcagcagc gacaccgatt ccaggtgccc aacgcggtcg acgtgaagc     540 ccatcgccgt cgcctgtagg cgcgacaggc attcctcggc cttcgtgtaa taccggccat    600
tgatcgacca gcccaggtcc tggcaaagct cgtagaacgt gaaggtgatc ggctcgccga    660
taggggtgcg cttcgcgtac tccaacacct gctgccacac cagttcgtca tcgtcggccc    720
gcagctcgac gccggtgtag gtgatcttca cgtccttgtt gacgtggaaa atgaccttgt    780
tttgcagcgc ctcgcgcggg attttcttgt tgcgcgtggt gaacagggca gagcgggccg    840
tgtcgtttgg catcgctcgc atcgtgtccg gccacggcgc aatatcgaac aaggaaagct    900
gcatttcctt gatctgctgc ttcgtgtgtt tcagcaacgc ggcctgcttg gcctcgctga    960 cctgtttttgc caggtcctcg ccggcggttt ttcgcttctt ggtcgtcata gttcctcgcg   1020
tgtcgatggt catcgacttc gccaaacctg ccgcctcctg ttcgagacga cgcgaacgct   1080
ccacggcggc cgatggcgcg ggcagggcag ggggagccag ttgcacgctg tcgcgctcga   1140
tcttggccgt agcttgctgg accatcgagc cgacggactg gaaggtttcg cggggcgcac   1200
gcatgacggt gcggcttgcg atggtttcgg catcctcggc ggaaaacccc gcgtcgatca   1260
gttcttgcct gtatgccttc cggtcaaacg tccgattcat tcaccctcct tgcgggattg   1320
ccccgactca cgccggggca atgtgccctt attcctgatt tgaccgcct ggtgccttgg    1380 tgtccagata atccaccta tcggcaatga agtcggtccc gtagaccgtc tggccgtcct   1440
tctcgtactt ggtattccga atcttgccct gcacgaatac cagcgacccc ttgcccaaat   1500
acttgccgtg ggcctcggcc tgagagccaa acacttgat gcggaagaag tcggtgcgct   1560
cctgcttgtc gccggcatcg ttgcgccaca tctaggtact aaaacaattc atccagtaaa   1620
atataatatt ttatttttctc ccaatcaggc ttgatcccca gtaagtcaaa aaatagctcg   1680
acatactgtt cttccccgat atcctccctg atcgaccgga cgcagaaggc aatgtcatac   1740
cacttgtccg ccctgccgct tctcccaaga tcaataaagc cacttacttt gccatctttc   1800
acaaagatgt tgctgtctcc caggtcgccg tgggaaaaga caagttcctc ttcgggcttt   1860
tccgtcttta aaaaatcata cagctcgcgc ggatctttaa atggagtgtc ttcttcccag    1920
ttttcgcaat ccacatcggc cagatcgtta ttcagtaagt aatccaattc ggctaagcgg   1980

```
ctgtctaagc tattcgtata gggacaatcc gatatgtcga tggagtgaaa gagcctgatg    2040
cactccgcat acagctcgat aatcttttca gggctttgtt catcttcata ctcttccgag    2100
caaaggacgc catcggcctc actcatgagc agattgctcc agccatcatg ccgttcaaag    2160
tgcaggacct ttggaacagg cagctttcct tccagccata gcatcatgtc cttttcccgt    2220
tccacatcat aggtggtccc tttataccgg ctgtccgtca tttttaaata taggttttca    2280
ttttctccca ccagcttata taccttagca ggagacattc cttccgtatc ttttacgcag    2340 cggtatttt cgatcagttt tttcaattcc ggtgatattc tcattttagc catttattat    2400
ttccttcctc ttttctacag tatttaaaga taccccaaga agctaattat aacaagacga    2460
actccaattc actgttcctt gcattctaaa accttaaata ccagaaaaca gcttttcaa    2520 agttgttttc aaagttggcg tataacatag tatcgacgga gccgattttg aaaccacaat    2580
tatgggtgat gctgccaact cgagagcggg ccgggagggt tcgagaaggg ggggcacccc    2640
ccttcggcgt gcgcggtcac gcgcacaggg cgcagccctg gttaaaaaca aggtttataa    2700
atattggttt aaaagcaggt taaaagacag gttagcggtg gccgaaaaac gggcggaaac    2760
ccttgcaaat gctggatttt ctgcctgtgg acagccctc aaatgtcaat aggtgcgccc    2820
ctcatctgtc agcactctgc ccctcaagtg tcaaggatcg cgccctcat ctgtcagtag    2880 tcgcgcccct caagtgtcaa taccgcaggg cacttatccc caggcttgtc cacatcatct    2940
gtgggaaact cgcgtaaaat caggcgtttt cgccgatttg cgaggctggc cagctccacg    3000
tcgccggccg aaatcgagcc tgcccctcat ctgtcaacgc cgcgccgggt gagtcggccc    3060
ctcaagtgtc aacgtccgcc cctcatctgt cagtgagggc caagttttcc gcgaggtatc    3120
cacaacgccg gcggccggcc gcggtgtctc gcacacggct tcgacggcgt ttctggcgcg    3180
tttgcagggc catagacggc cgccagccca gcggcgaggg caaccagccc ggtgagctct    3240
agtggactga tgggctgcct gtatcgagtg gtgattttgt gccgagctgc cggtcgggga    3300
gctgttggct ggctgg                                                    3316

<210> SEQ ID NO 31
<211> LENGTH: 25
<212> TYPE: DNA
<213> ORGANISM: Artificial sequence
<220> FEATURE:
<223> OTHER INFORMATION: FECT40 vector: T-DNA left border

<400> SEQUENCE: 31
tggcaggata tattgtggtg taaac                                           25

<210> SEQ ID NO 32
<211> LENGTH: 88
<212> TYPE: DNA
<213> ORGANISM: Artificial sequence
<220> FEATURE:
<223> OTHER INFORMATION: FECT40 vector: miscellaneous sequence 2

<400> SEQUENCE: 32
gggtggtttt ggtaccgggc ccccctcga ggtcgacggt atcgataagc ttgatatcga     60
attcctgcag gtcaacatgg tggagcac                                        88

<210> SEQ ID NO 33
<211> LENGTH: 728
<212> TYPE: DNA
<213> ORGANISM: Artificial sequence
<220> FEATURE:
<223> OTHER INFORMATION: FECT40: 35S promoter
```

<400> SEQUENCE: 33

| | | | | | |
|---|---|---|---|---|---|
| gacactctcg | tctactccaa | gaatatcaaa | gatacagtct | cagaagacca | aagggctatt | 60 |
| gagactttc | aacaaagggt | aatatcggga | aacctcctcg | gattccattg | cccagctatc | 120 |
| tgtcacttca | tcaaaaggac | agtagaaaag | gaaggtggca | cctacaaatg | ccatcattgc | 180 |
| gataaaggaa | aggctatcgt | tcaagatgcc | tctgccgaca | gtggtcccaa | agatggaccc | 240 |
| ccacccacga | ggagcatcgt | ggaaaagaa | gacgttccaa | ccacgtcttc | aaagcaagtg | 300 |
| gattgatgtg | ataacatggt | ggagcacgac | actctcgtct | actccaagaa | tatcaaagat | 360 |
| acagtctcag | aagaccaaag | ggctattgag | acttttcaac | aaagggtaat | atcgggaaac | 420 |
| ctcctcggat | tccattgccc | agctatctgt | cacttcatca | aaaggacagt | agaaaaggaa | 480 |
| ggtggcacct | acaaatgcca | tcattgcgat | aaaggaaagg | ctatcgttca | agatgcctct | 540 |
| gccgacagtg | gtcccaaaga | tggaccccca | cccacgagga | gcatcgtgga | aaagaagac | 600 |
| gttccaacca | cgtcttcaaa | gcaagtggat | tgatgtgata | tctccactga | cgtaagggat | 660 |
| gacgcacaat | cccactatcc | ttcgcaagac | cttcctctat | ataaggaagt | tcatttcatt | 720 |
| tggagagg | | | | | | 728 |

<210> SEQ ID NO 34
<211> LENGTH: 8905
<212> TYPE: DNA
<213> ORGANISM: Artificial Sequence
<220> FEATURE:
<223> OTHER INFORMATION: FECT40 vector: full sequence

<400> SEQUENCE: 34

| | | | | | |
|---|---|---|---|---|---|
| gaaaactctt | ccgaaaccga | aactgactga | aactacctcg | accgacctta | gaacccaaga | 60 |
| acccaacggg | tgcggccact | atgtctatcg | aggcagtttt | cgaccaggtt | acagacccat | 120 |
| cgctccgcgc | tgtgattcag | gaggaagcgc | acaaacagat | caaagatttg | tttaaggaaa | 180 |
| cgacgcgctg | caatccctac | tccataccgc | aagctgggcg | caaggttttg | gaaaagtacg | 240 |
| ccatccccta | caacccgtac | tctctcaaac | tacaccctca | cgcagcctca | aaagcgtttg | 300 |
| aagtgtcgct | ctacgaggct | gcgtctaact | acctcccctc | cacctcctca | actcctgtca | 360 |
| cattcatgtt | cacaaaaccg | ggcaagctca | gattctttag | gcgccgaggt | cacgtggaca | 420 |
| aattcgttaa | tgctgacata | gttccaagag | acttggctag | atacccacgc | gacacagtct | 480 |
| acagttatct | gcccgagatc | accaccacac | acgctttcat | ggcgacacc | ctacatcact | 540 |
| tcggtgagga | ctttctcgtc | gaggttttct | ccaggtcacc | gaaactagaa | gtgcttctag | 600 |
| ccaccatggt | attaccaccc | gaagcctttt | acagaatgga | gtcccttcat | ccctcggttt | 660 |
| acactctcct | ctacagggac | gaccgattcc | tatacctgcc | tggtggcctg | tctggcggtg | 720 |
| agtacgaaca | tcgctataag | gacctaaact | ggctaacatt | tggcacagtt | acgcacggcg | 780 |
| ggatcactat | cacaggagaa | cgcattgaga | ctaaggccgc | gaatcatctt | ttcctcttca | 840 |
| gacgagggcg | actagcgaca | ccaaaattcc | gctcattcga | catgcccgag | cctatggtcc | 900 |
| tgcttcccaa | ggttttccgc | cccgcaaagt | acaatgtaca | gaagccaatt | ccccgggaga | 960 |
| aagcaaacaa | atggttgatg | tacgttaaat | ccatcggcaa | tgccaccatt | cgtgacgtat | 1020 |
| gggctaagct | gaggcaaacc | atagccaatg | cagacattgg | actcttctcg | cccactgagc | 1080 |
| tcgtgcatct | cacgaattac | ttcctgctcc | tgggccggct | tgactcacac | aattccttcg | 1140 |
| accaagtact | ggccgacagt | gtgctgaaag | catggttcag | accaatggtc | gcaaagcttc | 1200 |
| aggagattaa | gcacaaactc | atggggcaga | cccaattcat | gcaactctgc | caagcgctag | 1260 |

```
agatgacgga ggtggacctc gtctttgagg tccgggactc caagactccc cacaaacaag    1320
ctgtgccgtt ggaccgtgaa attgaaaacg ttttgttgga aggagtctca tcggagccaa    1380
cttacactga aaccgaaggc gttgctgatg gtccacttcc cccccaatg caaactgcag     1440 ccgagccgtc cgcgacctca gacgagcccg agagctctag ctcgcgtgaa attgagcatc    1500
aaccggcgcc tgagatcacg cttgacgagg aagaacctca gcgagacgat ctgccttggg    1560
acgcttggag aacacaatta agggcgcttg gctttgaggc ctccgaaagg cagtatgacc    1620
cggacggtga actgatctct cctatcctga gcacccgaag gttgcctaaa actcccatag    1680
acacaacact ctacgccacg ctagacaaga ttgcacgctg cccaactttc tacaagcctg    1740
acacagatcg cgcgcagact tacgctcgcg atgtcatggc ggggaaaacc ggtgccattc    1800
tcaagcaaca acccttgag tggaaaacca cgctcaagcg caagactaaa gaggaaccga     1860
aggaaattca ccttgcggtg ttgcatggtg cgggcgggtc gggcaaatcc tacgcactgc    1920
aggaatttat gcggaacaac tctgacacac cgattacggt catcctgccg actaacgagc    1980
tcagggccga ctggaagaaa aaattgcccg cccacgacaa agacacattt atgacatacg    2040
aaaacgcgct cttgtgccct cgtggagaca tcttcattat ggacgattac acaaaattgc    2100 ccagggcta cattgaggct ttcgtgcaga atgcacctgc cctctcactt ctgatactca     2160
ccggtgaccc caaccaagcc gaacactttg agaccactga ggacaatgaa attaacagcc    2220 tcgccccgc ctcagtggtc ttcggcaagt tctctaggta ccacataaat gccacacacc     2280
gcaaccccag aaacttggca aacgcccctcg gtgtttactc cgagacgccc ggggaggtta   2340
aagtgcttta cacgaggaac atcaagaccg gttatcacaa tctcgtgccc tcacaaatga    2400
agatgagaaa ttacgcctca ctcgggcagc gagcgtccac ctatgcgggt tgtcagggga    2460
tcaccgcgcc ccgcgttcaa atcatcctag actccgacac accccggtgc accaggcaag    2520
tcatgtacac tgcactctca agggccacga cggaagtggt gctctgcaac acgatgccgg    2580
atgagaaaag cttttttccag aaggttgaag caacaccgta cctcaaagcc atcctcaacc   2640
tcaacaaaga gattaaagtc actgagggcg acttgacaga agaaccgccg agggagcccg    2700
ctcctcccac cacacacctg cctgttgaaa acagaatcat tcttaatgag gccctagtcg    2760
aaccgctgcc cgacaaacat gaccgcgaga tctactccaa ctccactggc ttttcaaact    2820
gcatacagac tcaagacccg tacatccaag ccttccaaca tcagcaagcc aaggacgaga    2880
cattgttctg ggcaaccgtc gagaagaggc tcgcagcatc tacgccgaag gacaactgga    2940
cagaattcaa gaccaagaga cctctggggtg acgtgctttg gctcgcgtac aagcgggcga    3000
tggtgctccc agatgagccc atcaaattta acccagagct ctggtgggca tgtgcagatg    3060
aggtgcaaaa gacctacctc tccaagccca tacacgcgct caagaacgga attcttcggc    3120 aatcaccccga ctttgactgg aacaaactgc agattttcct caagtcacag tgggttaaga    3180
aaattgacaa aatcgggaaa attgacgtca acgctggaca gacaattgcc gccttttacc    3240
aaccaactgt tatgctgttt ggaaccatgg cgagatacat gcgccgcatc cgcgacactt    3300
atcaacccgg cgaaatactc atcaattgcg agaagaacca gaagcacatt tcgaagtggg    3360
tcgagagcaa ttggaaccac cgcctacctg cttacaccaa tgacttcact gcttacgacc    3420 aaaagccaaga cggggctatg ttacagtttg aggtactgaa agcccctgcac catgatatcc    3480 ctcatgaggt tgtggaagct tacgtagccc ttaaactcaa ctcaaaaatg tttctgggca    3540
cactggcgat tatgagatta actggtgagg gaccccacctt cgacgctaac acagagtgca    3600
acattgctta cacacacgcc cggttcgaga tcccaaagaa tgtggcgcaa atgtacgcgg    3660
```

```
gtgacgactg tgcgctcaac tgcaggcccg ttgaacggca gtccttcctg cctcttgtgg    3720
agaaattcac cctgaaatca aacctaaag tatttgagca aaaagttggg tcatggcctg     3780
agttctgcgg caatctgatc accccacggg gctacctcaa ggatcccatg aagctacaac    3840
actgcctgca actggcacag aggaagaaac catccgaacc tgggtcgctt aaagacgttg    3900
ctgagaacta cgctatggac ttgctaccca catacgagct aggtgatgca ctctacgaaa    3960
tcttcgacga gagacaaatg aacgcgcact atcagtcggt caggacgctt atcacatgcg    4020
cccacaccaa agtcctccga gttgcacagg cacttcagga agactgcacc ttctttagct    4080
ccatctaaca ggttttgagt taggctaact ccactgacga attaaataac aatggatagt    4140
gaaatagttg aacgactaac aaagcttggt taattaaagt cctaggctac caaacaacgg    4200
gcagtacttc atcgaggcac ctcagtgatc agtagtatga taccaataaa taaatcgggc    4260
gaatccgcgc ctcctgacta tgggcaggtt tacggaccaa gctgtatcga gatacgacct    4320
aacagtaacg cagctaaggg gtgaatgcac acatcgctta taaaaaaaaa aaaaaaaaaa    4380
aaaaaaaaaa aaaaaaaaaa aaaaaaaaaa aaaaaaaaaa aaaaaaaaaa aaaaaaaaaa    4440
atctagagtc cgcaaatcac cagtctctct ctacaaatct atctctctct attttctcca    4500
gaataatgtg tgagtagttc ccagataagg gaattagggt tcttataggg tttcgctcat    4560
gtgttgagca tataagaaac ccttagtatg tatttgtatt tgtaaaatac ttctatcaat    4620
aaaatttcta attcctaaaa ccaaaatcca gtgacctgca gcccggccgg gggatccact    4680
agcagattgt cgtttcccgc cttcagttta aactatcagt gtttgacagg atatattggc    4740
gggtaaacct aagagaaaag agcgtttatt agaataatcg gatatttaaa agggcgtgaa    4800
aaggtttatc cgttcgtcca tttgtatgtg catgccaacc acaggagatc tcagtaaagc    4860
gctggctgaa cccccagccg gaactgaccc cacaaggccc tagcgtttgc aatgcaccag    4920
gtcatcattg acccaggcgt gttccaccag gccgctgcct cgcaactctt cgcaggcttc    4980
gccgacctgc tcgcgccact tcttcacgcg ggtggaatcc gatccgcaca tgaggcggaa    5040
ggtttccagc ttgagcgggt acggctcccg gtgcgagctg aaatagtcga acatccgtcg    5100
ggccgtcggc gacagcttgc ggtacttctc ccatatgaat ttcgtgtagt ggtcgccagc    5160
aaacagcacg acgatttcct cgtcgatcag gacctggcaa cgggacgttt tcttgccacg    5220
gtccaggacg cggaagcggt gcagcagcga caccgattcc aggtgcccaa cgcggtcgga    5280
cgtgaagccc atcgccgtcg cctgtaggcg cgacaggcat tcctcggcct tcgtgtaata    5340
ccggccattg atcgaccagc ccaggtcctg gcaaagctcg tagaacgtga aggtgatcgg    5400
ctcgccgata ggggtgcgct tcgcgtactc caacacctgc tgccacacca gttcgtcatc    5460
gtcggcccgc agctcgacgc cggtgtaggt gatcttcacg tccttgttga cgtggaaaat    5520
gaccttgttt tgcagcgcct cgcgcgggat tttcttgttg cgcgtggtga acagggcaga    5580
gcgggccgtg tcgtttggca tcgctcgcat cgtgtccggc cacggcgcaa tatcgaacaa    5640
ggaaagctgc atttccttga tctgctgctt cgtgtgtttc agcaacgcgg cctgcttggc    5700
ctcgctgacc tgttttgcca ggtcctcgcc ggcggttttt cgcttcttgg tcgtcatagt    5760
tcctcgcgtg tcgatggtca tcgacttcgc caaacctgcc gcctcctgtt cgagacgacg    5820
cgaacgctcc acggcggccg atggcgcggg cagggcaggg ggagccagtt gcacgctgtc    5880
gcgctcgatc ttggccgtag cttgctggac catcgagccg acggactgga aggtttcgcg    5940
gggcgcacgc atgacggtgc ggcttgcgat ggtttcggca tcctcggcgg aaaaccccgc    6000
gtcgatcagt tcttgcctgt atgccttccg gtcaaacgtc cgattcattc accctccttg    6060
```

```
cgggattgcc ccgactcacg ccggggcaat gtgcccttat tcctgatttg acccgcctgg   6120
tgccttggtg tccagataat ccaccttatc ggcaatgaag tcggtcccgt agaccgtctg   6180
gccgtccttc tcgtacttgg tattccgaat cttgccctgc acgaatacca gcgacccctt   6240
gcccaaatac ttgccgtggg cctcggcctg agagccaaaa cacttgatgc ggaagaagtc   6300
ggtgcgctcc tgcttgtcgc cggcatcgtt gcgccacatc taggtactaa aacaattcat   6360
ccagtaaaat ataatatttt attttctccc aatcaggctt gatccccagt aagtcaaaaa   6420
atagctcgac atactgttct ccccgatat cctccctgat cgaccggacg cagaaggcaa    6480
tgtcatacca cttgtccgcc ctgccgcttc tcccaagatc aataaagcca cttactttgc   6540
catctttcac aaagatgttg ctgtctccca ggtcgccgtg ggaaaagaca agttcctctt   6600
cgggcttttc cgtctttaaa aaatcataca gctcgcgcgg atctttaaat ggagtgtctt   6660
cttcccagtt ttcgcaatcc acatcggcca gatcgttatt cagtaagtaa tccaattcgg   6720
ctaagcggct gtctaagcta ttcgtatagg gacaatccga tatgtcgatg gagtgaagaa   6780
gcctgatgca ctccgcatac agctcgataa tcttttcagg gctttgttca tcttcatact   6840
cttccgagca aaggacgcca tcggcctcac tcatgagcag attgctccag ccatcatgcc   6900
gttcaaagtg caggaccttt ggaacaggca gctttccttc cagccatagc atcatgtcct   6960
tttcccgttc cacatcatag gtggtccctt tataccggct gtccgtcatt tttaaatata   7020
ggttttcatt ttctcccacc agcttatata ccttagcagg agacattcct tccgtatctt   7080
ttacgcagcg gtattttcg atcagttttt tcaattccgg tgatattctc attttagcca    7140
tttattattt ccttcctctt ttctacagta tttaaagata ccccaagaag ctaattataa   7200
caagacgaac tccaattcac tgttccttgc attctaaaac cttaaatacc agaaaacagc   7260 ttttcaaag ttgttttcaa agttggcgta taacatagta tcgacggagc cgattttgaa    7320
accacaatta tgggtgatgc tgccaactcg agagcgggcc gggagggttc gagaaggggg   7380 ggcaccccc ttcggcgtgc gcggtcacgc gcacagggcg cagccctggt taaaaacaag    7440
gtttataaat attggtttaa aagcaggtta aagacaggt tagcggtggc cgaaaaacgg    7500
gcggaaaccc ttgcaaatgc tggattttct gcctgtggac agcccctcaa atgtcaatag   7560
gtgcgcccct catctgtcag cactctgccc ctcaagtgtc aaggatcgcg cccctcatct   7620
gtcagtagtc gcgcccctca agtgtcaata ccgcagggca cttatcccca ggcttgtcca   7680
catcatctgt gggaaactcg cgtaaaatca ggcgttttcg ccgatttgcg aggctggcca   7740
gctccacgtc gccggccgaa atcgagcctg cccctcatct gtcaacgccg cgccgggtga   7800
gtcggcccct caagtgtcaa cgtccgcccc tcatctgtca gtgagggcca gttttccgc    7860 gaggtatcca caacgccggc ggccggccgc ggtgtctcgc acacggcttc gacggcgttt   7920
ctggcgcgtt tgcagggcca tagacggccg ccagcccagc ggcgagggca accagcccgg   7980
tgagctctag tggactgatg ggctgcctgt atcgagtggt gattttgtgc cgagctgccg   8040
gtcggggagc tgttggctgg ctggtggcag gatatattgt ggtgtaaacg gttggttttg   8100
gtaccgggcc cccctcgag gtcgacggta tcgataagct tgatatcgaa ttcctgcagg    8160
tcaacatggt ggagcacgac actctcgtct actccaagaa tatcaaagat acagtctcag   8220
aagaccaaag ggctattgag acttttcaac aaagggtaat atcgggaaac ctcctcggat   8280
tccattgccc agctatctgt cacttcatca aaggacagt agaaaaggaa ggtggcacct    8340
acaaatgcca tcattgcgat aaaggaaagg ctatcgttca agatgcctct gccgacagtg   8400
gtcccaaaga tggaccccca cccacgagga gcatcgtgga aaaagaagac gttccaacca   8460
```

-continued

```
cgtcttcaaa gcaagtggat tgatgtgata acatggtgga gcacgacact ctcgtctact      8520
ccaagaatat caaagataca gtctcagaag accaaagggc tattgagact tttcaacaaa      8580
gggtaatatc gggaaacctc ctcggattcc attgcccagc tatctgtcac ttcatcaaaa      8640
ggacagtaga aaaggaaggt ggcacctaca aatgccatca ttgcgataaa ggaaaggcta      8700
tcgttcaaga tgcctctgcc gacagtggtc ccaaagatgg accccacccc acgaggagca      8760
tcgtggaaaa agaagacgtt ccaaccacgt cttcaaagca agtggattga tgtgatatct      8820
ccactgacgt aagggatgac gcacaatccc actatccttc gcaagacctt cctctatata      8880
aggaagttca tttcatttgg agagg                                            8905
```

<210> SEQ ID NO 35
<211> LENGTH: 25
<212> TYPE: DNA
<213> ORGANISM: Artificial Sequence
<220> FEATURE:
<223> OTHER INFORMATION: FBest vector: T-DNA left border

<400> SEQUENCE: 35

```
tggcaggata tattgtggtg taaac                                              25
```

<210> SEQ ID NO 36
<211> LENGTH: 52
<212> TYPE: DNA
<213> ORGANISM: Artificial Sequence
<220> FEATURE:
<223> OTHER INFORMATION: FBest vector: miscellaneous sequence

<400> SEQUENCE: 36

```
gggtggtttt ggtaccgggc cccccctcga ggtcgacggt atcgataagc tt                52
```

<210> SEQ ID NO 37
<211> LENGTH: 333
<212> TYPE: DNA
<213> ORGANISM: Artificial Sequence
<220> FEATURE:
<223> OTHER INFORMATION: FBest vector: Nos promoter

<400> SEQUENCE: 37

```
aggcgggaaa cgacaatctg atcatgagcg gagaattaag ggagtcacgt tatgacccccc       60 gccgatgacg cgggacaagc cgttttacgt ttggaactga cagaaccgca acgattgaag      120
gagccactca gccgcgggtt tctggagttt aatgagctaa gcacatacgt cagaaaccat      180
tattgcgcgt tcaaaagtcg cctaaggtca ctatcagcta gcaaatattt cttgtcaaaa      240
atgctccact gacgttccat aaattcccct cggtatccaa ttagagtctc atattcactc      300
tcaatccaaa taatctgcac cggatcccct aga                                    333
```

<210> SEQ ID NO 38
<211> LENGTH: 552
<212> TYPE: DNA
<213> ORGANISM: Artificial Sequence
<220> FEATURE:
<223> OTHER INFORMATION: FBest vector: bar gene

<400> SEQUENCE: 38

```
atgagcccag aacgacgccc ggccgacatc cgccgtgcca ccgaggcgga catgccggcg       60
gtctgcacca tcgtcaacca ctacatcgag acaagcacgg tcaacttccg taccgagccg      120
caggaaccgc aggagtggac ggacgacctc gtccgtctgc gggagcgcta tccctggctc      180
gtcgccgagg tggacggcga ggtcgccggc atcgcctacg cgggccccctg gaaggcacgc      240
```

```
aacgcctacg actggacggc cgagtcgacc gtgtacgtct cccccgcca ccagcggacg    300 ggactgggct ccacgctcta cacccacctg ctgaagtccc tggaggcaca gggcttcaag    360
agcgtggtcg ctgtcatcgg gctgcccaac gacccgagcg tgcgcatgca cgaggcgctc    420
ggatatgccc ccgcggcat gctgcgggcg gccggcttca agcacgggaa ctggcatgac     480 gtgggttttct ggcagctgga cttcagcctg ccggtaccgc ccgtccggt cctgcccgtc    540 accgagatct ga                                                         552

<210> SEQ ID NO 39
<211> LENGTH: 332
<212> TYPE: DNA
<213> ORGANISM: Artificial Sequence
<220> FEATURE:
<223> OTHER INFORMATION: FBest vector: Nos terminator

<400> SEQUENCE: 39
cgatcgttca aacatttggc aataaagttt cttaagattg aatcctgttg ccggtcttgc     60
gatgattatc atataatttc tgttgaatta cgttaagcat gtaataatta acatgtaatg   120
catgacgtta tttatgagat ggggttttat gattagagtc ccgcaattat acatttaata   180
cgcgatagaa acaaaatat agcgcgcaaa ctaggataaa ttatcgcgcg cggtgtcatc    240
tatgttacta gatcggggaa ttgatccccc ctcgacagga attccatgtt actagatcgg   300
ggaattgatc cccctcgac agcttgcatg cc                                    332

<210> SEQ ID NO 40
<211> LENGTH: 292
<212> TYPE: DNA
<213> ORGANISM: Artificial Sequence
<220> FEATURE:
<223> OTHER INFORMATION: FBest vector: Lex operator

<400> SEQUENCE: 40
agcttgggct gcaggtcgag gctaaaaaac taatcgcatt atcatcccct cgacgtactg     60
tacatataac cactggtttt atatacagca gtactgtaca tataaccact ggttttatat   120
acagcagtcg acgtactgta catataacca ctggttttat atacagcagt actgtacata   180
taaccactgg ttttatatac agcagtcgag gtaagattag atatggatat gtatatggat   240
atgtatatgg tggtaatgcc atgtaatatg ctcgactcta ggatcttcgc aa           292

<210> SEQ ID NO 41
<211> LENGTH: 42
<212> TYPE: DNA
<213> ORGANISM: Artificial Sequence
<220> FEATURE:
<223> OTHER INFORMATION: FBest vector: 35S core promoter segment

<400> SEQUENCE: 41
gacccttcct ctatataagg aagttcattt catttggaga gg                        42

<210> SEQ ID NO 42
<211> LENGTH: 1628
<212> TYPE: DNA
<213> ORGANISM: Artificial Sequence
<220> FEATURE:
<223> OTHER INFORMATION: FBest vector: full sequence

<400> SEQUENCE: 42
tggcaggata tattgtggtg taaacgggtg gttttggtac cgggcccccc ctcgaggtcg     60
acggtatcga taagcttagg cgggaaacga caatctgatc atgagcggag aattaaggga   120
```

```
gtcacgttat gaccccngcc gatgacgcgg gacaagccgt tttacgtttg gaactgacag        180
aaccgcaacg attgaaggag ccactcagcc gcgggtttct ggagtttaat gagctaagca        240
catacgtcag aaaccattat tgcgcgttca aaagtcgcct aaggtcacta tcagctagca        300
aatatttctt gtcaaaaatg ctccactgac gttccataaa ttcccctcgg tatccaatta        360
gagtctcata ttcactctca atccaaataa tctgcaccgg atccctaga atgagcccag          420 aacgacgccc ggccgacatc cgccgtgcca ccgaggcgga catgccggcg gtctgcacca        480
tcgtcaacca ctacatcgag acaagcacgg tcaacttccg taccgagccg caggaaccgc        540
aggagtggac ggacgacctc gtccgtctgc gggagcgcta tccctggctc gtcgccgagg        600
tggacggcga ggtcgccggc atcgcctacg cgggcccctg gaaggcacgc aacgcctacg        660
actggacggc cgagtcgacc gtgtacgtct ccccccgcca ccagcggacg ggactgggct        720
ccacgctcta cacccacctg ctgaagtccc tggaggcaca gggcttcaag agcgtggtcg        780
ctgtcatcgg gctgcccaac gacccgagcg tgcgcatgca cgaggcgctc ggatatgccc        840
cccgcggcat gctgcgggcg gccggcttca agcacgggaa ctggcatgac gtgggtttct        900
ggcagctgga cttcagcctg ccggtaccgc ccgtccggt cctgcccgtc accgagatct         960
gacgatcgtt caaacatttg gcaataaagt ttcttaagat tgaatcctgt tgccggtctt       1020
gcgatgatta tcatataatt tctgttgaat tacgttaagc atgtaataat taacatgtaa       1080
tgcatgacgt tatttatgag atgggttttt atgattagag tcccgcaatt atacatttaa       1140
tacgcgatag aaaacaaaat atagcgcgca aactaggata aattatcgcg cgcggtgtca       1200
tctatgttac tagatcgggg aattgatccc ccctcgacag gaattccatg ttactagatc       1260
ggggaattga tccccctcg acagcttgca tgccagcttg gctgcaggt cgaggctaaa         1320 aaactaatcg cattatcatc ccctcgacgt actgtacata taaccactgg ttttatatac       1380
agcagtactg tacatataac cactggtttt atatacagca gtcgacgtac tgtacatata       1440
accactggtt ttatatacag cagtactgta catataacca ctggttttat atacagcagt       1500
cgaggtaaga ttagatatgg atatgtatat ggatatgtat atggtggtaa tgccatgtaa       1560
tatgctcgac tctaggatct tcgcaagacc cttcctctat ataaggaagt tcatttcatt       1620
tggagagg                                                                 1628

<210> SEQ ID NO 43
<211> LENGTH: 74
<212> TYPE: DNA
<213> ORGANISM: Artificial Sequence
<220> FEATURE:
<223> OTHER INFORMATION: SHEC74 vector: 5'UTR

<400> SEQUENCE: 43
gtatgattaa cttcacaaca cggttgaagt tataagacca acatttacat ttacatttac        60
aacaaacatt caca                                                           74

<210> SEQ ID NO 44
<211> LENGTH: 4882
<212> TYPE: DNA
<213> ORGANISM: Artificial Sequence
<220> FEATURE:
<223> OTHER INFORMATION: SHEC74 vector: replicase ORF

<400> SEQUENCE: 44
atgtctacat ctacactcat taacaaagca caaactaact cctgcggtga cgttggcgtt        60
gtggaccttc tgaaaagaaa ggtctacgat gacactgtca aaaccatgca ggggttagat       120
```

```
cgcagggcca agtaccggtt aaaccaatgc ttgggacctg aacagtgtag gactgtcaga    180
ggtggctacc ctgaatttca aattgaattc acaggagcat cgaacacgtc gcatgcaatg    240
gcggcgggtt tgagaggact tgaactcgag tatctttata ctcttgttcc gtacggggcc    300
gtgtcttacg acattggtgg aaacttcccc gcacacatga tgaagggtcg ttcgtacgtt    360
cattgctgca atccggcttt agacgcccgc gacctagcca gaaacgagaa ctacagaatc    420
tccattgaga actatttgtc acgcttcgag gacaaatccg gtgattattg tcaatggcaa    480
cggaaaaaac caaaggtttc aaaaccgtta ccaaggtatc aaaaggcctg tttcgacagg    540
tacaatgaag atccggaaca tgttacttgt agcgaaacat ttgagaaatg taggatctcg    600
ccacctgctg aaagggatga tatctacgcc acgagtttac actcgttata cgatatccct    660
taccaaaacc tcggtcctgc tttagccagg aagaggatca aagttcttca cgctgcattt    720
cattttagtg aagatctact actcggtgcc tctgaagggt tgttgaccca gattggtggt    780
actttccaac ggaacggtga tgttctcacc ttttcgtttt tggatgagtc ttctttaatt    840
tacaccccata gtttccgtaa tgtgtttgag tatgttacca gaactttctt cgtggcgtgc    900
aataggtacg cctacatgaa ggaatttcgt agtagacgcg tggatactgt tttctgtagc    960
tttattagga tagacactta ttgtctgtac agaagtgtgt caaagactg cgacgaacat   1020
gtgttcgcgg ccatggacga tgcatggag tttaaaaaga aaagagtgat gttggaagct   1080
tcaagaccca tctttaacga cgtcgcacaa ttcaacgtct acttcccgaa tgcaaaggac   1140
aaggtttgct tacccatttt cgcagtcaaa tctgtttctg gtgcacctgt taccacgcgc   1200
cacatacttg ttgagaagga cttctactgg acggctttga accatatctt aacatatcct   1260
gatggaaaag ccgatttcag aggagtgatg agcttcttgg agagcatcag gtcaagggtt   1320
gttatcaatg gtacaaccac agcatctcaa tgggaggtgg ataagagtca acttaaggac   1380
attgccttga gtttactgct gattgcaaaa ctcgaaaagc tgaagatctc agtgatcgag   1440
aagcggatca aaattgaaag acagggtttg gtatcgttac tcaaagagtt ccttcatggc   1500
ctcctggacg agtacacgca gacaatggcc gagtgggttg tagagaaggg ttgggtgaag   1560
tctgtagacc aagttctaca ggtgacaatt cctgacctgg ttctgaactt tagggatcac   1620
ttcagatgtg agttccgtac ttccgctaac gtctccgagg tgaatgtctc cgagcatctt   1680
gttgcaacga atgagtatta cgctaaggtc agtgatctcg ttgaccgtaa cccgaccctg   1740
gcttttgatt ttgaaaagtt tcaagactac tgtgagaaac tcggtgttga tatcgacacc   1800
gtcacagaac tgatcgacgc tatatcgaca gggcgtgccg gtatcacgct ggaccacaca   1860
gatgataaag aagagcaatt gccaagaaca ctcgcaggta gcagttctta tcttgaggaa   1920
gaaccatcag acgatttggt ttgtctgtct gataaggcca ttgtaaaccg atcaaccatt   1980
ctgggcgagc tgaaaaacaa tgtagttatc ttcgaaggca cactcccaaa gaacagtgtc   2040
ttcgtgagcg cccctgacga cccgtcagta acaatagagt tatctgaatt acacgcccgt   2100
cccgtctcag acttttgag tatgcaaaag cccgtcaaca ttgtttacac gggcgaagta   2160
caaatttgtc aaatgcagaa ctacctggac tatttgtccg cttctctggt agcatgcata   2220
agcaatctca agaagtatct gcaggaccaa tggttgaacc ctggtgaaaa gttccagaag   2280
attggtgtct gggacaatct taacaacaag tggatcgttg tccccaaaa gaagaaatat   2340
gcctggggac tcgcggctga tgtcgacggc aaccaaaaga ccgtcatact gaactacgac   2400
gaacacggga tgccgattct cgaaaagtcg tatgtgaggt tggttgtctc gacagacaca   2460
tacctctttta cggtcgtctc gatgcttggg tatctcaggc atctcgacca aaaaaaaccc   2520
```

```
accgccacta taacactagt tgacggggtc cctgggtgtg gaaagactca agaaatattg    2580
agtcgtttcg acgctaacag tgacctcata ctagtacagg gtagggaggc atgtgaaatg    2640
atcagacgca gagctaatga taacgtaccc ggttccgcca caaggaaaaa cgttagaacg    2700
ttcgattctt tcgttatgaa cagaaaacca ggaaagttta aaactctgtg ggttgatgag    2760
gggttgatgg tgcaccccgg attaatcaat ttttgtataa acatttcgtg tgtttcctct    2820
gtatatattt ttggtgatag aaaacagatt ccctttatta atagagtaat gaattttca     2880
attcccgata acctagcaaa actgtattac gatgagattg tctcccgtga tacaacaaaa    2940
agatgtccgt tagatgtgac acatttcttg aacagtgtct atgaaaagag ggttatgtcg    3000
tacagcaatg tacaacgttc cctcgagtgc aaaatgataa gtggtaaggc caaaatcaac    3060
gactatcgta gtatcttggc agaagggaag ttgttgacgt ttacccagga agataaagaa    3120
tatcttttga aggccgggtt taaagatgtc aacaccgttc atgaagcgca gggtgaaact    3180
tatcgggatg tgaatctcat aagagtcacc gccacgccct taaccattgt cagtgctggg    3240
tcacctcatg tgacggttgc actctcaaga cacacgaata gatttgtgta ctatacagta    3300
gtacctgatg tagttatgac aactgtacag aagactcagt gtgtaagtaa cttccttctg    3360
gatatgtacg ccgtggcgta cacccaaaaa tagcaattac agatctcgcc cttctacacc    3420
catgatatac catttgtgga gacgaacaag gtaggtcaaa tctctgattt acaatatttc    3480
tatgacagtt ggctaccagg gaactcattt gtccagaaca ccacgatca atggtcgatc     3540
atttcatcgg acattaatct tcattccgaa gccgtccgtt tggatatgaa caaacgccat    3600
attcctagga caaaaggtga gtttctgagg ccgttgttga acacggctgt cgaacctcca    3660
agaataccgg gttattggaa aaatctgctg gcgttgatta aagaaatttt taatgcgccg    3720
gatctagccg gtcaattgga ttacgacttt ctctccagaa aggtttgtga tgggtttttc    3780
gggaagctct tgcccccgga tgtagaagcg agcgaactgt tgaggttacc ggtcgatcac    3840
atgtattcgg tgcaaaaactt tgatgactgg ttgaacaagc aggaacctgg agtcgtaggg    3900
caattagcga actgggacca catcggtatg cccgcggccg accaatacag gcatatgatt    3960
aaaaggactc ctaaggccaa attagatttg tccatacaga gcgaataccc cgctctgcaa    4020
acgattgtgt atcacagcaa gcatgtgaac gcagttttgt gaccgatctt ttcatgtctg    4080
acggaacgat tactgtctgt ggtcgatcct ttgaggttca aattcttcac aagaactacc    4140
cctgcagatc ttgaattttt ttttagggat atggttgtcg gtgacatgga gatcctagaa    4200
ctcgacatct cgaagtacga caaaagtcaa aacaagtttc attttgaagt cgagatgaga    4260
atatgggaga tgctgggcat cgacaagtat atagaaaagg tgtgggaaaa cggtcaccgg    4320
aaaacgcatt tgcgtgacta tacagctggt attaagacgg tgatcgagta ccagagaaag    4380
agtggcgacg taacaacgtt cattgggaac actatcatta tcgccgcctg tctctgcagt    4440
attctaccaa tggagaaggt gtttaaagct gggttctgtg gtgatgactc gataatttac    4500
ttgccgagaa atcttctcta cccagatatc caatcggtct ccaacaacat gtggaatttt    4560
gaggcaaagc ttttcaagaa gctgcacggt tacttctgtg gtaggtatat tctacgcaac    4620
ggaaggtacc tgaggctttt accagacccc ctcaaaatta tcacaaaact gggttgtaaa    4680
gccatcaagg actgggatca cctggaggaa ttcaggtat  ctatgttcga catggcatgt    4740
gaatataaaa attgttttgg ttttgatgtt ttggagtcgg cagttaagga atcttttcca    4800
aaagctgaag gctgcaacgt tgcttttgt gctatttata aatttttaag taataaatat      4860
ttgtttagaa cttta tttag tg                                             4882
```

<210> SEQ ID NO 45
<211> LENGTH: 823
<212> TYPE: DNA
<213> ORGANISM: Artificial Sequence
<220> FEATURE:
<223> OTHER INFORMATION: SHEC74 vector: movement protein ORF

<400> SEQUENCE: 45

| | | | | | |
|---|---|---|---|---|---|
| atgtctgagg | tgtctaaaat | ctccactttg | ttggctccgg | aaaagtttgt | aaaactttcc | 60 |
| gtttccgaca | agtttaaatg | gaaggcacct | tcgagagttt | gtagtatagt | acagagtgat | 120 |
| accatatcta | tgactgcgaa | cggaagatca | ttgtttacgt | ttgatgtttt | gaaggacgtg | 180 |
| ttaaaacacg | cagaggagta | cacatatgtc | gatgttcttg | gcgttgtgtt | atctggacag | 240 |
| tggttgctcc | cgaaagggac | gcccggttcg | gcagagatca | ttctcttaga | ctcgcgcctt | 300 |
| aagggaaagg | cttctgtcct | cgcggttttt | aactgtagag | ctgccacgca | agaatttcag | 360 |
| ttcctgattt | caccagggta | ctctctgact | tgtgcgacg | ctcttaagaa | acccttcgaa | 420 |
| atatcatgta | atgtgatcga | cctgccggtc | aaagatggtt | tcactccttt | gtctgtcgag | 480 |
| attgcgtgtt | tagtgcagtt | ttctaattgt | gttataacaa | ggtctttgac | catgaaatta | 540 |
| aaagaaaacc | cagcgaccag | gacattctct | gctgaagagg | tcgacgaact | tttgggttcg | 600 |
| atgactactt | tacggagtat | cgagggttg | cgaaaaaaga | aagaacccaa | cgacgttgta | 660 |
| caaggacatc | tgagtgccga | gtacgatgtg | aaaaggagtg | ttaaaaggac | aaaatctgaa | 720 |
| aacactccgg | gaaaaagaag | ggtgaatgtt | gatagtgtga | gtttgggatt | aggaagggga | 780 |
| aagagtgtgt | ctgctaaaaa | cgaagacaca | gagtctgtat | ttg | | 823 |

<210> SEQ ID NO 46
<211> LENGTH: 74
<212> TYPE: DNA
<213> ORGANISM: Artificial Sequence
<220> FEATURE:
<223> OTHER INFORMATION: SHEC74 vector: initial 74bp of coat protein
with first two codons mutated (ATG->ACG)

<400> SEQUENCE: 46

| | | | | | |
|---|---|---|---|---|---|
| acgacggcat | actcgattcc | gactcctagt | caacttgtgt | attttactga | aaattacgct | 60 |
| gattacattc | catt | | | | | 74 |

<210> SEQ ID NO 47
<211> LENGTH: 226
<212> TYPE: DNA
<213> ORGANISM: Artificial Sequence
<220> FEATURE:
<223> OTHER INFORMATION: SHEC74 vector: PacI/Bss HII cloning site and 3'
UTR

<400> SEQUENCE: 47

| | | | | | |
|---|---|---|---|---|---|
| ttaattaaat | cgcgcgctct | agtgtaaaag | tttggtcgta | cttaacgacc | tagggcttaa | 60 |
| ccgaaataag | ccgtgtttaa | gagtccacgc | aaatcgaact | ctagaactta | tgaacagtca | 120 |
| tggtttccat | gccgtaaagt | tcataaccgc | gaagtcgcgg | cgccgtcaag | acacgacggt | 180 |
| gagtggggag | cattaccccc | ccaaaaccct | ggggatacag | ggccca | | 226 |

<210> SEQ ID NO 48
<211> LENGTH: 213
<212> TYPE: DNA
<213> ORGANISM: Artificial Sequence
<220> FEATURE:
<223> OTHER INFORMATION: SHEC74 vector: 35S terminator

<400> SEQUENCE: 48

```
tctagagtcc gcaaatcacc agtctctctc tacaaatcta tctctctcta ttttctccag    60
aataatgtgt gagtagttcc cagataaggg aattagggtt cttatagggt ttcgctcatg   120
tgttgagcat ataagaaacc cttagtatgt atttgtattt gtaaaatact tctatcaata   180
aaatttctaa ttcctaaaac caaaatccag tga                                213
```

<210> SEQ ID NO 49
<211> LENGTH: 69
<212> TYPE: DNA
<213> ORGANISM: Artificial Sequence
<220> FEATURE:
<223> OTHER INFORMATION: SHEC74 vector: miscellaneous sequence

<400> SEQUENCE: 49

```
cctgcagccc ggccggggga tccactagca gattgtcgtt tcccgccttc agtttaaact    60
atcagtgtt                                                            69
```

<210> SEQ ID NO 50
<211> LENGTH: 25
<212> TYPE: DNA
<213> ORGANISM: Artificial Sequence
<220> FEATURE:
<223> OTHER INFORMATION: SHEC74 vector: T-DNA right border

<400> SEQUENCE: 50

```
tgacaggata tattggcggg taaac                                          25
```

<210> SEQ ID NO 51
<211> LENGTH: 3316
<212> TYPE: DNA
<213> ORGANISM: Artificial Sequence
<220> FEATURE:
<223> OTHER INFORMATION: SHEC74 vector: JL22 sequence

<400> SEQUENCE: 51

```
ctaagagaaa agagcgttta ttagaataat cggatattta aaagggcgtg aaaaggttta    60
tccgttcgtc catttgtatg tgcatgccaa ccacaggaga tctcagtaaa gcgctggctg   120
aacccccagc cggaactgac cccacaaggc cctagcgttt gcaatgcacc aggtcatcat   180
tgacccaggc gtgttccacc aggccgctgc ctcgcaactc ttcgcaggct tcgccgacct   240
gctcgcgcca cttcttcacg cgggtggaat ccgatccgca catgaggcgg aaggtttcca   300
gcttgagcgg gtacggctcc cggtgcgagc tgaaatagtc gaacatccgt cgggccgtcg   360
gcgacagctt gcggtacttc tcccatatga atttcgtgta gtggtcgcca gcaaacagca   420
cgacgatttc ctcgtcgatc aggacctggc aacgggacgt tttcttgcca cggtccagga   480
cgcggaagcg gtgcagcagc gacaccgatt ccaggtgccc aacgcggtcg acgtgaagc    540
ccatcgccgt cgcctgtagg cgcgacaggc attcctcggc cttcgtgtaa taccggccat   600
tgatcgacca gcccaggtcc tggcaaagct cgtagaacgt gaaggtgatc ggctcgccga   660
taggggtgcg cttcgcgtac tccaacacct gctgccacac cagttcgtca tcgtcggccc   720
gcagctcgac gccggtgtag gtgatcttca cgtccttgtt gacgtggaaa atgaccttgt   780
tttgcagcgc ctcgcgcggg attttcttgt tgcgcgtggt gaacagggca gagcgggccc   840
tgtcgtttgg catcgctcgc atcgtgtccg gccacggcgc aatatcgaac aaggaaagct   900
gcatttcctt gatctgctgc ttcgtgtgtt tcagcaacgc ggcctgcttg gcctcgctga   960
cctgttttgc caggtcctcg ccggcggttt ttcgcttctt ggtcgtcata gttcctcgcg  1020
```

```
tgtcgatggt catcgacttc gccaaacctg ccgcctcctg ttcgagacga cgcgaacgct   1080
ccacggcggc cgatggcgcg ggcagggcag ggggagccag ttgcacgctg tcgcgctcga   1140
tcttggccgt agcttgctgg accatcgagc cgacggactg gaaggtttcg cggggcgcac   1200
gcatgacggt gcggcttgcg atggtttcgg catcctcggc ggaaaacccc gcgtcgatca   1260
gttcttgcct gtatgccttc cggtcaaacg tccgattcat tcaccctcct tgcgggattg   1320
ccccgactca cgccggggca atgtgccctt attcctgatt tgacccgcct ggtgccttgg   1380
tgtccagata atccacctta tcggcaatga agtcggtccc gtagaccgtc tggccgtcct   1440
tctcgtactt ggtattccga atcttgccct gcacgaatac cagcgacccc ttgcccaaat   1500
acttgccgtg ggcctcggcc tgagagccaa aacacttgat gcggaagaag tcggtgcgct   1560
cctgcttgtc gccggcatcg ttgcgccaca tctaggtact aaaacaattc atccagtaaa   1620
atataatatt ttattttctc ccaatcaggc ttgatcccca gtaagtcaaa aaatagctcg   1680
acatactgtt cttccccgat atcctccctg atcgaccgga cgcagaaggc aatgtcatac   1740
cacttgtccg ccctgccgct tctcccaaga tcaataaagc cacttacttt gccatctttc   1800
acaaagatgt tgctgtctcc caggtcgccg tgggaaaaga caagttcctc ttcgggcttt   1860
tccgtcttta aaaaatcata cagctcgcgc ggatctttaa atggagtgtc ttcttcccag   1920
ttttcgcaat ccacatcggc cagatcgtta ttcagtaagt aatccaattc ggctaagcgg   1980
ctgtctaagc tattcgtata gggacaatcc gatatgtcga tggagtgaaa gagcctgatg   2040
cactccgcat acagctcgat aatcttttca gggctttgtt catcttcata ctcttccgag   2100
caaaggacgc catcggcctc actcatgagc agattgctcc agccatcatg ccgttcaaag   2160
tgcaggacct ttggaacagg cagctttcct tccagccata gcatcatgtc cttttcccgt   2220
tccacatcat aggtggtccc tttataccgg ctgtccgtca ttttttaaata taggttttca   2280
ttttctccca ccagcttata taccttagca ggagacattc cttccgtatc ttttacgcag   2340
cggtattttt cgatcagttt tttcaattcc ggtgatattc tcatttttagc catttattat   2400
ttccttcctc ttttctacag tatttaaaga taccccaaga agctaattat aacaagacga   2460
actccaattc actgttcctt gcattctaaa accttaaata ccagaaaaca gctttttcaa   2520
agttgttttc aaagttggcg tataacatag tatcgacgga gccgattttg aaaccacaat   2580
tatgggtgat gctgccaact cgagagcggg ccggagggt tcgagaaggg ggggcacccc   2640
ccttcggcgt gcgcggtcac gcgcacaggg cgcagccctg gttaaaaaca aggtttataa   2700
atattggttt aaaagcaggt taaaagacag gttagcggtg gccgaaaaac gggcggaaac   2760
ccttgcaaat gctggatttt ctgcctgtgg acagcccctc aaatgtcaat aggtgcgccc   2820
ctcatctgtc agcactctgc ccctcaagtg tcaaggatcg cgccctcat ctgtcagtag   2880
tcgcgcccct caagtgtcaa taccgcaggg cacttatccc caggcttgtc cacatcatct   2940
gtgggaaact cgcgtaaaat caggcgtttt cgccgatttg cgaggctggc cagctccacg   3000
tcgccggccg aaatcgagcc tgcccctcat ctgtcaacgc cgcgccgggt gagtcggccc   3060
ctcaagtgtc aacgtccgcc cctcatctgt cagtgagggc caagttttcc gcgaggtatc   3120
cacaacgccg cggcggcc gcggtgtctc gcacacggct tcgacggcgt ttctggcgcg   3180
tttgcagggc catagacggc cgccagccca gcggcgaggg caaccagccc ggtgagctct   3240
agtggactga tgggctgcct gtatcgagtg gtgattttgt gccgagctgc cggtcgggga   3300
gctgttggct ggctgg                                                  3316
```

<210> SEQ ID NO 52
<211> LENGTH: 25
<212> TYPE: DNA
<213> ORGANISM: Artificial Sequence
<220> FEATURE:
<223> OTHER INFORMATION: SHEC74 vector: T-DNA left border

<400> SEQUENCE: 52
tggcaggata tattgtggtg taaac                                         25

<210> SEQ ID NO 53
<211> LENGTH: 88
<212> TYPE: DNA
<213> ORGANISM: Artificial Sequence
<220> FEATURE:
<223> OTHER INFORMATION: SHEC74 vector: miscellaneous sequence 2

<400> SEQUENCE: 53
gggtggtttt ggtaccgggc cccccctcga ggtcgacggt atcgataagc ttgatatcga    60
attcctgcag gtcaacatgg tggagcac                                      88

<210> SEQ ID NO 54
<211> LENGTH: 728
<212> TYPE: DNA
<213> ORGANISM: Artificial Sequence
<220> FEATURE:
<223> OTHER INFORMATION: SHEC74 vector: 35S promoter

<400> SEQUENCE: 54
gacactctcg tctactccaa gaatatcaaa gatacagtct cagaagacca aagggctatt    60 gagactttc aacaaggggt aatatcggga aacctcctcg gattccattg cccagctatc    120
tgtcacttca tcaaaaggac agtagaaaag gaaggtggca cctacaaatg ccatcattgc    180
gataaaggaa aggctatcgt tcaagatgcc tctgccgaca gtggtcccaa agatggaccc    240
ccacccacga ggagcatcgt ggaaaaagaa gacgttccaa ccacgtcttc aaagcaagtg    300
gattgatgtg ataacatggt ggagcacgac actctcgtct actccaagaa tatcaaagat    360
acagtctcag aagaccaaag ggctattgag acttttcaac aaagggtaat atcgggaaac    420
ctcctcggat tccattgccc agctatctgt cacttcatca aaaggacagt agaaaggaa    480 ggtggcacct acaaatgcca tcattgcgat aaaggaaagg ctatcgttca agatgcctct    540
gccgacagtg gtcccaaaga tggaccccca ccacgagga gcatcgtgga aaaagaagac    600
gttccaacca cgtcttcaaa gcaagtggat tgatgtgata tctccactga cgtaagggat    660
gacgcacaat cccactatcc ttcgcaagac cttcctctat ataaggaagt tcatttcatt    720
tggagagg                                                            728

<210> SEQ ID NO 55
<211> LENGTH: 10543
<212> TYPE: DNA
<213> ORGANISM: Artificial Sequence
<220> FEATURE:
<223> OTHER INFORMATION: SHEC74 vector: full sequence

<400> SEQUENCE: 55
gtatgattaa cttcacaaca cggttgaagt tataagacca acatttacat ttacatttac    60
aacaaacatt cacaatgtct acatctacac tcattaacaa agcacaaact aactcctgcg    120
gtgacgttgg cgttgtggac cttctgaaaa gaaaggtcta cgatgacact gtcaaaacca    180
tgcaggggtt agatcgcagg gccaagtacc ggttaaacca atgcttggga cctgaacagt    240
gtaggactgt cagaggtggc taccctgaat ttcaaattga attcacagga gcatcgaaca    300

```
cgtcgcatgc aatggcggcg ggtttgagag gacttgaact cgagtatctt tatactcttg    360
ttccgtacgg ggccgtgtct tacgacattg gtggaaactt ccccgcacac atgatgaagg    420
gtcgttcgta cgttcattgc tgcaatccgg ctttagacgc ccgcgaccta gccagaaacg    480
agaactacag aatctccatt gagaactatt tgtcacgctt cgaggacaaa tccggtgatt    540
attgtcaatg gcaacggaaa aaaccaaagg tttcaaaacc gttaccaagg tatcaaaagg    600
cctgtttcga caggtacaat gaagatccgg aacatgttac ttgtagcgaa acatttgaga    660
aatgtaggat ctcgccacct gctgaaaggg atgatatcta cgccacgagt ttacactcgt    720
tatacgatat cccttaccaa aacctcggtc ctgctttagc caggaagagg atcaaagttc    780
ttcacgctgc atttcatttt agtgaagatc tactactcgg tgcctctgaa gggttgttga    840
cccagattgg tggtactttc caacggaacg gtgatgttct cacctttcg ttttggatg      900 agtcttcttt aatttacacc catagtttcc gtaatgtgtt tgagtatgtt accagaactt    960
tcttcgtggc gtgcaatagg tacgcctaca tgaaggaatt tcgtagtaga cgcgtggata   1020
ctgttttctg tagctttatt aggatagaca cttattgtct gtacagaagt gtgttcaaag   1080
actgcgacga acatgtgttc gcggccatgg acgatgcatg ggagtttaaa agaaaagag    1140 tgatgttgga agcttcaaga cccatcttta cgacgtcgc acaattcaac gtctacttcc     1200
cgaatgcaaa ggacaaggtt tgcttaccca ttttcgcagt caaatctgtt tctggtgcac   1260
ctgttaccac gcgccacata cttgttgaga aggacttcta ctggacggct ttgaaccata   1320
tcttaacata tcctgatgga aaagccgatt tcagaggagt gatgagcttc ttggagagca   1380
tcaggtcaag ggttgttatc aatggtacaa ccacagcatc tcaatgggag gtggataaga   1440
gtcaacttaa ggacattgcc ttgagtttac tgctgattgc aaaactcgaa agctgaaga    1500 tctcagtgat cgagaagcgg atcaaaattg aaagacaggg tttggtatcg ttactcaaag   1560
agttccttca tggcctcctg gacgagtaca cgcagacaat ggccgagtgg gttgtagaga   1620
agggttgggt gaagtctgta gaccaagttc tacaggtgac aattcctgac ctggttctga   1680
actttaggga tcacttcaga tgtgagttcc gtacttccgc taacgtctcc gaggtgaatg   1740
tctccgagca tcttgttgca acgaatgagt attacgctaa ggtcagtgat ctcgttgacc   1800
gtaacccgac cctggctttt gattttgaaa agtttcaaga ctactgtgag aaactcggtg   1860
ttgatatcga caccgtcaca gaactgatcg acgctatatc gacagggcgt gccggtatca   1920
cgctggacca cacagatgat aaagaagagc aattgccaag aacactcgca ggtagcagtt   1980
cttatcttga ggaagaacca tcagacgatt tggtttgtct gtctgataag gccattgtaa   2040
accgatcaac cattctgggc gagctgaaaa acaatgtagt tatcttcgaa ggcacactcc   2100
caaagaacag tgtcttcgtg agcgcccctg acgacccgtc agtaacaata gagttatctg   2160
aattacacgc ccgtcccgtc tcagactttt tgagtatgca aaagcccgtc aacattgttt   2220
acacgggcga agtacaaatt tgtcaaatgc agaactacct ggactatttg tccgcttctc   2280
tggtagcatg cataagcaat ctcaagaagt atctgcagga ccaatggttg aaccctggtg   2340
aaaagttcca gaagattggt gtctgggaca atcttaacaa caagtggatc gttgtccccc   2400
aaaagaagaa atatgcctgg ggactcgcgg ctgatgtcga cggcaaccaa aagaccgtca   2460
tactgaacta cgacgaacac gggatgccga ttctcgaaaa gtcgtatgtg aggttggttg   2520
tctcgacaga cacataccct tttacggtcg tctcgatgct tgggtatctc aggcatctcg   2580
accaaaaaaa acccaccgcc actataacac tagttgacgg ggtccctggg tgtgaaaga    2640 ctcaagaaat attgagtcgt ttcgacgcta acagtgacct catactagta cagggtaggg   2700
```

```
aggcatgtga aatgatcaga cgcagagcta atgataacgt acccggttcc gccacaaagg    2760
aaaacgttag aacgttcgat tctttcgtta tgaacagaaa accaggaaag tttaaaactc    2820
tgtgggttga tgaggggttg atggtgcacc ccggattaat caattttgt ataaacattt     2880 cgtgtgtttc ctctgtatat attttggtg atagaaaaca gattccctt attaatagag     2940 taatgaattt ttcaattccc gataacctag caaaactgta ttacgatgag attgtctccc    3000
gtgatacaac aaaagatgt ccgttagatg tgacacattt cttgaacagt gtctatgaaa     3060
agagggttat gtcgtacagc aatgtacaac gttccctcga gtgcaaaatg ataagtggta    3120
aggccaaaat caacgactat cgtagtatct tggcagaagg gaagttgttg acgtttaccc    3180
aggaagataa agaatatctt ttgaaggccg ggtttaaaga tgtcaacacc gttcatgaag    3240
cgcagggtga aacttatcgg gatgtgaatc tcataagagt caccgccacg cccttaacca    3300
ttgtcagtgc tgggtcacct catgtgacgg ttgcactctc aagacacacg aatagatttg    3360
tgtactatac agtagtacct gatgtagtta tgacaactgt acagaagact cagtgtgtaa    3420
gtaacttcct tctggatatg tacgccgtgg cgtacaccca aaaatagcaa ttacagatct    3480
cgcccttcta cacccatgat ataccatttg tggagacgaa caaggtaggt caaatctctg    3540
atttacaata tttctatgac agttggctac cagggaactc atttgtccag aacaaccacg    3600
atcaatggtc gatcatttca tcggacatta atcttcattc cgaagccgtc cgtttggata    3660
tgaacaaacg ccatattcct aggacaaaag gtgagtttct gaggccgttg ttgaacacgg    3720
ctgtcgaacc tccaagaata ccgggtttat tggaaaatct gctggcgttg attaaaagaa    3780
attttaatgc gccggatcta gccggtcaat tggattacga cttctctcc agaaaggttt    3840 gtgatgggtt tttcgggaag ctcttgcccc cggatgtaga agcgagcgaa ctgttgaggt    3900
taccggtcga tcacatgtat tcggtgcaaa actttgatga ctggttgaac aagcaggaac    3960
ctggagtcgt agggcaatta gcgaactggg accacatcgg tatgcccgcg gccgaccaat    4020
acaggcatat gattaaaagg actcctaagg ccaaattaga tttgtccata cagagcgaat    4080
accccgctct gcaaacgatt gtgtatcaca gcaagcatgt gaacgcagtt tttggaccga    4140 tctttcatg tctgacggaa cgattactgt ctgtggtcga tcctttgagg ttcaaattct     4200
tcacaagaac taccctgca gatcttgaat ttttttttag ggatatggtt gtcggtgaca     4260
tggagatcct agaactcgac atctcgaagt acgacaaaag tcaaaacaag tttcattttg    4320
aagtcgagat gagaatatgg gagatgctgg gcatcgacaa gtatatagaa aaggtgtggg    4380
aaaacggtca ccggaaaacg catttgcgtg actatacagc tggtattaag acggtgatcg    4440
agtaccagag aaagagtggc gacgtaacaa cgttcattgg gaacactatc attatcgccg    4500
cctgtctctg cagtattcta ccaatggaga aggtgtttaa agctgggttc tgtggtgatg    4560
actcgataat ttacttgccg agaaatcttc tctacccaga tatccaatcg gtctccaaca    4620
acatgtggaa ttttgaggca aagcttttca agaagctgca cggttacttc tgtggtaggt    4680
atattctacg caacggaagg tacctgaggc ttttaccaga ccccctcaaa attatcacaa    4740 aactggggttg taaagccatc aaggactggg atcacctgga ggaattcagg atatctatgt    4800
tcgacatggc atgtgaatat aaaaattgtt ttggttttga tgttttggag tcggcagtta    4860
aggaatcttt tccaaaagct gaaggctgca acgttgcttt ttgtgctatt tataaatttt    4920
taagtaataa atatttgttt agaactttat ttagtgatgt ctgaggtgtc taaaatctcc    4980
actttgttgg ctccggaaaa gtttgtaaaa ctttccgttt ccgacaagtt taaatggaag    5040
gcaccttcga gagtttgtag tatagtacag agtgatacca tatctatgac tgcgaacgga    5100
```

```
agatcattgt ttacgtttga tgttttgaag gacgtgttaa aacacgcaga ggagtacaca    5160
tatgtcgatg ttcttggcgt tgtgttatct ggacagtggt tgctcccgaa agggacgccc    5220
ggttcggcag agatcattct cttagactcg cgccttaagg gaaaggcttc tgtcctcgcg    5280
gtttttaact gtagagctgc cacgcaagaa tttcagttcc tgatttcacc agggtactct    5340
ctgacttgtg cggacgctct taagaaaccc ttcgaaatat catgtaatgt gatcgacctg    5400
ccggtcaaag atggtttcac tcctttgtct gtcgagattg cgtgtttagt gcagttttct    5460
aattgtgtta taacaaggtc tttgaccatg aaattaaaag aaaacccagc gaccaggaca    5520
ttctctgctg aagaggtcga cgaacttttg ggttcgatga ctactttacg gagtatcgag    5580
gggttgcgaa aaagaaaga acccaacgac gttgtacaag gacatctgag tgccgagtac    5640
gatgtgaaaa ggagtgttaa aaggacaaaa tctgaaaaca ctccgggaaa aagaagggtg    5700
aatgttgata tgtgtgagttt gggattagga aagggaaaga gtgtgtctgc taaaaacgaa    5760
gacacagagt ctgtatttga cgacggcata ctcgattccg actcctagtc aacttgtgta    5820
ttttactgaa aattacgctg attacattcc atttttaatta aatcgcgcgc tctagtgtaa    5880
aagtttggtc gtacttaacg acctaggggc ttaccgaaat aagccgtgtt taagagtcca    5940
cgcaaatcga actctagaac ttatgaacag tcatggtttc catgccgtaa agttcataac    6000
cgcgaagtcg cggcgccgtc aagacacgac ggtgagtggg gagcattacc ccccaaaac    6060
cctggggata cagggcccat ctagagtccg caaatcacca gtctctctct acaaatctat    6120
ctctctctat tttctccaga ataatgtgtg agtagttccc agataaggga attagggttc    6180
ttatagggtt tcgctcatgt gttgagcata taagaaaccc ttagtatgta tttgtatttg    6240
taaaatactt ctatcaataa aatttctaat tcctaaaacc aaaatccagt gacctgcagc    6300
ccggccgggg gatccactag cagattgtcg tttcccgcct tcagtttaaa ctatcagtgt    6360
ttgacaggat atattggcgg gtaaacctaa gagaaaagag cgtttattag aataatcgga    6420
tatttaaaag ggcgtgaaaa ggtttatccg ttcgtccatt tgtatgtgca tgccaaccac    6480
aggagatctc agtaaagcgc tggctgaacc cccagccgga actgacccca caaggcccta    6540
gcgtttgcaa tgcaccaggt catcattgac ccaggcgtgt tccaccaggc cgctgcctcg    6600
caactcttcg caggcttcgc cgacctgctc gcgccacttc ttcacgcggg tggaatccga    6660
tccgcacatg aggcggaagg tttccagctt gagcgggtac ggctcccggt gcgagctgaa    6720
atagtcgaac atccgtcggg ccgtcggcga cagcttgcgg tacttctccc atatgaattt    6780
cgtgtagtgg tcgccagcaa acagcacgac gatttcctcg tcgatcagga cctggcaacg    6840
ggacgttttc ttgccacggt ccaggacgcg gaagcggtgc agcagcgaca ccgattccag    6900
gtgcccaacg cggtcggacg tgaagcccat cgccgtcgcc tgtaggcgcg acaggcattc    6960
ctcggccttc gtgtaatacc ggccattgat cgaccagccc aggtcctggc aaagctcgta    7020
gaacgtgaag gtgatcggct cgccgatagg ggtgcgcttc gcgtactcca acacctgctg    7080
ccacaccagt tcgtcatcgt cggcccgcag ctcgacgccg gtgtaggtga tcttcacgtc    7140
cttgttgacg tggaaaatga ccttgttttg cagcgcctcg cgcgggattt tcttgttgcg    7200
cgtggtgaac agggcagagc gggccgtgtc gtttggcatc gctcgcatcg tgtccggcca    7260
cggcgcaata tcgaacaagg aaagctgcat ttccttgatc tgctgcttcg tgtgtttcag    7320
caacgcggcc tgcttggcct cgctgacctg ttttgccagg tcctcgccgg cggttttcg    7380
cttcttggtc gtcatagttc ctcgcgtgtc gatggtcatc gacttcgcca aacctgccgc    7440
ctcctgtttcg agacgacgcg aacgctccac ggcggccgat ggcgcgggca gggcagggggg    7500
```

```
agccagttgc acgctgtcgc gctcgatctt ggccgtagct tgctggacca tcgagccgac   7560
ggactggaag gtttcgcggg gcgcacgcat gacggtgcgg cttgcgatgg tttcggcatc   7620
ctcggcggaa aaccccgcgt cgatcagttc ttgcctgtat gccttccggt caaacgtccg   7680
attcattcac cctccttgcg ggattgcccc gactcacgcc ggggcaatgt gcccttattc   7740
ctgatttgac ccgcctggtg ccttggtgtc cagataatcc accttatcgg caatgaagtc   7800
ggtcccgtag accgtctggc cgtccttctc gtacttggta ttccgaatct tgccctgcac   7860
gaataccagc gacccttgcc ccaaatactt gccgtgggcc tcggcctgag agccaaaaca   7920
cttgatgcgg aagaagtcgg tgcgctcctg cttgtcgccg gcatcgttgc gccacatcta   7980
ggtactaaaa caattcatcc agtaaaatat aatattttat tttctcccaa tcaggcttga   8040
tccccagtaa gtcaaaaaat agctcgacat actgttcttc cccgatatcc tccctgatcg   8100
accggacgca gaaggcaatg tcataccact tgtccgccct gccgcttctc caagatcaa   8160 taaagccact tactttgcca tctttcacaa agatgttgct gtctcccagg tcgccgtggg   8220
aaaagacaag ttcctcttcg ggcttttccg tctttaaaaa atcatacagc tcgcgcggat   8280 cttaaatgg agtgtcttct tcccagtttt cgcaatccac atcggccaga tcgttattca   8340
gtaagtaatc caattcggct aagcggctgt ctaagctatt cgtataggga caatccgata   8400
tgtcgatgga gtgaaagagc ctgatgcact ccgcatacag ctcgataatc ttttcagggc   8460
tttgttcatc ttcatactct tccgagcaaa ggacgccatc ggcctcactc atgagcagat   8520
tgctccagcc atcatgccgt tcaaagtgca ggacctttgg aacaggcagc tttccttcca   8580
gccatagcat catgtccttt tcccgttcca catcataggt ggtcccttta taccggctgt   8640
ccgtcatttt taaatatagg ttttcatttt ctcccaccag cttatatacc ttagcaggag   8700
acattccttc cgtatctttt acgcagcggt attttcgat cagttttttc aattccggtg   8760
atattctcat tttagccatt tattatttcc ttcctctttt ctacagtatt taagatacc   8820 ccaagaagct aattataaca agacgaactc caattcactg ttccttgcat tctaaaacct   8880
taaataccag aaaacagctt tttcaaagtt gttttcaaag ttggcgtata acatagtatc   8940
gacggagccg attttgaaac cacaattatg ggtgatgctg ccaactcgag agcgggccgg   9000
gagggttcga gaagggggg caccccccctt cggcgtgcgc ggtcacgcgc acagggcgca   9060
gccctggtta aaaacaaggt ttataaatat tggtttaaaa gcaggttaaa agacaggtta   9120
gcggtggccg aaaaacgggc ggaaaccctt gcaaatgctg gattttctgc ctgtggacag   9180
cccctcaaat gtcaataggt gcgcccctca tctgtcagca ctctgcccct caagtgtcaa   9240
ggatcgcgcc cctcatctgt cagtagtcgc gcccctcaag tgtcaatacc gcagggcact   9300
tatccccagg cttgtccaca tcatctgtgg gaaactcgcg taaaatcagg cgttttcgcc   9360
gatttgcgag gctggccagc tccacgtcgc cggccgaaat cgagcctgcc cctcatctgt   9420
caacgccgcg ccgggtgagt cggcccctca agtgtcaacg tccgcccctc atctgtcagt   9480
gagggccaag ttttccgcga ggtatccaca acgccggcgg ccggccgcgg tgtctcgcac   9540
acggcttcga cggcgtttct ggcgcgtttg cagggccata gacggccgcc agcccagcgg   9600
cgagggcaac cagcccggtg agctctagtg gactgatggg ctgcctgtat cgagtggtga   9660
ttttgtgccg agctgccggt cggggagctg ttggctggct ggtggcagga tatattgtgg   9720
tgtaaacggg tggttttggt accgggcccc cctcgaggt cgacggtatc gataagcttg   9780
atatcgaatt cctgcaggtc aacatggtgg agcacgacac tctcgtctac tccaagaata   9840
tcaaagatac agtctcagaa gaccaaaggg ctattgagac ttttcaacaa agggtaatat   9900
```

| | |
|---|---|
| cgggaaacct cctcggattc cattgcccag ctatctgtca cttcatcaaa aggacagtag | 9960 |
| aaaaggaagg tggcacctac aaatgccatc attgcgataa aggaaaggct atcgttcaag | 10020 |
| atgcctctgc cgacagtggt cccaaagatg acccccacc cacgaggagc atcgtggaaa | 10080 |
| aagaagacgt tccaaccacg tcttcaaagc aagtggattg atgtgataac atggtggagc | 10140 |
| acgacactct cgtctactcc aagaatatca aagatacagt ctcagaagac caaagggcta | 10200 |
| ttgagacttt tcaacaaagg gtaatatcgg gaaacctcct cggattccat tgcccagcta | 10260 |
| tctgtcactt catcaaaagg acagtagaaa aggaaggtgg cacctacaaa tgccatcatt | 10320 |
| gcgataaagg aaaggctatc gttcaagatg cctctgccga cagtggtccc aaagatggac | 10380 |
| ccccacccac gaggagcatc gtggaaaaag aagacgttcc aaccacgtct caaagcaag | 10440 |
| tggattgatg tgatatctcc actgacgtaa gggatgacgc acaatcccac tatccttcgc | 10500 |
| aagaccttcc tctatataag gaagttcatt tcatttggag agg | 10543 |

<210> SEQ ID NO 56
<211> LENGTH: 74
<212> TYPE: DNA
<213> ORGANISM: Artificial Sequence
<220> FEATURE:
<223> OTHER INFORMATION: SHAC74 vector: 5' UTR

<400> SEQUENCE: 56

| | |
|---|---|
| gtatgattaa cttcacaaca cggttgaagt tataagacca acatttacat ttacatttac | 60 |
| aacaaacatt caca | 74 |

<210> SEQ ID NO 57
<211> LENGTH: 4882
<212> TYPE: DNA
<213> ORGANISM: Artificial Sequence
<220> FEATURE:
<223> OTHER INFORMATION: SHAC74 vector: replicase ORF

<400> SEQUENCE: 57

| | |
|---|---|
| atgtctacat ctacactcat taacaaagca caaactaact cctgcggtga cgttggcgtt | 60 |
| gtggaccttc tgaaaagaaa ggtctacgat gacactgtca aaaccatgca ggggttagat | 120 |
| cgcagggcca agtaccggtt aaaccaatgc ttgggacctg aacagtgtag gactgtcaga | 180 |
| ggtggctacc ctgaatttca aattgaattc acaggagcat cgaacacgtc gcatgcaatg | 240 |
| gcggcgggtt tgagaggact tgaactcgag tatctttata ctcttgttcc gtacggggcc | 300 |
| gtgtcttacg acattggtgg aaacttcccc gcacacatga tgaagggtcg ttcgtacgtt | 360 |
| cattgctgca atccggcttt agacgcccgc gacctagcca gaaacgagaa ctacagaatc | 420 |
| tccattgaga actatttgtc acgcttcgag gacaaatccg gtgattattg tcaatggcaa | 480 |
| cggaaaaaac caaggtttc aaaccgtta ccaaggtatc aaaaggcctg tttcgacagg | 540 |
| tacaatgaag atccggaaca tgttacttgt agcgaaacat ttgagaaatg taggatctcg | 600 |
| ccacctgctg aaagggatga tatctacgcc acgagtttac actcgttata cgatatccct | 660 |
| taccaaaacc tcggtcctgc tttagccagg aagaggatca agttcttca cgctgcattt | 720 |
| cattttagtg aagatctact actccggtgcc tctgaagggt tgttgaccca gattggtggt | 780 |
| actttccaac ggaacggtga tgttctcacc ttttcgtttt tggatgagtc ttctttaatt | 840 |
| tacacccata gtttccgtaa tgtgtttgag tatgttacca gaactttctt cgtggcgtgc | 900 |
| aataggtacg cctacatgaa ggaatttcgt agtgacgcg tggatactgt tttctgtagc | 960 |
| tttattagga tagacactta ttgtctgtac agaagtgtgt tcaaagactg cgacgaacat | 1020 |

```
gtgttcgcgg ccatggacga tgcatgggag tttaaaaaga aaagagtgat gttggaagct   1080
tcaagaccca tctttaacga cgtcgcacaa ttcaacgtct acttcccgaa tgcaaaggac   1140
aaggttttgct tacccatttt cgcagtcaaa tctgtttctg gtgcacctgt taccacgcgc   1200
cacatacttg ttgagaagga cttctactgg acggctttga accatatctt aacatatcct   1260
gatggaaaag ccgatttcag aggagtgatg agcttcttgg agagcatcag gtcaagggtt   1320
gttatcaatg gtacaaccac agcatctcaa tgggaggtgg ataagagtca acttaaggac   1380
attgccttga gtttactgct gattgcaaaa ctcgaaaagc tgaagatctc agtgatcgag   1440
aagcggatca aaattgaaag acagggtttg gtatcgttac tcaaagagtt ccttcatggc   1500
ctcctggacg agtacacgca gacaatggcc gagtgggttg tagagaaggg ttgggtgaag   1560
tctgtagacc aagttctaca ggtgacaatt cctgacctgg ttctgaactt tagggatcac   1620
ttcagatgtg agttccgtac ttccgctaac gtctccgagg tgaatgtctc cgagcatctt   1680
gttgcaacga atgagtatta cgctaaggtc agtgatctcg ttgaccgtaa cccgaccctg   1740
gcttttgatt ttgaaaagtt tcaagactac tgtgagaaac tcggtgttga tatcgacacc   1800
gtcacagaac tgatcgacgc tatatcgaca gggcgtgccg gtatcacgct ggaccacaca   1860
gatgataaag aagagcaatt gccaagaaca ctcgcaggta gcagttctta tcttgaggaa   1920
gaaccatcag acgatttggt ttgtctgtct gataaggcca ttgtaaaccg atcaaccatt   1980
ctgggcgagc tgaaaaacaa tgtagttatc ttcgaaggca cactcccaaa gaacagtgtc   2040
ttcgtgagcg cccctgacga cccgtcagta acaatagagt tatctgaatt acacgcccgt   2100
cccgtctcag acttttttgag tatgcaaaag cccgtcaaca ttgtttacac gggcgaagta   2160
caaatttgtc aaatgcagaa ctacctggac tatttgtccg cttctctggt agcatgcata   2220
agcaatctca agaagtatct gcaggaccaa tggttgaacc ctggtgaaaa gttccagaag   2280
attggtgtct gggacaatct taacaacaag tggatcgttg tccccaaaa gaagaaatat   2340
gcctggggac tcgcggctga tgtcgacggc aaccaaaaga ccgtcatact gaactacgac   2400
gaacacggga tgccgattct cgaaaagtcg tatgtgaggt tggttgtctc gacagacaca   2460
tacctcttta cggtcgtctc gatgcttggg tatctcaggc atctcgacca aaaaaaaccc   2520
accgccacta taacactagt tgacggggtc cctgggtgtg aaagactca agaaatattg   2580
agtcgtttcg acgctaacag tgacctcata ctagtacagg gtagggaggc atgtgaaatg   2640
atcagacgca gagctaatga taacgtaccc ggttccgcca caaggaaaa cgttagaacg   2700
ttcgattctt tcgttatgaa cagaaaacca ggaaagttta aaactctgtg ggttgatgag   2760
gggttgatgg tgcaccccgg attaatcaat ttttgtataa acatttcgtg tgtttcctct   2820
gtatatattt ttggtgatag aaaacagatt cccttttatta atagagtaat gaattttttca   2880
attcccgata acctagcaaa actgtattac gatgagattg tctcccgtga tacaacaaaa   2940
agatgtccgt tagatgtgac acatttcttg aacagtgtct atgaaaagag ggttatgtcg   3000
tacagcaatg tacaacgttc cctcgagtgc aaaatgataa gtggtaaggc caaaatcaac   3060
gactatcgta gtatcttggc agaagggaag ttgttgacgt ttacccagga agataaagaa   3120
tatcttttga aggccgggtt taaagatgtc aacaccgttc atgaagcgca gggtgaaact   3180
tatcgggatg tgaatctcat aagagtcacc gccacgccct taaccattgt cagtgctggg   3240
tcacctcatg tgacggttgc actctcaaga cacacgaata gatttgtgta ctatacagta   3300
gtacctgatg tagttatgac aactgtacag aagactcagt gtgtaagtaa cttccttctg   3360
gatatgtacg ccgtggcgta cacccaaaaa tagcaattac agatctcgcc cttctacacc   3420
```

```
catgatatac catttgtgga gacgaacaag gtaggtcaaa tctctgattt acaatatttc    3480
tatgacagtt ggctaccagg gaactcattt gtccagaaca accacgatca atggtcgatc    3540
atttcatcgg acattaatct tcattccgaa gccgtccgtt tggatatgaa caaacgccat    3600
attcctagga caaaaggtga gttctgaggg ccgttgttga acacggctgt cgaacctcca    3660
agaataccgg gtttattgga aaatctgctg gcgttgatta aaagaaattt taatgcgccg    3720
gatctagccg gtcaattgga ttacgacttt ctctccagaa aggtttgtga tgggttttc    3780 gggaagctct tgcccccgga tgtagaagcg agcgaactgt tgaggttacc ggtcgatcac    3840
atgtattcgg tgcaaaactt tgatgactgg ttgaacaagc aggaacctgg agtcgtaggg    3900
caattagcga actgggacca catcggtatg cccgcggccg accaatacag gcatatgatt    3960
aaaaggactc ctaaggccaa attagatttg tccatacaga gcgaataccc cgctctgcaa    4020
acgattgtgt atcacagcaa gcatgtgaac gcagttttg gaccgatctt ttcatgtctg    4080
acggaacgat tactgtctgt ggtcgatcct ttgaggttca aattcttcac aagaactacc    4140
cctgcagatc ttgaattttt ttttagggat atggttgtcg gtgacatgga gatcctagaa    4200
ctcgacatct cgaagtacga caaaagtcaa aacaagtttc attttgaagt cgagatgaga    4260
atatgggaga tgctgggcat cgacaagtat atagaaaagg tgtgggaaaa cggtcaccgg    4320
aaaacgcatt tgcgtgacta tacagctggt attaagacgg tgatcgagta ccagagaaag    4380
agtggcgacg taacaacgtt cattgggaac actatcatta tcgccgcctg tctctgcagt    4440
attctaccaa tggagaaggt gtttaaagct gggttctgtg gtgatgactc gataatttac    4500
ttgccgagaa atcttctcta cccagatatc caatcggtct ccaacaacat gtggaatttt    4560
gaggcaaagc ttttcaagaa gctgcacggt tacttctgtg gtaggtatat tctacgcaac    4620
ggaaggtacc tgaggcttt accagacccc ctcaaaatta tcacaaaact gggttgtaaa    4680
gccatcaagg actgggatca cctggaggaa ttcaggatat ctatgttcga catggcatgt    4740
gaatataaaa attgttttgg ttttgatgtt ttggagtcgg cagttaagga atcttttcca    4800
aaagctgaag gctgcaacgt tgcttttgt gctatttata aattttaag taataaatat    4860 ttgtttagaa ctttatttag tg                                           4882

<210> SEQ ID NO 58
<211> LENGTH: 823
<212> TYPE: DNA
<213> ORGANISM: Artificial Sequence
<220> FEATURE:
<223> OTHER INFORMATION: SHAC74: movement protein ORF

<400> SEQUENCE: 58
atgtctgagg tgtctaaaat ctccactttg ttggctccgg aaaagtttgt aaaactttcc      60
gtttccgaca gtttaaatg gaaggcacct tcgagagttt gtagtatagt acagagtgat     120
accatatcta tgactgcgaa cggaagatca ttgtttacgt ttgatgtttt gaaggacgtg     180
ttaaaacacg cagaggagta cacatatgtc gatgttcttg gcgttgtgtt atctggacag     240
tggttgctcc cgaaagggac gcccggttcg gcagagatca ttctcttaga ctcgcgcctt     300
aagggaaagg cttctgtcct cgcggttttt aactgtagag ctgccacgca agaatttcag     360
ttcctgattt caccagggta ctctctgact tgtgcgacg ctcttaagaa acccttcgaa     420
atatcatgta atgtgatcga cctgccggtc aaagatggtt tcactccttt gtctgtcgag     480
attgcgtgtt tagtgcagtt ttctaattgt gttataacaa ggtctttgac catgaaatta     540
aaagaaaacc cagcgaccag gacattctct gctgaagagg tcgacgaact tttgggttcg     600
```

```
atgactactt tacggagtat cgaggggttg cgaaaaaaga aagaacccaa cgacgttgta      660
caaggacatc tgagtgccga gtacgatgtg aaaaggagtg ttaaaaggac aaaatctgaa      720
aacactccgg gaaaaagaag ggtgaatgtt gatagtgtga gtttgggatt aggaaaggga      780
aagagtgtgt ctgctaaaaa cgaagacaca gagtctgtat ttg                        823
```

```
<210> SEQ ID NO 59
<211> LENGTH: 74
<212> TYPE: DNA
<213> ORGANISM: Artificial Sequence
<220> FEATURE:
<223> OTHER INFORMATION: SHAC74 vector: Initial 74 bp of coat protein
      ORF with first two codon mutated (ATG --> ACG)

<400> SEQUENCE: 59
acgacggcat actcgattcc gactcctagt caacttgtgt attttactga aaattacgct      60
gattacattc catt                                                        74

<210> SEQ ID NO 60
<211> LENGTH: 30
<212> TYPE: DNA
<213> ORGANISM: Artificial Sequence
<220> FEATURE:
<223> OTHER INFORMATION: SHAC74 vector: Pac I and Avr II cloning sites

<400> SEQUENCE: 60
ttaattaacg gcctagggcg gccgctcgag                                       30

<210> SEQ ID NO 61
<211> LENGTH: 175
<212> TYPE: DNA
<213> ORGANISM: Artificial Sequence
<220> FEATURE:
<223> OTHER INFORMATION: SHAC74 vector: TMV-U1 3' UTR

<400> SEQUENCE: 61
gggtagtcaa gatgcataat aaataacgga ttgtgtccgt aatcacacgt ggtgcgtacg      60
ataacgcata gtgtttttcc ctccacttaa atcgaagggt tgtgtcttgg atcgcgcggg     120
tcaaatgtat atggttcata tacatccgca ggcacgtaat aaagcgaggg gttcg          175

<210> SEQ ID NO 62
<211> LENGTH: 179
<212> TYPE: DNA
<213> ORGANISM: Artificial Sequence
<220> FEATURE:
<223> OTHER INFORMATION: SHAC74 vector: Tobacco mild green mottle virus
      subgenomic promoter

<400> SEQUENCE: 62
ggtcgaggtc ggctgtgaaa ctcgaaaagg ttccggaaaa caaaaaagag agtggtaggt      60
aatagtgtta ataataagaa aataaataat agtggtaaga aaggtttgaa agttgaggaa     120
attgaggata atgtaagtga tgacgagtct atcgcgtcat cgagtacgtt ttaatcaat     179

<210> SEQ ID NO 63
<211> LENGTH: 480
<212> TYPE: DNA
<213> ORGANISM: Artificial Sequence
<220> FEATURE:
<223> OTHER INFORMATION: SHAC74 vector: Tobacco mild green mottle virus
      CP ORF

<400> SEQUENCE: 63
```

```
atgccttata caatcaactc tccgagccaa tttgtttact taagttccgc ttatgcagat    60
cctgtgcagc tgatcaatct gtgtacaaat gcattgggta accagtttca aacgcaacaa   120
gctaggacaa cagtccaaca gcaatttgcg gatgcctgga aacctgtgcc tagtatgaca   180
gtgagatttc ctgcatcgga tttctatgtg tatagatata attcgacgct tgatccgttg   240
atcacggcgt tattaaatag cttcgatact agaaatagaa aatagaggt tgataatcaa   300 cccgcaccga atactactga aatcgttaac gcgactcaga gggtagacga tgcgactgta   360
gctataaggg cttcaatcaa taatttggct aatgaactgg ttcgtggaac tggcatgttc   420
aatcaagcaa gctttgagac tgctagtgga cttgtctgga ccacaactcc ggctacttag   480
```

<210> SEQ ID NO 64
<211> LENGTH: 209
<212> TYPE: DNA
<213> ORGANISM: Artificial Sequence
<220> FEATURE:
<223> OTHER INFORMATION: SHAC74 vector: SHMV 3' UTR

<400> SEQUENCE: 64

```
tctagtgtaa agtttggtc gtacttaacg acctagggc ttaccgaaat aagccgtgtt    60
taagagtcca cgcaaatcga actctagaac ttatgaacag tcatggtttc catgccgtaa   120
agttcataac cgcgaagtcg cggcgccgtc aagacacgac ggtgagtggg gagcattacc   180
cccccaaaac cctggggata cagggccca                                     209
```

<210> SEQ ID NO 65
<211> LENGTH: 213
<212> TYPE: DNA
<213> ORGANISM: Artificial Sequence
<220> FEATURE:
<223> OTHER INFORMATION: SHAC74 vector: 35S terminator

<400> SEQUENCE: 65

```
tctagagtcc gcaaatcacc agtctctctc tacaaatcta tctctctcta ttttctccag    60
aataatgtgt gagtagttcc cagataaggg aattagggtt cttatagggt ttcgctcatg   120
tgttgagcat ataagaaacc cttagtatgt atttgtattt gtaaaatact tctatcaata   180
aaatttctaa ttcctaaaac caaaatccag tga                                213
```

<210> SEQ ID NO 66
<211> LENGTH: 69
<212> TYPE: DNA
<213> ORGANISM: Artificial Sequence
<220> FEATURE:
<223> OTHER INFORMATION: SHAC74 vector: miscellaneous sequence

<400> SEQUENCE: 66

```
cctgcagccc ggccggggga tccactagca gattgtcgtt tcccgccttc agtttaaact    60
atcagtgtt                                                           69
```

<210> SEQ ID NO 67
<211> LENGTH: 25
<212> TYPE: DNA
<213> ORGANISM: Artificial Sequence
<220> FEATURE:
<223> OTHER INFORMATION: SHAC74 vector: T-DNA right border

<400> SEQUENCE: 67

```
tgacaggata tattggcggg taaac                                         25
```

<210> SEQ ID NO 68

<211> LENGTH: 3316
<212> TYPE: DNA
<213> ORGANISM: Artificial Sequence
<220> FEATURE:
<223> OTHER INFORMATION: SHAC74 vector: JL22 sequence

<400> SEQUENCE: 68

| | |
|---|---|
| ctaagagaaa agagcgttta ttagaataat cggatattta aaagggcgtg aaaaggttta | 60 |
| tccgttcgtc catttgtatg tgcatgccaa ccacaggaga tctcagtaaa gcgctggctg | 120 |
| aaccccagc cggaactgac cccacaaggc cctagcgttt gcaatgcacc aggtcatcat | 180 |
| tgacccaggc gtgttccacc aggccgctgc ctcgcaactc ttcgcaggct tcgccgacct | 240 |
| gctcgcgcca cttcttcacg cgggtggaat ccgatccgca catgaggcgg aaggtttcca | 300 |
| gcttgagcgg gtacggctcc cggtgcgagc tgaaatagtc gaacatccgt cgggccgtcg | 360 |
| gcgacagctt gcggtacttc tcccatatga atttcgtgta gtggtcgcca gcaaacagca | 420 |
| cgacgatttc ctcgtcgatc aggacctggc aacgggacgt tttcttgcca cggtccagga | 480 |
| cgcggaagcg gtgcagcagc gacaccgatt ccaggtgccc aacgcggtcg acgtgaagc | 540 |
| ccatcgccgt cgcctgtagg cgcgacaggc attcctcggc cttcgtgtaa taccggccat | 600 |
| tgatcgacca gcccaggtcc tggcaaagct cgtagaacgt gaaggtgatc ggctcgccga | 660 |
| taggggtgcg cttcgcgtac tccaacacct gctgccacac cagttcgtca tcgtcggccc | 720 |
| gcagctcgac gccggtgtag gtgatcttca cgtccttgtt gacgtggaaa atgaccttgt | 780 |
| tttgcagcgc ctcgcgcggg attttcttgt tgcgcgtggt gaacagggca gagcgggccg | 840 |
| tgtcgtttgg catcgctcgc atcgtgtccg gccacggcgc aatatcgaac aaggaaagct | 900 |
| gcatttcctt gatctgctgc ttcgtgtgtt tcagcaacgc ggcctgcttg gcctcgctga | 960 |
| cctgttttgc caggtcctcg ccggcggttt ttcgcttctt ggtcgtcata gttcctcgcg | 1020 |
| tgtcgatggt catcgacttc gccaaacctg ccgcctcctg ttcgagacga cgcgaacgct | 1080 |
| ccacggcggc cgatggcgcg ggcagggcag ggggagccag ttgcacgctg tcgcgctcga | 1140 |
| tcttggccgt agcttgctgg accatcgagc cgacggactg gaaggtttcg cggggcgcac | 1200 |
| gcatgacggt gcggcttgcg atggtttcgg catcctcggc ggaaaacccc gcgtcgatca | 1260 |
| gttcttgcct gtatgccttc cggtcaaacg tccgattcat tcaccctcct gcgggattg | 1320 |
| ccccgactca cgccggggca atgtgccctt attcctgatt tgacccgcct ggtgccttgg | 1380 |
| tgtccagata atccaccta tcggcaatga agtcggtccc gtagaccgtc tggccgtcct | 1440 |
| tctcgtactt ggtattccga atcttgccct gcacgaatac cagcgacccc ttgcccaaat | 1500 |
| acttgccgtg ggcctcggcc tgagagccaa acacttgat gcggaagaag tcggtgcgct | 1560 |
| cctgcttgtc gccggcatcg ttgcgccaca tctaggtact aaaacaattc atccagtaaa | 1620 |
| atataatatt ttattttctc ccaatcaggc ttgatcccca gtaagtcaaa aaatagctcg | 1680 |
| acatactgtt cttccccgat atcctccctg atcgaccgga cgcagaaggc aatgtcatac | 1740 |
| cacttgtccg ccctgccgct tctcccaaga tcaataaagc cacttacttt gccatctttc | 1800 |
| acaaagatgt tgctgtctcc caggtcgccg tgggaaaaga caagttcctc ttcgggcttt | 1860 |
| tccgtcttta aaaaatcata cagctcgcgc ggatctttaa atggagtgtc ttcttcccag | 1920 |
| ttttcgcaat ccacatcggc cagatcgtta ttcagtaagt aatccaattc ggctaagcgg | 1980 |
| ctgtctaagc tattcgtata gggacaatcc gatatgtcga tggagtgaaa gagcctgatg | 2040 |
| cactccgcat acagctcgat aatcttttca gggctttgtt catcttcata ctcttccgag | 2100 |
| caaaggacgc catcggcctc actcatgagc agattgctcc agccatcatg ccgttcaaag | 2160 |

-continued

```
tgcaggacct ttggaacagg cagctttcct tccagccata gcatcatgtc cttttcccgt    2220
tccacatcat aggtggtccc tttataccgg ctgtccgtca ttttttaaata taggttttca   2280 ttttctccca ccagcttata taccttagca ggagacattc cttccgtatc ttttacgcag   2340 cggtatttt cgatcagttt tttcaattcc ggtgatattc tcattttagc catttattat    2400
ttccttcctc ttttctacag tatttaaaga taccccaaga agctaattat aacaagacga   2460
actccaattc actgttcctt gcattctaaa accttaaata ccagaaaaca gcttttcaa    2520 agttgttttc aaagttggcg tataacatag tatcgacgga gccgattttg aaaccacaat   2580
tatgggtgat gctgccaact cgagagcggg ccggggagggt tcgagaaggg ggggcaccccc  2640 ccttcggcgt gcgcggtcac gcgcacaggg cgcagccctg gttaaaaaca aggtttataa   2700
atattggttt aaaagcaggt taaaagacag gttagcggtg gccgaaaaac gggcggaaac   2760
ccttgcaaat gctggatttt ctgcctgtgg acagcccctc aaatgtcaat aggtgcgccc   2820
ctcatctgtc agcactctgc ccctcaagtg tcaaggatcg cgcccctcat ctgtcagtag   2880
tcgcgcccct caagtgtcaa taccgcaggg cacttatccc caggcttgtc cacatcatct   2940
gtgggaaact cgcgtaaaat caggcgtttt cgccgatttg cgaggctggc cagctccacg   3000
tcgccggccg aaatcgagcc tgcccctcat ctgtcaacgc cgcgccgggt gagtcggccc   3060
ctcaagtgtc aacgtccgcc cctcatctgt cagtgagggc caagttttcc gcgaggtatc   3120
cacaacgccg gcggccggcc gcggtgtctc gcacacggct tcgacggcgt ttctggcgcg   3180
tttgcagggc catagacggc cgccagccca gcggcgaggg caaccagccc ggtgagctct   3240
agtggactga tgggctgcct gtatcgagtg gtgattttgt gccgagctgc cggtcgggga   3300
gctgttggct ggctgg                                                    3316
```

<210> SEQ ID NO 69
<211> LENGTH: 25
<212> TYPE: DNA
<213> ORGANISM: Artificial Sequence
<220> FEATURE:
<223> OTHER INFORMATION: SHAC74 vector: T-DNA left border

<400> SEQUENCE: 69

```
tggcaggata tattgtggtg taaac                                          25
```

<210> SEQ ID NO 70
<211> LENGTH: 88
<212> TYPE: DNA
<213> ORGANISM: Artificial Sequence
<220> FEATURE:
<223> OTHER INFORMATION: SHAC74 vector: miscellaneous sequence 2

<400> SEQUENCE: 70

```
gggtggtttt ggtaccgggc ccccccctcga ggtcgacggt atcgataagc ttgatatcga   60
attcctgcag gtcaacatgg tggagcac                                       88
```

<210> SEQ ID NO 71
<211> LENGTH: 728
<212> TYPE: DNA
<213> ORGANISM: Artificial Sequence
<220> FEATURE:
<223> OTHER INFORMATION: SHAC74 vector: 35S promoter

<400> SEQUENCE: 71

```
gacactctcg tctactccaa gaatatcaaa gatacagtct cagaagacca aagggctatt   60
gagacttttc aacaaagggt aatatcggga aacctcctcg gattccattg cccagctatc  120
```

| | |
|---|---|
| tgtcacttca tcaaaaggac agtagaaaag gaaggtggca cctacaaatg ccatcattgc | 180 |
| gataaaggaa aggctatcgt tcaagatgcc tctgccgaca gtggtcccaa agatggaccc | 240 |
| ccacccacga ggagcatcgt ggaaaaagaa gacgttccaa ccacgtcttc aaagcaagtg | 300 |
| gattgatgtg ataacatggt ggagcacgac actctcgtct actccaagaa tatcaaagat | 360 |
| acagtctcag aagaccaaag ggctattgag acttttcaac aaagggtaat atcgggaaac | 420 |
| ctcctcggat tccattgccc agctatctgt cacttcatca aaaggacagt agaaaaggaa | 480 |
| ggtggcacct acaaatgcca tcattgcgat aaaggaaagg ctatcgttca agatgcctct | 540 |
| gccgacagtg gtcccaaaga tggaccccca cccacgagga gcatcgtgga aaagaagac | 600 |
| gttccaacca cgtcttcaaa gcaagtggat tgatgtgata tctccactga cgtaagggat | 660 |
| gacgcacaat cccactatcc ttcgcaagac cttcctctat ataaggaagt tcatttcatt | 720 |
| tggagagg | 728 |

<210> SEQ ID NO 72
<211> LENGTH: 11390
<212> TYPE: DNA
<213> ORGANISM: Artificial Sequence
<220> FEATURE:
<223> OTHER INFORMATION: SHAC74 vector: full sequence

<400> SEQUENCE: 72

| | |
|---|---|
| gtatgattaa cttcacaaca cggttgaagt tataagacca acatttacat ttacatttac | 60 |
| aacaaacatt cacaatgtct acatctacac tcattaacaa agcacaaact aactcctgcg | 120 |
| gtgacgttgg cgttgtggac cttctgaaaa gaaaggtcta cgatgacact gtcaaaacca | 180 |
| tgcagggggtt agatcgcagg gccaagtacc ggttaaacca atgcttggga cctgaacagt | 240 |
| gtaggactgt cagaggtggc taccctgaat ttcaaattga attcacagga gcatcgaaca | 300 |
| cgtcgcatgc aatggcggcg ggtttgagag gacttgaact cgagtatctt tatactcttg | 360 |
| ttccgtacgg ggccgtgtct tacgacattg gtggaaactt ccccgcacac atgatgaagg | 420 |
| gtcgttcgta cgttcattgc tgcaatccgg ctttagacgc ccgcgaccta gccagaaacg | 480 |
| agaactacag aatctccatt gagaactatt tgtcacgctt cgaggacaaa tccggtgatt | 540 |
| attgtcaatg gcaacggaaa aaaccaaagg tttcaaaacc gttaccaagg tatcaaaagg | 600 |
| cctgtttcga caggtacaat gaagatccgg aacatgttac ttgtagcgaa acatttgaga | 660 |
| aatgtaggat ctcgccacct gctgaaaggg atgatatcta cgccacgagt ttacactcgt | 720 |
| tatacgatat cccttaccaa aacctcggtc ctgctttagc caggaagagg atcaaagttc | 780 |
| ttcacgctgc atttcatttt agtgaagatc tactactcgg tgcctctgaa gggttgttga | 840 |
| cccagattgg tggtacttc caacggaacg gtgatgttct cacctttcg tttttggatg | 900 |
| agtcttcttt aatttacacc catagtttcc gtaatgtgtt tgagtatgtt accagaactt | 960 |
| tcttcgtggc gtgcaatagg tacgcctaca tgaaggaatt tcgtagtaga cgcgtggata | 1020 |
| ctgtttctg tagctttatt aggatagaca cttattgtct gtacagaagt gtgttcaaag | 1080 |
| actgcgacga acatgtgttc gcggccatgg acgatgcatg ggagtttaaa aagaaaagag | 1140 |
| tgatgttgga agcttcaaga cccatctta cgacgtcgc acaattcaac gtctacttcc | 1200 |
| cgaatgcaaa ggacaaggtt tgcttaccca ttttcgcagt caaatctgtt tctggtgcac | 1260 |
| ctgttaccac gcgccacata cttgttgaga aggacttcta ctggacggct ttgaaccata | 1320 |
| tcttaacata tcctgatgga aaagccgatt tcagagagt gatgagcttc ttggagagca | 1380 |
| tcaggtcaag ggttgttatc aatggtacaa ccacagcatc tcaatgggag gtggataaga | 1440 |

```
gtcaacttaa ggacattgcc ttgagtttac tgctgattgc aaaactcgaa aagctgaaga    1500
tctcagtgat cgagaagcgg atcaaaattg aaagacaggg tttggtatcg ttactcaaag    1560
agttccttca tggcctcctg gacgagtaca cgcagacaat ggccgagtgg gttgtagaga    1620
agggttgggt gaagtctgta gaccaagttc tacaggtgac aattcctgac ctggttctga    1680
actttaggga tcacttcaga tgtgagttcc gtacttccgc taacgtctcc gaggtgaatg    1740
tctccgagca tcttgttgca acgaatgagt attacgctaa ggtcagtgat ctcgttgacc    1800
gtaacccgac cctggctttt gattttgaaa agtttcaaga ctactgtgag aaactcggtg    1860
ttgatatcga caccgtcaca gaactgatcg acgctatatc gacagggcgt gccggtatca    1920
cgctggacca cacagatgat aaagaagagc aattgccaag aacactcgca ggtagcagtt    1980
cttatcttga ggaagaacca tcagacgatt tggtttgtct gtctgataag gccattgtaa    2040
accgatcaac cattctgggc gagctgaaaa acaatgtagt tatcttcgaa ggcacactcc    2100
caaagaacag tgtcttcgtg agcgcccctg acgacccgtc agtaacaata gagttatctg    2160
aattacacgc ccgtcccgtc tcagacttt tgagtatgca aaagcccgtc aacattgttt    2220
acacgggcga agtacaaatt tgtcaaatgc agaactacct ggactatttg tccgcttctc    2280
tggtagcatg cataagcaat ctcaagaagt atctgcagga ccaatggttg aaccctggtg    2340
aaaagttcca gaagattggt gtctgggaca atcttaacaa caagtggatc gttgtccccc    2400
aaaagaagaa atatgcctgg ggactcgcgg ctgatgtcga cggcaaccaa aagaccgtca    2460
tactgaacta cgacgaacac gggatgccga ttctcgaaaa gtcgtatgtg aggttggttg    2520
tctcgacaga cacatacctc tttacggtcg tctcgatgct tgggtatctc aggcatctcg    2580
accaaaaaaa acccaccgcc actataacac tagttgacgg ggtccctggg tgtggaaaga    2640
ctcaagaaat attgagtcgt ttcgacgcta acagtgacct catactagta cagggtaggg    2700
aggcatgtga aatgatcaga cgcagagcta atgataacgt acccggttcc gccacaaagg    2760
aaaacgttag aacgttcgat tctttcgtta tgaacagaaa accaggaaag tttaaaactc    2820
tgtgggttga tgaggggttg atggtgcacc ccggattaat caattttgt ataaacattt    2880 cgtgtgtttc ctctgtatat attttttggtg atagaaaaca gattcccttt attaatagag    2940
taatgaattt ttcaattccc gataacctag caaaactgta ttacgatgag attgtctccc    3000
gtgatacaac aaaaagatgt ccgttagatg tgacacattt cttgaacagt gtctatgaaa    3060
agagggttat gtcgtacagc aatgtacaac gttccctcga gtgcaaaatg ataagtggta    3120
aggccaaaat caacgactat cgtagtatct tggcagaagg gaagttgttg acgtttaccc    3180
aggaagataa agaatatctt ttgaaggccg ggtttaaaga tgtcaacacc gttcatgaag    3240
cgcagggtga aacttatcgg gatgtgaatc tcataagagt caccgccacg cccttaacca    3300
ttgtcagtgc tgggtcacct catgtgacgg ttgcactctc aagacacacg aatagatttg    3360
tgtactatac agtagtacct gatgtagtta tgacaactgt acagaagact cagtgtgtaa    3420
gtaacttcct tctggatatg tacgccgtgg cgtacaccca aaaatagcaa ttacagatct    3480
cgcccttcta cacccatgat ataccatttg tggagacgaa caaggtaggt caaatctctg    3540
atttacaata tttctatgac agttggctac cagggaactc atttgtccag aacaaccacg    3600
atcaatggtc gatcatttca tcggacatta atcttcattc cgaagccgtc cgtttggata    3660
tgaacaaacg ccatattcct aggacaaaag gtgagtttct gaggccgttg ttgaacacgg    3720
ctgtcgaacc tccaagaata ccgggtttat tggaaaatct gctggcgttg attaaaagaa    3780
attttaatgc gccggatcta gccggtcaat tggattacga ctttctctcc agaaaggttt    3840
```

```
gtgatgggtt tttcgggaag ctcttgcccc cggatgtaga agcgagcgaa ctgttgaggt    3900
taccggtcga tcacatgtat tcggtgcaaa actttgatga ctggttgaac aagcaggaac    3960
ctggagtcgt agggcaatta gcgaactggg accacatcgg tatgcccgcg gccgaccaat    4020
acaggcatat gattaaaagg actcctaagg ccaaattaga tttgtccata cagagcgaat    4080
accccgctct gcaaacgatt gtgtatcaca gcaagcatgt gaacgcagtt tttggaccga    4140
tcttttcatg tctgacggaa cgattactgt ctgtggtcga tcctttgagg ttcaaattct    4200
tcacaagaac taccccctgca gatcttgaat ttttttttag ggatatggtt gtcggtgaca    4260
tggagatcct agaactcgac atctcgaagt acgacaaaag tcaaaacaag tttcattttg    4320
aagtcgagat gagaatatgg gagatgctgg gcatcgacaa gtatatagaa aaggtgtggg    4380
aaaacggtca ccggaaaacg catttgcgtg actatacagc tggtattaag acggtgatcg    4440
agtaccagag aaagagtggc gacgtaacaa cgttcattgg gaacactatc attatcgccg    4500
cctgtctctg cagtattcta ccaatggaga aggtgtttaa agctgggttc tgtggtgatg    4560
actcgataat ttacttgccg agaaatcttc tctacccaga tatccaatcg gtctccaaca    4620
acatgtggaa ttttgaggca aagcttttca agaagctgca cggttacttc tgtggtaggt    4680
atattctacg caacggaagg tacctgaggc ttttaccaga ccccctcaaa attatcacaa    4740
aactggggtt g taaagccatc aaggactggg atcacctgga ggaattcagg atatctatgt    4800
tcgacatggc atgtgaatat aaaaattgtt ttggttttga tgttttggag tcggcagtta    4860
aggaatcttt tccaaaagct gaaggctgca acgttgcttt ttgtgctatt tataaatttt    4920
taagtaataa atatttgttt agaactttat ttagtgatgt ctgaggtgtc taaaatctcc    4980
actttgttgg ctccggaaaa gtttgtaaaa ctttccgttt ccgacaagtt taaatggaag    5040
gcaccttcga gagtttgtag tatagtacag agtgatacca tatctatgac tgcgaacgga    5100
agatcattgt ttacgtttga tgttttgaag gacgtgttaa aacacgcaga ggagtacaca    5160
tatgtcgatg ttcttggcgt tgtgttatct ggacagtggt tgctcccgaa agggacgccc    5220
ggttcggcag agatcattct cttagactcg cgccttaagg gaaaggcttc tgtcctcgcg    5280 gttttttaact gtagagctgc cacgcaagaa tttcagttcc tgatttcacc agggtactct    5340
ctgacttgtg cggacgctct taagaaaccc ttcgaaatat catgtaatgt gatcgacctg    5400
ccggtcaaag atggtttcac tcctttgtct gtcgagattg cgtgtttagt gcagtttttct    5460 aattgtgtta taacaaggtc tttgaccatg aaattaaaag aaaacccagc gaccaggaca    5520
ttctctgctg aagaggtcga cgaacttttg ggttcgatga ctactttacg gagtatcgag    5580
gggttgcgaa aaagaaaga acccaacgac gttgtacaag gacatctgag tgccgagtac    5640
gatgtgaaaa ggagtgttaa aaggacaaaa tctgaaaaca ctccgggaaa aagaagggtg    5700
aatgttgata gtgtgagttt gggattagga aagggaaaga gtgtgtctgc taaaaacgaa    5760
gacacagagt ctgtatttga cgacggcata ctcgattccg actcctagtc aacttgtgta    5820
ttttactgaa aattacgctg attacattcc attttaatta acggcctagg gcggccgctc    5880
gaggggtagt caagatgcat aataaataac ggattgtgtc cgtaatcaca cgtggtgcgt    5940
acgataacgc atagtgtttt tccctccact taaatcgaag ggttgtgtct tggatcgcgc    6000
gggtcaaatg tatatggttc atatacatcc gcaggcacgt aataaagcga ggggttcggg    6060
tcgaggtcgg ctgtgaaact cgaaaaggtt ccggaaaaca aaaagagag tggtaggtaa    6120 tagtgttaat aataagaaaa taataatag tggtaagaaa ggtttgaaag ttgaggaaat    6180
tgaggataat gtaagtgatg acgagtctat cgcgtcatcg agtacgtttt aatcaatatg    6240
```

```
ccttatacaa tcaactctcc gagccaattt gtttacttaa gttccgctta tgcagatcct    6300
gtgcagctga tcaatctgtg tacaaatgca ttgggtaacc agtttcaaac gcaacaagct    6360
aggacaacag tccaacagca atttgcggat gcctggaaac ctgtgcctag tatgacagtg    6420
agatttcctg catcggattt ctatgtgtat agatataatt cgacgcttga tccgttgatc    6480
acggcgttat taaatagctt cgatactaga aatagaataa tagaggttga taatcaaccc    6540
gcaccgaata ctactgaaat cgttaacgcg actcagaggg tagacgatgc gactgtagct    6600
ataagggctt caatcaataa tttggctaat gaactggttc gtggaactgg catgttcaat    6660
caagcaagct ttgagactgc tagtggactt gtctggacca caactccggc tacttagtct    6720
agtgtaaaag tttggtcgta cttaacgacc taggggctta ccgaaataag ccgtgtttaa    6780
gagtccacgc aaatcgaact ctagaactta tgaacagtca tggtttccat gccgtaaagt    6840
tcataaccgc gaagtcgcgg cgccgtcaag acacgacggt gagtggggag cattaccccc    6900
ccaaaaccct ggggatacag ggcccatcta gagtccgcaa atcaccagtc tctctctaca    6960
aatctatctc tctctatttt ctccagaata atgtgtgagt agttcccaga taagggaatt    7020
agggttctta tagggtttcg ctcatgtgtt gagcatataa gaaaccctta gtatgtatt    7080
gtatttgtaa aatacttcta tcaataaaat ttctaattcc taaaaccaaa atccagtgac    7140
ctgcagcccg gccgggggat ccactagcag attgtcgttt cccgccttca gtttaaacta    7200
tcagtgtttg acaggatata ttggcgggta aacctaagag aaaagagcgt ttattagaat    7260
aatcggatat ttaaaagggc gtgaaaaggt ttatccgttc gtccatttgt atgtgcatgc    7320
caaccacagg agatctcagt aaagcgctgg ctgaaccccc agccggaact gaccccacaa    7380
ggccctagcg tttgcaatgc accaggtcat cattgaccca ggcgtgttcc accaggccgc    7440
tgcctcgcaa ctcttcgcag gcttcgccga cctgctcgcg ccacttcttc acgcgggtgg    7500
aatccgatcc gcacatgagg cggaaggttt ccagcttgag cgggtacggc tcccggtgcg    7560
agctgaaata gtcgaacatc cgtcgggccg tcggcgacag cttgcggtac ttctcccata    7620
tgaatttcgt gtagtggtcg ccagcaaaca gcacgacgat ttcctcgtcg atcaggacct    7680
ggcaacggga cgttttcttg ccacggtcca ggacgcggaa gcggtgcagc agcgacaccg    7740
attccaggtg cccaacgcgg tcggacgtga agcccatcgc cgtcgcctgt aggcgcgaca    7800
ggcattcctc ggccttcgtg taataccggc cattgatcga ccagcccagg tcctggcaaa    7860
gctcgtagaa cgtgaaggtg atcggctcgc cgatagggt gcgcttcgcg tactccaaca    7920
cctgctgcca caccagttcg tcatcgtcgg cccgcagctc gacgccggtg taggtgatct    7980
tcacgtcctt gttgacgtgg aaaatgacct tgttttgcag cgcctcgcgc gggattttct    8040
tgttgcgcgt ggtgaacagg gcagagcggg ccgtgtcgtt tggcatcgct cgcatcgtgt    8100
ccggccacgg cgcaatatcg aacaaggaaa gctgcatttc cttgatctgc tgcttcgtgt    8160
gtttcagcaa cgcggcctgc ttggcctcgc tgacctgttt tgccaggtcc tcgccggcgg    8220
tttttcgctt cttggtcgtc atagttcctc gcgtgtcgat ggtcatcgac ttcgccaaac    8280
ctgccgcctc ctgttcgaga cgacgcgaac gctccacggc ggccgatggc gcgggcaggg    8340
caggggagc cagttgcacg ctgtcgcgct cgatcttggc cgtagcttgc tggaccatcg    8400
agccgacgga ctgaaggtt tcgcggggcg cacgcatgac ggtgcggctt gcgatggttt    8460
cggcatcctc ggcggaaaac cccgcgtcga tcagttcttg cctgtatgcc ttccggtcaa    8520
acgtccgatt cattcaccct ccttgcggga ttgccccgac tcacgccggg gcaatgtgcc    8580
cttattcctg atttgacccg cctggtgcct tggtgtccag ataatccacc ttatcggcaa    8640
```

```
tgaagtcggt cccgtagacc gtctggccgt ccttctcgta cttggtattc cgaatcttgc    8700
cctgcacgaa taccagcgac cccttgccca aatacttgcc gtgggcctcg gcctgagagc    8760
caaaacactt gatgcggaag aagtcggtgc gctcctgctt gtcgccggca tcgttgcgcc    8820
acatctaggt actaaaacaa ttcatccagt aaaatataat attttatttt ctcccaatca    8880
ggcttgatcc ccagtaagtc aaaaaatagc tcgacatact gttcttcccc gatatcctcc    8940
ctgatcgacc ggacgcagaa ggcaatgtca taccacttgt ccgccctgcc gcttctccca    9000
agatcaataa agccacttac tttgccatct ttcacaaaga tgttgctgtc tcccaggtcg    9060
ccgtgggaaa agacaagttc ctcttcgggc ttttccgtct ttaaaaaatc atacagctcg    9120
cgcggatctt taaatggagt gtcttcttcc cagttttcgc aatccacatc ggccagatcg    9180
ttattcagta agtaatccaa ttcggctaag cggctgtcta agctattcgt atagggacaa    9240
tccgatatgt cgatggagtg aaagagcctg atgcactccg catacagctc gataatcttt    9300
tcagggcttt gttcatcttc atactcttcc gagcaaagga cgccatcggc ctcactcatg    9360
agcagattgc tccagccatc atgccgttca aagtgcagga cctttggaac aggcagcttt    9420
ccttccagcc atagcatcat gtccttttcc cgttccacat cataggtggt ccctttatac    9480
cggctgtccg tcattttaa atataggttt tcattttctc ccaccagctt atataccttca    9540 gcaggagaca ttccttccgt atcttttacg cagcggtatt tttcgatcag ttttttcaat    9600
tccggtgata ttctcatttt agccatttat tatttccttc ctctttcta cagtatttaa     9660 agataccca agaagctaat tataacaaga cgaactccaa ttcactgttc cttgcattct     9720
aaaaccttaa ataccagaaa acagcttttt caaagttgtt ttcaaagttg gcgtataaca    9780
tagtatcgac ggagccgatt ttgaaaccac aattatgggt gatgctgcca actcgagagc    9840
gggccgggag ggttcgagaa gggggggcac cccccttcgg cgtgcgcggt cacgcgcaca    9900
gggcgcagcc ctggttaaaa acaaggttta taaatattgg tttaaaagca ggttaaaaga    9960
caggttagcg gtggccgaaa aacgggcgga aacccttgca aatgctggat tttctgcctg    10020
tggacagccc ctcaaatgtc aataggtgcg cccctcatct gtcagcactc tgcccctcaa    10080
gtgtcaagga tcgcgcccct catctgtcag tagtcgcgcc cctcaagtgt caataccgca    10140 ggcacttat ccccaggctt gtccacatca tctgtgggaa actcgcgtaa aatcaggcgt     10200
tttcgccgat ttgcgaggct ggccagctcc acgtcgccgg ccgaaatcga gcctgcccct    10260
catctgtcaa cgccgcgccg ggtgagtcgg cccctcaagt gtcaacgtcc gcccctcatc    10320
tgtcagtgag ggccaagttt ccgcgcaggt atccacaacg ccggcggccg gccgcggtgt    10380
ctcgcacacg gcttcgacgg cgtttctggc gcgtttgcag ggccatagac ggccgccagc    10440
ccagcggcga gggcaaccag cccggtgagc tctagtggac tgatgggctg cctgtatcga    10500
gtggtgattt tgtgccgagc tgccggtcgg ggagctgttg gctggctggt ggcaggatat    10560
attgtggtgt aaacgggtgg ttttggtacc gggcccccc tcgaggtcga cggtatcgat     10620
aagcttgata tcgaattcct gcaggtcaac atggtggagc acgacactct cgtctactcc    10680
aagaatatca agatacagt ctcagaagac caaagggcta ttgagacttt tcaacaaagg     10740
gtaatatcgg gaaacctcct cggattccat tgcccagcta tctgtcactt catcaaaagg    10800
acagtagaaa aggaaggtgg cacctacaaa tgccatcatt gcgataaagg aaaggctatc    10860
gttcaagatg cctctgccga cagtggtccc aaagatggac ccccacccac gaggagcatc    10920
gtggaaaaag aagacgttcc aaccacgtct caaagcaag tggattgatg tgataacatg     10980
gtggagcacg acactctcgt ctactccaag aatatcaaag atacagtctc agaagaccaa    11040
```

```
agggctattg agacttttca acaaagggta atatcgggaa acctcctcgg attccattgc  11100
ccagctatct gtcacttcat caaaaggaca gtagaaaagg aaggtggcac ctacaaatgc  11160
catcattgcg ataaaggaaa ggctatcgtt caagatgcct ctgccgacag tggtcccaaa  11220
gatggacccc cacccacgag gagcatcgtg gaaaagaag acgttccaac cacgtcttca   11280
aagcaagtgg attgatgtga tatctccact gacgtaaggg atgacgcaca atcccactat  11340
ccttcgcaag accttcctct atataaggaa gttcatttca tttggagagg             11390
```

<210> SEQ ID NO 73
<211> LENGTH: 107
<212> TYPE: DNA
<213> ORGANISM: Artificial Sequence
<220> FEATURE:
<223> OTHER INFORMATION: WECT40 vector: 5' UTR

<400> SEQUENCE: 73

```
gaaaacaaga cgagacgaac ccaaacagaa cgagccatcc gcagaaaaac taaaccatcc   60
caggttttct ttgaacataa ccaatccgta gtttgacaaa ggctgcc                107
```

<210> SEQ ID NO 74
<211> LENGTH: 3887
<212> TYPE: DNA
<213> ORGANISM: Artificial Sequence
<220> FEATURE:
<223> OTHER INFORMATION: WECT40 vector: replicase ORF

<400> SEQUENCE: 74

```
atggctaaag ttcgtgccgc tcttgacaga atcactgatc catcggttaa agctgtactc   60
aatgaagagg catacagcca catccgaccg gttcttcgtg aatccctaac caacaacccc  120
tacgccatcg caccgatgc tgctgatacg ctagaaaagt atggaattgc tactaatcca   180
ttcgcagtga agtacattc ccatggagca gttaaagta ttgaaaacac cctacttgag    240
agagttgggt ttaacttgcc gaaagagcca tgtaccttcc tcttcctcaa aagaagtaag   300
ctgcgttacc tcagacgtgg acctagcaac aatgacatct ttatcaatct agcgatcgaa   360
ccccgcgacc tccaaagata cgaggaagac actcttgttg agagtggac acgtatcacc   420 actaggtatg catatattag tgacactttc cacttcttca ctaggaagat gttggctgac   480
cttttctttc ataatccggc cttagatgta ttatatgcca ctttagtact tccacccgaa   540
gccctccaca acatcctag catagaacct gacttataca ctattaacta taactttaat   600
ggtttccaat acatcccagg caatcatggt ggtggttcct actcccatga attcaaacaa   660
ctggagtggc tcaaagttgg acatctcaaa tctccagaac tatgcctcac tttccagatg   720
atcgaatcca ttggtgccaa ccacctttc atgattaccc gcggtattaa aataaccct    780 agggtcagga ctttcaccaa agactcttac gtgctctttc cccaaatctt ccaccctcga   840
aacctcaatc cctcaaaacc attcccgaaa gtcaaagcaa tgcaactatt cacttatgtg   900
aagtctgtca agaatccaac tgaacgagac atctatgcca aaattcgaca gctaatcaag   960
acttctgagc tatctgatta tcatccagat gaaattgtgc acattgtaaa ttactttgtg  1020
ttcatctcca gttagatag catcaactct tattctgaca tactctcgct acccatctgg  1080
tctaaagcat tgctacccat caaaaccaaa attacacaac tttgggaaaa gctcaccggc  1140
gcaagagcct tcaatcaact cttagatgca ctccaatgga aacattcac ttatccttta   1200 gaggtagttg attctccaca gccccttcag accggagatt gcttcattga agacgagaga 1260
ttagagattg acacacttga ggatgaaatc ccaccaaatc gaacgacaa cacttcaatg  1320
```

```
agtccacaga gcattgagga ggctgttaaa acaaccctg atttaccctg gcaccatgg    1380 ttactcatct tgcaggctca taatgctgac tgcactgaaa agcagtatga ccctgagaat    1440
aacctcattc ttcctataca agagatcaac accctcccca agcaccaaca ccctgacatc    1500
ccaactgacc ttctaacact cctaaccaaa ttacacagag agccaactac agtctcactt    1560
gacaaccatc gagctcgtgc ctatggttct gacgttaaga atctgcgaat aggcgctcta    1620
ctcaaaaaac aaagcaaaga ttggttagct agtttcgctc tcaaaacgga aaatattgaa    1680
cgtgaagttt tgatgtctgt catccatggt gccggcggct ctgggaaatc acatgccatt    1740
caaacttgga tgcgctccct gaaccgaaga accgtcatg tcacaatcat tttaccaacg    1800
acagacttgc ggaatgactg gaccaacaaa gtgcccaatc tggagcaagc aaatttcaaa    1860
acttttgaga aagctctttg tcaaccttgt ggtaaaatta tcgtatttga tgactactcc    1920
aagcttcctc aaggctacat cgaagcattc cttgctatca accaaaatgt cattttagcc    1980
attcttaccg gagattctaa gcagagcttt catcatgaat ccaatgagga tgcctacact    2040
gccaccctag aacccagcat tatcacatac caacccttct gccgctacta cctaaacata    2100
acccatagaa acaaaccaga cctagctaac aaactgggtg tttactcctg ttctagtggc    2160
accacctcct tcacaatgtc atcccaagct ctcaagggta tgccaattct ctcccccagt    2220
ataatgaaga aaactgctct tggagaaatg ggccaaaaaa gcatgacata cgctggctgc    2280
caaggtctca aactaaagc tgtccaaatt ctcttggata ccaataccccc tttgtgcagt    2340 tccaacgtca tatacactgc tctcagccgt gctgttgacc acatacattt tattaacact    2400
ggacccaact caacagactt ctgggagaaa cttgattcca cccctacct caaaactttc    2460 ttggactgtg ttcgagaaga aaaaatgaat gagatcatcg ctgctgaaga accacctact    2520
cctgtgcagg ctcctaccac ccacttccca aaagtgaacc ccaccacagt gattgaatca    2580
tatgtccacg atcttcccga aaacatgat cgtgaaatct tttcagagac tcatggtcac    2640
tcaaatgcaa ttcaaactga caatcctgtg gttcaactct ttccccacca acaagccaaa    2700
gatgaaactc tttattgggc taccatcgaa gctagactac aatgcacttc atctgaagaa    2760
aaccttaaag aatttcatct caaacatgat attggtgaca ttctcttcct taattacaaa    2820
caagccatga accttcctca agaccccata ccatttaacc cagacctatg gacccctttgc    2880 agacaggaaa ttgagaacac atacctcaag aaaagtgctg ctgcccttgt taatgctgcc    2940
acccgccaat cacctgattt tgactcacat gcgatagcac tctttctcaa atcacaatgg    3000
gtcaagaaaa ctgaaaaaat tggttgcctt aaaatcaaag ctggccaaac tattgctgcc    3060
ttcatgcaac aaactgtcat gatttatggc acaatggctc gatacatgag aaaatttaga    3120
aaccaatatt gccccaggaa aatctttgtg aactgtgaaa ccacaccagc cgacttcaac    3180
tctttcatcc tcgacgagtg gaatttttaat agaacttgct tttcaaatga cttcactgca    3240
tttgatcaaa gtcaagatgg ctccatcctc caattcgaag tcattaaagc aaagtttcac    3300
aacatacccg aggatgttat tgaaggctat atccaaatca aaacacatgc caagatcttc    3360
ctgggcaccc ttagtatcat gagactctct ggtgaaggtc ccacttttga tgctaacact    3420
gaagcaaaca ttgcttatac acacaccaag tttaacatac cctgcgatgc tgcacaggtg    3480
tacgctggtg atgatatgtc cattgactac gtggcttcag tcaagcccag tttcaacatg    3540
attgaacatc tgatgaaact caaaggtaaa ccagtttta acacacaaac tcagggagac    3600
ttcgctgaat tttgcgggtg gacaatctca ccaaaaggca ttatcaagaa accagaaaaa    3660
atgaacatga gcattgaact ccaaaagaac atcaacaagt ttcatgaagt caaaagaagt    3720
```

-continued

```
tatgctctag accatgcctt cgcataccaa cttggtgatg aattacatga gctatacaat    3780
gagaatgaag cagaacacca ccaacttgct acaaggtcac tcattctcgc tggtcaagcc    3840
accgccctag acatacttga ttacgggtta agagacctaa agtagcg                  3887

<210> SEQ ID NO 75
<211> LENGTH: 40
<212> TYPE: DNA
<213> ORGANISM: Artificial Sequence
<220> FEATURE:
<223> OTHER INFORMATION: WECT40 vector: 40 bp of TGB1 ORF

<400> SEQUENCE: 75
atggatcaca ttcaccacct cctcagctcc cacggtttta                            40

<210> SEQ ID NO 76
<211> LENGTH: 71
<212> TYPE: DNA
<213> ORGANISM: Artificial Sequence
<220> FEATURE:
<223> OTHER INFORMATION: WECT40 vector: Pac I and Mlu I cloning sites
      followed by the last 60 bp of CP ORF

<400> SEQUENCE: 76
attaaacgcg tgttgaaatc actaacggtc gctccgaccc tattggtccc cttattacct      60
atccccagta a                                                           71

<210> SEQ ID NO 77
<211> LENGTH: 53
<212> TYPE: DNA
<213> ORGANISM: Artificial Sequence
<220> FEATURE:
<223> OTHER INFORMATION: WECT40 vector: 3' UTR

<400> SEQUENCE: 77
ttgccttatc acttcactta atatgtgtgg ctttctgttt aataaaattt cag             53

<210> SEQ ID NO 78
<211> LENGTH: 213
<212> TYPE: DNA
<213> ORGANISM: Artificial Sequence
<220> FEATURE:
<223> OTHER INFORMATION: WECT40 vector: 35S terminator

<400> SEQUENCE: 78
tctagagtcc gcaaatcacc agtctctctc tacaaatcta tctctctcta ttttctccag      60
aataatgtgt gagtagttcc cagataaggg aattagggtt cttatagggt ttcgctcatg     120
tgttgagcat ataagaaacc cttagtatgt atttgtattt gtaaaatact tctatcaata    180
aaatttctaa ttcctaaaac caaaatccag tga                                  213

<210> SEQ ID NO 79
<211> LENGTH: 69
<212> TYPE: DNA
<213> ORGANISM: Artificial Sequence
<220> FEATURE:
<223> OTHER INFORMATION: WECT40 vector: miscellaneous sequence

<400> SEQUENCE: 79
cctgcagccc ggccggggga tccactagca gattgtcgtt tcccgccttc agtttaaact      60
atcagtgtt                                                              69

<210> SEQ ID NO 80
<211> LENGTH: 25
```

```
<212> TYPE: DNA
<213> ORGANISM: Artificial Sequence
<220> FEATURE:
<223> OTHER INFORMATION: WECT40 vector: T-DNA right border

<400> SEQUENCE: 80
tgacaggata tattggcggg taaac                                           25

<210> SEQ ID NO 81
<211> LENGTH: 3316
<212> TYPE: DNA
<213> ORGANISM: Artificial Sequence
<220> FEATURE:
<223> OTHER INFORMATION: WECT40 vector: JL22 sequence

<400> SEQUENCE: 81
ctaagagaaa agagcgttta ttagaataat cggatattta aaagggcgtg aaaaggttta    60
tccgttcgtc catttgtatg tgcatgccaa ccacaggaga tctcagtaaa gcgctggctg   120 aaccccagc cggaactgac cccacaaggc cctagcgttt gcaatgcacc aggtcatcat   180
tgacccaggc gtgttccacc aggccgctgc ctcgcaactc ttcgcaggct tcgccgacct   240
gctcgcgcca cttcttcacg cggggtggaat ccgatccgca catgaggcgg aaggtttcca   300
gcttgagcgg gtacggctcc cggtgcgagc tgaaatagtc gaacatccgt cgggccgtcg   360
gcgacagctt gcggtacttc tcccatatga atttcgtgta gtggtcgcca gcaaacagca   420
cgacgatttc ctcgtcgatc aggacctggc aacgggacgt tttcttgcca cggtccagga   480
cgcggaagcg gtgcagcagc gacaccgatt ccaggtgccc aacgcggtcg acgtgaagc   540 ccatcgccgt cgcctgtagg cgcgacaggc attcctcggc cttcgtgtaa taccggccat   600
tgatcgacca gcccaggtcc tggcaaagct cgtagaacgt gaaggtgatc ggctcgccga   660
taggggtgcg cttcgcgtac tccaacacct gctgccacac cagttcgtca tcgtcggccc   720
gcagctcgac gccggtgtag gtgatcttca cgtccttgtt gacgtggaaa atgaccttgt   780
tttgcagcgc ctcgcgcggg atttttcttgt tgcgcgtggt gaacagggca gagcgggccg   840
tgtcgtttgg catcgctcgc atcgtgtccg gccacgcgc aatatcgaac aaggaaagct   900
gcatttcctt gatctgctgc ttcgtgtgtt tcagcaacgc ggcctgcttg gcctcgctga   960
cctgttttgc caggtcctcg ccggcggttt ttcgcttctt ggtcgtcata gttcctcgcg  1020
tgtcgatggt catcgacttc gccaaacctg ccgcctcctg ttcgagacga cgcgaacgct  1080
ccacggcggc cgatggcgcg ggcagggcag ggggagccag ttgcacgctg tcgcgctcga  1140
tcttggccgt agcttgctgg accatcgagc cgacggactg gaaggtttcg cggggcgcac  1200
gcatgacggt gcggcttgcg atggtttcgg catcctcggc ggaaaacccc gcgtcgatca  1260
gttcttgcct gtatgccttc cggtcaaacg tccgattcat tcaccctcct tgcgggattg  1320
ccccgactca cgccggggca atgtgccctt attcctgatt tgaccgcct ggtgccttgg  1380 tgtccagata atccaccta tcggcaatga agtcggtccc gtagaccgtc tggccgtcct  1440
tctcgtactt ggtattccga atcttgccct gcacgaatac cagcgacccc ttgcccaaat  1500
acttgccgtg ggcctcggcc tgagagccaa aacacttgat gcggaagaag tcggtgcgct  1560
cctgcttgtc gccggcatcg ttgcgccaca tctaggtact aaaacaattc atccagtaaa  1620
atataatatt ttattttctc ccaatcaggc ttgatcccca gtaagtcaaa aaatagctcg  1680
acatactgtt cttccccgat atcctccctg atcgaccgga cgcagaaggc aatgtcatac  1740
cacttgtccg ccctgccgct tctcccaaga tcaataaagc cacttacttt gccatctttc  1800
acaaagatgt tgctgtctcc caggtcgccg tgggaaaaga caagttcctc ttcgggcttt  1860
```

-continued

```
tccgtctttα αααααtcαtα cαgctcgcgc ggαtctttαα αtggαgtgtc ttcttcccαg    1920 ttttcgcαα t ccαcαtcggc cαgαtcgttα ttcαgtααgt ααtccααttc ggctααgcgg    1980 ctgtctααgc tαttcgtαtα gggαcααtcc gαtαtgtcgα tggαgtgααα gαgcctgαtg    2040 cαctccgcαt αcαgctcgαt ααtcttttcα gggctttgtt cαtcttcαtα ctcttccgαg    2100 cαααggαcgc cαtcggcctc αctcαtgαgc αgαttgctcc αgccαtcαtg ccgttcαααg    2160 tgcαggαcct ttggααcαgg cαgctttcct tccαgccαtα gcαtcαtgtc cttttcccgt    2220 tccαcαtcαt αggtggtccc tttαtαccgg ctgtccgtcα ttttτααααtα tαggttttcα    2280 ttttctcccα ccαgcttαtα tαccttαgcα ggαgαcαttc cttccgtαtc ttttαcgcαg    2340 cggtαttttt cgαtcαgttt tttcααttcc ggtgαtαttc tcαtttτtαgc cαtttαttαt    2400 ttccttcctc ttttctαcαg tαtttααα gα tαccccααgα αgctααttαt ααcααgαcgα    2460

αctccααttc αctgttcctt gcαttctααα αccttααα tα ccαgααααcα gcttttcαα     2520

αgttgtttc ααα gttggcg tαtααcαtαg tαtcgαcggα gccgαttttg αααccαcααt    2580 tαtgggtgαt gctgccααct cgαgαgcggg ccgggαgggt cgαgααggg gggcαcccc     2640 ccttcggcgt gcgcggtcαc gcgcαcαggg cgcαgccctg gttααααα cα αggtttαtαα    2700

αtαttggttt αααα gcαggt tαααα gαcαg gttαgcggtg gccgααααα c gggcggαααc    2760 ccttgcααα t gctggαtttt ctgcctgtgg αcαgcccctc ααα tgtcααt αggtgcgccc    2820 ctcαtctgtc αgcαctctgc ccctcααgtg tcααggαtcg cgccctcαt ctgtcαgtαg     2880 tcgcgcccct cααgtgtcαα tαccgcαggg cαcttαtccc cαggcttgtc cαcαtcαtct    2940 gtgggαααct cgcgtαααα t cαggcgtttt cgccgαtttg cgαggctggc cαgctccαcg    3000 tcgccggccg αα tcgαgcc tgccctcαt ctgtcααcgc cgcgccgggt gαgtcggccc    3060 ctcααgtgtc ααcgtccgcc cctcαtctgt cαgtgαgggc cααgttttcc gcgαggtαtc    3120 cαcααcgccg gcgccggcc gcggtgtctc gcαcαcggct tcgαcggcgt ttctggcgcg    3180 tttgcαgggc cαtαgαcggc cgccαgcccα gcggcgαggg cααccαgccc ggtgαgctct    3240

αgtggαctgα tgggctgcct gtαtcgαgtg gtgαttttgt gccgαgctgc cggtcgggg α   3300 gctgttggct ggctgg                                                    3316
```

<210> SEQ ID NO 82
<211> LENGTH: 25
<212> TYPE: DNA
<213> ORGANISM: Artificial Sequence
<220> FEATURE:
<223> OTHER INFORMATION: WECT40 vector: T-DNA left border
<400> SEQUENCE: 82
tggcaggata tattgtggtg taaac    25

<210> SEQ ID NO 83
<211> LENGTH: 88
<212> TYPE: DNA
<213> ORGANISM: Artificial Sequence
<220> FEATURE:
<223> OTHER INFORMATION: WECT40 vector: miscellaneous sequence 2

<400> SEQUENCE: 83
gggtggtttt ggtaccgggc cccccctcga ggtcgacggt atcgataagc ttgatatcga    60
attcctgcag gtcaacatgg tggagcac    88

<210> SEQ ID NO 84
<211> LENGTH: 728

<212> TYPE: DNA
<213> ORGANISM: Artificial Sequence
<220> FEATURE:
<223> OTHER INFORMATION: WECT40 vector: 35S promoter

<400> SEQUENCE: 84

| | | | | | |
|---|---|---|---|---|---|
| gacactctcg | tctactccaa | gaatatcaaa | gatacagtct | cagaagacca | aagggctatt | 60 |
| gagacttttc | aacaagggt | aatatcggga | acctcctcg | gattccattg | cccagctatc | 120 |
| tgtcacttca | tcaaaggac | agtagaaaag | gaaggtggca | cctacaaatg | ccatcattgc | 180 |
| gataaaggaa | aggctatcgt | tcaagatgcc | tctgccgaca | gtggtcccaa | agatggaccc | 240 |
| ccacccacga | ggagcatcgt | ggaaaagaa | gacgttccaa | ccacgtcttc | aaagcaagtg | 300 |
| gattgatgtg | ataacatggt | ggagcacgac | actctcgtct | actccaagaa | tatcaaagat | 360 |
| acagtctcag | aagaccaaag | ggctattgag | acttttcaac | aaagggtaat | atcgggaaac | 420 |
| ctcctcggat | tccattgccc | agctatctgt | cacttcatca | aaggacagt | agaaaggaa | 480 |
| ggtggcacct | acaaatgcca | tcattgcgat | aaaggaaagg | ctatcgttca | agatgcctct | 540 |
| gccgacagtg | gtcccaaaga | tggaccccca | cccacgagga | gcatcgtgga | aaagaagac | 600 |
| gttccaacca | cgtcttcaaa | gcaagtggat | tgatgtgata | tctccactga | cgtaagggat | 660 |
| gacgcacaat | cccactatcc | ttcgcaagac | cttcctctat | ataaggaagt | tcatttcatt | 720 |
| tggagagg | | | | | | 728 |

<210> SEQ ID NO 85
<211> LENGTH: 8622
<212> TYPE: DNA
<213> ORGANISM: Artificial Sequence
<220> FEATURE:
<223> OTHER INFORMATION: WECT40 vector: full length sequence

<400> SEQUENCE: 85

| | | | | | |
|---|---|---|---|---|---|
| gaaaacaaga | cgagacgaac | ccaaacagaa | cgagccatcc | gcagaaaaac | taaaccatcc | 60 |
| caggttttct | ttgaacataa | ccaatccgta | gtttgacaaa | ggctgccatg | gctaaagttc | 120 |
| gtgccgctct | tgacagaatc | actgatccat | cggttaaagc | tgtactcaat | gaagaggcat | 180 |
| acagccacat | ccgaccggtt | cttcgtgaat | ccctaaccaa | caacccctac | gccatcgcac | 240 |
| ccgatgctgc | tgatacgcta | gaaaagtatg | gaattgctac | taatccattc | gcagtgaaag | 300 |
| tacattccca | tggagcagtt | aaaagtattg | aaaacaccct | acttgagaga | gttgggttta | 360 |
| acttgccgaa | agagccatgt | accttcctct | tcctcaaaag | aagtaagctg | cgttacctca | 420 |
| gacgtggacc | tagcaacaat | gacatcttta | tcaatctagc | gatcgaaccc | cgcgacctcc | 480 |
| aaagatacga | ggaagacact | cttgttgaga | gttggacacg | tatcaccact | aggtatgcat | 540 |
| atattagtga | cactttccac | ttcttcacta | ggaagatgtt | ggctgacctt | ttctttcata | 600 |
| atccggcctt | agatgtatta | tatgccactt | tagtacttcc | acccgaagcc | ctccacaaac | 660 |
| atcctagcat | agaacctgac | ttatacacta | ttaactataa | ctttaatggt | ttccaataca | 720 |
| tcccaggcaa | tcatggtggt | ggttcctact | cccatgaatt | caaacaactg | gagtggctca | 780 |
| aagttggaca | tctcaaatct | ccagaactat | gcctcacttt | ccagatgatc | gaatccattg | 840 |
| gtgccaacca | ccttttcatg | attacccgcg | gtattaaaat | aacccctagg | gtcaggactt | 900 |
| tcaccaaaga | ctcttacgtg | ctctttcccc | aaatcttcca | ccctcgaaac | ctcaatccct | 960 |
| caaaaccatt | cccgaaagtc | aaagcaatgc | aactattcac | ttatgtgaag | tctgtcaaga | 1020 |
| atccaactga | acgagacatc | tatgccaaaa | ttcgacagct | aatcaagact | tctgagctat | 1080 |
| ctgattatca | tccagatgaa | attgtgcaca | ttgtaaatta | ctttgtgttc | atctccaagt | 1140 |

```
tagatagcat caactcttat tctgacatac tctcgctacc catctggtct aaagcattgc   1200
tacccatcaa aaccaaaatt acacaacttt gggaaaagct caccggcgca agagccttca   1260
atcaactctt agatgcactc caatggaaaa cattcactta tcctttagag gtagttgatt   1320
ctccacagcc ccttcagacc cgagattgct tcattgaaga cgagagatta gagattgaca   1380
cacttgagga tgaaatccca ccaaatccga acgacaacac ttcaatgagt ccacagagca   1440
ttgaggaggc tgttaaaaac aaccctgatt taccctgggc accatggtta ctcatcttgc   1500
aggctcataa tgctgactgc actgaaaagc agtatgaccc tgagaataac ctcattcttc   1560
ctatacaaga gatcaacacc ctccccaagc accaacaccc tgacatccca actgaccttc   1620
taacactcct aaccaaatta cacagagagc caactacagt ctcacttgac aaccatcgag   1680
ctcgtgccta tggttctgac gttaagaatc tgcgaatagg cgctctactc aaaaaacaaa   1740
gcaaagattg gttagctagt ttcgctctca aaacggaaaa tattgaacgt gaagttttga   1800
tgtctgtcat ccatggtgcc ggcggctctg ggaaatcaca tgccattcaa acttggatgc   1860
gctccctgaa ccgaagagac cgtcatgtca caatcatttt accaacgaca gacttgcgga   1920
atgactggac caacaaagtg cccaatctgg agcaagcaaa tttcaaaact tttgagaaag   1980
ctctttgtca accttgtggt aaaattatcg tatttgatga ctactccaag cttcctcaag   2040
gctacatcga agcattcctt gctatcaacc aaaatgtcat tttagccatt cttaccggag   2100
attctaagca gagctttcat catgaatcca atgaggatgc ctacactgcc accctagaac   2160
ccagcattat cacataccaa cccttctgcc gctactacct aaacataacc catagaaaca   2220
aaccagacct agctaacaaa ctgggtgttt actcctgttc tagtggcacc acctccttca   2280
caatgtcatc ccaagctctc aagggtatgc caattctctc ccccagtata atgaagaaaa   2340
ctgctcttgg agaaatgggc caaaaaagca tgacatacgc tggctgccaa ggtctcacaa   2400
ctaaagctgt ccaaattctc ttggatacca atacccettt gtgcagttcc aacgtcatat   2460
acactgctct cagccgtgct gttgaccaca tacattttat taacactgga cccaactcaa   2520
cagacttctg ggagaaactt gattccacac cctacctcaa aactttcttg gactgtgttc   2580
gagaagaaaa aatgaatgag atcatcgctg ctgaagaacc acctactcct gtgcaggctc   2640
ctaccaccca cttcccaaaa gtgaacccca ccacagtgat tgaatcatat gtccacgatc   2700
ttcccgaaaa acatgatcgt gaaatctttt cagagactca tggtcactca aatgcaattc   2760
aaactgacaa tcctgtggtt caactctttc cccaccaaca agccaaagat gaaactcttt   2820
attgggctac catcgaagct agactacaat gcacttcatc tgaagaaaac cttaaagaat   2880
ttcatctcaa acatgatatt ggtgacattc tcttccttaa ttacaaacaa gccatgaacc   2940
ttcctcaaga ccccatacca tttaacccag acctatggac cctttgcaga caggaaattg   3000
agaacacata cctcaagaaa agtgctgctg cccttgttaa tgctgccacc cgccaatcac   3060
ctgattttga ctcacatgcg atagcactct ttctcaaatc acaatgggtc aagaaaactg   3120
aaaaaattgg ttgccttaaa atcaaagctg gccaaactat tgctgccttc atgcaacaaa   3180
ctgtcatgat ttatggcaca atggctcgat acatgagaaa atttagaaac caatattgcc   3240
ccaggaaaat ctttgtgaac tgtgaaacca caccagccga cttcaactct ttcatcctcg   3300
acgagtggaa ttttaataga acttgctttt caaatgactt cactgcattt gatcaaagtc   3360
aagatggctc catcctccaa ttcgaagtca ttaaagcaaa gtttcacaac atacccgagg   3420
atgttattga aggctatatc caaatcaaaa cacatgccaa gatcttcctg ggcacccta    3480 gtatcatgag actctctggt gaaggtccca cttttgatgc taacactgaa gcaaacattg   3540
```

-continued

```
cttatacaca caccaagttt aacataccct gcgatgctgc acaggtgtac gctggtgatg    3600
atatgtccat tgactacgtg gcttcagtca agcccagttt caacatgatt gaacatctga    3660
tgaaactcaa aggtaaacca gttttaaca cacaaactca gggagacttc gctgaatttt    3720
gcgggtggac aatctcacca aaaggcatta tcaagaaacc agaaaaaatg aacatgagca    3780
ttgaactcca aaagaacatc aacaagtttc atgaagtcaa aagaagttat gctctagacc    3840
atgccttcgc ataccaactt ggtgatgaat tacatgagct atacaatgag aatgaagcag    3900
aacaccacca acttgctaca aggtcactca ttctcgctgg tcaagccacc gcccctagaca   3960 tacttgatta cgggttaaga gacctaaagt agcgatggat cacattcacc acctcctcag    4020
ctcccacggt tttaattaaa cgcgtgttga atcactaac ggtcgctccg accctattgg     4080
tccccttatt acctatcccc agtaattgcc ttatcacttc acttaatatg tgtggctttc    4140
tgtttaataa aatttcagtc tagagtccgc aaatcaccag tctctctcta caaatctatc    4200
tctctctatt ttctccagaa taatgtgtga gtagttccca gataagggaa ttagggttct    4260
tatagggttt cgctcatgtg ttgagcatat aagaaaccct tagtatgtat ttgtatttgt    4320
aaaatacttc tatcaataaa atttctaatt cctaaaacca aaatccagtg acctgcagcc    4380
cggccggggg atccactagc agattgtcgt ttcccgcctt cagtttaaac tatcagtgtt    4440
tgacaggata tattggcggg taaacctaag agaaaagagc gtttattaga ataatcggat    4500
atttaaaagg gcgtgaaaag gtttatccgt tcgtccattt gtatgtgcat gccaaccaca    4560
ggagatctca gtaaagcgct ggctgaaccc ccagccggaa ctgaccccac aaggccctag    4620
cgtttgcaat gcaccaggtc atcattgacc caggcgtgtt ccaccaggcc gctgcctcgc    4680
aactcttcgc aggcttcgcc gacctgctcg cgccacttct tcacgcgggt ggaatccgat    4740
ccgcacatga ggcggaaggt ttccagcttg agcgggtacg gctcccggtg cgagctgaaa    4800
tagtcgaaca tccgtcgggc cgtcggcgac agcttgcggt acttctccca tatgaatttc    4860
gtgtagtggt cgccagcaaa cagcacgacg atttcctcgt cgatcaggac ctggcaacgg    4920
gacgttttct tgccacggtc caggacgcgg aagcggtgca gcagcgacac cgattccagg    4980
tgcccaacgc ggtcggacgt gaagcccatc gccgtcgcct gtaggcgcga caggcattcc    5040
tcggccttcg tgtaataccg gccattgatc gaccagccca ggtcctggca aagctcgtag    5100
aacgtgaagg tgatcggctc gccgataggg gtgcgcttcg cgtactccaa cacctgctgc    5160
cacaccagtt cgtcatcgtc ggcccgcagc tcgacgccgg tgtaggtgat cttcacgtcc    5220
ttgttgacgt ggaaaatgac cttgttttgc agcgcctcgc gcgggatttt cttgttgcgc    5280
gtggtgaaca gggcagagcg ggccgtgtcg tttggcatcg ctcgcatcgt gtccggccac    5340
ggcgcaatat cgaacaagga aagctgcatt tccttgatct gctgcttcgt gtgtttcagc    5400
aacgcggcct gcttggcctc gctgacctgt tttgccaggt cctcgccggc ggttttcgc     5460 ttcttggtcg tcatagttcc tcgcgtgtcg atggtcatcg acttcgccaa acctgccgcc    5520
tcctgttcga gacgacgcga acgctccacg gcggccgatg gcgcgggcag gcaggggga     5580 gccagttgca cgctgtcgcg ctcgatcttg ccgtagcttt gctggaccat cgagccgacg    5640
gactggaagg tttcgcgggg cgcacgcatg acggtgcggc ttgcgatggt tcggcatcc     5700 tcggcggaaa accccgcgtc gatcagttct tgcctgtatg ccttccggtc aaacgtccga    5760
ttcattcacc ctccttgcgg gattgccccg actcacgccg gggcaatgtg cccttattcc    5820
tgatttgacc cgcctggtgc cttggtgtcc agataatcca ccttatcggc aatgaagtcg    5880
gtcccgtaga ccgtctggcc gtccttctcg tacttggtat tccgaatctt gccctgcacg    5940
```

```
aataccagcg accccttgcc caaatacttg ccgtgggcct cggcctgaga gccaaaacac    6000
ttgatgcgga agaagtcggt gcgctcctgc ttgtcgccgg catcgttgcg ccacatctag    6060
gtactaaaac aattcatcca gtaaaatata atattttatt ttctcccaat caggcttgat    6120
ccccagtaag tcaaaaaata gctcgacata ctgttcttcc ccgatatcct ccctgatcga    6180
ccggacgcag aaggcaatgt cataccactt gtccgccctg ccgcttctcc caagatcaat    6240
aaagccactt actttgccat cttttcacaaa gatgttgctg tctcccaggt cgccgtggga    6300
aaagacaagt tcctcttcgg cttttccgt ctttaaaaaa tcatacagct cgcgcggatc    6360
tttaaatgga gtgtcttctt cccagttttc gcaatccaca tcggccagat cgttattcag    6420
taagtaatcc aattcggcta agcggctgtc taagctattc gtatagggac aatccgatat    6480
gtcgatggag tgaaagagcc tgatgcactc cgcatacagc tcgataatct tttcagggct    6540
ttgttcatct tcatactctt ccgagcaaag gacgccatcg gcctcactca tgagcagatt    6600
gctccagcca tcatgccgtt caaagtgcag gacctttgga acaggcagct ttccttccag    6660
ccatagcatc atgtccttt cccgttccac atcataggtg gtccctttat accggctgtc    6720
cgtcattttt aaatataggt tttcattttc tcccaccagc ttatatacct tagcaggaga    6780
cattccttcc gtatctttta cgcagcggta tttttcgatc agttttttca attccggtga    6840
tattctcatt ttagccattt attatttcct tcctcttttc tacagtattt aaagatacccc    6900 caagaagcta attataacaa gacgaactcc aattcactgt tccttgcatt ctaaaacctt    6960
aaataccaga aaacagcttt ttcaaagttg ttttcaaagt tggcgtataa catagtatcg    7020
acggagccga ttttgaaacc acaattatgg gtgatgctgc caactcgaga gcgggccggg    7080
agggttcgag aaggggggc acccccttc ggcgtgcgcg tcacgcgca cagggcgcag    7140 ccctggttaa aaacaaggtt tataaatatt ggtttaaaag caggttaaaa gacaggttag    7200
cggtggccga aaaacgggcg gaaacccttg caaatgctgg attttctgcc tgtggacagc    7260
ccctcaaatg tcaataggtg cgcccctcat ctgtcagcac tctgcccctc aagtgtcaag    7320
gatcgcgccc ctcatctgtc agtagtcgcg cccctcaagt gtcaataccg cagggcactt    7380
atccccaggc ttgtccacat catctgtggg aaactcgcgt aaaatcaggc gttttcgccg    7440
atttgcgagg ctggccagct ccacgtcgcc ggccgaaatc gagcctgccc ctcatctgtc    7500
aacgccgcgc cgggtgagtc ggcccctcaa gtgtcaacgt ccgcccctca tctgtcagtg    7560
agggccaagt tttccgcgag gtatccacaa cgccggcggc cggccgcggt gtctcgcaca    7620
cggcttcgac ggcgtttctg gcgcgtttgc agggccatag acgccgcca gcccagcggc    7680 gagggcaacc agcccggtga gctctagtgg actgatgggc tgcctgtatc gagtggtgat    7740
tttgtgccga gctgccggtc ggggagctgt tggctggctg gtggcaggat atattgtggt    7800
gtaaacgggt ggttttggta ccgggcccc cctcgaggtc gacggtatcg ataagcttga    7860
tatcgaattc ctgcaggtca acatggtgga gcacgacact ctcgtctact ccaagaatat    7920
caaagataca gtctcagaag accaaagggc tattgagact tttcaacaaa gggtaatatc    7980
gggaaacctc ctcggattcc attgcccagc tatctgtcac ttcatcaaaa ggacagtaga    8040
aaaggaaggt ggcacctaca aatgccatca ttgcgataaa ggaaaggcta tcgttcaaga    8100
tgcctctgcc gacagtggtc ccaaagatgg acccccaccc acgaggagca tcgtggaaaa    8160
agaagacgtt ccaaccacgt cttcaaagca agtggattga tgtgataaca tggtggagca    8220
cgacactctc gtctactcca agaatatcaa agatacagtc tcagaagacc aaagggctat    8280
tgagactttt caacaaaggg taatatcggg aaacctcctc ggattccatt gcccagctat    8340
```

```
ctgtcacttc atcaaaagga cagtagaaaa ggaaggtggc acctacaaat gccatcattg    8400
cgataaagga aaggctatcg ttcaagatgc ctctgccgac agtggtccca agatggacc     8460 cccacccacg aggagcatcg tggaaaaaga agacgttcca accacgtctt caaagcaagt    8520
ggattgatgt gatatctcca ctgacgtaag ggatgacgca caatcccact atccttcgca    8580
agaccttcct ctatataagg aagttcattt catttggaga gg                       8622
```

<210> SEQ ID NO 86
<211> LENGTH: 32
<212> TYPE: DNA
<213> ORGANISM: Artificial Sequence
<220> FEATURE:
<223> OTHER INFORMATION: EcoLex Up primer

<400> SEQUENCE: 86

```
ggaaaggaat tcatgttact agatcgggga at                                  32
```

<210> SEQ ID NO 87
<211> LENGTH: 22
<212> TYPE: DNA
<213> ORGANISM: Artificial Sequence
<220> FEATURE:
<223> OTHER INFORMATION: 35term Up primer

<400> SEQUENCE: 87

```
aagttcattt catttggaga gg                                             22
```

<210> SEQ ID NO 88
<211> LENGTH: 22
<212> TYPE: DNA
<213> ORGANISM: Artificial Sequence
<220> FEATURE:
<223> OTHER INFORMATION: 35termAS Down primer

<400> SEQUENCE: 88

```
cctctccaaa tgaaatgaac tt                                             22
```

<210> SEQ ID NO 89
<211> LENGTH: 28
<212> TYPE: DNA
<213> ORGANISM: Artificial Sequence
<220> FEATURE:
<223> OTHER INFORMATION: JL22 RB Down primer

<400> SEQUENCE: 89

```
tctaataaac gctcttttct cttaggtt                                       28
```

<210> SEQ ID NO 90
<211> LENGTH: 21
<212> TYPE: DNA
<213> ORGANISM: Artificial Sequence
<220> FEATURE:
<223> OTHER INFORMATION: TMV p1-21 UP primer
<220> FEATURE:
<221> NAME/KEY: misc_feature
<222> LOCATION: (1)..(21)
<223> OTHER INFORMATION: where "n" is a phosphate group

<400> SEQUENCE: 90

```
ngtatttta caacaattac c                                               21
```

<210> SEQ ID NO 91
<211> LENGTH: 34
<212> TYPE: DNA
<213> ORGANISM: Artificial Sequence

```
<220> FEATURE:
<223> OTHER INFORMATION: TMV1008 NotDN primer

<400> SEQUENCE: 91
attattgcgg ccgcttgtac aaaagaaaag tatc                              34

<210> SEQ ID NO 92
<211> LENGTH: 22
<212> TYPE: DNA
<213> ORGANISM: Artificial Sequence
<220> FEATURE:
<223> OTHER INFORMATION: FoMV 5' term UP primer
<220> FEATURE:
<221> NAME/KEY: misc_feature
<222> LOCATION: (1)..(22)
<223> OTHER INFORMATION: where "n" is a phosphate group

<400> SEQUENCE: 92
ngaaaactct tccgaaaccg aa                                           22

<210> SEQ ID NO 93
<211> LENGTH: 34
<212> TYPE: DNA
<213> ORGANISM: Artificial Sequence
<220> FEATURE:
<223> OTHER INFORMATION: FoMV756 NotI DOWN primer

<400> SEQUENCE: 93 tttttttgcgg ccgcttagcc agtttaggtc ctta                             34

<210> SEQ ID NO 94
<211> LENGTH: 31
<212> TYPE: DNA
<213> ORGANISM: Artificial Sequence
<220> FEATURE:
<223> OTHER INFORMATION: p19XhoI UP primer

<400> SEQUENCE: 94
taataactcg agatggaacg agctatacaa g                                 31

<210> SEQ ID NO 95
<211> LENGTH: 35
<212> TYPE: DNA
<213> ORGANISM: Artificial Sequence
<220> FEATURE:
<223> OTHER INFORMATION: p19SpeI DOWN primer

<400> SEQUENCE: 95 tttttttacta gtttactcgc tttcttttc gaagg                             35

<210> SEQ ID NO 96
<211> LENGTH: 20
<212> TYPE: DNA
<213> ORGANISM: Artificial Sequence
<220> FEATURE:
<223> OTHER INFORMATION: FoMV Up primer

<400> SEQUENCE: 96
gtgggcatgt gcagatgagg                                              20

<210> SEQ ID NO 97
<211> LENGTH: 43
<212> TYPE: DNA
<213> ORGANISM: Artificial Sequence
<220> FEATURE:
<223> OTHER INFORMATION: FoMV+0sgp Down primer

<400> SEQUENCE: 97
```

```
aacctaccta ggactttaat taatgttatt taattcgtca gtg            43
```

<210> SEQ ID NO 98
<211> LENGTH: 41
<212> TYPE: DNA
<213> ORGANISM: Artificial Sequence
<220> FEATURE:
<223> OTHER INFORMATION: FoMV+22sgp Down primer

<400> SEQUENCE: 98

```
gcttttaatt aagttcaact atttcactat cgattgttat t              41
```

<210> SEQ ID NO 99
<211> LENGTH: 32
<212> TYPE: DNA
<213> ORGANISM: Artificial Sequence
<220> FEATURE:
<223> OTHER INFORMATION: FoMV+40sgp Down primer

<400> SEQUENCE: 99

```
gtctttaatt aaccaagctt tgttagtcgt tc                        32
```

<210> SEQ ID NO 100
<211> LENGTH: 33
<212> TYPE: DNA
<213> ORGANISM: Artificial Sequence
<220> FEATURE:
<223> OTHER INFORMATION: PacGFPUp primer

<400> SEQUENCE: 100

```
ttgtcattaa ttaagctagc aaaggagaag aac                       33
```

<210> SEQ ID NO 101
<211> LENGTH: 32
<212> TYPE: DNA
<213> ORGANISM: Artificial Sequence
<220> FEATURE:
<223> OTHER INFORMATION: GFPAvrDown primer

<400> SEQUENCE: 101

```
tttactccta ggttatttgt agagctcatc ca                        32
```

<210> SEQ ID NO 102
<211> LENGTH: 33
<212> TYPE: DNA
<213> ORGANISM: Artificial Sequence
<220> FEATURE:
<223> OTHER INFORMATION: PacDsRedUP primer

<400> SEQUENCE: 102

```
ggatggttaa ttaaatggcc tcctccgaga acg                       33
```

<210> SEQ ID NO 103
<211> LENGTH: 30
<212> TYPE: DNA
<213> ORGANISM: Artificial Sequence
<220> FEATURE:
<223> OTHER INFORMATION: AvrDsRedDN primer

<400> SEQUENCE: 103

```
tttactccta ggctacagga acaggtggtg                           30
```

<210> SEQ ID NO 104
<211> LENGTH: 34
<212> TYPE: DNA
<213> ORGANISM: Artificial Sequence

```
<220> FEATURE:
<223> OTHER INFORMATION: PacLangLCUP

<400> SEQUENCE: 104
ggatggttaa ttaaatgaag ttgcctgtta ggct                              34

<210> SEQ ID NO 105
<211> LENGTH: 31
<212> TYPE: DNA
<213> ORGANISM: Artificial Sequence
<220> FEATURE:
<223> OTHER INFORMATION: AvrLangLCDN primer

<400> SEQUENCE: 105
aatactccta ggctaacact ctcccctgtt g                                 31

<210> SEQ ID NO 106
<211> LENGTH: 34
<212> TYPE: DNA
<213> ORGANISM: Artificial Sequence
<220> FEATURE:
<223> OTHER INFORMATION: PacLangHCUP primer

<400> SEQUENCE: 106
atatggttaa ttaaatggaa tggaggatct ttct                              34

<210> SEQ ID NO 107
<211> LENGTH: 32
<212> TYPE: DNA
<213> ORGANISM: Artificial Sequence
<220> FEATURE:
<223> OTHER INFORMATION: AvrLangHCDN primer

<400> SEQUENCE: 107
tttactccta ggtcagctag ctttacccag ag                                32

<210> SEQ ID NO 108
<211> LENGTH: 36
<212> TYPE: DNA
<213> ORGANISM: Artificial Sequence
<220> FEATURE:
<223> OTHER INFORMATION: ApaI Pnos UP primer

<400> SEQUENCE: 108
atatgagggc ccaactgaag gcgggaaacg acaatc                            36

<210> SEQ ID NO 109
<211> LENGTH: 43
<212> TYPE: DNA
<213> ORGANISM: Artificial Sequence
<220> FEATURE:
<223> OTHER INFORMATION: PnosBsiWI-overlapDN primer

<400> SEQUENCE: 109
gaccacttta tggaggttcg tacgtctagg ggatccggtg cag                    43

<210> SEQ ID NO 110
<211> LENGTH: 42
<212> TYPE: DNA
<213> ORGANISM: Artificial Sequence
<220> FEATURE:
<223> OTHER INFORMATION: TnosSpeI-overlapUP primer

<400> SEQUENCE: 110
aacctccata aagtggtcac tagtatcgtt caaacatttg gc                     42
```

```
<210> SEQ ID NO 111
<211> LENGTH: 37
<212> TYPE: DNA
<213> ORGANISM: Artificial Sequence
<220> FEATURE:
<223> OTHER INFORMATION: SbfI Tnos DN primer

<400> SEQUENCE: 111
attatgcctg caggagctgg catgcaagct gtcgagg                              37

<210> SEQ ID NO 112
<211> LENGTH: 31
<212> TYPE: DNA
<213> ORGANISM: Artificial Sequence
<220> FEATURE:
<223> OTHER INFORMATION: BsiWI/p19 UP primer

<400> SEQUENCE: 112
taataacgta cgatggaacg agctatacaa g                                    31

<210> SEQ ID NO 113
<211> LENGTH: 35
<212> TYPE: DNA
<213> ORGANISM: Artificial Sequence
<220> FEATURE:
<223> OTHER INFORMATION: p19SpeI DOWN primer

<400> SEQUENCE: 113 tttttttacta gtttactcgc tttcttttc gaagg                                35

<210> SEQ ID NO 114
<211> LENGTH: 34
<212> TYPE: DNA
<213> ORGANISM: Artificial Sequence
<220> FEATURE:
<223> OTHER INFORMATION: Xba/GFP UP primer

<400> SEQUENCE: 114
taagcatcta gaatggctag caaaggagaa gaac                                 34

<210> SEQ ID NO 115
<211> LENGTH: 32
<212> TYPE: DNA
<213> ORGANISM: Artificial Sequence
<220> FEATURE:
<223> OTHER INFORMATION: GFP/SpeI DOWN primer

<400> SEQUENCE: 115 tttttttacta gtttatttgt agagctcatc ca                                  32

<210> SEQ ID NO 116
<211> LENGTH: 25
<212> TYPE: DNA
<213> ORGANISM: Artificial Sequence
<220> FEATURE:
<223> OTHER INFORMATION: SHMV 4658 Up primer

<400> SEQUENCE: 116
cagatatcca atcggtctcc aacaa                                           25

<210> SEQ ID NO 117
<211> LENGTH: 33
<212> TYPE: DNA
<213> ORGANISM: Artificial Sequence
<220> FEATURE:
<223> OTHER INFORMATION: dCP-SHMV Down primer

<400> SEQUENCE: 117
```

```
tcggaatcga gtatgccgtc gtcaaataca gac                           33
```

<210> SEQ ID NO 118
<211> LENGTH: 33
<212> TYPE: DNA
<213> ORGANISM: Artificial Sequence
<220> FEATURE:
<223> OTHER INFORMATION: dCP-SHMV Up primer

<400> SEQUENCE: 118

```
gtctgtattt gacgacggca tactcgattc cga                           33
```

<210> SEQ ID NO 119
<211> LENGTH: 28
<212> TYPE: DNA
<213> ORGANISM: Artificial Sequence
<220> FEATURE:
<223> OTHER INFORMATION: JL22 RB Down primer

<400> SEQUENCE: 119

```
tctaataaac gctcttttct cttaggtt                                 28
```

<210> SEQ ID NO 120
<211> LENGTH: 30
<212> TYPE: DNA
<213> ORGANISM: Artificial Sequence
<220> FEATURE:
<223> OTHER INFORMATION: SHMV Pac5838 Down primer

<400> SEQUENCE: 120

```
tggaatttaa ttaacgtaat tttcagtaaa                               30
```

<210> SEQ ID NO 121
<211> LENGTH: 30
<212> TYPE: DNA
<213> ORGANISM: Artificial Sequence
<220> FEATURE:
<223> OTHER INFORMATION: SHMV Pac5854 Down primer

<400> SEQUENCE: 121

```
aacctattaa ttaatggaat gtaatcagcg                               30
```

<210> SEQ ID NO 122
<211> LENGTH: 31
<212> TYPE: DNA
<213> ORGANISM: Artificial Sequence
<220> FEATURE:
<223> OTHER INFORMATION: SHMV Pac5869 Down primer

<400> SEQUENCE: 122

```
ctgcgttaat taatcaacct attaacaaat g                             31
```

<210> SEQ ID NO 123
<211> LENGTH: 43
<212> TYPE: DNA
<213> ORGANISM: Artificial Sequence
<220> FEATURE:
<223> OTHER INFORMATION: SHMV PacBss3UTR Up primer

<400> SEQUENCE: 123

```
tgctcgttaa ttaaactgcg cgctctagtg taaaagtttg gtc                43
```

<210> SEQ ID NO 124
<211> LENGTH: 32
<212> TYPE: DNA
<213> ORGANISM: Artificial Sequence

```
<220> FEATURE:
<223> OTHER INFORMATION: GFPBssDown primer

<400> SEQUENCE: 124
tttactccta ggttatttgt agagctcatc ca                              32

<210> SEQ ID NO 125
<211> LENGTH: 34
<212> TYPE: DNA
<213> ORGANISM: Artificial Sequence
<220> FEATURE:
<223> OTHER INFORMATION: PacGUSUp primer

<400> SEQUENCE: 125
ggatggttaa ttaaatgtta cgtcctgtag aaac                            34

<210> SEQ ID NO 126
<211> LENGTH: 31
<212> TYPE: DNA
<213> ORGANISM: Artificial Sequence
<220> FEATURE:
<223> OTHER INFORMATION: GUSBssDown primer

<400> SEQUENCE: 126
tttactgcgc gctcattgtt tgcctccctg c                               31

<210> SEQ ID NO 127
<211> LENGTH: 31
<212> TYPE: DNA
<213> ORGANISM: Artificial Sequence
<220> FEATURE:
<223> OTHER INFORMATION: TMGMVCPBssDown primer

<400> SEQUENCE: 127
tttactgcgc gcctaagtag ccggagttgt g                               31

<210> SEQ ID NO 128
<211> LENGTH: 32
<212> TYPE: DNA
<213> ORGANISM: Artificial Sequence
<220> FEATURE:
<223> OTHER INFORMATION: BssSHMVUp15 primer

<400> SEQUENCE: 128
tttactgcgc gcccacgtac cgcttagtct ag                              32

<210> SEQ ID NO 129
<211> LENGTH: 33
<212> TYPE: DNA
<213> ORGANISM: Artificial Sequence
<220> FEATURE:
<223> OTHER INFORMATION: BssSHMVUp40 primer

<400> SEQUENCE: 129
tttactgcgc gctctgacat ggttggtgac aac                             33

<210> SEQ ID NO 130
<211> LENGTH: 32
<212> TYPE: DNA
<213> ORGANISM: Artificial Sequence
<220> FEATURE:
<223> OTHER INFORMATION: XbaGUSUp primer

<400> SEQUENCE: 130
ggatggtcta gaatgttacg tcctgtagaa ac                              32
```

```
<210> SEQ ID NO 131
<211> LENGTH: 31
<212> TYPE: DNA
<213> ORGANISM: Artificial Sequence
<220> FEATURE:
<223> OTHER INFORMATION: SpeGUSDown primer

<400> SEQUENCE: 131
tttactacta gttcattgtt tgcctccctg c                              31

<210> SEQ ID NO 132
<211> LENGTH: 22
<212> TYPE: DNA
<213> ORGANISM: Artificial Sequence
<220> FEATURE:
<223> OTHER INFORMATION: WClMV 5' term UP primer
<220> FEATURE:
<221> NAME/KEY: misc_feature
<222> LOCATION: (1)..(21)
<223> OTHER INFORMATION: where "n" is a phosphate group

<400> SEQUENCE: 132
ngaaaacaag acgagacgaa cc                                        22

<210> SEQ ID NO 133
<211> LENGTH: 34
<212> TYPE: DNA
<213> ORGANISM: Artificial Sequence
<220> FEATURE:
<223> OTHER INFORMATION: WClMV1089 NotI DN primer

<400> SEQUENCE: 133
aaaaaagcgg ccgcgataat cagatagctc agaa                           34

<210> SEQ ID NO 134
<211> LENGTH: 34
<212> TYPE: DNA
<213> ORGANISM: Artificial Sequence
<220> FEATURE:
<223> OTHER INFORMATION: WClMV4822 NotI UP primer

<400> SEQUENCE: 134
tattatgcgg ccgcttggag gtgaatacaa agac                           34

<210> SEQ ID NO 135
<211> LENGTH: 32
<212> TYPE: DNA
<213> ORGANISM: Artificial Sequence
<220> FEATURE:
<223> OTHER INFORMATION: WClMV5846 XbaI DN primer

<400> SEQUENCE: 135
aatgaatcta gactgaaatt ttattaaaca ga                             32

<210> SEQ ID NO 136
<211> LENGTH: 32
<212> TYPE: DNA
<213> ORGANISM: Artificial Sequence
<220> FEATURE:
<223> OTHER INFORMATION: WClMV2608XmaUP primer

<400> SEQUENCE: 136
agagtacccg ggagatcatc gctgctgaag aa                             32

<210> SEQ ID NO 137
<211> LENGTH: 35
<212> TYPE: DNA
<213> ORGANISM: Artificial Sequence
```

```
<220> FEATURE:
<223> OTHER INFORMATION: WClMVsg26PacDN primer

<400> SEQUENCE: 137
gaagtcttaa ttaactgagg aggtggtgaa tgtga                              35

<210> SEQ ID NO 138
<211> LENGTH: 35
<212> TYPE: DNA
<213> ORGANISM: Artificial Sequence
<220> FEATURE:
<223> OTHER INFORMATION: WCMVsg40PacDN primer

<400> SEQUENCE: 138
gaagtcttaa ttaataaaac cgtgggagct gagga                              35

<210> SEQ ID NO 139
<211> LENGTH: 39
<212> TYPE: DNA
<213> ORGANISM: Artificial Sequence
<220> FEATURE:
<223> OTHER INFORMATION: WCMVPacI MluI 3'CP UP primer

<400> SEQUENCE: 139
aagttgttaa ttaaacgcgt gttgaaatca ctaacggtc                          39

<210> SEQ ID NO 140
<211> LENGTH: 28
<212> TYPE: DNA
<213> ORGANISM: Artificial Sequence
<220> FEATURE:
<223> OTHER INFORMATION: JL22RB DN primer

<400> SEQUENCE: 140
tctaataaac gctctttttct cttaggtt                                      28

<210> SEQ ID NO 141
<211> LENGTH: 33
<212> TYPE: DNA
<213> ORGANISM: Artificial Sequence
<220> FEATURE:
<223> OTHER INFORMATION: PacGFP UP primer

<400> SEQUENCE: 141
ttgtcattaa ttaagctagc aaaggagaag aac                                33

<210> SEQ ID NO 142
<211> LENGTH: 32
<212> TYPE: DNA
<213> ORGANISM: Artificial Sequence
<220> FEATURE:
<223> OTHER INFORMATION: GFP Bss DN primer

<400> SEQUENCE: 142
tttactgcgc gcttatttgt agagctcatc ca                                 32

<210> SEQ ID NO 143
<211> LENGTH: 34
<212> TYPE: DNA
<213> ORGANISM: Artificial Sequence
<220> FEATURE:
<223> OTHER INFORMATION: WCMV2590 XmaI UP primer

<400> SEQUENCE: 143
tgcgtacccg ggaaatgaat gagatcatcg ctgc                               34
```

```
<210> SEQ ID NO 144
<211> LENGTH: 43
<212> TYPE: DNA
<213> ORGANISM: Artificial Sequence
<220> FEATURE:
<223> OTHER INFORMATION: WECT+22ORF PacDN primer

<400> SEQUENCE: 144
gtactattaa ttaaggaggt ggtgaatgtg atcgatcgct act                43

<210> SEQ ID NO 145
<211> LENGTH: 47
<212> TYPE: DNA
<213> ORGANISM: Artificial Sequence
<220> FEATURE:
<223> OTHER INFORMATION: WECT+40ORF PacDN primer

<400> SEQUENCE: 145
gactacttaa ttaaaaccgt gggagctgag gaggtggtga atgtgat            47

<210> SEQ ID NO 146
<211> LENGTH: 18
<212> TYPE: DNA
<213> ORGANISM: Artificial Sequence
<220> FEATURE:
<223> OTHER INFORMATION: WECT UPscreen primer

<400> SEQUENCE: 146
gaatgagatc atcgctgc                                            18

<210> SEQ ID NO 147
<211> LENGTH: 18
<212> TYPE: DNA
<213> ORGANISM: Artificial Sequence
<220> FEATURE:
<223> OTHER INFORMATION: WECTscreen AUC primer

<400> SEQUENCE: 147
aggtggtgaa tgtgatcg                                            18

<210> SEQ ID NO 148
<211> LENGTH: 18
<212> TYPE: DNA
<213> ORGANISM: Artificial Sequence
<220> FEATURE:
<223> OTHER INFORMATION: WECT40screen primer

<400> SEQUENCE: 148
taaaaccgtg ggagctga                                            18
```